US011951100B2

United States Patent
Lin et al.

(10) Patent No.: US 11,951,100 B2
(45) Date of Patent: Apr. 9, 2024

(54) FORMULATIONS OF RBP4 INHIBITORS AND METHODS OF USE

(71) Applicant: Belite Bio, LLC, San Diego, CA (US)

(72) Inventors: Yu-Hsin Tom Lin, San Diego, CA (US); Cheng-Chi Irene Wang, San Diego, CA (US)

(73) Assignee: Belite Bio, LLC, San Diego, CA (US)

( * ) Notice: Subject to any disclaimer, the term of this patent is extended or adjusted under 35 U.S.C. 154(b) by 0 days.

(21) Appl. No.: 18/460,080

(22) Filed: Sep. 1, 2023

(65) Prior Publication Data

US 2023/0404984 A1    Dec. 21, 2023

Related U.S. Application Data

(63) Continuation of application No. 17/620,427, filed as application No. PCT/US2020/040919 on Jul. 6, 2020.

(60) Provisional application No. 62/871,622, filed on Jul. 8, 2019.

(51) Int. Cl.
| | |
|---|---|
| *A61K 31/437* | (2006.01) |
| *A61K 9/10* | (2006.01) |
| *A61K 9/16* | (2006.01) |
| *A61K 9/48* | (2006.01) |
| *A61P 27/02* | (2006.01) |
| *C07D 471/04* | (2006.01) |
| *C07D 487/04* | (2006.01) |

(52) U.S. Cl.
CPC ............ *A61K 31/437* (2013.01); *A61K 9/10* (2013.01); *A61K 9/1635* (2013.01); *A61K 9/1652* (2013.01); *A61K 9/4866* (2013.01); *A61P 27/02* (2018.01); *C07D 471/04* (2013.01); *C07D 487/04* (2013.01); *C07B 2200/13* (2013.01)

(58) Field of Classification Search
CPC ...... A61K 31/437; A61K 9/10; A61K 9/1635; A61K 9/1652; A61K 9/4866; A61P 27/02; C07D 471/04; C07D 487/04; C07B 2200/13
See application file for complete search history.

(56) References Cited

U.S. PATENT DOCUMENTS

| | | | |
|---|---|---|---|
| 5,846,514 A | 12/1998 | Foster et al. | |
| 6,334,997 B1 | 1/2002 | Foster et al. | |
| 7,632,837 B2 | 12/2009 | Sun et al. | |
| 8,648,038 B2 | 2/2014 | Defossa et al. | |
| 8,680,137 B2 | 3/2014 | Sun et al. | |
| 8,980,924 B2 | 3/2015 | Petrukhin et al. | |
| 9,333,202 B2 | 5/2016 | Petrukhin et al. | |
| 9,434,727 B2 | 9/2016 | Petrukhin et al. | |
| 9,487,509 B2 | 11/2016 | Kasai et al. | |
| 9,637,450 B2 | 5/2017 | Petrukhin et al. | |
| 9,777,010 B2 | 10/2017 | Petrukhin et al. | |
| 9,926,271 B2 | 3/2018 | Petrukhin et al. | |
| 9,938,291 B2 | 4/2018 | Petrukhin et al. | |
| 9,944,644 B2 | 4/2018 | Petrukhin et al. | |
| 10,245,259 B2 | 4/2019 | Lin et al. | |
| 11,007,186 B2 | 5/2021 | Lin et al. | |
| 11,389,444 B2 | 7/2022 | Lin et al. | |
| 2008/0063708 A1 | 3/2008 | Perlman et al. | |
| 2010/0022530 A1 | 1/2010 | Schiemann et al. | |
| 2011/0123521 A1 | 5/2011 | Monia et al. | |
| 2014/0066420 A1 | 3/2014 | Kasai et al. | |
| 2015/0315197 A1 | 11/2015 | Petrukhin et al. | |
| 2016/0004668 A1 | 1/2016 | Rowles et al. | |
| 2016/0046648 A1 | 2/2016 | Petrukhin et al. | |
| 2016/0046649 A1 | 2/2016 | Petrukhin et al. | |
| 2017/0114072 A1 | 4/2017 | Yang et al. | |
| 2018/0354957 A1 | 12/2018 | Petrukhin et al. | |
| 2021/0228563 A1 | 7/2021 | Lin et al. | |
| 2022/0354844 A1 | 11/2022 | Lin et al. | |
| 2022/0387400 A1 | 12/2022 | Lin et al. | |

FOREIGN PATENT DOCUMENTS

| | | | |
|---|---|---|---|
| CN | 101294956 A | 10/2008 | |
| EP | 2202223 A1 | 6/2010 | |
| WO | WO-0174164 A1 | 10/2001 | |
| WO | WO-2009143390 A2 | 11/2009 | |
| WO | WO-2012007172 A1 | 1/2012 | |
| WO | WO-2012071369 A2 | 5/2012 | |
| WO | WO-2013166037 A1 | 11/2013 | |
| WO | WO-2014151936 A1 | 9/2014 | |
| WO | WO-2014151959 A1 | 9/2014 | |
| WO | WO-2014152013 A1 | 9/2014 | |
| WO | WO-2014152018 A1 | 9/2014 | |
| WO | WO-2014160409 A1 | 10/2014 | |
| WO | WO-2015168286 A1 * | 11/2015 | ........... A61K 31/437 |

(Continued)

OTHER PUBLICATIONS

Aguilera CM, et al. Alterations in plasma and tissue lipids associated with obesity and metabolic syndrome. Clin Sci (Lond). Feb. 2008;114(3):183-193.
Anon, Diagnosis and Classification of Diabetes Mellitus. 2012 Diabetes care, 35 Suppl 1, pp. S64-S71.
Attie AD, et al. Adipocyte metabolism and obesity. J Lipid Res. Apr. 2009;50 Suppl:S395-S399.
Berge et al.: Pharmaceutical Salts. Journal of Pharmaceutical Science. 66:1-19 (1997).
Bundgard, H. Design of Prodrugs. 1985; pp. 7-9, 21-24 (Elsevier, Amsterdam).
Cannon, Burger's Medicinal Chemistry and Drug Discovery 1995, Fifth Edition, I: Principles and Practice, Chap. 19, John Wiley & Sons, Inc., 783-802 (1995).

(Continued)

*Primary Examiner* — Michael Barker
*Assistant Examiner* — Jed A Kucharczk
(74) *Attorney, Agent, or Firm* — Wilson Sonsini Goodrich & Rosati

(57) ABSTRACT

Provided herein are heterocyclic derivative compounds and pharmaceutical compositions comprising said compounds that are useful for the treatment of retinal binding protein (RBP4) related diseases, such as macular degeneration and the like.

20 Claims, 29 Drawing Sheets

(56) References Cited

FOREIGN PATENT DOCUMENTS

| WO | WO-2018232154 A1 | 12/2018 |
|---|---|---|
| WO | WO-2020028723 A1 | 2/2020 |

OTHER PUBLICATIONS

Chalasani et al.: The diagnosis and management of non-alcoholic fatty liver disease: Practice guideline by the American Association for the Study of Liver Diseases, American College of Gastroenterology, and the American Gastroenterological Association. Hepatology. 55:2005-2023 (2012).
Choe SS, et al. Adipose Tissue Remodeling Its Role in Energy Metabolism and Metabolic Disorders. Front Endocrinol (Lausanne). Apr. 13, 2016;7:30.
Cooke DW, et al. Type 1 diabetes mellitus in pediatrics. Pediatr Rev. Nov. 2008;29(11):374-384; quiz 385.
European Application No. 20836592.4 extended European Search Report dated Jun. 15, 2023.
European Patent Application No. EP18817386.8 Extended European Search Report dated Feb. 5, 2021.
Fabbrini E, et al. Alterations in adipose tissue and hepatic lipid kinetics in obese men and women with nonalcoholic fatty liver disease. Gastroenterology 2008;134:424-431.
Goto T, et al. Farnesol, an isoprenoid, improves metabolic abnormalities in mice via both PPAR-dependent and- independent pathways. Am J Physiol Endocrinol Metab. Nov. 2011;301(5):E1022-1032.
Graham et al.: Retinol-Binding Protein 4 and Insulin Resistance in Lean, Obese, and Diabetic Subjects. N. Engl J Med. 354:2552-2563 (2006).
Higuchi et al. Pro-drugs as Novel Delivery Systems, vol. 14 of the A.C.S. Symposium Series; and in Bioreversible Carriers in Drug Design, ed. Edward B. Roche, American Pharmaceutical Association and Pergamon Press (1987).
International Application No. PCT/US2019/044754 International Search Report and Written Opinion dated Nov. 27, 2019.
Johansson H, et al. Effect of fenretinide and low-dose tamoxifen on insulin sensitivity in premenopausal women at high risk for breast cancer. Cancer Res. Nov. 15, 2008;68(22):9512-9518.
Jung UJ, et al. Obesity and Its Metabolic Complications: The Role of Adipokines and the Relationship between Obesity, Inflammation, Insulin Resistance, Dyslipidemia and Nonalcoholic Fatty Liver Disease. Int J Mol Sci. Apr. 11, 2014;15(4):6184-6223.
Kahn SE, et al. Mechanisms linking obesity to insulin resistance and type 2 diabetes. Nature. Dec. 14, 2006;444(7121):840-846.
Koh Iu, et al. Fenretinide ameliorates insulin resistance and fatty liver in obese mice. Biol Pharm Bull. 2012;35(3):369-375.
Li et al.: Nanomilling of Drugs for Bioavailability Enhancement: A Holistic Formulation-Process Perspective. Pharmaceutics. 8(2):17 1-35 (2016).
Li et al., Serum retinol-binding protein 4 levels in patients with diabetic retinopathy. The Journal of International Medical Research, 38:95-99, 2010.
Moon RC, et al. N-(4-Hydroxyphenyl)retinamide, a new retinoid for prevention of breast cancer in the rat. Cancer Res. Apr. 1979;39(4):1339-1346.
Moraes-Vieira PM, et al. RBP4 Activates Antigen-Presenting Cells, Leading to Adipose Tissue Inflammation and Systemic Insulin Resistance. Cell Metab. Mar. 4, 2014;19(3):512-526.
Okada-Iwabu M, et al. Perspective of Small-Molecule AdipoR Agonist for Type 2 Diabetes and Short Life in Obesity. Diabetes Metab J. Oct. 2015;39(5):363-372.
Paudel et al.: Manufacturing of solid dispersions of poorly water soluble drugs by spray drying: Formulation and process considerations. International Journal of Pharmaceutics. 453(1):253-284 (2013).
PCT/US2018/037593 International Search Report and Written Opinion dated Aug. 30, 2018.
PCT/US2018/037597 International Search Report and Written Opinion dated Aug. 28, 2018.
PCT/US2018/037606 International Preliminary Report on Patentability dated Dec. 17, 2019.
PCT/US2018/037606 International Search Report and Written Opinion dated Aug. 28, 2018.
PCT/US2020/040919 International Preliminary Report on Patentability dated Jan. 20, 2022.
PCT/US2020/040919 International Search Report and Written Opinion dated Nov. 17, 2020.
PCT/US2020/040919 Invitation to Pay Additional Fees dated Sep. 9, 2020.
Postic C, Girard J. Contribution of de novo fatty acid synthesis to hepatic steatosis and insulin resistance: lessons from genetically engineered mice. J. J Clin Invest 2008;118:829-838.
Preitner F, et al. Long-term Fenretinide treatment prevents high-fat diet-induced obesity, insulin resistance, and hepatic steatosis. Am J Physiol Endocrinol Metab. Dec. 2009;297(6):E1420-E1429.
Savage DB, et al. Disordered Lipid Metabolism and the Pathogenesis of Insulin Resistance. Physiol Rev. Apr. 2007;87(2):507-520.
Taiwan Patent Application No. 107120497 Office Action/Search Report.
Taiwan Patent Application No. 107120499 Office Action.
Taiwan Patent Application No. 107120499 Office Action/Search Report.
Tilg H, et al. Evolution of inflammation in nonalcoholic fatty liver disease: the multiple parallel hits hypothesis. Hepatology. Nov. 2010;52(5):1836-1846.
U.S. Appl. No. 16/008,838 Restriction Requirement dated Sep. 21, 2018.
U.S. Appl. No. 16/272,911 Restriction Requirement dated Mar. 23, 2020.
U.S. Appl. No. 16/622,252 Final Office Action dated Oct. 20, 2021.
U.S. Appl. No. 16/622,252 Office Action dated Jun. 29, 2021.
U.S. Appl. No. 17/228,590 Office Action dated Jun. 7, 2023.
U.S. Appl. No. 17/228,590 Restriction Requirement dated Apr. 7, 2023.
Venkatesh et al. Role of the Development Scientist in Compound Lead Selection and Optimization. J. Pharm. Sci. 89(2):145-154 (Feb. 2000).
Wang. Correlation of retinol binding protein 4 with metabolic indexes of glucose and lipid, bile cholesterol saturation index. 40(6):657-665 (2015) DOI:10.11817/j.issn.1672-7347.2015.06.014.
West. Solid Solutions. Solid State Chemistry and Its Applications. John Wiley & Sons. Chapter 10:358 (1984).
Wolff. Burger's Medicinal Chemistry and Drug Discovery. 5th Ed. Part 1, pp. 975-977 (1995).
Yang et al.: Serum retinol binding protein 4 contributes to insulin resistance in obesity and type 2 diabetes. Nature 436(7049):356-362 (2005).

\* cited by examiner

FORMULATIONS OF RBP4 INHIBITORS AND METHODS OF USE

CROSS REFERENCE

This application is a continuation of U.S. application Ser. No. 17/620,427, filed Dec. 17, 2021, which is a § 371 U.S. national stage entry of International Application No. PCT/US2020/040919 filed Jul. 6, 2020, which claims the benefit of U.S. Provisional Application No. 62/871,622 filed Jul. 8, 2019, which application is incorporated herein by reference in its entirety.

BACKGROUND

A need exists in the medicinal arts for the effective treatment of visual diseases and disorders associated with retinol-binding protein 4 (RBP4).

BRIEF SUMMARY OF THE INVENTION

In one aspect, provided herein is a pharmaceutical composition comprising a compound of Formula (I), a pharmaceutically acceptable salt, solvate, polymorph, prodrug, metabolite, N-oxide, stereoisomer, or isomer thereof:

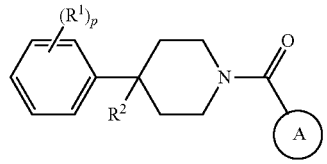

Formula (I)

wherein:

each $R^1$ is independently halogen, haloalkyl, or alkyl;

$R^2$ is —H, —OH, or halogen;

p is 0, 1, 2, 3, 4, or 5;

A has the structure:

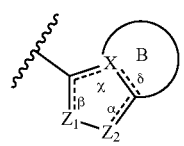

wherein:

α, β, χ, and δ are each independently absent or present, and when present each is a bond;

X is C;

$Z_1$ is S, O, or N;

$Z_2$ is S, O, N, or $NR^3$;

$R^3$ is H, $C_1$-$C_4$ alkyl, or oxetane; and

B is a substituted or unsubstituted fused 5-, 6-, or 7-membered ring structure;

wherein the composition comprises a solid dispersion comprising a dispersion polymer.

In certain embodiments, A has the structure

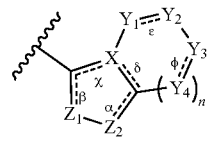

wherein:

n is 0, 1, or 2;

α, β, χ, δ, ε, and φ are each independently absent or present, and when present each is a bond;

$Z_1$ is S, O, or N;

$Z_2$ is S, O, N or $NR^3$,
  wherein $R^3$ is H, $C_1$-$C_4$ alkyl, or oxetane;

X is C;

$Y_1$, $Y_2$, $Y_3$ and each occurrence of $Y_4$ are each independently $CR^4$, $C(R^5)_2$, $NR^6$, O, N, $SO_2$, or —(C=O)—, wherein:

$R^4$ is H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$;

$R^5$ is H or $C_1$-$C_{10}$ alkyl; and $R^6$ is H, $C_1$-$C_{10}$ alkyl, $C_3$-$C_6$ cycloalkyl, —($C_1$-$C_{10}$ alkylene)$CF_3$, —($C_1$-$C_{10}$ alkylene)$OCH_3$, —($C_1$-$C_{10}$ alkylene)-halogen, —$SO_2$($C_1$-$C_{10}$ alkyl), —$SO_2$($C_1$-$C_{10}$ alkylene)-$CF_3$, —$SO_2$($C_1$-$C_{10}$ alkylene)$OCH_3$, —$SO_2$($C_1$-$C_{10}$ alkylene)-halogen, —C(O)($C_1$-$C_{10}$ alkyl), —C(O)($C_1$-$C_{10}$ alkylene)$CF_3$, —C(O)($C_1$-$C_{10}$ alkylene)$OCH_3$, —C(O)($C_1$-$C_{10}$ alkylene)-halogen, —C(O)NH($C_1$-$C_{10}$ alkyl), —C(O)N($C_1$-$C_{10}$ alkyl)$_2$, —($C_1$-$C_{10}$ alkyl)C(O)OH, —C(O)$NH_2$, or oxetane.

In certain embodiments, A has the structure

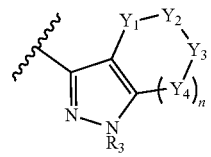

wherein:

n is 0;

$R^3$ is H, $C_1$-$C_4$ alkyl, or oxetane;

$Y_1$ and $Y_3$ are each $CH_2$ or $C(CH_3)_2$;

$Y_2$ is O, $SO_2$, or $NR^6$; and $R^6$ is H, $C_1$-$C_4$ alkyl, $C_3$-$C_6$ cycloalkyl, —($C_1$-$C_4$ alkylene)$CF_3$, —($C_1$-$C_4$ alkylene)$OCH_3$, —($C_1$-$C_4$ alkylene)-halogen, —$SO_2$($C_1$-$C_4$ alkyl), —$SO_2$($C_1$-$C_4$ alkylene)$CF_3$, —$SO_2$($C_1$-$C_4$ alkylene)$OCH_3$, —$SO_2$($C_1$-$C_4$ alkylene)-halogen, —C(O)($C_1$-$C_4$ alkyl), —C(O)($C_1$-$C_4$ alkylene)$CF_3$, —C(O)($C_1$-$C_4$ alkylene)$OCH_3$, —C(O)($C_1$-$C_4$ alkylene)-halogen, —C(O)NH($C_1$-$C_4$ alkyl), —C(O)N($C_1$-$C_4$ alkyl)$_2$, —($C_1$-$C_4$ alkylene)C(O)OH, —C(O)$NH_2$, or oxetane.

In certain embodiments, the compound of Formula (I) has the structure:

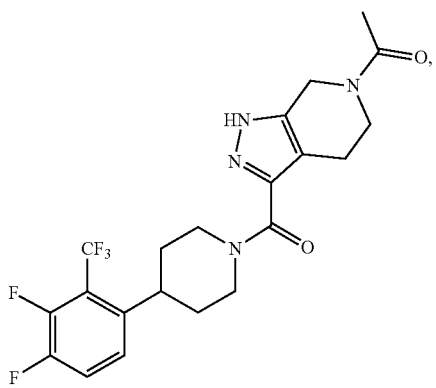 [SMILES: CC(=O)N1CCc2c(C(=O)N3CCC(c4ccc(F)c(F)c4C(F)(F)F)CC3)n[nH]c2C1]

or a pharmaceutically acceptable salt, solvate, polymorph, prodrug, metabolite, N-oxide, stereoisomer, or isomer thereof.

In certain embodiments, the compound of Formula (I) is effective to reduce RBP4 concentrations in dosages forms of 1 to 200 mg or 5 to 25 mg. In certain embodiments, the compound of Formula (I) is a micronized crystalline. In certain embodiments, the compound of Formula (I) is a polymorph exhibiting an x-ray powder diffraction pattern having at least three characteristic peaks expressed in degrees two theta (+/−0.5 degree theta) at 6.7, 9.3, 14.1, 17.2, 23.5, 27.1, and/or 29.0.

In certain embodiments, the compound of Formula (I) is molecularly dispersed in the dispersion polymer. In certain embodiments, the compound of Formula (I) is amorphous and molecularly dispersed in the dispersion polymer In some embodiments, the compound of Formula (I) is amorphous within the dispersion polymer. In certain embodiments, the dispersion polymer is selected from the group consisting of hydroxypropyl methylcellulose (HPMC), hydroxypropyl methylcellulose-acetate succinate (HPMC-AS or HPMCAS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, and combinations thereof. In certain embodiments, the dispersion polymer is HPMC. In certain embodiments, the dispersion polymer is HPMC-AS.

In certain embodiments, the dispersion polymer comprises about 1-99% by weight of the solid dispersion. In certain embodiments, the dispersion polymer comprises about 20-80% by weight of the solid dispersion. In certain embodiments, the dispersion polymer comprises about 40-60% by weight of the solid dispersion. In certain embodiments, the dispersion polymer comprises about 1-99% by weight, 20-80% by weight, or 40-60% by weight of the solid dispersion. In certain embodiments, the compound of Formula (I) comprises about 1-99% by weight of the solid dispersion. In certain embodiments, the compound of Formula (I) comprises 20-80% by weight of the solid dispersion. In certain embodiments, the compound of Formula (I) comprises about 40-60% by weight of the solid dispersion. In certain embodiments, the ratio of the compound of Formula (I):dispersion polymer is about 20:80 (w/w) in the solid dispersion. In certain embodiments, the ratio of the compound of Formula (I):dispersion polymer is about 40:60 (w/w) in the solid dispersion. In certain embodiments, the compound of Formula (I) comprises about 1-99% by weight, about 20-80% by weight, or about 40-60% by weight of the solid dispersion.

In certain embodiments, the ratio of the compound of Formula (I):dispersion polymer is about 20:80 (w/w) in the solid dispersion. In certain embodiments, the ratio of the compound of Formula (I):dispersion polymer is about 40:60 (w/w) in the solid dispersion.

In certain embodiments, the compound of Formula (I) is

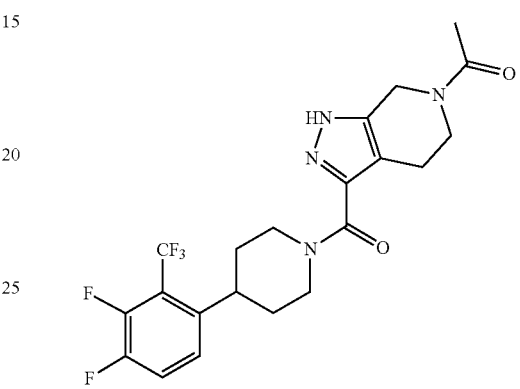

and the dispersion polymer is HPMC-AS.

In certain embodiments, the dispersion polymer is HPMC-AS, M or HPMC-AS, H. In certain embodiments, the dispersion polymer is HPMC-AS, M. In certain embodiments, the dispersion polymer is HPMC-AS, H. In certain embodiments, the dispersion polymer is HPMC-AS having an acetyl content from 7-11 wt %, a succinyl content from 10-14 wt %, a methoxyl content from 21-25 wt %, and a hydroxypropyl content from 5-9 wt %. In certain embodiments, the dispersion polymer is HPMC-AS having an acetyl content from 10-14 wt %, a succinyl content from 4-8 wt %, a methoxyl content from 22-26 wt %, and a hydroxypropyl content from 6-10 wt %.

In certain embodiments, the dispersion polymer comprises polyvinylpyrrolidone (PVP). In certain embodiments, the PVP is present in a ratio with the compound of Formula (I) from about 10:1 to about 1:1. In certain embodiments, the PVP is a present in a ratio with the compound of Formula (I) of about 2:1, about 3:1, or about 5:1. In certain embodiments, the PVP has a molecular weight average molecular weight from about 7,000 Daltons to about 11,000 Daltons.

In certain embodiments, the pharmaceutical composition further comprises a filler, a sweetener, a disintegrant, a wetting agent, a glidant, a lubricant, or a surfactant, or any combinations thereof. In certain embodiments, the solid dispersion further comprises a filler, a sweetener, a disintegrant, a wetting agent, a glidant, a lubricant, or a surfactant, or any combinations thereof.

In certain embodiments, the solid dispersion has an average particle size of less than 10 μm. In certain embodiments, the solid dispersion has an average particle size of less than 20 μm. In certain embodiments, the solid dispersion has an average particle size from about 10 μm to 20 μm. In certain embodiments, the solid dispersion has an average particle size of less than 10 μm or less than 20 μm.

In one aspect, provided herein, is a nanosuspension pharmaceutical composition comprising a compound of Formula (I), a pharmaceutically acceptable salt, crystalline, solvate, polymorph, prodrug, metabolite, N-oxide, stereoisomer, or isomer thereof, wherein the compound of Formula (I) is suspended in a pharmaceutically acceptable solvent. In some embodiments, the compound of Formula (I) is Compound 1, or a pharmaceutically acceptable salt, crystalline, solvate, polymorph, prodrug, metabolite, N-oxide, stereoisomer, or isomer thereof. In some embodiments, the compound of Formula (I) is a polymorph exhibiting an x-ray powder diffraction pattern having at least three characteristic peaks expressed in degrees two theta (+/−0.5 degree theta) at 6.7, 9.3, 14.1, 17.2, 23.5, 27.1, and/or 29.0. In some embodiments, the concentration of the compound of Formula (I) is from about 1 mg/mL to about 50 mg/mL. In some embodiments, the compound of Formula (I) is micronized. In some embodiments, the compound of Formula (I) has an average particle size of less than 1000 nm.

In some embodiments, the nanosuspension further comprises a surfactant. In some embodiments, the surfactant comprises sodium dodecyl sulfate, a poloxamer, or a polysorbate. In some embodiments, the nanosuspension further comprises an excipient. In some embodiments, the excipient comprises hydroxypropyl methylcellulose (HPMC), hydroxypropyl methylcellulose-acetate succinate (HPMC-AS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, or any combinations thereof. In some embodiments, the excipient is present at a concentration from about 0.1% to about 5%.

In certain embodiments, the pharmaceutical composition is encapsulated. In certain embodiments, the pharmaceutical composition is in the form of a tablet. In certain embodiments, the pharmaceutical composition is in the form of a capsule. In certain embodiments, the pharmaceutical composition is a liquid formulation. In certain embodiments, the pharmaceutical composition is formulated as an oral suspension.

In another aspect is a method of treating an eye disease comprising administering a therapeutically effective amount of a pharmaceutical composition of any of the preceding claims to a subject in need thereof. In certain embodiments, the eye disease is a disease characterized by excessive lipofuscin accumulation in the retina. In certain embodiments, the disease characterized by excessive lipofuscin accumulation is Age-Related Macular Degeneration, dry (atrophic) Age-Related Macular Degeneration, Juvenile Macular Degeneration (Stargardt Disease), Best disease, adult vitelliform maculopathy, Geographic Atrophy, Stargardt-like macular dystrophy, diabetic retinopathy, or an ABCA4 gene associated retinal disease.

In another aspect is a method for lowering the serum concentration of RBP4 in a subject, comprising administering to the subject a therapeutically effective amount of a pharmaceutical composition. In certain embodiments, the therapeutically effective amount of the pharmaceutical composition comprises about 0.1 mg to about 400 mg of the compound of Formula (I). In certain embodiments, the therapeutically effective amount of the pharmaceutical composition comprises about 0.5 mg to about 400 mg of the compound of Formula (I). In certain embodiments, the therapeutically effective amount of the pharmaceutical composition comprises about 0.5 mg to about 50 mg of the compound of Formula (I). In certain embodiments, the therapeutically effective amount of the pharmaceutical composition comprises about 0.1 mg of the compound of Formula (I). In certain embodiments, the therapeutically effective amount of the pharmaceutical composition comprises about 0.5 mg of the compound of Formula (I). In certain embodiments, the therapeutically effective amount of the pharmaceutical composition comprises about 1 mg of the compound of Formula (I). In certain embodiments, the therapeutically effective amount of the pharmaceutical composition comprises about 5 mg of the compound of Formula (I). In certain embodiments, the therapeutically effective amount of the pharmaceutical composition comprises about 10 mg of the compound of Formula (I). In certain embodiments, the therapeutically effective amount of the pharmaceutical composition comprises about 25 mg of the compound of Formula (I). In certain embodiments, the therapeutically effective amount of the pharmaceutical composition comprises about 50 mg of the compound of Formula (I). In certain embodiments, the therapeutically effective amount of the pharmaceutical composition comprises about 100 mg of the compound of Formula (I). In certain embodiments, the therapeutically effective amount of the pharmaceutical composition comprises about 200 mg of the compound of Formula (I). In certain embodiments, the therapeutically effective amount of the pharmaceutical composition comprises about 400 mg of the compound of Formula (I). In certain embodiments, the therapeutically effective amount of the pharmaceutical composition comprises about 0.1 mg, about 0.5 mg, about 1 mg, about 5 mg, about 10 mg, about 25 mg, about 50 mg, about 100 mg, about 200 mg, or about 400 mg of the compound of Formula (I).

In certain embodiments, the pharmaceutical composition is administered one, two, three, or four times daily. In certain embodiments, the pharmaceutical composition is administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In certain embodiments, the pharmaceutical composition is administered once daily. In certain embodiments, the pharmaceutical composition is administered orally. In certain embodiments, the serum RBP4 concentration of the subject is reduced to below 1 µM after treatment.

In another aspect, described herein, is a method of manufacturing a solid dispersion comprising the steps of adding a solvent to a vessel; adding a compound of Formula (I) or its pharmaceutically acceptable salt to the vessel; adding a dispersion polymer to the vessel to obtain a first mixture; mixing the first mixture until the compound of Formula (I) or its pharmaceutically acceptable salt and the dispersion polymer are dissolved in the solvent to obtain a first solution;

and dry spraying the first solution to obtain a first solid; wherein the compound of Formula (I) has the structure:

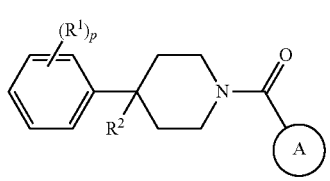

Formula (I)

wherein:

each $R^1$ is independently halogen, haloalkyl, or alkyl;

$R^2$ is —H, —OH, or halogen;

p is 0, 1, 2, 3, 4, or 5;

A has the structure:

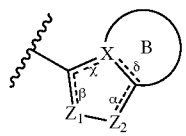

wherein:

α, β, χ, and δ are each independently absent or present, and when present each is a bond;

X is C;

$Z_1$ is S, O, or N;

$Z_2$ is S, O, N, or $NR^3$;

$R^3$ is H, $C_1$-$C_4$ alkyl, or oxetane; and

B is a substituted or unsubstituted fused 5-, 6-, or 7-membered ring structure;

wherein the composition comprises a solid dispersion comprising a dispersion polymer.

In certain embodiments, the solvent comprises an organic solvent. In certain embodiments, the solvent is selected from the group consisting of ethanol, methanol, acetone, isopropyl alcohol, n-butanol, tetrahydrofuran, dichloromethane, ethyl acetate, methyl acetate, acetonitrile, chloroform, carbon tetrachloride, benzene, toluene, diethyl ether, dioxane, pentane, hexane, cyclohexane, heptane, methyl t-butyl ether, petroleum ether, 1-propanol, and combinations thereof. In certain embodiments, the solvent is 90:10 dichloromethane:methanol (v/v).

In certain embodiments, the dispersion polymer selected from the group consisting of hydroxypropyl methylcellulose (HPMC), hydroxypropyl methylcellulose-acetate succinate (HPMC-AS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, and combinations thereof. In certain embodiments, the dispersion polymer is HPMC-AS. In certain embodiments, the dispersion polymer is HPMC. In some embodiments, the dispersion polymer is polyvinyl pyrrolidine.

In certain embodiments, the compound of Formula (I) has the structure:

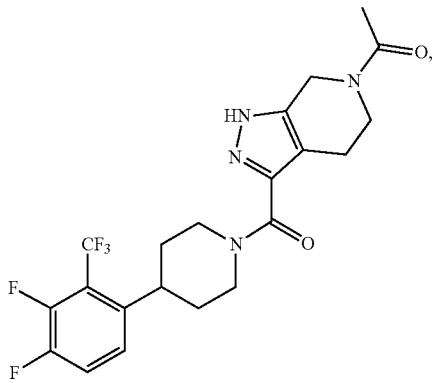 [SMILES: CC(=O)N1CCc2c(C(=O)N3CCC(c4ccc(F)c(F)c4C(F)(F)F)CC3)n[nH]c2C1]

or a pharmaceutically acceptable salt, solvate, polymorph, prodrug, metabolite, N-oxide, stereoisomer, or isomer thereof. In certain embodiments, the solvent comprises acetic acid, acetone, acetonitrile, benzene, tert-butyl alcohol, tert-butyl methyl ether, carbon tetrachloride, chloroform, cyclohexane, 1,2-dichloroethane, dichloromethane, diethyl ether, diglyme, 1,2,-dimethoxyethane, dimethyl acetamide, dimethylformamide, dimethyl sulfoxide, dioxane, ethanol, ethyl acetate, ethyl methyl ketone, ethylene glycol, hexanes, hexamethylphosphoramide, methanol, nitromethane, pentanes, 2-proponal, pyridine, tetrahydrofuran, toluene, xylenes, or any combination thereof.

In another aspect, described herein, is a method for lowering the serum concentration of RBP4 in a subject, comprising administering to the subject a pharmaceutical composition comprising a therapeutically effective amount of a compound having the structure

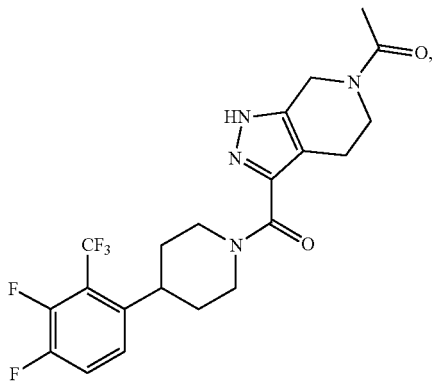 [SMILES: CC(=O)N1CCc2c(C(=O)N3CCC(c4ccc(F)c(F)c4C(F)(F)F)CC3)n[nH]c2C1]

or a pharmaceutically acceptable salt, solvate, polymorph, prodrug, metabolite, N-oxide, stereoisomer, or isomer thereof; wherein the pharmaceutical composition comprises the compound in an amount of about 10 mg; wherein the pharmaceutical composition is administered daily; and wherein the serum or plasma levels of RBP4 of the subject are reduced to below 1 μM.

In one aspect, provided herein, is a polymorph of Compound 1, wherein the polymorph exhibits an x-ray powder diffraction pattern having at least three characteristic peaks expressed in degrees two theta (+/−0.5 degree theta) at 6.7, 9.3, 14.1, 17.2, 23.5, 27.1, and/or 29.0. In some embodiments, the polymorph is crystalline. In some embodiments, the polymorph exhibits an x-ray powder diffraction pattern having at least five characteristic peaks expressed in degrees two theta (+/−0.5 degree theta) at 6.7, 9.3, 14.1, 17.2, 23.5, 27.1, and/or 29.0. In some embodiments, the polymorph exhibits an x-ray powder diffraction pattern having characteristic peaks expressed in degrees two theta (+/−0.5 degree theta) at 6.7, 9.3, 14.1, 17.2, 23.5, 27.1, and/or 29.0. In some embodiments, the polymorph is micronized. In some embodiments, the polymorph has an average particle size of less than 20 μm, less than 10 μm, less than 1 μm, or less than 100 nm.

INCORPORATION BY REFERENCE

All publications, patents, and patent applications mentioned in this specification are herein incorporated by reference for the specific purposes identified herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
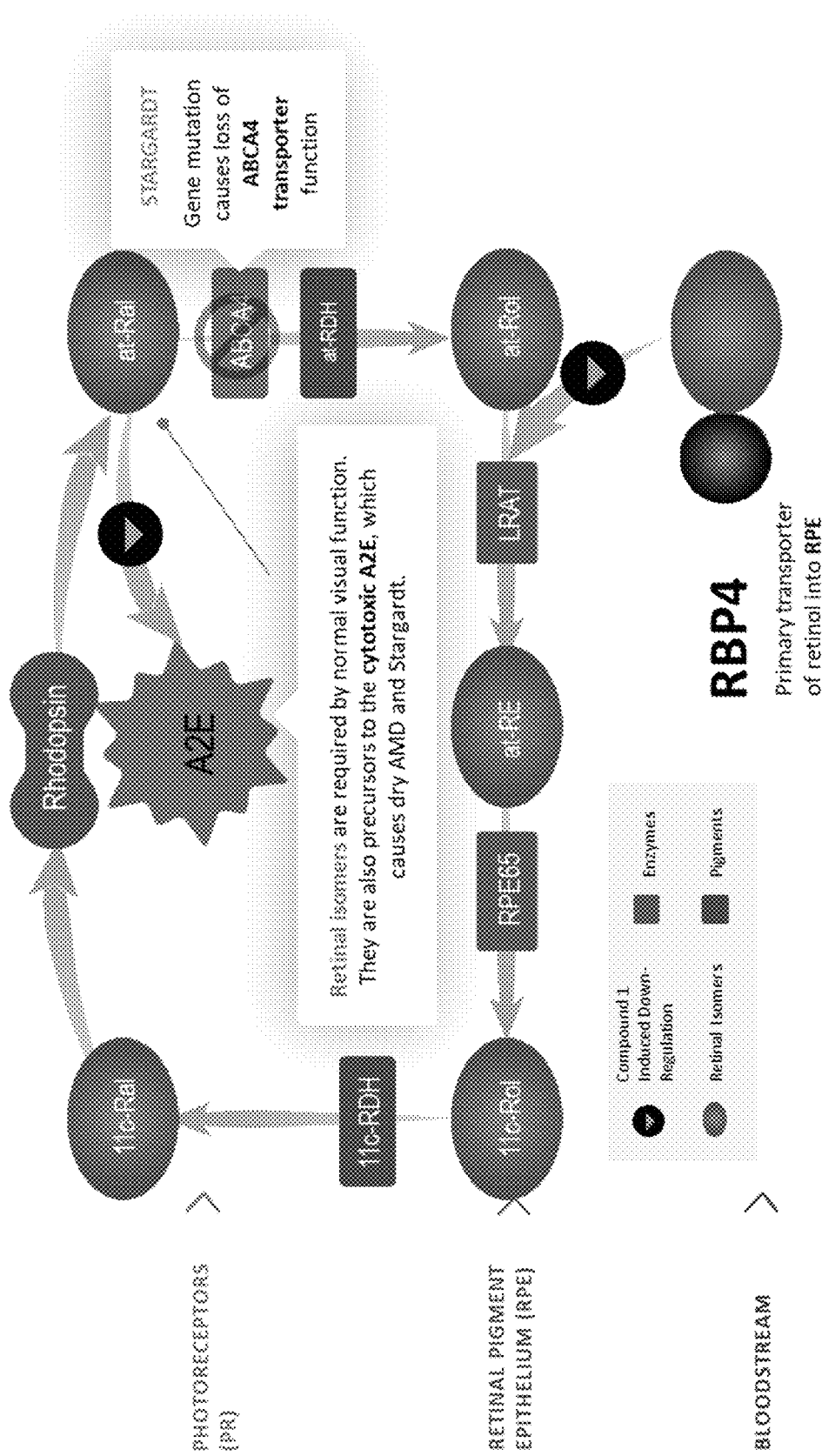
FIG. 1 illustrates a schematic of a mechanism of action for dry (atrophic) macular degeneration and Stargardt disease. Without being bound by theory, RBP4 transports retinol (a precursor to cytotoxic A2E) into the retina by way of the visual cycle. RBP4 inhibitors, such as Compound 1, are in some instances used to treat RBP4-related visual diseases and disorders.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g., $C_5$-$C_8$ alkenylene). In other embodiments, an alkenylene comprises two to five carbon atoms (e.g., $C_2$-$C_5$ alkenylene). In other embodiments, an alkenylene comprises three to five carbon atoms (e.g., $C_3$-$C_5$ alkenylene). Unless stated otherwise specifically in the specification, an alkenylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —$N(R^a)$C(O)O$R^a$, —OC(O)—N($R^a)_2$, —$N(R^a)$C(O)$R^a$, —$N(R^a)$S(O)$_tR^a$ (where t is 1 or 2), —S(O)$_t$O$R^a$ (where t is 1 or 2), —S(O)$_tR^a$ (where t is 1 or 2) and —S(O)$_t$N($R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —$N(R^a)$C(O)O$R^a$, —OC(O)—N($R^a)_2$, —$N(R^a)$C(O)$R^a$, —$N(R^a)$S(O)$_tR^a$ (where t is 1 or 2), —S(O)$_t$O$R^a$ (where t is 1 or 2), —S(O)$_tR^a$ (where t is 1 or 2) and —S(O)$_t$N($R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a)_2$, —$R^b$—N($R^a)_2$, —$R^b$—C(O)$R^a$, —$R^b$—C(O)O$R^a$, —$R^b$—C(O)N($R^a)_2$, —$R^b$—O—$R^c$—C(O)N($R^a)_2$, —$R^b$—N($R^a$)C(O)O$R^a$, —$R^b$—N($R^a$)C(O)$R^a$, —$R^b$—N($R^a$)S(O)$_tR^a$ (where t is 1 or 2), —$R^b$—S(O)$_tR^a$ (where t is 1 or 2), —$R^b$—S(O)$_t$O$R^a$ (where t is 1 or 2) and —$R^b$—S(O)$_t$N($R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Carbocyclylalkynyl" refers to a radical of the formula-$R^c$-carbocyclyl where $R^c$ is an alkynylene chain as defined above. The alkynylene chain and the carbocyclyl radical are optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical are optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

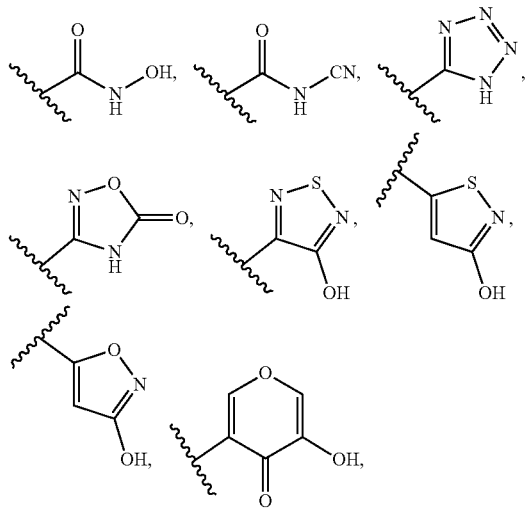

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoro alkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula $-O-R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

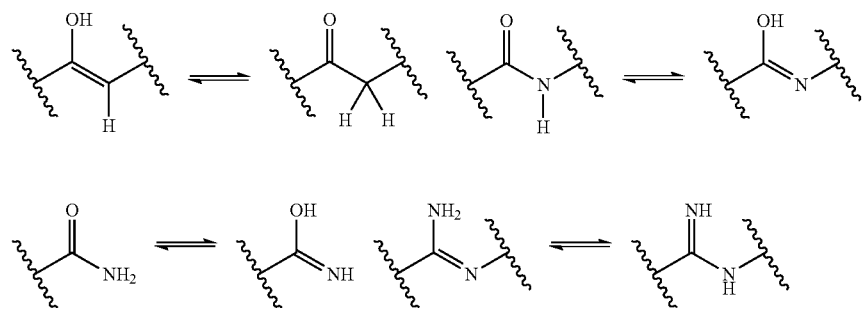

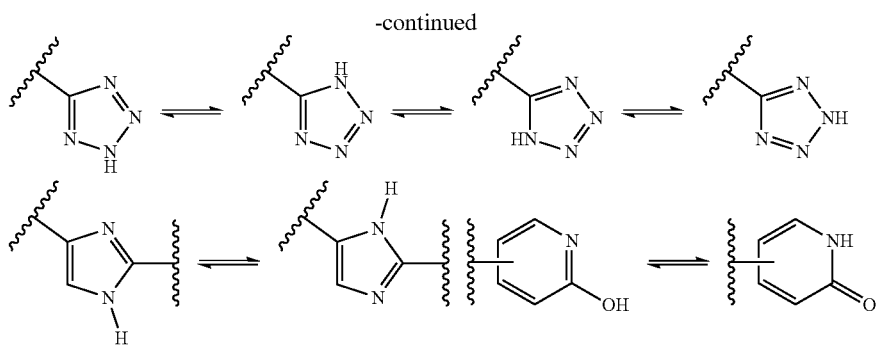

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

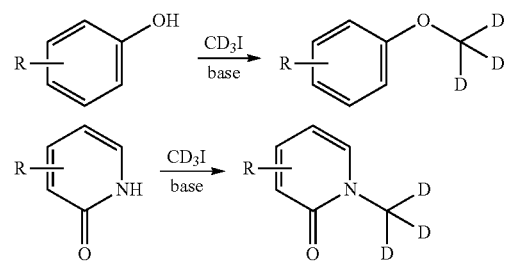

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

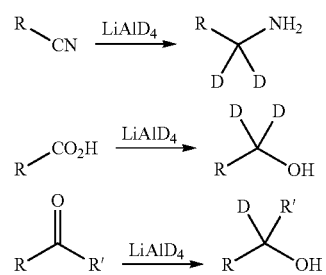

Deuterium gas and palladium catalyst are employed to reduce unsaturated carbon-carbon linkages and to perform a reductive substitution of aryl carbon-halogen bonds as illustrated, by way of example only, in the reaction schemes below.

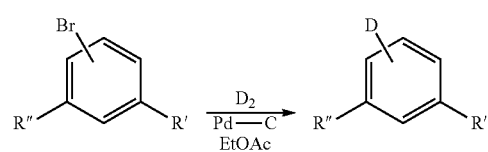

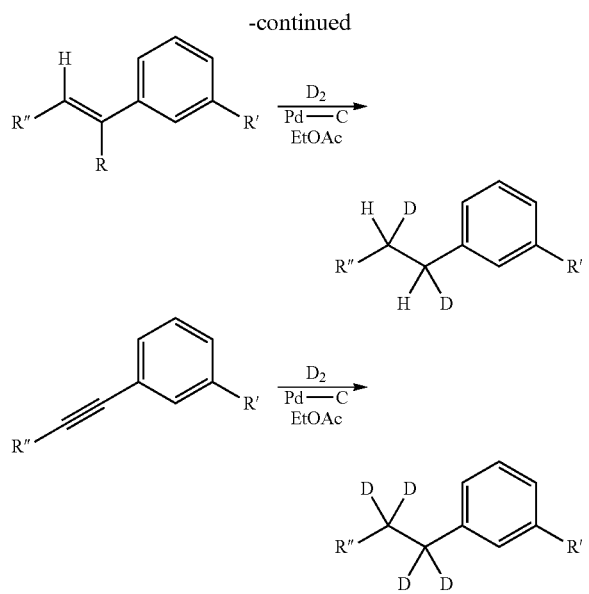

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1H$ hydrogen atoms. In one embodiment, the level of deuterium incorporation is determined by synthetic methods in which a deuterated synthetic building block is used as a starting material.

Throughout the specification, examples, and claims, various components are expressed as being present in ratios, e.g. 1:2, 1:3, 1:4, or 1:5 and the like. Unless otherwise specified, such ratios refer to the ratio of each component by weight.

"Pharmaceutically acceptable salt" includes both acid and base addition salts. A pharmaceutically acceptable salt of any one of the heterocyclic RBP4 inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogen phosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or"palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like Throughout the specification and claims, x-ray powder diffraction (XRPD) peaks are described. XRPD peak values in the application refer to those obtained using a copper source with a wavelength of 1.5406 angstrom unless otherwise noted.

As used herein, "Compound 1" or "CMPD-1" refers to Compound No. 1 as indicated in Table 1. Compound 1 has the structure

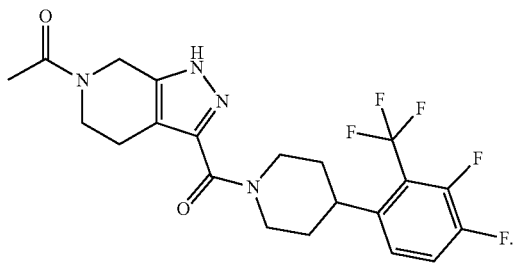 [SMILES: CC(=O)N1CCc2c(C(=O)N3CCC(c4ccc(F)c(F)c4C(F)(F)F)CC3)n[nH]c2C1]

Compound 1 is also referred to by its full chemical name of 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)ethan-1-one.

RBP4 Inhibitory Compounds

Provided herein in some embodiments are RBP4 inhibitory compounds and pharmaceutical compositions comprising said compounds. The subject compounds and compositions are useful for inhibiting RPB4 and for the treatment of eye diseases or disorders, such as Age-Related Macular Degeneration, dry (atrophic) Age-Related Macular Degeneration, Juvenile Macular Degeneration (Stargardt Disease), Best disease, adult vitelliform maculopathy, Geographic Atrophy, Stargardt-like macular dystrophy, diabetic retinopathy, or ABCA4 gene associated retinal diseases.

Some embodiments provided herein describe a compound, or a pharmaceutically acceptable salt, solvate, polymorph, prodrug, metabolite, N-oxide, stereoisomer, or isomer thereof, for use in treating a metabolic disease or disorder, having the structure of Formula (I):

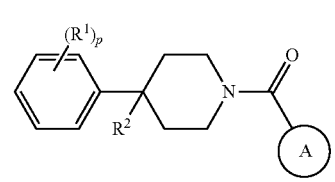

Formula (I)

wherein:
each $R^1$ is independently halogen, optionally substituted alkyl, optionally substituted cycloalkyl, optionally substituted heterocyclyl, optionally substituted heterocycloalkyl, —$COR^7$, —$CON(R^7)_2$, optionally substituted ($C_0$-$C_4$ alkylene)-CN, optionally substituted ($C_0$-$C_4$ alkylene)-$OR^7$, optionally substituted ($C_0$-$C_4$ alkylene)-$N(R^7)_2$, optionally substituted ($C_0$-$C_4$ alkylene)$N(R^8)$—$COR^7$, optionally substituted ($C_0$-$C_4$ alkylene)-$SO_2N(R^7)_2$, optionally substituted ($C_0$-$C_4$ alkylene)-$SO_2R^7$, optionally substituted ($C_0$-$C_4$ alkylene)$N(R^8)$—$SO_2N(R^7)_2$, or optionally substituted ($C_0$-$C_4$ alkylene)$N(R^8)$—$SO_2R^7$;

each $R^7$ is independently selected from H, optionally substituted alkyl, optionally substituted alkenyl, optionally substituted carbocyclyl, optionally substituted carbocyclylalkyl, optionally substituted aryl, optionally substituted aralkyl, optionally substituted heterocyclyl, optionally substituted heterocyclylalkyl, optionally substituted heteroaryl, or optionally substituted heteroarylalkyl; or two $R^{11}$ groups together with the nitrogen to which they are attached join to form an optionally substituted N-heterocyclyl;

each $R^8$ is independently selected from H or optionally substituted alkyl;

$R^2$ is —H, —OH, optionally substituted alkyl, or halogen;
p is 0, 1, 2, 3, 4, or 5;
A has the structure:

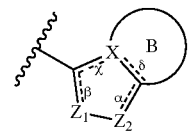

wherein:
α, β, χ, and δ are each independently absent or present, and when present each is a bond;
X is C;
$Z_1$ is S, O, or N;
$Z_2$ is S, O, N, or $NR^3$;
$R^3$ is H, optionally substituted alkyl, or oxetane; and
B is a substituted or unsubstituted fused 5-, 6-, or 7-membered ring structure.

Some embodiments provided herein describe a compound, or a pharmaceutically acceptable salt, solvate, polymorph, prodrug, metabolite, N-oxide, stereoisomer, or isomer thereof, having the structure of Formula (I) wherein:
each $R^1$ is independently halogen, optionally substituted $C_{1-6}$ alkyl, optionally substituted $C_{3-6}$ cycloalkyl, optionally substituted $C_{2-6}$ heterocyclyl, optionally substituted $C_{3-10}$ heterocycloalkyl, —$COR^7$, —CON $(R^7)_2$, optionally substituted $(C_0\text{-}C_4$ alkylene)-CN, optionally substituted $(C_0\text{-}C_4$ alkylene)-$OR^7$, optionally substituted $(C_0\text{-}C_4$ alkylene)-$N(R^7)_2$, optionally substituted $(C_0\text{-}C_4$ alkylene)$N(R^8)$—$COR^7$, optionally substituted $(C_0\text{-}C_4$ alkylene)-$SO_2N(R^7)_2$, optionally substituted $(C_0\text{-}C_4$ alkylene)-$SO_2R^7$, optionally substituted $(C_0\text{-}C_4$ alkylene)$N(R^8)$—$SO_2N(R^7)_2$, or optionally substituted $(C_0\text{-}C_4$ alkylene)$N(R^8)$—$SO_2R^7$;

each $R^7$ is independently selected from H, optionally substituted $C_{1-6}$ alkyl, optionally substituted $C_{3-6}$ carbocyclyl, optionally substituted $C_{3-10}$ carbocyclylalkyl, optionally substituted $C_{2-6}$ heterocyclyl, optionally substituted $C_{2-10}$ heterocyclylalkyl; or two $R^{11}$ groups together with the nitrogen to which they are attached join to form an optionally substituted $C_{2-6}$ N-heterocyclyl;

each $R^8$ is independently selected from H or optionally substituted $C_{1-6}$ alkyl;

$R^2$ is —H, —OH, optionally substituted $C_{1-6}$ alkyl, or halogen;

p is 0, 1, 2, 3, 4, or 5;

A has the structure:

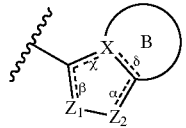

wherein:
α, β, χ, and δ are each independently absent or present, and when present each is a bond;
X is C;
$Z_1$ is S, O, or N;
$Z_2$ is S, O, N, or $NR^3$;
$R^3$ is H, optionally substituted $C_{1-6}$ alkyl, or oxetane; and
B is a substituted or unsubstituted fused 5-, 6-, or 7-membered ring structure.

Certain embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently halogen, $C_{1-6}$ alkyl, $C_{1-6}$ haloalkyl, $C_{3-6}$ cycloalkyl, $C_{2-6}$ heterocyclyl, $C_{3-10}$ heterocloalkyl, —$COR^7$, —$CON(R^7)_2$, $(C_0\text{-}C_4$ alkylene)-CN, $(C_0\text{-}C_4$ alkylene)-$OR^7$, $(C_0\text{-}C_4$ alkylene)-$N(R^7)_2$, $(C_0\text{-}C_4$ alkylene)$N(R^8)$—$COR^7$, $(C_0\text{-}C_4$ alkylene)-$SO_2N(R^7)_2$, $(C_0\text{-}C_4$ alkylene)-$SO_2R^7$, $(C_0\text{-}C_4$ alkylene)$N(R^8)$—$SO_2N(R^7)_2$, or $(C_0\text{-}C_4$ alkylene)$N(R^8)$—$SO_2R^7$;

each $R^7$ is independently selected from H, $C_{1-6}$ alkyl, $C_{3-6}$ carbocyclyl, $C_{3-10}$ carbocyclylalkyl, $C_{2-6}$ heterocyclyl, $C_{2-10}$ heterocyclylalkyl; or two $R^{11}$ groups together with the nitrogen to which they are attached join to form a $C_{2-6}$ N-heterocyclyl;

each $R^8$ is independently selected from H or $C_{1-6}$ alkyl;

$R^2$ is —H, —OH, $C_{1-6}$ alkyl, or halogen;

p is 0, 1, 2, 3, 4, or 5;

A has the structure:

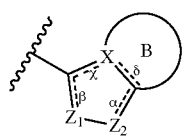

wherein:
α, β, χ, and δ are each independently absent or present, and when present each is a bond;
X is C;
$Z_1$ is S, O, or N;
$Z_2$ is S, O, N, or $NR^3$;
$R^3$ is H, $C_{1-6}$ alkyl, or oxetane; and
B is a substituted or unsubstituted fused 5-, 6-, or 7-membered ring structure.

Some embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently halogen, haloalkyl, or alkyl;
$R^2$ is —H, —OH, or halogen;
p is 0, 1, 2, 3, 4, or 5;
A has the structure:

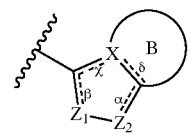

wherein:
α, β, χ, and δ are each independently absent or present, and when present each is a bond;
X is C;
$Z_1$ is S, O, or N;
$Z_2$ is S, O, N, or $NR^3$;
$R^3$ is H, $C_1\text{-}C_4$ alkyl, or oxetane; and
B is a substituted or unsubstituted fused 5-, 6-, or 7-membered ring structure.

Certain embodiments provided herein describe a compound, or a pharmaceutically acceptable salt, solvate, polymorph, prodrug, metabolite, N-oxide, stereoisomer, or isomer thereof, having the structure of Formula (I) wherein:

each $R^1$ is independently Br, Cl, F, $C_{1-6}$ fluoroalkyl, or $C_{1-6}$ alkyl;
$R^2$ is —H, —OH, Br, Cl, or F;
p is 0, 1, 2, 3, 4, or 5;
A has the structure:

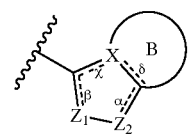

wherein:
α, β, χ, and δ are each independently absent or present, and when present each is a bond;
X is C;
$Z_1$ is S, O, or N;
$Z_2$ is S, O, N, or $NR^3$;
$R^3$ is H, $C_1\text{-}C_4$ alkyl, or oxetane; and
B is a substituted or unsubstituted fused 5-, 6-, or 7-membered ring structure.

For any and all of the embodiments of Formula (I), substituents are selected from among a subset of the listed alternatives.

In some embodiments, each $R^1$ is independently halogen, optionally substituted $C_{1-6}$ alkyl, optionally substituted $C_{3-6}$ cycloalkyl, optionally substituted $C_{2-6}$ heterocyclyl, optionally substituted C$_{3-10}$ heterocycloalkyl, —COR$^7$, —CON(R$^7$)$_2$, optionally substituted (C$_0$-C$_4$ alkylene)-CN, optionally substituted (C$_0$-C$_4$ alkylene)-OR$^7$, optionally substituted (C$_0$-C$_4$ alkylene)-N(R$^7$)$_2$, optionally substituted (C$_0$-C$_4$ alkylene)N(R$^8$)—COR$^7$, optionally substituted (C$_0$-C$_4$ alkylene)-SO$_2$N(R$^7$)$_2$, optionally substituted (C$_0$-C$_4$ alkylene)-SO$_2$R$^7$, optionally substituted (C$_0$-C$_4$ alkylene)N(R$^8$)—SO$_2$N(R$^7$)$_2$, or optionally substituted (C$_0$-C$_4$ alkylene)N(R$^8$)—SO$_2$R$^7$. In certain embodiments, each R$^1$ is independently halogen, C$_{1-6}$ alkyl, C$_{1-6}$ haloalkyl, C$_{3-6}$ cycloalkyl, C$_{2-6}$ heterocyclyl, C$_{3-10}$ heterocycloalkyl, —COR$^7$, —CON(R$^7$)$_2$, (C$_0$-C$_4$ alkylene)-CN, (C$_0$-C$_4$ alkylene)-OR$^7$, (C$_0$-C$_4$ alkylene)-N(R$^7$)$_2$, (C$_0$-C$_4$ alkylene)N(R$^8$)—COR$^7$, (C$_0$-C$_4$ alkylene)-SO$_2$N(R$^7$)$_2$, (C$_0$-C$_4$ alkylene)-SO$_2$R$^7$, (C$_0$-C$_4$ alkylene)N(R$^8$)—SO$_2$N(R$^7$)$_2$, or (C$_0$-C$_4$ alkylene)N(R$^8$)—SO$_2$R$^7$. In some embodiments, each R$^1$ is independently halogen, C$_{1-6}$ alkyl, C$_{1-6}$ haloalkyl, —COR$^7$, —CON(R$^7$)$_2$, (C$_0$-C$_4$ alkylene)-CN, (C$_0$-C$_4$ alkylene)-OR$^7$, or (C$_0$-C$_4$ alkylene)-N(R$^7$)$_2$. In other embodiments, each R$^1$ is independently (C$_0$-C$_4$ alkylene)N(R$^8$)—COR$^7$, (C$_0$-C$_4$ alkylene)-SO$_2$N(R$^7$)$_2$, (C$_0$-C$_4$ alkylene)-SO$_2$R$^7$, (C$_0$-C$_4$ alkylene)N(R$^8$)—SO$_2$N(R$^7$)$_2$, or (C$_0$-C$_4$ alkylene)N(R$^8$)—SO$_2$R$^7$. In some embodiments, each R$^1$ is independently halogen, C$_{1-6}$ alkyl, C$_{1-6}$ haloalkyl, —COR$^7$, —CON(R$^7$)$_2$, —CN, (C$_0$-C$_4$ alkylene)-OR$^7$, or (C$_0$-C$_4$ alkylene)-N(R$^7$)$_2$. In some embodiments, each R$^1$ is independently halogen, C$_{1-6}$ alkyl, C$_{1-6}$ haloalkyl, or —CN. In certain embodiments, each R$^1$ is independently F, Br, Cl, C$_{1-6}$ haloalkyl, or C$_{1-6}$ alkyl. In specific embodiments, each R$^1$ is independently F or CF$_3$.

In some embodiments, each R$^7$ is independently selected from H, optionally substituted C$_{1-6}$ alkyl, optionally substituted C$_{3-6}$ carbocyclyl, optionally substituted C$_{3-10}$ carbocyclylalkyl, optionally substituted C$_{2-6}$ heterocyclyl, optionally substituted C$_{2-10}$ heterocyclylalkyl; or two R$^{11}$ groups together with the nitrogen to which they are attached join to form an optionally substituted C$_{2-6}$ N-heterocyclyl. In some embodiments, each R$^7$ is independently selected from H, C$_{1-6}$ alkyl, C$_{3-6}$ carbocyclyl, C$_{3-10}$ carbocyclylalkyl, C$_{2-6}$ heterocyclyl, C$_{2-10}$ heterocyclylalkyl; or two R$^{11}$ groups together with the nitrogen to which they are attached join to form a C$_{2-6}$ N-heterocyclyl. In some embodiments, each R$^7$ is independently selected from H, C$_{1-6}$ alkyl, or C$_{3-6}$ carbocyclyl. In certain embodiments, two R$^{11}$ groups together with the nitrogen to which they are attached join to form an optionally substituted C$_{2-6}$ N-heterocyclyl. In some embodiments, each R$^7$ is independently selected from H or C$_{1-6}$ alkyl. In some embodiments, each R$^7$ is H or Me.

In some embodiments, each R$^8$ is independently selected from H, C$_{1-6}$ alkyl, or C$_{1-6}$ haloalkyl. In some embodiments, each R$^8$ is independently selected from H or C$_{1-6}$ alkyl. In some embodiments, each R$^8$ is independently selected from H or Me. In some embodiments, each R$^8$ is H.

In some embodiments, p is 0, 1, 2, 3, or 4. In some embodiments, p is 0, 1, 2, or 3. In some embodiments, p is 0, 1 or 2. In some embodiments, p is 0 or 1. In some embodiments, p is 1, 2, or 3. In some embodiments, p is 1 or 2. In some embodiments, p is 1, 2, 3, or 4. In some embodiments, p is 2, 3, or 4. In some embodiments, p is 2 or 3. In some embodiments, p is 0. In some embodiments, p is 1. In some embodiments, p is 2. In some embodiments, p is 3. In some embodiments, p is 4. In some embodiments, p is 5. In some embodiments, p is 1.

In some embodiments, R$^2$ is —H, —OH, optionally substituted alkyl, or halogen. In some embodiments, R$^2$ is —H, —OH, alkyl, haloalkyl, or halogen. In some embodiments, R$^2$ is —H, —OH, C$_{1-6}$ alkyl, C$_{1-6}$ haloalkyl, or halogen. In some embodiments, R$^2$ is —H, —OH, Me, CF$_3$, or halogen. In some embodiments, R$^2$ is —H, —OH, Me, CF$_3$, Cl, or F. In some embodiments, R$^2$ is —H, —OH, Me, CF$_3$, or F. In some embodiments, R$^2$ is —H, —OH, or halogen. In some embodiments, R$^2$ is —H, —OH, or F. In some embodiments, R$^2$ is —H. In some embodiments, R$^2$ is —OH. In some embodiments, R$^2$ is F. In some embodiments, R$^2$ is Cl.

In some embodiments, when α is present, then Z$_1$ is O or S, Z$_2$ is N, X is C, χ is present, and β and δ are absent. In other embodiments, when α is absent, then Z$_1$ is N, Z$_2$ is NR$^3$, X is C, β and δ are present, and χ is absent. In certain embodiments, when α is absent, then Z$_1$ is N, Z$_2$ is O or S, X is C, β and δ are present, and χ is absent.

In some embodiments, A has the structure

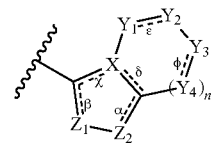

wherein:
n is 0, 1, or 2;
α, β, χ, δ, ε, and φ are each independently absent or present, and when present each is a bond;
Z$_1$ is S, O, or N;
Z$_2$ is S, O, N or NR$^3$,
 wherein R$^3$ is H, C$_1$-C$_4$ alkyl, or oxetane;
X is C;
Y$_1$, Y$_2$, Y$_3$ and each occurrence of Y$_4$ are each independently CR$^4$, C(R$^5$)$_2$, NR$^6$, O, N, SO$_2$, or —(C═O)—,
 wherein:
 R$^4$ is H, halogen, C$_1$-C$_{10}$ alkyl, C$_1$-C$_{10}$ cycloalkyl, —O(C$_1$-C$_{10}$ alkyl), —C(O)OH, —C(O)O(C$_1$-C$_{10}$ alkyl), —C(O)NH$_2$, —C(O)NH(C$_1$-C$_4$ alkyl), —C(O)N(C$_1$-C$_4$ alkyl)$_2$, —NHC(O)NH(C$_1$-C$_{10}$ alkyl), —NHC(O)N(C$_1$-C$_4$ alkyl)$_2$, —SO$_2$NH(C$_1$-C$_{10}$ alkyl), —SO$_2$N(C$_1$-C$_{10}$ alkyl)$_2$, —CN, or —CF$_3$;
 R$^5$ is H or C$_1$-C$_{10}$ alkyl; and
 R$^6$ is H, C$_1$-C$_{10}$ alkyl, C$_3$-C$_6$ cycloalkyl, —(C$_1$-C$_{10}$ alkylene)CF$_3$, —(C$_1$-C$_{10}$ alkylene)OCH$_3$, —(C$_1$-C$_{10}$ alkylene)-halogen, —SO$_2$(C$_1$-C$_{10}$ alkyl), —SO$_2$(C$_1$-C$_{10}$ alkylene)-CF$_3$, —SO$_2$(C$_1$-C$_{10}$ alkylene)OCH$_3$, —SO$_2$(C$_1$-C$_{10}$ alkylene)-halogen, —C(O)(C$_1$-C$_{10}$ alkyl), —C(O)(C$_1$-C$_{10}$ alkylene)CF$_3$, —C(O)(C$_1$-C$_{10}$ alkylene)OCH$_3$, —C(O)(C$_1$-C$_{10}$ alkylene)-halogen, —C(O)NH(C$_1$-C$_{10}$ alkyl), —C(O)N(C$_1$-C$_{10}$ alkyl)$_2$, —(C$_1$-C$_{10}$ alkylene)C(O)OH, —C(O)NH$_2$, or oxetane.

In some embodiments, when α is present, then Z$_1$ is O or S, Z$_2$ is N, X is C, χ is present, and β and δ are absent. In other embodiments, when α is absent, then Z$_1$ is N, Z$_2$ is N, X is C, β and δ are present, and χ is absent. In certain embodiments, when α is absent, then Z$_1$ is N, Z$_2$ is O or S, X is C, β and δ are present, and χ is absent. In further or additional embodiments, when ε and φ are each present, then n=1, and each of Y$_1$, Y$_2$, Y$_3$, and Y$_4$, are independently —CR$^4$— or N. In other embodiments, when ε and φ are each absent, then n=0, 1 or 2, each of Y$_1$, Y$_2$, Y$_3$, and each occurrence of Y$_4$ are independently C(R$^5$)$_2$, NR$^6$, O, or SO$_2$.

In some embodiments, β and δ are present. In some embodiments, α, χ, ε, and φ are absent. In some embodiments, Z$_1$ is N. In some embodiments, Z$_2$ is O, S, or NR$^3$;

wherein $R^3$ is H, $C_1$-$C_4$ alkyl, or oxetane. In some embodiments, X is C. In certain embodiments, β and δ are present; α, χ, ε, and φ are absent; $Z_1$ is N; $Z_2$ is O, S, or $NR^3$; $R^3$ is H, $C_1$-$C_4$ alkyl, or oxetane; and X is C.

In some embodiments, β, δ, ε, and φ are present. In some embodiments, α, and χ are absent. In some embodiments, $Z_1$ is N. In some embodiments, $Z_2$ is O or $NR_3$, wherein $R^3$ is H, $C_1$-$C_4$ alkyl, or oxetane. In some embodiments, X is C. In certain embodiments, β, δ, ε, and φ are present; α, and χ are absent; $Z_1$ is N; $Z_2$ is O or $NR_3$; $R^3$ is H, $C_1$-$C_4$ alkyl, or oxetane; and X is C.

In some embodiments, A has the structure:

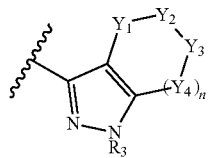

wherein
n is 0;
$R^3$ is H, $C_1$-$C_4$ alkyl, or oxetane;
$Y_1$ and $Y_3$ are each $CH_2$ or $C(CH_3)_2$;
$Y_2$ is O, $SO_2$, or $NR^6$; and
$R^6$ is H, $C_1$-$C_4$ alkyl, $C_3$-$C_6$ cycloalkyl, —($C_1$-$C_4$ alkylene)$CF_3$, —($C_1$-$C_4$ alkylene)$OCH_3$, —($C_1$-$C_4$ alkylene)-halogen, —$SO_2$($C_1$-$C_4$ alkyl), —$SO_2$($C_1$-$C_4$ alkylene)$CF_3$, —$SO_2$($C_1$-$C_4$ alkylene)$OCH_3$, —$SO_2$($C_1$-$C_4$ alkylene)-halogen, —C(O)($C_1$-$C_4$ alkyl), —C(O)($C_1$-$C_4$ alkylene)$CF_3$, —C(O)($C_1$-$C_4$ alkylene)$OCH_3$, —C(O)($C_1$-$C_4$ alkylene)-halogen, —C(O)NH($C_1$-$C_4$ alkyl), —C(O)N($C_1$-$C_4$ alkyl)$_2$, —($C_1$-$C_4$ alkylene)C(O)OH, —C(O)$NH_2$, or oxetane.

In some embodiments, A has the structure:

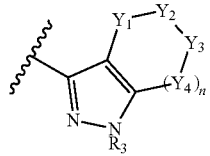

n is 1;
$R^3$ is H, $C_1$-$C_4$ alkyl, or oxetane;
$Y_1$ and $Y_4$ are $CH_2$ or $C(CH_3)_2$;
$Y_2$ and $Y_3$ are each $CH_2$ or $C(CH_3)_2$, O, $SO_2$, or $NR^6$; and
$R^6$ is H, $C_1$-$C_4$ alkyl, $C_3$-$C_6$ cycloalkyl, —($C_1$-$C_4$ alkylene)$CF_3$, —($C_1$-$C_4$ alkylene)$OCH_3$, —($C_1$-$C_4$ alkylene)-halogen, —$SO_2$($C_1$-$C_4$ alkyl), —$SO_2$($C_1$-$C_4$ alkylene)$CF_3$, —$SO_2$($C_1$-$C_4$ alkylene)$OCH_3$, —$SO_2$($C_1$-$C_4$ alkylene)-halogen, —C(O)($C_1$-$C_4$ alkyl), —C(O)($C_1$-$C_4$ alkylene)$CF_3$, —C(O)($C_1$-$C_4$ alkylene)$OCH_3$, —C(O)($C_1$-$C_4$ alkylene)-halogen, —C(O)NH($C_1$-$C_4$ alkyl), —C(O)N($C_1$-$C_4$ alkyl)$_2$, —($C_1$-$C_4$ alkylene)C(O)OH, —C(O)$NH_2$, or oxetane.

In some embodiments, A has the structure:

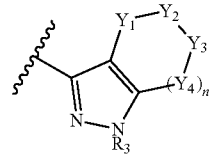

n is 2;
$R^3$ is H, $C_1$-$C_4$ alkyl, or oxetane;
$Y_1$ and $Y_4$ are $CH_2$ or $C(CH_3)_2$;
$Y_2$ and $Y_3$ are each $CH_2$ or $C(CH_3)_2$, O, $SO_2$, or $NR^6$; and
$R^6$ is H, $C_1$-$C_4$ alkyl, $C_3$-$C_6$ cycloalkyl, —($C_1$-$C_4$ alkylene)$CF_3$, —($C_1$-$C_4$ alkylene)$OCH_3$, —($C_1$-$C_4$ alkylene)-halogen, —$SO_2$($C_1$-$C_4$ alkyl), —$SO_2$($C_1$-$C_4$ alkylene)$CF_3$, —$SO_2$($C_1$-$C_4$ alkylene)$OCH_3$, —$SO_2$($C_1$-$C_4$ alkylene)-halogen, —C(O)($C_1$-$C_4$ alkyl), —C(O)($C_1$-$C_4$ alkylene)$CF_3$, —C(O)($C_1$-$C_4$ alkylene)$OCH_3$, —C(O)($C_1$-$C_4$ alkylene)-halogen, —C(O)NH($C_1$-$C_4$ alkyl), —C(O)N($C_1$-$C_4$ alkyl)$_2$, —($C_1$-$C_4$ alkylene)C(O)OH, —C(O)$NH_2$, or oxetane.

In some embodiments, A has the structure:

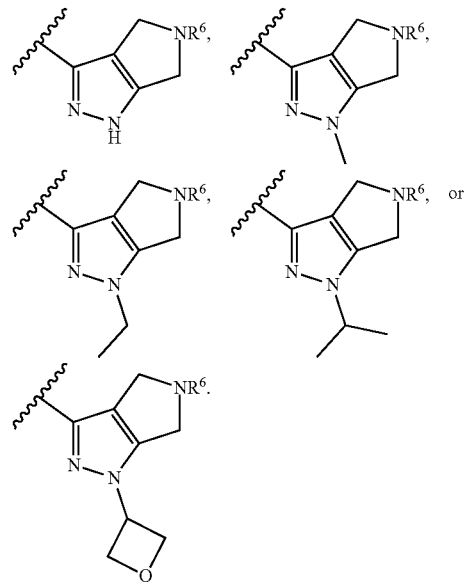

In certain embodiments, A has the structure:

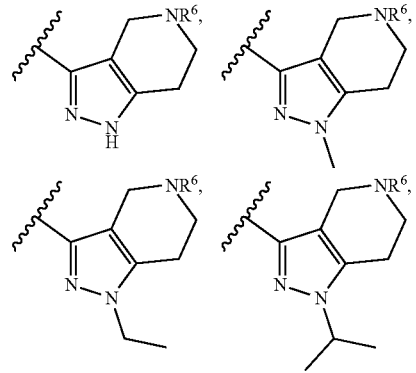

-continued

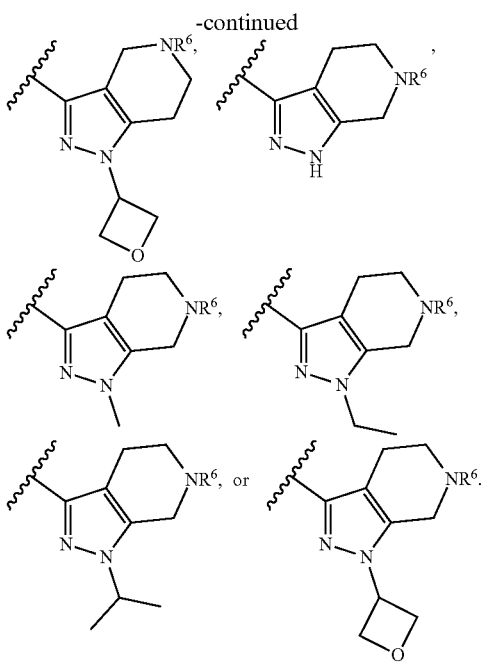

In certain embodiments, A has the structure:

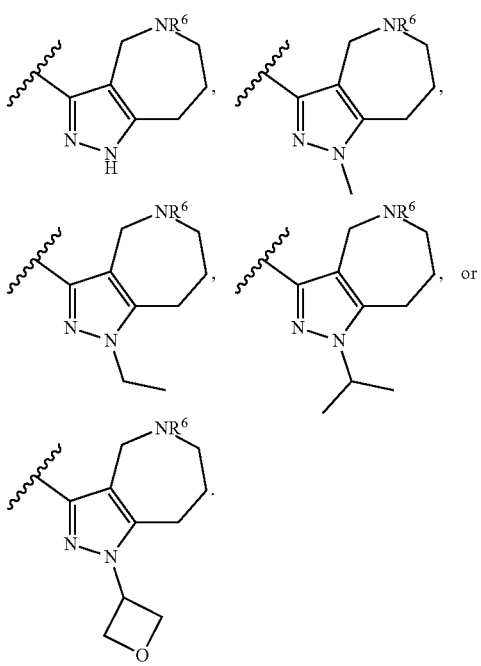

In certain embodiments, A has the structure:

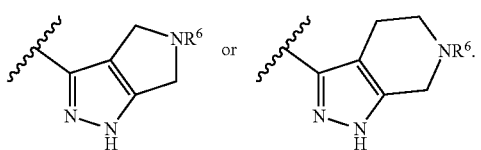

In certain embodiments, A has the structure:

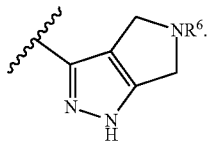

In certain embodiments, A has the structure:

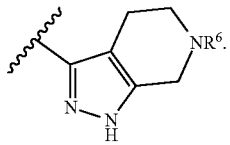

In some embodiments, $R^6$ is H, $C_1$-$C_6$ alkyl, $C_3$-$C_6$ cycloalkyl, —($C_1$-$C_6$ alkylene)$CF_3$, —($C_1$-$C_6$ alkylene)$OCH_3$, —($C_1$-$C_6$ alkylene)-halogen, —$SO_2$—$C_1$-$C_6$ alkyl, —$SO_2$($C_1$-$C_6$ alkylene)-$CF_3$, —$SO_2$($C_1$-$C_6$ alkylene)$OCH_3$, —$SO_2$($C_1$-$C_6$ alkylene)-halogen, —C(O)($C_1$-$C_6$ alkyl), —C(O)($C_1$-$C_6$ alkylene)$CF_3$, —C(O)($C_1$-$C_6$ alkylene)$OCH_3$, —C(O)($C_1$-$C_6$ alkylene)-halogen, —C(O)NH($C_1$-$C_6$ alkyl), —C(O)N($C_1$-$C_6$ alkyl)$_2$, —($C_1$-$C_6$ alkylene)C(O)OH, —C(O)$NH_2$, or oxetane. In some embodiments, $R^6$ is $C_1$-$C_6$ alkyl, $C_3$-$C_6$ cycloalkyl, —($C_1$-$C_6$ alkylene)$CF_3$, —($C_1$-$C_6$ alkylene)$OCH_3$, —($C_1$-$C_6$ alkylene)-halogen, —$SO_2$—$C_1$-$C_6$ alkyl, —$SO_2$($C_1$-$C_6$ alkylene)-$CF_3$, —$SO_2$($C_1$-$C_6$ alkylene)$OCH_3$, —$SO_2$($C_1$-$C_6$ alkylene)-halogen, —C(O)($C_1$-$C_6$ alkyl), —C(O)($C_1$-$C_6$ alkylene)$CF_3$, —C(O)($C_1$-$C_6$ alkylene)$OCH_3$, —C(O)($C_1$-$C_6$ alkylene)-halogen, —C(O)NH($C_1$-$C_6$ alkyl), —C(O)N($C_1$-$C_6$ alkyl)$_2$, —($C_1$-$C_6$ alkylene)C(O)OH, —C(O)$NH_2$, or oxetane. In some embodiments, $R^6$ is —C(O)($C_1$-$C_6$ alkyl). In some embodiments, $R^6$ is H, $C_1$-$C_4$ alkyl, —$CH_2CH_2CH_3$, —$CH(CH_3)_2$, —$CH_2CH(CH_3)_2$, t-Bu, —$CH_2OCH_3$, —$CH_2CF_3$, —$CH_2Cl$, —$CH_2F$, —$CH_2CH_2OCH_3$, —$CH_2CH_2CF_3$, —$CH_2CH_2Cl$, —$CH_2CH_2F$,

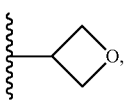 [SMILES: *C1COC1]

$SO_2CH_3$, —$SO_2CH_2CH_3$, —$SO_2CH_2CH_2CH_3$, —$SO_2CH(CH_3)_2$, —$SO_2CH_2CH(CH_3)_2$, —$SO_2$(t-Bu), —$SO_2CH_2OCH_3$, —$SO_2CH_2CF_3$, —$SO_2CH_2Cl$, —$SO_2CH_2F$, —$SO_2CH_2CH_2OCH_3$, —$SO_2CH_2CH_2CF_3$, —$SO_2CH_2CH_2Cl$, —$SO_2CH_2CH_2F$,

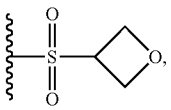 [SMILES: *S(=O)(=O)C1COC1]

$C(O)CH_3$, $C(O)CH_2CH_3$, —$C(O)CH_2CH_2CH_3$, —$C(O)CH(CH_3)_2$, —$C(O)CH_2CH(CH_3)_2$, —C(O)t-Bu, —$C(O)CH_2OCH_3$, —$C(O)CH_2CF_3$, —$C(O)CH_2Cl$, —$C(O)CH_2F$, —$C(O)CH_2CH_2OCH_3$, —$C(O)CH_2CH_2CF_3$, —$C(O)CH_2CH_2Cl$, —$C(O)CH_2CH_2F$,

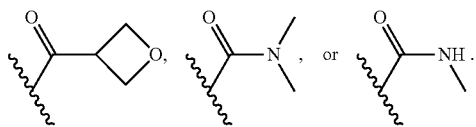

In some embodiments, $R^6$ is —C(O)($C_1$-$C_6$ alkyl). In some embodiments, $R^6$ is H, $C_1$-$C_4$ alkyl, —$CH_2CH_2CH_3$, —CH($CH_3$)$_2$, —$CH_2CH(CH_3)_2$, t-Bu, —$CH_2OCH_3$, —$CH_2CF_3$, —$CH_2Cl$, —$CH_2F$, —$CH_2CH_2OCH_3$, —$CH_2CH_2CF_3$, —$CH_2CH_2Cl$, —$CH_2CH_2F$, or

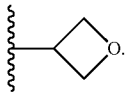

In other embodiments, $R^6$ is —$SO_2CH_3$, —$SO_2CH_2CH_3$, —$SO_2CH_2CH_2CH_3$, —$SO_2CH(CH_3)_2$, —$SO_2CH_2CH(CH_3)_2$, —$SO_2$(t-Bu), —$SO_2CH_2OCH_3$, —$SO_2CH_2CF_3$, —$SO_2CH_2Cl$, —$SO_2CH_2F$, —$SO_2CH_2CH_2OCH_3$, —$SO_2CH_2CH_2CF_3$, —$SO_2CH_2CH_2Cl$, —$SO_2CH_2CH_2F$, or

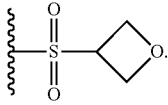

In certain embodiments, $R^6$ is C(O)$CH_3$, C(O)$CH_2CH_3$, —C(O)$CH_2CH_2CH_3$, —C(O)CH($CH_3$)$_2$, —C(O)$CH_2CH(CH_3)_2$, —C(O)t-Bu, —C(O)$CH_2OCH_3$, —C(O)$CH_2CF_3$, —C(O)$CH_2Cl$, —C(O)$CH_2F$, —C(O)$CH_2CH_2OCH_3$, —C(O)$CH_2CH_2CF_3$, —C(O)$CH_2CH_2Cl$, —C(O)$CH_2CH_2F$,

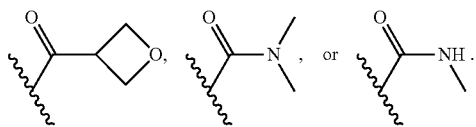

In some embodiments, A has the structure:

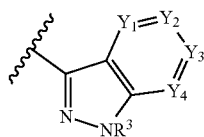

wherein:

$Y_1$, $Y_2$, $Y_3$ and each occurrence of $Y_4$ are each independently $CR^4$, or N;

wherein:

$R^3$ is H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$.

In some embodiments, $Y_1$, $Y_2$, $Y_3$ and $Y_4$ are CH. In some embodiments, $Y_1$, $Y_2$, $Y_3$ are CH and $Y_4$ is N. In some embodiments, $Y_1$, $Y_2$, $Y_4$ are CH and $Y_3$ is N. In some embodiments, $Y_1$, $Y_3$, $Y_4$ are CH and $Y_2$ is N. In some embodiments, $Y_2$, $Y_3$, $Y_4$ are CH and $Y_1$ is N.

In certain embodiments, A has the structure:

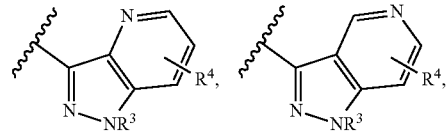

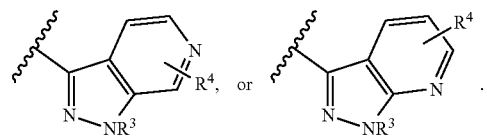

In some embodiments, $R^3$ is H, halogen, $C_1$-$C_{10}$ alkyl, $C_1$-$C_{10}$ cycloalkyl, —O($C_1$-$C_{10}$ alkyl), —C(O)OH, —C(O)O($C_1$-$C_{10}$ alkyl), —C(O)$NH_2$, —C(O)NH($C_1$-$C_4$ alkyl), —C(O)N($C_1$-$C_4$ alkyl)$_2$, —NHC(O)NH($C_1$-$C_{10}$ alkyl), —NHC(O)N($C_1$-$C_4$ alkyl)$_2$, —$SO_2$NH($C_1$-$C_{10}$ alkyl), —$SO_2$N($C_1$-$C_{10}$ alkyl)$_2$, —CN, or —$CF_3$. In some embodiments, $R^3$ is H, halogen, $C_1$-$C_6$ alkyl, $C_1$-$C_6$ cycloalkyl, —O($C_1$-$C_6$ alkyl), —C(O)OH, —C(O)O($C_1$-$C_6$ alkyl), —C(O)$NH_2$, —C(O)NH($C_1$-$C_4$ alkyl), —C(O)N($C_1$-$C_4$ alkyl)$_2$, —NHC(O)NH($C_1$-$C_6$ alkyl), —NHC(O)N($C_1$-$C_4$ alkyl)$_2$, —$SO_2$NH($C_1$-$C_6$ alkyl), —$SO_2$N($C_1$-$C_6$ alkyl)$_2$, —CN, or —$CF_3$. In some embodiments, $R_4$ is H, halogen, $C_1$-$C_4$ alkyl, $C_3$-$C_6$ cycloalkyl, —O($C_1$-$C_4$ alkyl), —CN, —$CF_3$, —C(O)OH, —C(O)$NH_2$, —C(O)N($CH_3$)$_2$, —C(O)NH$CH_3$, or —NHC(O)N($CH_3$)$_2$. In some embodiments, $R_4$ is H, halogen, methyl, methoxy, —CN, —$CF_3$, —C(O)N($CH_3$)$_2$, —C(O)NH$CH_3$, or —C(O)Me.

In some embodiments, the heterocyclic compounds of Formula (I) are provided in Table 1.

TABLE 1

| Compound No. | Name | Structure |
| --- | --- | --- |
| 1 | 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)ethan-1-one | 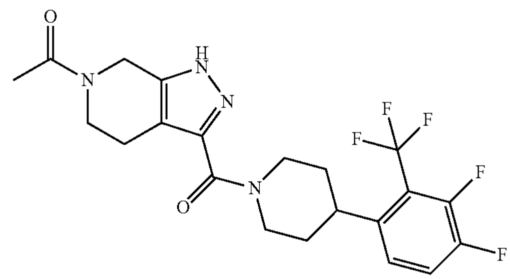 [SMILES: CC(=O)N1CCc2c(C(=O)N3CCC(c4ccc(F)c(F)c4C(F)(F)F)CC3)n[nH]c2C1] |
| 2 | 1-(3-(4-(3,4-difluoro-2-(trifluoromethyl)phenyl)piperidine-1-carbonyl)-4,6-dihydropyrrolo[3,4-c]pyrazol-5(1H)-yl)ethan-1-one | 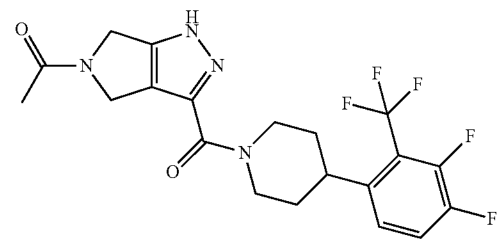 [SMILES: CC(=O)N1Cc2[nH]nc(C(=O)N3CCC(c4ccc(F)c(F)c4C(F)(F)F)CC3)c2C1] |
| 12 | (4-(3,4-difluoro-2-(trifluoromethyl)phenyl)piperidin-1-yl)(6-ethyl-4,5,6,7-tetrahydro-1H-pyrazolo[3,4-c]pyridin-3-yl)methanone | 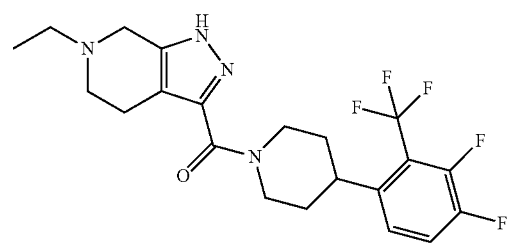 [SMILES: CCN1CCc2c(C(=O)N3CCC(c4ccc(F)c(F)c4C(F)(F)F)CC3)n[nH]c2C1] |
| 13 | (4-(4-fluoro-2-(trifluoromethyl)phenyl)piperidin-1-yl)(5-(methylsulfonyl)-4,5,6,7-tetrahydro-1H-pyrazolo[4,3-c]pyridin-3-yl)methanone | 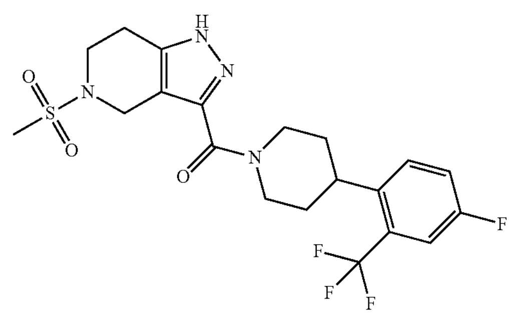 [SMILES: CS(=O)(=O)N1CCc2[nH]nc(C(=O)N3CCC(c4ccc(F)cc4C(F)(F)F)CC3)c2C1] |
| 14 | 1-(3-(4-(2-fluoro-6-(trifluoromethyl)phenyl)piperidine-1-carbonyl)-1,4,5,7-tetrahydro-6H-pyrazolo[3,4-c]pyridin-6-yl)ethan-1-one | 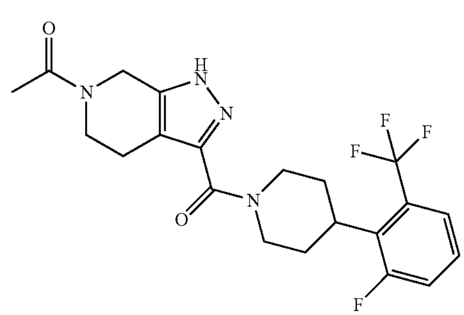 [SMILES: CC(=O)N1CCc2c(C(=O)N3CCC(c4c(F)cccc4C(F)(F)F)CC3)n[nH]c2C1] |

TABLE 1-continued

| Compound No. | Name | Structure |
|---|---|---|
| 17 | (4-(3,5-bis(trifluoromethyl)phenyl)piperidin-1-yl)(5-(methylsulfonyl)-4,5,6,7-tetrahydro-1H-pyrazolo[4,3-c]pyridin-3-yl)methanone | 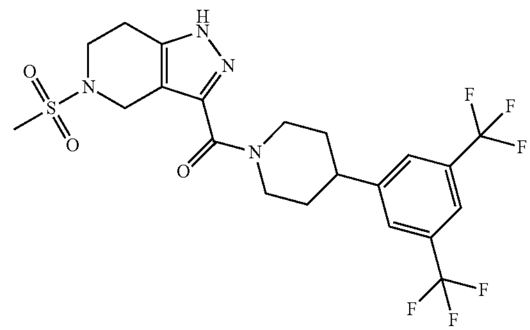 [SMILES: CS(=O)(=O)N1CCc2[nH]nc(C(=O)N3CCC(c4cc(C(F)(F)F)cc(C(F)(F)F)c4)CC3)c2C1] |
| 22 | 3-(4-(3,5-difluoro-2-(trifluoromethyl)phenyl)piperidine-1-carbonyl)-N-methyl-1,4,5,7-tetrahydro-6H-pyrazolo[3,4-c]pyridine-6-carboxamide | 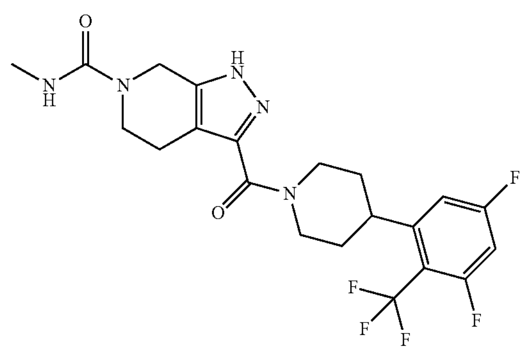 [SMILES: CNC(=O)N1CCc2c(C(=O)N3CCC(c4cc(F)cc(F)c4C(F)(F)F)CC3)n[nH]c2C1] |
| 23 | (6-(cyclopropylmethyl)-4,5,6,7-tetrahydro-1H-pyrazolo[3,4-c]pyridin-3-yl)(4-(3,4-difluoro-2-(trifluoromethyl)phenyl)piperidin-1-yl)methanone | 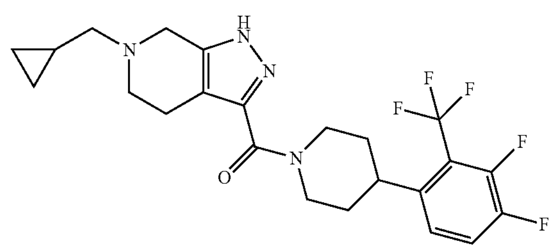 [SMILES: O=C(c1n[nH]c2c1CCN(CC1CC1)C2)N1CCC(c2ccc(F)c(F)c2C(F)(F)F)CC1] |
| 26 | (4-(3,4-difluoro-2-(trifluoromethyl)phenyl)piperidin-1-yl)(5-neopentyl-4,5,6,7-tetrahydro-1H-pyrazolo[4,3-c]pyridin-3-yl)methanone | 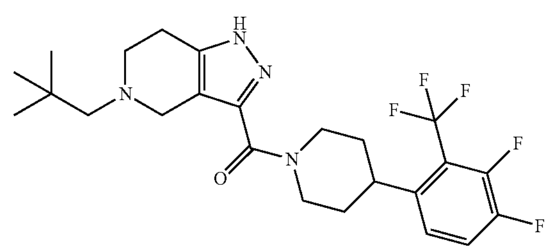 [SMILES: CC(C)(C)CN1CCc2[nH]nc(C(=O)N3CCC(c4ccc(F)c(F)c4C(F)(F)F)CC3)c2C1] |
| 27 | (4-(2-chloro-5-fluorophenyl)piperidin-1-yl)(5-(methylsulfonyl)-4,5,6,7-tetrahydro-1H-pyrazolo[4,3-c]pyridin-3-yl)methanone | 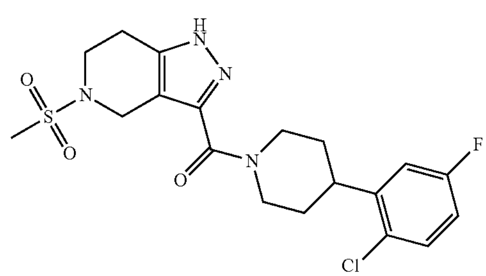 [SMILES: CS(=O)(=O)N1CCc2[nH]nc(C(=O)N3CCC(c4cc(F)ccc4Cl)CC3)c2C1] |

TABLE 1-continued

| Compound No. | Name | Structure |
|---|---|---|
| 31 | 3-(4-(3,4-difluoro-2-(trifluoromethyl)phenyl)piperidine-1-carbonyl)-N-methyl-1,4,5,7-tetrahydro-6H-pyrazolo[3,4-c]pyridine-6-carboxamide | 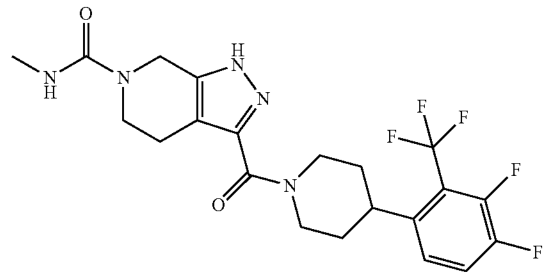 [SMILES: CNC(=O)N1CCc2c(C(=O)N3CCC(c4ccc(F)c(F)c4C(F)(F)F)CC3)n[nH]c2C1] |
| 32 | (4-(3,4-difluoro-2-(trifluoromethyl)phenyl)piperidin-1-yl)(6-neopentyl-4,5,6,7-tetrahydro-1H-pyrazolo[3,4-c]pyridin-3-yl)methanone | 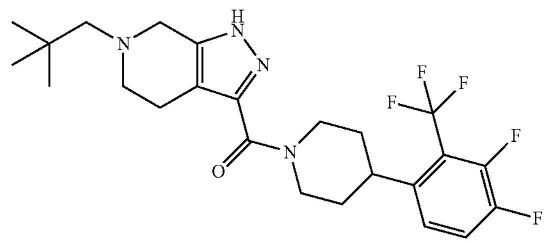 [SMILES: CC(C)(C)CN1CCc2c(C(=O)N3CCC(c4ccc(F)c(F)c4C(F)(F)F)CC3)n[nH]c2C1] |
| 35 | 1-(3-(4-(3,5-difluoro-2-(trifluoromethyl)phenyl)piperidine-1-carbonyl)-1,4,5,7-tetrahydro-6H-pyrazolo[3,4-c]pyridin-6-yl)ethan-1-one | 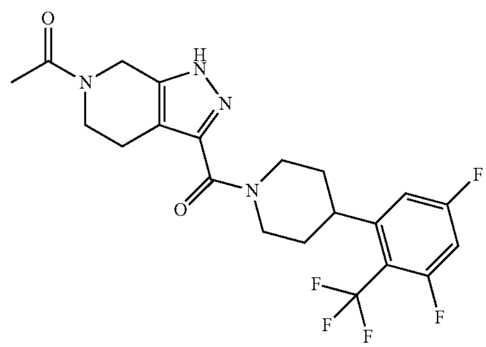 [SMILES: CC(=O)N1CCc2c(C(=O)N3CCC(c4cc(F)cc(F)c4C(F)(F)F)CC3)n[nH]c2C1] |
| 38 | 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)-3-methylbutan-1-one | 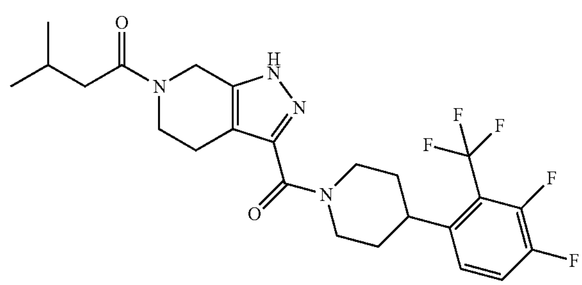 [SMILES: CC(C)CC(=O)N1CCc2c(C(=O)N3CCC(c4ccc(F)c(F)c4C(F)(F)F)CC3)n[nH]c2C1] |
| 39 | 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)propan-1-one | 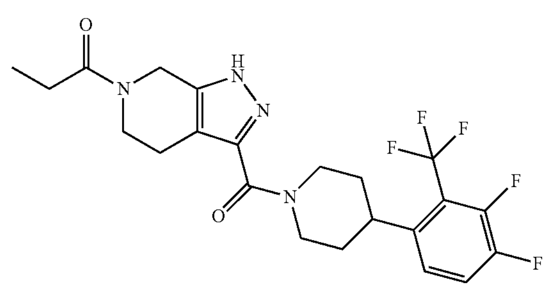 [SMILES: CCC(=O)N1CCc2c(C(=O)N3CCC(c4ccc(F)c(F)c4C(F)(F)F)CC3)n[nH]c2C1] |

TABLE 1-continued

| Compound No. | Name | Structure |
|---|---|---|
| 41 | 3-(4-(3,4-difluoro-2-(trifluoromethyl)phenyl)piperidine-1-carbonyl)-1,4,5,7-tetrahydro-6H-pyrazolo[3,4-c]pyridine-6-carbonitrile | 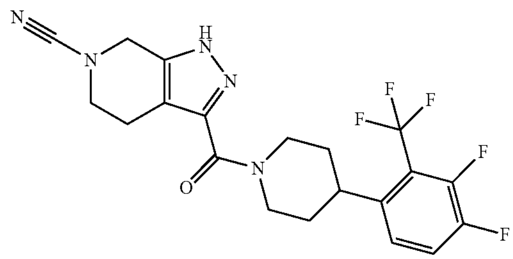 [SMILES: N#CN1CCc2c(C(=O)N3CCC(c4ccc(F)c(F)c4C(F)(F)F)CC3)n[nH]c2C1] |
| 44 | (4-(3,4-difluoro-2-(trifluoromethyl)phenyl)piperidin-1-yl)(5-(3,3,3-trifluoropropyl)-4,5,6,7-tetrahydro-1H-pyrazolo[4,3-c]pyridin-3-yl)methanone | 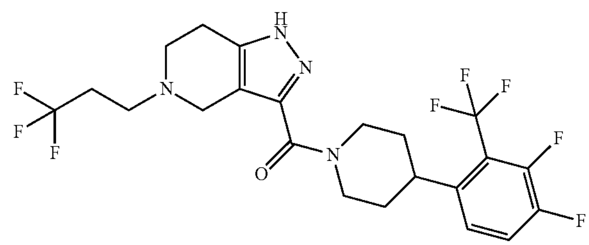 [SMILES: O=C(c1n[nH]c2c1CN(CCC(F)(F)F)CC2)N1CCC(c2ccc(F)c(F)c2C(F)(F)F)CC1] |
| 52 | 3-(4-(3-fluoro-2-(trifluoromethyl)phenyl)piperidine-1-carbonyl)-N-methyl-1,4,6,7-tetrahydro-5H-pyrazolo[4,3-c]pyridine-5-carboxamide | 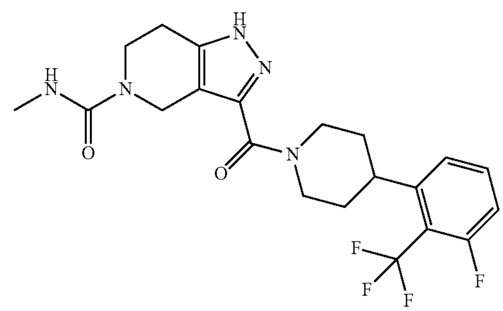 [SMILES: CNC(=O)N1CCc2[nH]nc(C(=O)N3CCC(c4cccc(F)c4C(F)(F)F)CC3)c2C1] |
| 57 | 3-(4-(3,4-difluoro-2-(trifluoromethyl)phenyl)piperidine-1-carbonyl)-1,4,6,7-tetrahydro-5H-pyrazolo[4,3-c]pyridine-5-carbonitrile | 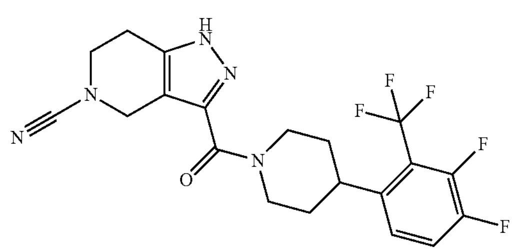 [SMILES: N#CN1CCc2[nH]nc(C(=O)N3CCC(c4ccc(F)c(F)c4C(F)(F)F)CC3)c2C1] |
| 63 | (4-(3-fluoro-2-(trifluoromethyl)phenyl)piperidin-1-yl)(5-(3,3,3-trifluoropropyl)-4,5,6,7-tetrahydro-1H-pyrazolo[4,3-c]pyridin-3-yl)methanone | 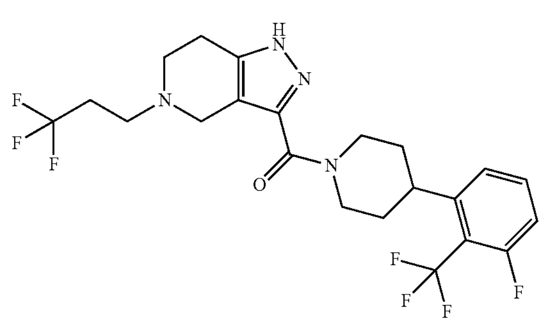 [SMILES: O=C(c1n[nH]c2c1CN(CCC(F)(F)F)CC2)N1CCC(c2cccc(F)c2C(F)(F)F)CC1] |

TABLE 1-continued

| Compound No. | Name | Structure |
|---|---|---|
| 67 | 1-(3-(4-(3,4-difluoro-2-(trifluoromethyl)phenyl)piperidine-1-carbonyl)-1,4,6,7-tetrahydro-5H-pyrazolo[4,3-c]pyridin-5-yl)ethan-1-one | 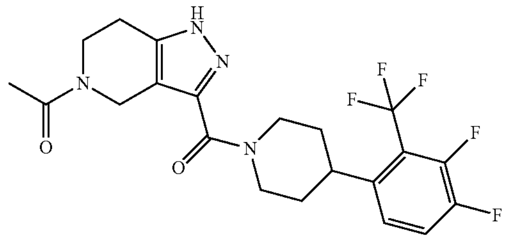 [SMILES: CC(=O)N1CCc2[nH]nc(C(=O)N3CCC(c4ccc(F)c(F)c4C(F)(F)F)CC3)c2C1] |
| 69 | 3-(4-(3-fluoro-2-(trifluoromethyl)phenyl)piperidine-1-carbonyl)-N-methyl-1,4,5,7-tetrahydro-6H-pyrazolo[3,4-c]pyridine-6-carboxamide | 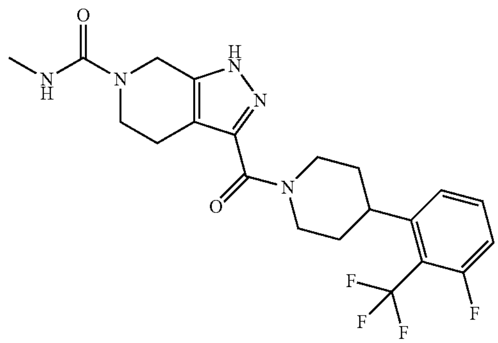 [SMILES: CNC(=O)N1CCc2c(C(=O)N3CCC(c4cccc(F)c4C(F)(F)F)CC3)n[nH]c2C1] |
| 70 | (4-(3-fluoro-2-(trifluoromethyl)phenyl)piperidin-1-yl)(5-(methylsulfonyl)-4,5,6,7-tetrahydro-1H-pyrazolo[4,3-c]pyridin-3-yl)methanone | 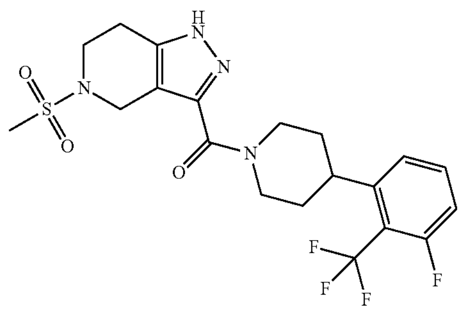 [SMILES: CS(=O)(=O)N1CCc2[nH]nc(C(=O)N3CCC(c4cccc(F)c4C(F)(F)F)CC3)c2C1] |
| 75 | (4-(3,4-difluoro-2-(trifluoromethyl)phenyl)piperidin-1-yl)(4,5,6,7-tetrahydro-1H-pyrazolo[4,3-c]pyridin-3-yl)methanone | 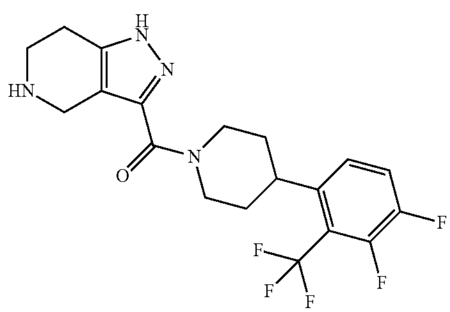 [SMILES: O=C(c1n[nH]c2c1CNCC2)N1CCC(c2ccc(F)c(F)c2C(F)(F)F)CC1] |
| 76 | (4-(3,4-difluoro-2-(trifluoromethyl)phenyl)piperidin-1-yl)(4,5,6,7-tetrahydro-1H-pyrazolo[3,4-c]pyridin-3-yl)methanone | 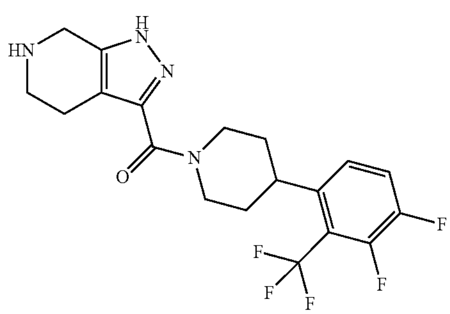 [SMILES: O=C(c1n[nH]c2c1CCNC2)N1CCC(c2ccc(F)c(F)c2C(F)(F)F)CC1] |

TABLE 1-continued

| Compound No. | Name | Structure |
|---|---|---|
| 82 | 1-(3-(4-(3-fluoro-2-(trifluoromethyl)phenyl)piperidine-1-carbonyl)-1,4,5,7-tetrahydro-6H-pyrazolo[3,4-c]pyridin-6-yl)ethan-1-one | 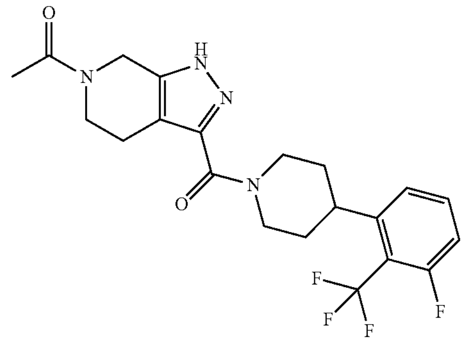 [SMILES: CC(=O)N1CCc2c(C(=O)N3CCC(c4cccc(F)c4C(F)(F)F)CC3)n[nH]c2C1] |
| 84 | 1-(3-(4-(3,5-bis(trifluoromethyl)phenyl)piperidine-1-carbonyl)-1,4,5,7-tetrahydro-6H-pyrazolo[3,4-c]pyridin-6-yl)ethan-1-one | 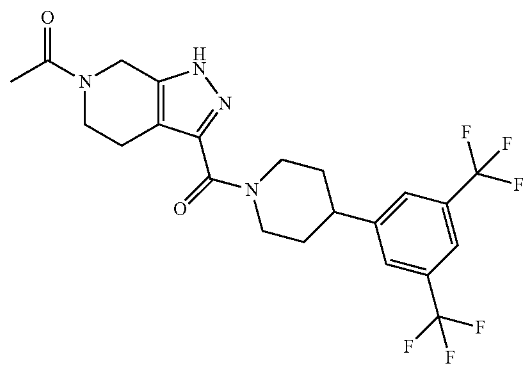 [SMILES: CC(=O)N1CCc2c(C(=O)N3CCC(c4cc(C(F)(F)F)cc(C(F)(F)F)c4)CC3)n[nH]c2C1] |
| 85 | 1-(3-(4-(4-fluoro-2-(trifluoromethyl)phenyl)piperidine-1-carbonyl)-1,4,5,7-tetrahydro-6H-pyrazolo[3,4-c]pyridin-6-yl)ethan-1-one | 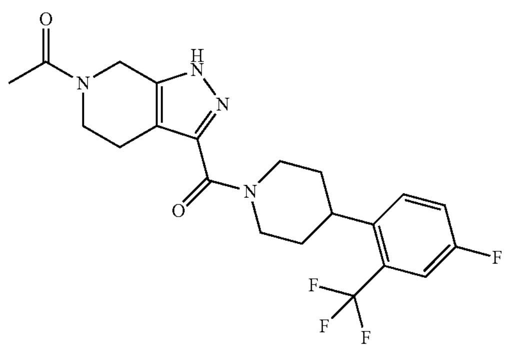 [SMILES: CC(=O)N1CCc2c(C(=O)N3CCC(c4ccc(F)cc4C(F)(F)F)CC3)n[nH]c2C1] |
| 88 | (5-(cyclopropylmethyl)-4,5,6,7-tetrahydro-1H-pyrazolo[4,3-c]pyridin-3-yl)(4-(3-fluoro-2-(trifluoromethyl)phenyl)piperidin-1-yl)methanone | 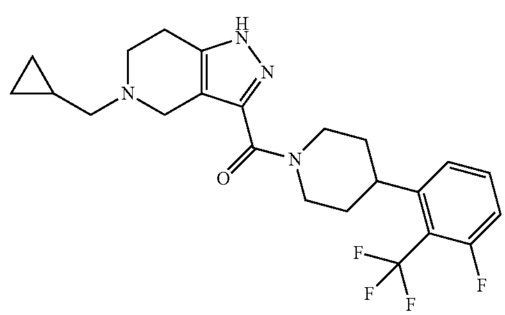 [SMILES: O=C(c1n[nH]c2c1CN(CC1CC1)CC2)N1CCC(c2cccc(F)c2C(F)(F)F)CC1] |

In certain embodiments, the heterocyclic compound of Formula (I) is 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)ethan-1-one; 1-(3-(4-(3,4-difluoro-2-(trifluoromethyl)phenyl)piperidine-1-carbonyl)-4,6-dihydropyrrolo[3,4-c]pyrazol-5(1H)-yl)ethan-1-one; (4-(3-fluoro-2,5-bis(trifluoromethyl)phenyl)piperidin-1-yl)(4, 5, 6,7-tetrahydro-1H-pyrazolo[4,3-c]pyridin-3-yl)methanone; (4-(2-chloro-3-fluorophenyl)piperidin-1-yl)(5-(2-methoxyethyl)-4,5,6,7-tetrahydro-1H-pyrazolo[4,3-c]pyridin-3-yl)methanone; (4-(2-chloro-3-fluorophenyl)piperidin-1-yl)(5-(3,3,3-trifluoropropyl)-4,5,6,7-tetrahydro-1H-pyrazolo[4,3-c]pyridin-3-yl)methanon e; (4-(2-chloro-3-fluorophenyl)piperidin-1-yl)(5-(2,2,2-trifluoroethyl)-4,5,6,7-tetrahydro-1H-pyrazolo[4,3-c]pyridin-3-yl)methanone; (4-(2-chloro-3-fluorophenyl)piperidin-1-yl)(5-(oxetan-3-yl)-4,5,6,7- tetrahydro-1H-pyrazolo[4,3-c]pyridin-3-yl)methanone; (4-(4-fluoro-2-(trifluoromethyl)phenyl)piperidin-1-yl)(4,5,6,7-tetrahydro-1H-pyrazolo[4,3-c]pyridin-3-yl)methanone; (4-(4-fluoro-2-(trifluoromethyl)phenyl)piperidin-1-yl)(4,5,6,7-tetrahydro-1H-pyrazolo[3,4-c]pyridin-3-yl)methanone; (4-(2-chloro-3-fluorophenyl)piperidin-1-yl)(5-(cyclopropylmethyl)-4,5,6,7-tetrahydro-1H-pyrazolo[4,3-c]pyridin-3-yl)methanone; (4-(2-chloro-3-fluorophenyl)piperidin-1-yl)(5-ethyl-4,5,6,7-tetrahydro-1H-pyrazolo[4,3-c]pyridin-3-yl)methanone; (4-(3,4-difluoro-2-(trifluoromethyl)phenyl)piperidin-1-yl)(6-ethyl-4,5,6,7-tetrahydro-1H-pyrazolo[3,4-c]pyridin-3-yl)methanone; (4-(4-fluoro-2-(trifluoromethyl)phenyl)piperidin-1-yl)(5-(methylsulfonyl)-4,5,6,7-tetrahydro-1H-pyrazolo[4,3-c]pyridin-3-yl)methanone; 1-(3-(4-(2-fluoro-6-(trifluoromethyl)phenyl)piperidine-1-carbonyl)-1,4,5,7-tetrahydro-6H-pyrazolo[3,4-c]pyridin-6-yl)ethan-1-one; (4-(3-fluoro-2,5-bis(trifluoromethyl)phenyl)piperidin-1-yl)(4,5,6,7-tetrahydro-1H-pyrazolo[3,4-c]pyridin-3-yl)methanone; (4-(2-chloro-3-fluorophenyl)piperidin-1-yl)(6-(cyclopropylmethyl)-4,5,6,7-tetrahydro-1H-pyrazolo[3,4-c]pyridin-3-yl)methanone; (4-(3,5-bis(trifluoromethyl)phenyl)piperidin-1-yl)(5-(methylsulfonyl)-4,5,6,7-tetrahydro-1H-pyrazolo[4,3-c]pyridin-3-yl)methanone; (4-(2-chloro-3-fluorophenyl)piperidin-1-yl)(5-(methylsulfonyl)-4,5,6,7-tetrahydro-1H-pyrazolo[4,3-c]pyridin-3-yl)methanone; (4-(2-chloro-3-fluorophenyl)piperidin-1-yl)(6-(oxetan-3-yl)-4,5,6,7-tetrahydro-1H-pyrazolo[3,4-c]pyridin-3-yl)methanone; 3-(4-(2-chloro-3-fluorophenyl)piperidine-1-carbonyl)-1,4,5,7-tetrahydro-6H-pyrazolo[3,4-c]pyridine-6-carbonitrile(4-(5-fluoro-2-(trifluoromethyl)phenyl)piperidin-1-yl)(5-(methylsulfonyl)-4,5,6,7-tetrahydro-1H-pyrazolo[4,3-c]pyridin-3-yl)methanone; 3-(4-(3,5-difluoro-2-(trifluoromethyl)phenyl)piperidine-1-carbonyl)-N-methyl-1,4,5,7-tetrahydro-6H-pyrazolo[3,4-c]pyridine-6-carboxamide(6-(cyclopropylmethyl)-4,5,6,7-tetrahydro-1H-pyrazolo[3,4-c]pyridin-3-yl)(4-(3,4-difluoro-2-(trifluoromethyl)phenyl)piperidin-1-yl)methanone; methyl 3-(4-(3,5-difluoro-2-(trifluoromethyl)phenyl)piperidine-1-carbonyl)-1,4,5,7-tetrahydro-6H-pyrazolo[3,4-c]pyridine-6-carboxylate; (4-(3,5-difluoro-2-(trifluoromethyl)phenyl)piperidin-1-yl)(5-(3,3,3-trifluoropropyl)-4,5,6,7-tetrahydro-1H-pyrazolo[4,3-c]pyridin-3-yl)methanone; (4-(3,4-difluoro-2-(trifluoromethyl)phenyl)piperidin-1-yl)(5-neopentyl-4,5,6,7-tetrahydro-1H-pyrazolo[4,3-c]pyridin-3-yl)methanone; (4-(2-chloro-5-fluorophenyl)piperidin-1-yl)(5-(methylsulfonyl)-4,5,6,7-tetrahydro-1H-pyrazolo[4,3-c]pyridin-3-yl)methanone; (4-(3,5-difluoro-2-(trifluoromethyl)phenyl)piperidin-1-yl)(6-(2,2,2-trifluoroethyl)-4,5,6,7-tetrahydro-1H-pyrazolo[3,4-c]pyridin-3-yl)methanone; 3-(4-(3,5-difluoro-2-(trifluoromethyl)phenyl)piperidine-1-carbonyl)-1,4,5,7-tetrahydro-6H-pyrazolo[3,4-c]pyridine-6-carbonitrile; (4-(3,5-difluoro-2-(trifluoromethyl)phenyl)piperidin-1-yl)(6-(oxetan-3-yl)-4,5,6,7-tetrahydro-1H-pyrazolo[3,4-c]pyridin-3-yl)methanone; 3-(4-(3,4-difluoro-2-(trifluoromethyl)phenyl)piperidine-1-carbonyl)-N-methyl-1,4,5,7-tetrahydro-6H-pyrazolo[3,4-c]pyridine-6-carboxamide; (4-(3,4-difluoro-2-(trifluoromethyl)phenyl)piperidin-1-yl)(6-neopentyl-4,5,6,7-tetrahydro-1H-pyrazolo[3,4-c]pyridin-3-yl)methanone; (4-(3,4-difluoro-2-(trifluoromethyl)phenyl)piperidin-1-yl)(6-(2,2,2-trifluoroethyl)-4,5,6,7-tetrahydro-1H-pyrazolo[3,4-c]pyridin-3-yl)methanone; methyl 3-(4-(2-chloro-3-fluorophenyl)piperidine-1-carbonyl)-1,4,5,7-tetrahydro-6H-pyrazolo[3,4-c]pyridine-6-carboxylate; 1-(3-(4-(3,5-difluoro-2-(trifluoromethyl)phenyl)piperidine-1-carbonyl)-1,4,5,7-tetrahydro-6H-pyrazolo[3,4-c]pyridin-6-yl)ethan-1-one; (6-(cyclopropylmethyl)-4,5,6,7-tetrahydro-1H-pyrazolo[3,4-c]pyridin-3-yl)(4-(3,5-difluoro-2-(trifluoromethyl)phenyl)piperidin-1-yl)methanone; (4-(3,4-difluoro-2-(trifluoromethyl)phenyl)piperidin-1-yl)(6-(2-methoxyethyl)-4,5,6,7-tetrahydro-1H-pyrazolo[3,4-c]pyridin-3-yl)methanone; 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)-3-methylbutan-1-one; 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)propan-1-one; 1-(3-(4-(3,4-difluoro-2-(trifluoromethyl)phenyl)piperidine-1-carbonyl)-1,4,5,7-tetrahydro-6H-pyrazolo[3,4-c]pyridin-6-yl)-2-methylpropan-1-one; 3-(4-(3,4-difluoro-2-(trifluoromethyl)phenyl)piperidine-1-carbonyl)-1,4,5,7-tetrahydro-6H-pyrazolo[3,4-c]pyridine-6-carbonitrile; (4-(3,4-difluoro-2-(trifluoromethyl)phenyl)piperidin-1-yl)(6-(3,3,3-trifluoropropyl)-4,5,6,7-tetrahydro-1H-pyrazolo[3,4-c]pyridin-3-yl)methanone; (4-(3,4-difluoro-2-(trifluoromethyl)phenyl)piperidin-1-yl)(5-(2-methoxyethyl)-4,5,6,7-tetrahydro-1H-pyrazolo[4,3-c]pyridin-3-yl)methanone; (4-(3,4-difluoro-2-(trifluoromethyl)phenyl)piperidin-1-yl)(5-(3,3,3-trifluoropropyl)-4,5,6,7-tetrahydro-1H-pyrazolo[4,3-c]pyridin-3-yl)methanone; 3-(4-(3,4-difluoro-2-(trifluoromethyl)phenyl)piperidine-1-carbonyl)-N-methyl-1,4,6,7-tetrahydro-5H-pyrazolo[4,3-c]pyridine-5-carboxamide; (4-(3,4-difluoro-2-(trifluoromethyl)phenyl)piperidin-1-yl)(6-(oxetan-3-yl)-4,5,6,7-tetrahydro-1H-pyrazolo[3,4-c]pyridin-3-yl)methanone; methyl 3-(4-(3,4-difluoro-2-(trifluoromethyl)phenyl)piperidine-1-carbonyl)-1,4,5,7-tetrahydro-6H-pyrazolo[3,4-c]pyridine-6-carboxylate; 2-(3-(4-(3,4-difluoro-2-(trifluoromethyl)phenyl)piperidine-1-carbonyl)-1,4,5,7-tetrahydro-6H-pyrazolo[3,4-c]pyridin-6-yl)acetic acid; (4-(3,4-difluoro-2-(trifluoromethyl)phenyl)piperidin-1-yl)(5-(oxetan-3-yl)-4,5,6,7-tetrahydro-1H-pyrazolo[4,3-c]pyridin-3-yl)methanone; (5-(cyclopropylmethyl)-4,5,6,7-tetrahydro-1H-pyrazolo[4,3-c]pyridin-3-yl)(4-(3,4-difluoro-2-(trifluoromethyl)phenyl)piperidin-1-yl)methanone; (4-(3,4-difluoro-2-(trifluoromethyl)phenyl)piperidin-1-yl)(5-ethyl-4,5,6,7-tetrahydro-1H-pyrazolo[4,3-c]pyridin-3-yl)methanone; 3-(4-(3-fluoro-2-(trifluoromethyl)phenyl)piperidine-1-carbonyl)-N-methyl-1,4,6,7-tetrahydro-5H-pyrazolo[4,3-c]pyridine-5-carboxamide; (4-(3,4-difluoro-2-(trifluoromethyl)phenyl)piperidin-1-yl)(6-methyl-4,5,6,7-tetrahydro-1H-pyrazolo[3,4-c]pyridin-3-yl)methanone; methyl 3-(4-(3,5-difluoro-2-(trifluoromethyl)phenyl)piperidine-1-carbonyl)-1,4,6,7-tetrahydro-5H-pyrazolo[4,3-c]pyridine-5-carboxylate; (4-(3,5-difluoro-2-(trifluoromethyl)phenyl)piperidin-1-yl)(5-ethyl-4,5,6,7-tetrahydro-1H-pyrazolo[4,3-c]pyridin-3-yl)methanone; (4-(3,5-difluoro-2-(trifluoromethyl)phenyl)piperidin-1-yl)(5-(2-methoxyethyl)-4,5,6,7-tetrahydro-1H-pyrazolo[4,3-c]pyridin-3-yl)methanone; 3-(4-(3,4-difluoro-2-(trifluoromethyl)phenyl)piperidine-1-carbonyl)-1,4,6,7-tetrahydro-5H-pyrazolo[4,3-c]pyridine-5-carbonitrile; methyl 3-(4-(3,4-difluoro-2-(trifluoromethyl)phenyl)piperidine-1-carbonyl)-1,4,6,7-tetrahydro-5H-pyrazolo[4,3-c]pyridine-5-carboxylate; (4-(3-fluoro-2-(trifluoromethyl)phenyl)piperidin-1-yl)(6-(3,3,3-trifluoropropyl)-4,5,6,7-tetrahydro-1H-pyrazolo[3,4-c]pyridin-3-yl)methanone; (6-ethyl-4,5,6,7-tetrahydro-1H-pyrazolo[3,4-c]pyridin-3-yl)(4-(3-fluoro-2-(trifluoromethyl)phenyl)piperidin-1-yl)methanone; (4-(3-fluoro-2-(trifluoromethyl)phenyl)piperidin-1-yl)(5-(oxetan-3-yl)-4,5,6,7-tetrahydro-1H-pyrazolo[4,3-c]pyridin-3-yl)methanone; (4-(3-fluoro-2-

(trifluoromethyl)phenyl)piperidin-1-yl)(5-(2-methoxyethyl)-4,5,6,7-tetrahydro-1H-pyrazolo[4,3-c]pyridin-3-yl)methanone; (4-(3-fluoro-2-(trifluoromethyl)phenyl)piperidin-1-yl)(5-(3,3,3-trifluoropropyl)-4,5,6,7-tetrahydro-1H-pyrazolo[4,3-c]pyridin-3-yl)methanone; (4-(2-chloro-5-fluorophenyl)piperidin-1-yl)(4,5,6,7-tetrahydro-1H-pyrazolo[3,4-c]pyridin-3-yl)methanone; imidazo[1,2-a]pyridin-2-yl(4-(2-(trifluoromethyl)phenyl)piperidin-1-yl)methanone; (4-(5-fluoro-2-(trifluoromethyl)phenyl)piperidin-1-yl)(4,5,6,7-tetrahydro-1H-pyrazolo[4,3-c]pyridin-3-yl)methanone; 1-(3-(4-(3,4-difluoro-2-(trifluoromethyl)phenyl)piperidine-1-carbonyl)-1,4,6,7-tetrahydro-5H-pyrazolo[4,3-c]pyridin-5-yl)ethan-1-one; (5-ethyl-4,5,6,7-tetrahydro-1H-pyrazolo[4,3-c]pyridin-3-yl)(4-(3-fluoro-2-(trifluoromethyl)phenyl)piperidin-1-yl)methanone; 3-(4-(3-fluoro-2-(trifluoromethyl)phenyl)piperidine-1-carbonyl)-N-methyl-1,4,5,7-tetrahydro-6H-pyrazolo[3,4-c]pyridine-6-carboxamide; (4-(3-fluoro-2-(trifluoromethyl)phenyl)piperidin-1-yl)(5-(methylsulfonyl)-4,5,6,7-tetrahydro-1H-pyrazolo[4,3-c]pyridin-3-yl)methanone; (4-(3,5-difluoro-2-(trifluoromethyl)phenyl)piperidin-1-yl)(4,5,6,7-tetrahydro-1H-pyrazolo[4,3-c]pyridin-3-yl)methanone; (4-(3,5-difluoro-2-(trifluoromethyl)phenyl)piperidin-1-yl)(4,5,6,7-tetrahydro-1H-pyrazolo[4,3-c]pyridin-3-yl)methanone; (4-(2-chloro-3-fluorophenyl)piperidin-1-yl)(4,5,6,7-tetrahydro-1H-pyrazolo[3,4-c]pyridin-3-yl)methanone; (4-(2-chloro-3-fluorophenyl)piperidin-1-yl)(4,5,6,7-tetrahydro-1H-pyrazolo[3,4-c]pyridin-3-yl)methanone; (4-(3,4-difluoro-2-(trifluoromethyl)phenyl)piperidin-1-yl)(4,5,6,7-tetrahydro-1H-pyrazolo[3,4-c]pyridin-3-yl)methanone; (4-(3,4-difluoro-2-(trifluoromethyl)phenyl)piperidin-1-yl)(4,5,6,7-tetrahydro-1H-pyrazolo[3,4-c]pyridin-3-yl)methanone; (4-(3,5-bis(trifluoromethyl)phenyl)piperidin-1-yl)(4,5,6,7-tetrahydro-1H-pyrazolo[3,4-c]pyridin-3-yl)methanone; (4-(3,5-bis(trifluoromethyl)phenyl)piperidin-1-yl)(4,5,6,7-tetrahydro-1H-pyrazolo[3,4-c]pyridin-3-yl)methanone; (4-(3-fluoro-2-(trifluoromethyl)phenyl)piperidin-1-yl)(4,5,6,7-tetrahydro-1H-pyrazolo[3,4-c]pyridin-3-yl)methanone; (4-(3-fluoro-2-(trifluoromethyl)phenyl)piperidin-1-yl)(4,5,6,7-tetrahydro-1H-pyrazolo[3,4-c]pyridin-3-yl)methanone; 1-(3-(4-(2-chloro-3-fluorophenyl)piperidine-1-carbonyl)-1,4,5,7-tetrahydro-6H-pyrazolo[3,4-c]pyridin-6-yl)ethan-1-one; 1-(3-(4-(3-fluoro-2-(trifluoromethyl)phenyl)piperidine-1-carbonyl)-1,4,5,7-tetrahydro-6H-pyrazolo[3,4-c]pyridin-6-yl)ethan-1-one; 1-(3-(4-(5-fluoro-2-(trifluoromethyl)phenyl)piperidine-1-carbonyl)-1,4,5,7-tetrahydro-6H-pyrazolo[3,4-c]pyridin-6-yl)ethan-1-one; 1-(3-(4-(3,5-bis(trifluoromethyl)phenyl)piperidine-1-carbonyl)-1,4,5,7-tetrahydro-6H-pyrazolo[3,4-c]pyridin-6-yl)ethan-1-one; 1-(3-(4-(4-fluoro-2-(trifluoromethyl)phenyl)piperidine-1-carbonyl)-1,4,5,7-tetrahydro-6H-pyrazolo[3,4-c]pyridin-6-yl)ethan-1-one; (4-(2-fluoro-6-(trifluoromethyl)phenyl)piperidin-1-yl)(4,5,6,7-tetrahydro-1H-pyrazolo[4,3-c]pyridin-3-yl)methanone; (4-(3-fluoro-2-(trifluoromethyl)phenyl)piperidin-1-yl)(5-(2,2,2-trifluoroethyl)-4,5,6,7-tetrahydro-1H-pyrazolo[4,3-c]pyridin-3-yl)methanone; (5-(cyclopropylmethyl)-4,5,6,7-tetrahydro-1H-pyrazolo[4,3-c]pyridin-3-yl)(4-(3-fluoro-2-(trifluoromethyl)phenyl)piperidin-1-yl)methanone; methyl 3-(4-(3-fluoro-2-(trifluoromethyl)phenyl)piperidine-1-carbonyl)-1,4,6,7-tetrahydro-5H-pyrazolo[4,3-c]pyridine-5-carboxylate; 3-(4-(3-fluoro-2-(trifluoromethyl)phenyl)piperidine-1-carbonyl)-1,4,6,7-tetrahydro-5H-pyrazolo[4,3-c]pyridine-5-carbonitrile; 1-(3-(4-(2-chloro-5-fluorophenyl)piperidine-1-carbonyl)-1,4,5,7-tetrahydro-6H-pyrazolo[3,4-c]pyridin-6-yl)ethan-1-one; (4-(2-fluoro-6-(trifluoromethyl)phenyl)piperidin-1-yl)(4,5,6,7-tetrahydro-1H-pyrazolo[3,4-c]pyridin-3-yl)methanone; tert-butyl 2-(3-(4-(3,4-difluoro-2-(trifluoromethyl)phenyl)piperidine-1-carbonyl)-1,4,5,7-tetrahydro-6H-pyrazolo[3,4-c]pyridin-6-yl)acetate; tert-butyl 3-(4-(3,5-difluoro-2-(trifluoromethyl)phenyl)piperidine-1-carbonyl)-1,4,6,7-tetrahydro-5H-pyrazolo[4,3-c]pyridine-5-carboxylate; tert-butyl 3-(4-(3,5-difluoro-2-(trifluoromethyl)phenyl)piperidine-1-carbonyl)-1,4,5,7-tetrahydro-6H-pyrazolo[3,4-c]pyridine-6-carboxylate; tert-butyl 3-(4-(2-fluoro-6-(trifluoromethyl)phenyl)piperidine-1-carbonyl)-1,4,6,7-tetrahydro-5H-pyrazolo[4,3-c]pyridine-5-carboxylate; tert-butyl 3-(4-(5-fluoro-2-(trifluoromethyl)phenyl)piperidine-1-carbonyl)-1,4,6,7-tetrahydro-5H-pyrazolo[4,3-c]pyridine-5-carboxylate; tert-butyl 3-(4-(5-fluoro-2-(trifluoromethyl)phenyl)piperidine-1-carbonyl)-1,4,5,7-tetrahydro-6H-pyrazolo[3,4-c]pyridine-6-carboxylate; tert-butyl 3-(4-(2-chloro-3-fluorophenyl)piperidine-1-carbonyl)-1,4,6,7-tetrahydro-5H-pyrazolo[4,3-c]pyridine-5-carboxylate; tert-butyl 3-(4-(2-fluoro-6-(trifluoromethyl)phenyl)piperidine-1-carbonyl)-1,4,5,7-tetrahydro-6H-pyrazolo[3,4-c]pyridine-6-carboxylate tert-butyl 3-(4-(3,5-bis(trifluoromethyl)phenyl)piperidine-1-carbonyl)-1,4,6,7-tetrahydro-5H-pyrazolo[4,3-c]pyridine-5-carboxylate; tert-butyl 3-(4-(3,5-bis(trifluoromethyl)phenyl)piperidine-1-carbonyl)-1,4,5,7-tetrahydro-6H-pyrazolo[3,4-c]pyridine-6-carboxylate; tert-butyl 3-(4-(2-chloro-5-fluorophenyl)piperidine-1-carbonyl)-1,4,6,7-tetrahydro-5H-pyrazolo[4,3-c]pyridine-5-carboxylate; tert-butyl 3-(4-(2-chloro-5-fluorophenyl)piperidine-1-carbonyl)-1,4,5,7-tetrahydro-6H-pyrazolo[3,4-c]pyridine-6-carboxylate; tert-butyl 3-(4-(4-fluoro-2-(trifluoromethyl)phenyl)piperidine-1-carbonyl)-1,4,5,7-tetrahydro-6H-pyrazolo[3,4-c]pyridine-6-carboxylate; tert-butyl 3-(4-(3-fluoro-2-(trifluoromethyl)phenyl)piperidine-1-carbonyl)-1,4,5,7-tetrahydro-6H-pyrazolo[3,4-c]pyridine-6-carboxylate; tert-butyl 3-(4-(3,4-difluoro-2-(trifluoromethyl)phenyl)piperidine-1-carbonyl)-1,4,6,7-tetrahydro-5H-pyrazolo[4,3-c]pyridine-5-carboxylate; tert-butyl 3-(4-(3,4-difluoro-2-(trifluoromethyl)phenyl)piperidine-1-carbonyl)-1,4,5,7-tetrahydro-6H-pyrazolo[3,4-c]pyridine-6-carboxylate; tert-butyl 3-(4-(3-fluoro-2-(trifluoromethyl)phenyl)piperidine-1-carbonyl)-1,4,6,7-tetrahydro-5H-pyrazolo[4,3-c]pyridine-5-carboxylate; tert-butyl 3-(4-(4-fluoro-2-(trifluoromethyl)phenyl)piperidine-1-carbonyl)-1,4,6,7-tetrahydro-5H-pyrazolo[4,3-c]pyridine-5-carboxylate; tert-butyl 3-(4-(2-chloro-3-fluorophenyl)piperidine-1-carbonyl)-1,4,5,7-tetrahydro-6H-pyrazolo[3,4-c]pyridine-6-carboxylate; (6,6-dimethyl-1,4,6,7-tetrahydropyrano[4,3-c]pyrazol-3-yl)(4-(2-(trifluoromethyl)phenyl)piperidin-1-yl)methanone; (6,6-dioxido-1,4,5,7-tetrahydrothiopyrano[3,4-c]pyrazol-3-yl)(4-(2-(trifluoromethyl)phenyl)piperidin-1-yl)methanone; (1,4,6,7-tetrahydropyrano[4,3-c]pyrazol-3-yl)(4-(2-(trifluoromethyl)phenyl)piperidin-1-yl)methanone; (1,4,5,7-tetrahydropyrano[3,4-c]pyrazol-3-yl)(4-(2-(trifluoromethyl)phenyl)piperidin-1-yl)methanone; (1-methyl-4,5,6,7-tetrahydro-1H-pyrazolo[4,3-c]pyridin-3-yl)(4-(2-(trifluoromethyl)phenyl)piperidin-1-yl)methanone; (1-methyl-4,5,6,7-tetrahydro-1H-pyrazolo[3,4-c]pyridin-3-yl)(4-(2-(trifluoromethyl)phenyl)piperidin-1-yl)methanone; 1-ethyl-N,N-dimethyl-3-(4-(2-(trifluoromethyl)phenyl)piperidine-1-carbonyl)-1,4,5,7-tetrahydro-6H-pyrazolo[3,4-c]pyridine-6-carboxamide; (5-(2,2,2-trifluoroethyl)-4,5,6,7-tetrahydro-1H-pyrazolo[4,3-c]pyridin-3-yl)(4-(2-(trifluoromethyl)phenyl)piperidin-1-yl)methanone; (6-(2,2,2-trifluoroethyl)-4,5,6,7-tetrahydro-1H-pyrazolo[3,4-c]pyridin-3-yl)(4-(2-(trifluoromethyl)phenyl)piperidin-1-yl)methanone; (5-chloro-1H-indazol-3-yl)(4-(2-

(trifluoromethyl)phenyl)piperidin-1-yl)methanone; (1H-pyrazolo[3,4-b]pyridin-3-yl)(4-(2-(trifluoromethyl)phenyl)piperidin-1-yl)methanone; (6-chloro-1H-indazol-3-yl)(4-(2-(trifluoromethyl)phenyl)piperidin-1-yl)methanone; (5-(methylsulfonyl)-4,5,6,7-tetrahydro-1H-pyrazolo[4,3-c]pyridin-3-yl)(4-(2-(trifluoromethyl)phenyl)piperidin-1-yl)methanone; 1-(3-(4-(2-(trifluoromethyl)phenyl)piperidine-1-carbonyl)-1,4,6,7-tetrahydro-5H-pyrazolo[4,3-c]pyridin-5-yl)ethan-1-one; (4,5,6,7-tetrahydro-1H-pyrazolo[4,3-c]pyridin-3-yl)(4-(2-(trifluoromethyl)phenyl)piperidin-1-yl)methanone; (6-fluoro-1-(oxetan-3-yl)-1H-indazol-3-yl)(4-(2-(trifluoromethyl)phenyl)piperidin-1-yl)methanone; (1-ethyl-6-fluoro-1H-indazol-3-yl)(4-(2-(trifluoromethyl)phenyl)piperidin-1-yl)methanone; (6-fluoro-1-isopropyl-1H-indazol-3-yl)(4-(2-(trifluoromethyl)phenyl)piperidin-1-yl)methanone; 1-(3-(4-fluoro-4-(2-(trifluoromethyl)phenyl)piperidine-1-carbonyl)-1,4,6,7-tetrahydro-5H-pyrazolo[4,3-c]pyridin-5-yl)ethan-1-one; (5-fluoro-1-methyl-1H-indazol-3-yl)(4-(2-(trifluoromethyl)phenyl)piperidin-1-yl)methanone; (6-fluoro-1H-indazol-3-yl)(4-(2-(trifluoromethyl)phenyl)piperidin-1-yl)methanone; (6-methyl-4,5,6,7-tetrahydro-1H-pyrazolo[3,4-c]pyridin-3-yl)(4-(2-(trifluoromethyl)phenyl)piperidin-1-yl)methanone; (6-(methylsulfonyl)-4,5,6,7-tetrahydro-1H-pyrazolo[3,4-c]pyridin-3-yl)(4-(2-(trifluoromethyl)phenyl)piperidin-1-yl)methanone; 1-(3-(4-(2-(trifluoromethyl)phenyl)piperidine-1-carbonyl)-1,4,5,7-tetrahydro-6H-pyrazolo[3,4-c]pyridin-6-yl)ethan-1-one; (5-fluoro-1H-indazol-3-yl)(4-(2-(trifluoromethyl)phenyl)piperidin-1-yl)methanone; (5-((chloromethyl)sulfonyl)-4,5,6,7-tetrahydro-1H-pyrazolo[4,3-c]pyridin-3-yl)(4-(2-(trifluoromethyl)phenyl)piperidin-1-yl)methanone; (5-(2-methoxyethyl)-4,5,6,7-tetrahydro-1H-pyrazolo[4,3-c]pyridin-3-yl)(4-(2-(trifluoromethyl)phenyl)piperidin-1-yl)methanone; (4-fluoro-4-(2-(trifluoromethyl)phenyl)piperidin-1-yl)(4,5,6,7-tetrahydro-1H-pyrazolo[4,3-c]pyridin-3-yl)methanone; 1-(3-(4-(4-fluoro-2-(trifluoromethyl)phenyl)piperidine-1-carbonyl)-1,4,5,7-tetrahydro-6H-pyrazolo[3,4-c]pyridin-6-yl)ethan-1-one; (1-ethyl-5-fluoro-1H-indazol-3-yl)(4-(2-(trifluoromethyl)phenyl)piperidin-1-yl)methanone; (6-fluoro-1-methyl-1H-indazol-3-yl)(4-(2-(trifluoromethyl)phenyl)piperidin-1-yl)methanone; 3-(4-(2-(trifluoromethyl)phenyl)piperidine-1-carbonyl)-1,4,5,7-tetrahydro-6H-pyrazolo[4,3-c]pyridin-6-one; 3-(4-(2-(trifluoromethyl)phenyl)piperidine-1-carbonyl)-1,4,6,7-tetrahydro-5H-pyrazolo[3,4-c]pyridin-5-one; 6-methyl-3-(4-(2-(trifluoromethyl)phenyl)piperidine-1-carbonyl)-1,4,6,7-tetrahydro-5H-pyrazolo[3,4-c]pyridin-5-one; 5-methyl-3-(4-(2-(trifluoromethyl)phenyl)piperidine-1-carbonyl)-1,4,5,7-tetrahydro-6H-pyrazolo[4,3-c]pyridin-6-one; (5,5-dioxido-1,4,6,7-tetrahydrothiopyrano[4,3-c]pyrazol-3-yl)(4-(2-(trifluoromethyl)phenyl)piperidin-1-yl)methanone; (1-methyl-5-(methylsulfonyl)-4,5,6,7-tetrahydro-1H-pyrazolo[4,3-c]pyridin-3-yl)(4-(2-(trifluoromethyl)phenyl)piperidin-1-yl)methanone; (1-methyl-6-(methylsulfonyl)-4,5,6,7-tetrahydro-1H-pyrazolo[3,4-c]pyridin-3-yl)(4-(2-(trifluoromethyl)phenyl)piperidin-1-yl)methanone; 1-(1-ethyl-3-(4-(2-(trifluoromethyl)phenyl)piperidine-1-carbonyl)-1,4,5,7-tetrahydro-6H-pyrazolo[3,4-c]pyridin-6-yl)ethan-1-one; (5-(methoxymethyl)-4,5,6,7-tetrahydro-1H-pyrazolo[4,3-c]pyridin-3-yl)(4-(2-(trifluoromethyl)phenyl)piperidin-1-yl)methanone; (6-(methoxymethyl)-4,5,6,7-tetrahydro-1H-pyrazolo[3,4-c]pyridin-3-yl)(4-(2-(trifluoromethyl)phenyl)piperidin-1-yl)methanone; (5-methoxy-1H-indazol-3-yl)(4-(2-(trifluoromethyl)phenyl)piperidin-1-yl)methanone; (5-(oxetan-3-yl)-4,5,6,7-tetrahydro-1H-pyrazolo[4,3-c]pyridin-3-yl)(4-(2-(trifluoromethyl)phenyl)piperidin-1-yl)methanone; (5-isobutyl-4,5,6,7-tetrahydro-1H-pyrazolo[4,3-c]pyridin-3-yl)(4-(2-(trifluoromethyl)phenyl)piperidin-1-yl)methanone; 1-(3-(4-(2-(trifluoromethyl)phenyl)piperidine-1-carbonyl)-1,4,6,7-tetrahydro-5H-pyrazolo[4,3-c]pyridin-5-yl)propan-1-one; (5-ethyl-4,5,6,7-tetrahydro-1H-pyrazolo[4,3-c]pyridin-3-yl)(4-(2-(trifluoromethyl)phenyl)piperidin-1-yl)methanone; 3-methyl-1-(3-(4-(2-(trifluoromethyl)phenyl)piperidine-1-carbonyl)-1,4,6,7-tetrahydro-5H-pyrazolo[4,3-c]pyridin-5-yl)butan-1-one; 2-methyl-1-(3-(4-(2-(trifluoromethyl)phenyl)piperidine-1-carbonyl)-1,4,6,7-tetrahydro-5H-pyrazolo[4,3-c]pyridin-5-yl)propan-1-one; 2,2-dimethyl-1-(3-(4-(2-(trifluoromethyl)phenyl)piperidine-1-carbonyl)-1,4,6,7-tetrahydro-5H-pyrazolo[4,3-c]pyridin-5-yl)propan-1-one; (5-(isopropylsulfonyl)-4,5,6,7-tetrahydro-1H-pyrazolo[4,3-c]pyridin-3-yl)(4-(2-(trifluoromethyl)phenyl)piperidin-1-yl)methanone; (5-(isobutylsulfonyl)-4,5,6,7-tetrahydro-1H-pyrazolo[4,3-c]pyridin-3-yl)(4-(2-(trifluoromethyl)phenyl)piperidin-1-yl)methanone; (5-(ethylsulfonyl)-4,5,6,7-tetrahydro-1H-pyrazolo[4,3-c]pyridin-3-yl)(4-(2-(trifluoromethyl)phenyl)piperidin-1-yl)methanone; 3-(4-(2-(trifluoromethyl)phenyl)piperidine-1-carbonyl)-1H-indazole-5-carbonitrile; (7-chloro-1H-indazol-3-yl)(4-(2-(trifluoromethyl)phenyl)piperidin-1-yl)methanone; (5,6-difluoro-1H-indazol-3-yl)(4-(2-(trifluoromethyl)phenyl)piperidin-1-yl)methanone; (6-(2-methoxyethyl)-4,5,6,7-tetrahydro-1H-pyrazolo[3,4-c]pyridin-3-yl)(4-(2-(trifluoromethyl)phenyl)piperidin-1-yl)methanone; 3,3,3-trifluoro-1-(3-(4-(2-(trifluoromethyl)phenyl)piperidine-1-carbonyl)-1,4,5,7-tetrahydro-6H-pyrazolo[3,4-c]pyridin-6-yl)propan-1-one; (5-(tert-butyl)-4,5,6,7-tetrahydro-1H-pyrazolo[4,3-c]pyridin-3-yl)(4-(2-(trifluoromethyl)phenyl)piperidin-1-yl)methanone; (5-isopropyl-4,5,6,7-tetrahydro-1H-pyrazolo[4,3-c]pyridin-3-yl)(4-(2-(trifluoromethyl)phenyl)piperidin-1-yl)methanone; N-methyl-3-(4-(2-(trifluoromethyl)phenyl)piperidine-1-carbonyl)-1,4,6,7-tetrahydro-5H-pyrazolo[4,3-c]pyridine-5-carboxamide; N-methyl-3-(4-(2-(trifluoromethyl)phenyl)piperidine-1-carbonyl)-1,4,5,7-tetrahydro-6H-pyrazolo[3,4-c]pyridine-6-carboxamide; (5-bromo-1H-indazol-3-yl)(4-(2-(trifluoromethyl)phenyl)piperidin-1-yl)methanone; tert-butyl 3-(4-(2-(trifluoromethyl)phenyl)piperidine-1-carbonyl)-1,4,5,7-tetrahydro-6H-pyrazolo[3,4-c]pyridine-6-carboxylate; tert-butyl 3-(4-(2-(trifluoromethyl)phenyl)piperidine-1-carbonyl)-1,4,6,7-tetrahydro-5H-pyrazolo[4,3-c]pyridine-5-carboxylate; (5-fluoro-1-isopropyl-1H-indazol-3-yl)(4-(2-(trifluoromethyl)phenyl)piperidin-1-yl)methanone; (7-fluoro-1H-indazol-3-yl)(4-(2-(trifluoromethyl)phenyl)piperidin-1-yl)methanone; (1H-pyrazolo[4,3-c]pyridin-3-yl)(4-(2-(trifluoromethyl)phenyl)piperidin-1-yl)methanone; (1H-pyrazolo[3,4-c]pyridin-3-yl)(4-(2-(trifluoromethyl)phenyl)piperidin-1-yl)methanone; (1H-pyrazolo[3,4-b]pyridin-3-yl)(4-(2-(trifluoromethyl)phenyl)piperidin-1-yl)methanone; (6-methoxy-1H-indazol-3-yl)(4-(2-(trifluoromethyl)phenyl)piperidin-1-yl)methanone; (5-fluoro-1-(oxetan-3-yl)-1H-indazol-3-yl)(4-(2-(trifluoromethyl)phenyl)piperidin-1-yl)methanone; (1-ethyl-5-(methylsulfonyl)-4,5,6,7-tetrahydro-1H-pyrazolo[4,3-c]pyridin-3-yl)(4-(2-(trifluoromethyl)phenyl)piperidin-1-yl)methanone; (1-ethyl-6-(methylsulfonyl)-4,5,6,7-tetrahydro-1H-pyrazolo[3,4-c]pyridin-3-yl)(4-(2-(trifluoromethyl)phenyl)piperidin-1-yl)methanone; 1-(1-methyl-3-(4-(2-(trifluoromethyl)phenyl)piperidine-1-carbonyl)-1,4,6,7-tetrahydro-5H-pyrazolo[4,3-c]pyridin-5-yl)ethan-1-one; 1-(1-methyl-3-(4-(2-(trifluoromethyl)phenyl)piperidine-1-carbonyl)-1,4,5,7-tetrahydro-6H-pyrazolo[3,4-c]pyridin-6-yl)ethan-1-one; N,N-dimethyl-3-(4-(2-(trifluoromethyl)phenyl)piperidine-1-carbonyl)-1,4,6,7-tetrahydro-5H-pyrazolo[4,3-c]pyridine-5-carboxamide; N,N-dimethyl-3-(4-(2-(trifluoromethyl)phenyl)piperidine-1-carbonyl)-1,4,5,7-tetrahydro-6H-pyrazolo[3,4-c]pyridine-6-carboxamide; (1-methyl-5,5-dioxido-1,4,6,7-tetrahydrothiopyrano[4,3-c]pyrazol-3-yl)(4-(2-(trifluoromethyl)phenyl)piperidin-1-yl)methanone; (4-(2-(trifluoromethyl)phenyl)piperidin-1-yl)(1,6,6-trimethyl-1,4,6,7-tetrahydropyrano[4,3-c]pyrazol-3-yl)methanone; (1-methyl-1,4,6,7-tetrahydropyrano[4,3-c]pyrazol-3-yl)(4-(2-(trifluoromethyl)phenyl)piperidin-1-yl)methanone; 2-methyl-1-(3-(4-(2-(trifluoromethyl)phenyl)piperidine-1-carbonyl)-1,4,5,7-tetrahydro-6H-pyrazolo[3,4-c]pyridin-6-yl)propan-1-one; (6-(isopropylsulfonyl)-4,5,6,7-tetrahydro-1H-pyrazolo[3,4-c]pyridin-3-yl)(4-(2-(trifluoromethyl)phenyl)piperidin-1-yl)methanone; (6-(ethylsulfonyl)-4,5,6,7-tetrahydro-1H-pyrazolo[3,4-c]pyridin-3-yl)(4-(2-(trifluoromethyl)phenyl)piperidin-1-yl)methanone; 1-(3-(4-(2-(trifluoromethyl)phenyl)piperidine-1-carbonyl)-1,4,5,7-tetrahydro-6H-pyrazolo[3,4-c]pyridin-6-yl)propan-1-one; 2-methoxy-1-(3-(4-(2-(trifluoromethyl)phenyl)piperidine-1-carbonyl)-1,4,6,7-tetrahydro-5H-pyrazolo[4,3-c]pyridin-5-yl)ethan-1-one; 3,3,3-trifluoro-1-(3-(4-(2-(trifluoromethyl)phenyl)piperidine-1-carbonyl)-1,4,6,7-tetrahydro-5H-pyrazolo[4,3-c]pyridin-5-yl)propan-1-one; (1H-indazol-3-yl)(4-(2-(trifluoromethyl)phenyl)piperidin-1-yl)methanone; (1-methyl-1H-indazol-3-yl)(4-(2-(trifluoromethyl)phenyl)piperidin-1-yl)methanone; (6-(oxetan-3-yl)-4,5,6,7-tetrahydro-1H-pyrazolo[3,4-c]pyridin-3-yl)(4-(2-(trifluoromethyl)phenyl)piperidin-1-yl)methanone; (6-(tert-butylsulfonyl)-4,5,6,7-tetrahydro-1H-pyrazolo[3,4-c]pyridin-3-yl)(4-(2-(trifluoromethyl)phenyl)piperidin-1-yl)methanone; 2,2-dimethyl-1-(3-(4-(2-(trifluoromethyl)phenyl)piperidine-1-carbonyl)-1,4,5,7-tetrahydro-6H-pyrazolo[3,4-c]pyridin-6-yl)propan-1-one; (6-(tert-butyl)-4,5,6,7-tetrahydro-1H-pyrazolo[3,4-c]pyridin-3-yl)(4-(2-(trifluoromethyl)phenyl)piperidin-1-yl)methanone; (6-(isobutylsulfonyl)-4,5,6,7-tetrahydro-1H-pyrazolo[3,4-c]pyridin-3-yl)(4-(2-(trifluoromethyl)phenyl)piperidin-1-yl)methanone; 3-methyl-1-(3-(4-(2-(trifluoromethyl)phenyl)piperidine-1-carbonyl)-1,4,5,7-tetrahydro-6H-pyrazolo[3,4-c]pyridin-6-yl)butan-1-one; (6-isobutyl-4,5,6,7-tetrahydro-1H-pyrazolo[3,4-c]pyridin-3-yl)(4-(2-(trifluoromethyl)phenyl)piperidin-1-yl)methanone; (6-isopropyl-4,5,6,7-tetrahydro-1H-pyrazolo[3,4-c]pyridin-3-yl)(4-(2-(trifluoromethyl)phenyl)piperidin-1-yl)methanone; (6-ethyl-4,5,6,7-tetrahydro-1H-pyrazolo[3,4-c]pyridin-3-yl)(4-(2-(trifluoromethyl)phenyl)piperidin-1-yl)methanone; (5-(tert-butylsulfonyl)-4,5,6,7-tetrahydro-1H-pyrazolo[4,3-c]pyridin-3-yl)(4-(2-(trifluoromethyl)phenyl)piperidin-1-yl)methanone; tert-butyl 3-(4-fluoro-4-(2-(trifluoromethyl)phenyl)piperidine-1-carbonyl)-1,4,6,7-tetrahydro-5H-pyrazolo[4,3-c]pyridine-5-carboxylate; (4-hydroxy-4-(2-(trifluoromethyl)phenyl)piperidin-1-yl)(1-methyl-1H-indazol-3-yl)methanone; 1-(3-(4-hydroxy-4-(2-(trifluoromethyl)phenyl)piperidine-1-carbonyl)-1,4,6,7-tetrahydro-5H-pyrazolo[4,3-c]pyridin-5-yl)ethan-1-one; 3-(4-(3,4-difluoro-2-(trifluoromethyl)phenyl)piperidine-1-carbonyl)-N-methyl-4,6-dihydropyrrolo[3,4-c]pyrazole-5(1H)-carboxamide; (4-(3,4-difluoro-2-(trifluoromethyl)phenyl)piperidin-1-yl)(5-neopentyl-1,4,5,6-tetrahydropyrrolo[3,4-c]pyrazol-3-yl)methanone; (4-(3,4-difluoro-2-(trifluoromethyl)phenyl)piperidin-1-yl)(5-(oxetan-3-yl)-1,4,5,6-tetrahydropyrrolo[3,4-c]pyrazol-3-yl)methanone; (5-(cyclopropylmethyl)-1,4,5,6-tetrahydropyrrolo[3,4-c]pyrazol-3-yl)(4-(3,4-difluoro-2-(trifluoromethyl)phenyl)piperidin-1-yl)methanone; (4-(3,4-difluoro-2-(trifluoromethyl)phenyl)piperidin-1-yl)(5-ethyl-1,4,5,6-tetrahydropyrrolo[3,4-c]pyrazol-3-yl)methanone; 1-(3-(4-(3,4-difluoro-2-(trifluoromethyl)phenyl)piperidine-1-carbonyl)-4,6-dihydropyrrolo[3,4-c]pyrazol-5(1H)-yl)-3-methylbutan-1-one; 1-(3-(4-(3,4-difluoro-2-(trifluoromethyl)phenyl)piperidine-1-carbonyl)-4,6-dihydropyrrolo[3,4-c]pyrazol-5(1H)-yl)-2-methylpropan-1-one; (4-(3,4-difluoro-2-(trifluoromethyl)phenyl)piperidin-1-yl)(5-picolinoyl-1,4,5,6-tetrahydropyrrolo[3,4-c]pyrazol-3-yl)methanone; 3-(4-(3,4-difluoro-2-(trifluoromethyl)phenyl)piperidine-1-carbonyl)-4,6-dihydropyrrolo[3,4-c]pyrazole-5(1H)-carbonitrile; (4-(3,4-difluoro-2-(trifluoromethyl)phenyl)piperidin-1-yl)(5-(2-methoxyethyl)-1,4,5,6-tetrahydropyrrolo[3,4-c]pyrazol-3-yl)methanone; (4-(3,4-difluoro-2-(trifluoromethyl)phenyl)piperidin-1-yl)(5-(3,3,3-trifluoropropyl)-1,4,5,6-tetrahydropyrrolo[3,4-c]pyrazol-3-yl)methanone; (5-benzoyl-1,4,5,6-tetrahydropyrrolo[3,4-c]pyrazol-3-yl)(4-(3,4-difluoro-2-(trifluoromethyl)phenyl)piperidin-1-yl)methanone; methyl 3-(4-(3,4-difluoro-2-(trifluoromethyl)phenyl)piperidine-1-carbonyl)-4,6-dihydropyrrolo[3,4-c]pyrazole-5(1H)-carboxylate; (4-(3,4-difluoro-2-(trifluoromethyl)phenyl)piperidin-1-yl)(1,4,5,6-tetrahydropyrrolo[3,4-c]pyrazol-3-yl)methanone; (4-(3,4-difluoro-2-(trifluoromethyl)phenyl)piperidin-1-yl)(5-(2,2,2-trifluoroethyl)-1,4,5,6-tetrahydropyrrolo[3,4-c]pyrazol-3-yl)methanone; (4-(3,4-difluoro-2-(trifluoromethyl)phenyl)piperidin-1-yl)(5-(pyrrolidine-1-carbonyl)-1,4,5,6-tetrahydropyrrolo[3,4-c]pyrazol-3-yl)methanone; (4-(3,4-difluoro-2-(trifluoromethyl)phenyl)piperidin-1-yl)(5-isonicotinoyl-1,4,5,6-tetrahydropyrrolo[3,4-c]pyrazol-3-yl)methanone; (4-(3,4-difluoro-2-(trifluoromethyl)phenyl)piperidin-1-yl)(5-nicotinoyl-1,4,5,6-tetrahydropyrrolo[3,4-c]pyrazol-3-yl)methanone; (4-(3,4-difluoro-2-(trifluoromethyl)phenyl)piperidin-1-yl)(5-(piperidine-1-carbonyl)-1,4,5,6-tetrahydropyrrolo[3,4-c]pyrazol-3-yl)methanone; (4-(3,4-difluoro-2-(trifluoromethyl)phenyl)piperidin-1-yl)(5-(piperazine-1-carbonyl)-1,4,5,6-tetrahydropyrrolo[3,4-c]pyrazol-3-yl)methanone; 1-(3-(4-(3,4-difluoro-2-(trifluoromethyl)phenyl)piperidine-1-carbonyl)-4,6-dihydropyrrolo[3,4-c]pyrazol-5(1H)-yl)propan-1-one; (5,5-dioxido-4,6-dihydro-1H-thieno[3,4-c]pyrazol-3-yl)(4-(2-(trifluoromethyl)phenyl)piperidin-1-yl)methanone; (4,6-dihydro-1H-furo[3,4-c]pyrazol-3-yl)(4-(2-(trifluoromethyl)phenyl)piperidin-1-yl)methanone; (1-ethyl-5-(methylsulfonyl)-1,4,5,6-tetrahydropyrrolo[3,4-c]pyrazol-3-yl)(4-(2-(trifluoromethyl)phenyl)piperidin-1-yl)methanone; (1-methyl-5-(methylsulfonyl)-1,4,5,6-tetrahydropyrrolo[3,4-c]pyrazol-3-yl)(4-(2-(trifluoromethyl)phenyl)piperidin-1-yl)methanone; (1-methyl-1,4,5,6-tetrahydropyrrolo[3,4-c]pyrazol-3-yl)(4-(2-(trifluoromethyl)phenyl)piperidin-1-yl)methanone; 2-methoxy-1-(3-(4-(2-(trifluoromethyl)phenyl)piperidine-1-carbonyl)-4,6-dihydropyrrolo[3,4-c]pyrazol-5(1H)-yl)ethan-1-one; (5-(2-methoxyethyl)-1,4,5,6-tetrahydropyrrolo[3,4-c]pyrazol-3-yl)(4-(2-(trifluoromethyl)phenyl)piperidin-1-yl)methanone; 3,3,3-trifluoro-1-(3-(4-(2-(trifluoromethyl)phenyl)piperidine-1-carbonyl)-4,6-dihydropyrrolo[3,4-c]pyrazol-5(1H)-yl)propan-1-one; (5-(oxetan-3-yl)-1,4,5,6-tetrahydropyrrolo[3,4-c]pyrazol-3-yl)(4-(2-(trifluoromethyl)phenyl)piperidin-1-yl)methanone; (5-(isobutylsulfonyl)-1,4,5,6-tetrahydropyrrolo[3,4-c]pyrazol-3-yl)(4-(2-(trifluoromethyl)phenyl)piperidin-1-yl)methanone; (5-(isopropylsulfonyl)-1,4,5,6-tetrahydropyrrolo[3,4-c]pyrazol-3-yl)(4-(2-(trifluoromethyl)phenyl)piperidin-1-yl)methanone; (5-(ethylsulfonyl)-1,4,5,6-tetrahydropyrrolo[3,4-c]pyrazol-3-yl)(4-(2-(trifluoromethyl)phenyl)piperidin-1-yl)methanone; tert-butyl 3-(4-(2-(trifluoromethyl)phenyl)piperidine-1- carbonyl)-4,6-dihydropyrrolo[3,4-c]pyrazole-5(1H)-carboxylate; (5-methyl-1,4,5,6-tetrahydropyrrolo[3,4-c]pyrazol-3-yl)(4-(2-(trifluoromethyl)phenyl)piperidin-1-yl)methanone; (5-(methylsulfonyl)-1,4,5,6-tetrahydropyrrolo[3,4-c]pyrazol-3-yl)(4-(2-(trifluoromethyl)phenyl)piperidin-1-yl)methanone; 1-(3-(4-(2-(trifluoromethyl)phenyl)piperidine-1-carbonyl)-4,6-dihydropyrrolo[3,4-c]pyrazol-5(1H)-yl)ethan-1-one; (5-(tert-butylsulfonyl)-1,4,5,6-tetrahydropyrrolo[3,4-c]pyrazol-3-yl)(4-(2-(trifluoromethyl)phenyl)piperidin-1-yl)methanone; (5-(tert-butyl)-1,4,5,6-tetrahydropyrrolo[3,4-c]pyrazol-3-yl)(4-(2-(trifluoromethyl)phenyl)piperidin-1-yl)methanone; (5-isobutyl-1,4,5,6-tetrahydropyrrolo[3,4-c]pyrazol-3-yl)(4-(2-(trifluoromethyl)phenyl)piperidin-1-yl)methanone; (5-isopropyl-1,4,5,6-tetrahydropyrrolo[3,4-c]pyrazol-3-yl)(4-(2-(trifluoromethyl)phenyl)piperidin-1-yl)methanone; (5-ethyl-1,4,5,6-tetrahydropyrrolo[3,4-c]pyrazol-3-yl)(4-(2-(trifluoromethyl)phenyl)piperidin-1-yl)methanone; N-methyl-3-(4-(2-(trifluoromethyl)phenyl)piperidine-1-carbonyl)-4,6-dihydropyrrolo[3,4-c]pyrazole-5(1H)-carboxamide; 1-(1-methyl-3-(4-(2-(trifluoromethyl)phenyl)piperidine-1-carbonyl)-4,6-dihydropyrrolo[3,4-c]pyrazol-5(1H)-yl)ethan-1-one; 2,2-dimethyl-1-(3-(4-(2-(trifluoromethyl)phenyl)piperidine-1-carbonyl)-4,6-dihydropyrrolo[3,4-c]pyrazol-5(1H)-yl)propan-1-one; 3-methyl-1-(3-(4-(2-(trifluoromethyl)phenyl)piperidine-1-carbonyl)-4,6-dihydropyrrolo[3,4-c]pyrazol-5(1H)-yl)butan-1-one; 2-methyl-1-(3-(4-(2-(trifluoromethyl)phenyl)piperidine-1-carbonyl)-4,6-dihydropyrrolo[3,4-c]pyrazol-5(1H)-yl)propan-1-one; 1-(3-(4-(2-(trifluoromethyl)phenyl)piperidine-1-carbonyl)-4,6-dihydropyrrolo[3,4-c]pyrazol-5(1H)-yl)propan-1-one; N,N-dimethyl-3-(4-(2-(trifluoromethyl)phenyl)piperidine-1-carbonyl)-4,6-dihydropyrrolo[3,4-c]pyrazole-5(1H)-carboxamide; (5-(2,2,2-trifluoroethyl)-1,4,5,6-tetrahydropyrrolo[3,4-c]pyrazol-3-yl)(4-(2-(trifluoromethyl)phenyl)piperidin-1-yl)methanone; (5-(methoxymethyl)-1,4,5,6-tetrahydropyrrolo[3,4-c]pyrazol-3-yl)(4-(2-(trifluoromethyl)phenyl)piperidin-1-yl)methanone; (1,4,5,6-tetrahydropyrrolo[3,4-c]pyrazol-3-yl)(4-(2-(trifluoromethyl)phenyl)piperidin-1-yl)methanone; tert-butyl 4-(3-(4-(3,4-difluoro-2-(trifluoromethyl)phenyl)piperidine-1-carbonyl)-1,4,5,6-tetrahydropyrrolo[3,4-c]pyrazole-5-carbonyl)piperazine-1-carboxylate; tert-butyl 3-(4-(3,4-difluoro-2-(trifluoromethyl)phenyl)piperidine-1-carbonyl)-4,6-dihydropyrrolo[3,4-c]pyrazol-5(1H)-carboxylate; (5,5-dioxido-4,6,7,8-tetrahydro-1H-thiepino[4,3-c]pyrazol-3-yl)(4-(2-(trifluoromethyl)phenyl)piperidin-1-yl)methanone; (4,6,7,8-tetrahydro-1H-oxepino[4,3-c]pyrazol-3-yl)(4-(2-(trifluoromethyl)phenyl)piperidin-1-yl)methanone; N-methyl-3-(4-(2-(trifluoromethyl)phenyl)piperidine-1-carbonyl)-4,6,7,8-tetrahydropyrazolo[4,3-c]azepine-5(1H)-carboxamide; (5-(2,2,2-trifluoroethyl)-1,4,5,6,7,8-hexahydropyrazolo[4,3-c]azepin-3-yl)(4-(2-(trifluoromethyl)phenyl)piperidin-1-yl)methanone; (5-(tert-butylsulfonyl)-1,4,5,6,7,8-hexahydropyrazolo[4,3-c]azepin-3-yl)(4-(2-(trifluoromethyl)phenyl)piperidin-1-yl)methanone; 2,2-dimethyl-1-(3-(4-(2-(trifluoromethyl)phenyl)piperidine-1-carbonyl)-4,6,7,8-tetrahydropyrazolo[4,3-c]azepin-5(1H)-yl)propan-1-one; (5-(tert-butyl)-1,4,5,6,7,8-hexahydropyrazolo[4,3-c]azepin-3-yl)(4-(2-(trifluoromethyl)phenyl)piperidin-1-yl)methanone; (5-(isobutylsulfonyl)-1,4,5,6,7,8-hexahydropyrazolo[4,3-c]azepin-3-yl)(4-(2-(trifluoromethyl)phenyl)piperidin-1-yl)methanone; 3-methyl-1-(3-(4-(2-(trifluoromethyl)phenyl)piperidine-1-carbonyl)-4,6,7,8-tetrahydropyrazolo[4,3-c]azepin-5(1H)-yl)butan-1-one; (5-isobutyl-1,4,5,6,7,8-hexahydropyrazolo[4,3-c]azepin-3-yl)(4-(2-(trifluoromethyl)phenyl)piperidin-1-yl)methanone; (5-(isopropylsulfonyl)-1,4,5,6,7,8-hexahydropyrazolo[4,3-c]azepin-3-yl)(4-(2-(trifluoromethyl)phenyl)piperidin-1-yl)methanone; 2-methyl-1-(3-(4-(2-(trifluoromethyl)phenyl)piperidine-1-carbonyl)-4,6,7,8-tetrahydropyrazolo[4,3-c]azepin-5(1H)-yl)propan-1-one; (1-ethyl-5-(methylsulfonyl)-1,4,5,6,7,8-hexahydropyrazolo[4,3-c]azepin-3-yl)(4-(2-(trifluoromethyl)phenyl)piperidin-1-yl)methanone; 1-(1-methyl-3-(4-(2-(trifluoromethyl)phenyl)piperidine-1-carbonyl)-4,6,7,8-tetrahydropyrazolo[4,3-c]azepin-5(1H)-yl)ethan-1-one; (5-(methoxymethyl)-1,4,5,6,7,8-hexahydropyrazolo[4,3-c]azepin-3-yl)(4-(2-(trifluoromethyl)phenyl)piperidin-1-yl)methanone; (5-methyl-1,4,5,6,7,8-hexahydropyrazolo[4,3-c]azepin-3-yl)(4-(2-(trifluoromethyl)phenyl)piperidin-1-yl)methanone; (5-isopropyl-1,4,5,6,7,8-hexahydropyrazolo[4,3-c]azepin-3-yl)(4-(2-(trifluoromethyl)phenyl)piperidin-1-yl)methanone; (5-(ethylsulfonyl)-1,4,5,6,7,8-hexahydropyrazolo[4,3-c]azepin-3-yl)(4-(2-(trifluoromethyl)phenyl)piperidin-1-yl)methanone; 1-(3-(4-(2-(trifluoromethyl)phenyl)piperidine-1-carbonyl)-4,6,7,8-tetrahydropyrazolo[4,3-c]azepin-5(1H)-yl)propan-1-one; (5-ethyl-1,4,5,6,7,8-hexahydropyrazolo[4,3-c]azepin-3-yl)(4-(2-(trifluoromethyl)phenyl)piperidin-1-yl)methanone; (5-(methylsulfonyl)-1,4,5,6,7,8-hexahydropyrazolo[4,3-c]azepin-3-yl)(4-(2-(trifluoromethyl)phenyl)piperidin-1-yl)methanone; 1-(3-(4-(2-(trifluoromethyl)phenyl)piperidine-1-carbonyl)-4,6,7,8-tetrahydropyrazolo[4,3-c]azepin-5(1H)-yl)ethan-1-one; (1,4,5,6,7,8-hexahydropyrazolo[4,3-c]azepin-3-yl)(4-(2-(trifluoromethyl)phenyl)piperidin-1-yl)methanone; (1-methyl-5-(methylsulfonyl)-1,4,5,6,7,8-hexahydropyrazolo[4,3-c]azepin-3-yl)(4-(2-(trifluoromethyl)phenyl)piperidin-1-yl)methanone; (1-methyl-1,4,5,6,7,8-hexahydropyrazolo[4,3-c]azepin-3-yl)(4-(2-(trifluoromethyl)phenyl)piperidin-1-yl)methanone; N,N-dimethyl-3-(4-(2-(trifluoromethyl)phenyl)piperidine-1-carbonyl)-4,6,7,8-tetrahydropyrazolo[4,3-c]azepine-5(1H)-carboxamide; (5-(2-methoxyethyl)-1,4,5,6,7,8-hexahydropyrazolo[4,3-c]azepin-3-yl)(4-(2-(trifluoromethyl)phenyl)piperidin-1-yl)methanone; 2-methoxy-1-(3-(4-(2-(trifluoromethyl)phenyl)piperidine-1-carbonyl)-4,6,7,8-tetrahydropyrazolo[4,3-c]azepin-5(1H)-yl)ethan-1-one; 3,3,3-trifluoro-1-(3-(4-(2-(trifluoromethyl)phenyl)piperidine-1-carbonyl)-4,6,7,8-tetrahydropyrazolo[4,3-c]azepin-5(1H)-yl)propan-1-one; (5-(oxetan-3-yl)-1,4,5,6,7,8-hexahydropyrazolo[4,3-c]azepin-3-yl)(4-(2-(trifluoromethyl)phenyl)piperidin-1-yl)methanone; tert-butyl 3-(4-(2-(trifluoromethyl)phenyl)piperidine-1-carbonyl)-4,6,7,8-tetrahydropyrazolo[4,3-c]azepine-5(1H)-carboxylate; (6-(trifluoromethyl)imidazo[1,2-b]pyridazin-2-yl)(4-(2-(trifluoromethyl)phenyl)piperidin-1-yl)methanone; (6-fluoroimidazo[1,2-b]pyridazin-2-yl)(4-(2-(trifluoromethyl)phenyl)piperidin-1-yl)methanone; (6-(pyrrolidin-1-yl)imidazo[1,2-b]pyridazin-2-yl)(4-(2-(trifluoromethyl)phenyl)piperidin-1-yl)methanone; (6-cyclopropylimidazo[1,2-b]pyridazin-2-yl)(4-(2-(trifluoromethyl)phenyl)piperidin-1-yl)methanone; (6-methoxyimidazo[1,2-b]pyridazin-2-yl)(4-(2-(trifluoromethyl)phenyl)piperidin-1-yl)methanone; (6-methylimidazo[1,2-b]pyridazin-2-yl)(4-(2-(trifluoromethyl)phenyl)piperidin-1-yl)methanone; (6-chloroimidazo[1,2-b]pyridazin-2-yl)(4-(2-(trifluoromethyl)phenyl)piperidin-1-yl)methanone; imidazo[1,2-b]pyridazin-2-yl(4-(2-(trifluoromethyl)phenyl)piperidin-1-yl)methanone; (6-chloro-2-methylimidazo[1,2-b]pyridazin-3-yl)(4-(2-(trifluoromethyl)phenyl)piperidin-1-yl)methanone; (1H-benzo[d]imidazol-2-yl)(4-(2-(trifluoromethyl)phenyl)piperidin-1-yl)methanone; (1H-imidazo[4,5-b]pyridin-2-yl)(4-(2-

(trifluoromethyl)phenyl)piperidin-1-yl)methanone; (4-(5-fluoro-2-(trifluoromethyl)phenyl)piperidin-1-yl)(4,5,6,7-tetrahydro-1H-pyrazolo[3,4-c]pyridin-3-yl)methanone; (4-(3-fluoro-2-(trifluoromethyl)phenyl)piperidin-1-yl)(6-(2-methoxyethyl)-4,5,6,7-tetrahydro-1H-pyrazolo[3,4-c]pyridin-3-yl)methanone; 6-methyl-2-(4-(2-(trifluoromethyl)phenyl)piperidine-1-carbonyl)pyrimidine-4-carboxylic acid; methyl 6-methyl-2-(4-(2-(trifluoromethyl)phenyl)piperidine-1-carbonyl)pyrimidine-4-carboxylate; N-(cyclopropylsulfonyl)-2-(4-(2-(trifluoromethyl)phenyl)piperidine-1-carbonyl)benzamide; N-(phenylsulfonyl)-2-(4-(2-(trifluoromethyl)phenyl)piperidine-1-carbonyl)benzamide; N-(methylsulfonyl)-2-(4-(2-(trifluoromethyl)phenyl)piperidine-1-carbonyl)benzamide; 3-(4-(2-(trifluoromethyl)phenyl)piperidine-1-carbonyl)benzamide; 2-(4-(2-(trifluoromethyl)phenyl)piperidine-1-carbonyl)benzamide; 4-(4-(2-(trifluoromethyl)phenyl)piperidine-1-carbonyl)benzoic acid; 3-(4-(2-(trifluoromethyl)phenyl)piperidine-1-carbonyl)benzoic acid; 2-(4-(2-(trifluoromethyl)phenyl)piperidine-1-carbonyl)benzoic acid; 4-(4-(2-(tert-butyl)phenyl)piperidine-1-carbonyl)benzoic acid; 2-(4-(2-(tert-butyl)phenyl)piperidine-1-carbonyl)benzoic acid; 3-(4-(2-(tert-butyl)phenyl)piperidine-1-carbonyl)benzoic acid; 4-(4-(2-(trifluoromethyl)phenyl)piperidine-1-carbonyl)benzamide; 1-(3-(4-(2-(trifluoromethyl)phenyl)piperidine-1-carbonyl)-4,7-dihydroisothiazolo[5,4-c]pyridin-6(5H)-yl)ethan-1-one; (4,5,6,7-tetrahydroisothiazolo[5,4-c]pyridin-3-yl)(4-(2-(trifluoromethyl)phenyl)piperidin-1-yl)methanone; (4,5,6,7-tetrahydroisothiazolo[4,5-c]pyridin-3-yl)(4-(2-(trifluoromethyl)phenyl)piperidin-1-yl)methanone; 1-(3-(4-(2-(trifluoromethyl)phenyl)piperidine-1-carbonyl)-6,7-dihydroisoxazolo[4,5-c]pyridin-5(4H)-yl)ethan-1-one; 1-(3-(4-(2-(trifluoromethyl)phenyl)piperidine-1-carbonyl)-4,7-dihydroisoxazolo[5,4-c]pyridin-6(5H)-yl)ethan-1-one; (4,5,6,7-tetrahydroisoxazolo[4,5-c]pyridin-3-yl)(4-(2-(trifluoromethyl)phenyl)piperidin-1-yl)methanone; benzo[c]isothiazol-3-yl(4-(2-(trifluoromethyl)phenyl)piperidin-1-yl)methanone; benzo[d]thiazol-2-yl(4-(2-(trifluoromethyl)phenyl)piperidin-1-yl)methanone; benzo[d]isoxazol-3-yl(4-(2-(trifluoromethyl)phenyl)piperidin-1-yl)methanone; 1-(3-(4-(2-(trifluoromethyl)phenyl)piperidine-1-carbonyl)-6,7-dihydroisothiazolo[4,5-c]pyridin-5(4H)-yl)ethan-1-one; benzo[d]oxazol-2-yl(4-(2-(trifluoromethyl)phenyl)piperidin-1-yl)methanone; (3-methyloxetan-3-yl)(4-(2-(trifluoromethyl)phenyl)piperidin-1-yl)methanone; oxetan-3-yl(4-(2-(trifluoromethyl)phenyl)piperidin-1-yl)methanone; 2-(2-hydroxyphenyl)-1-(4-(2-(trifluoromethyl)phenyl)piperidin-1-yl)ethan-1-one; (4-(2-(tert-butyl)phenyl)piperidin-1-yl)(tetrahydrothiophen-2-yl)methanone; rac-tert-butyl (2R,3R)-2-(4-(2-(tert-butyl)phenyl)piperidine-1-carbonyl)-3-hydroxypyrrolidine-1-carboxylate; (2R,4R)-2-(4-(2-(tert-butyl)phenyl)piperidine-1-carbonyl)-4-hydroxypyrrolidine-1-carboxylate 2-(2-oxo-2-(4-(2-(trifluoromethyl)phenyl)piperidin-1-yl)ethyl)phenyl sulfamate; (4-(2-(tert-butyl)phenyl)piperidin-1-yl)(1,1-dioxidotetrahydrothiophen-2-yl)methanone; rac-(4-(2-(tert-butyl)phenyl)piperidin-1-yl)((2R,3R)-3-hydroxypyrrolidin-2-yl)methanone; rac-(4-(2-(tert-butyl)phenyl)piperidin-1-yl)((2R,4R)-4-hydroxypyrrolidin-2-yl)methanone; rac-(R)-1-(2-(4-(2-(tert-butyl)phenyl)piperidine-1-carbonyl)pyrrolidin-1-yl)ethan-1-one; (6-bromo-1H-pyrrolo[3,2-b]pyridin-2-yl)(4-(2-(trifluoromethyl)phenyl)piperidin-1-yl)methanone; (5-morpholino-1H-pyrrolo[3,2-b]pyridin-2-yl)(4-(2-(trifluoromethyl)phenyl)piperidin-1-yl)methanone; (5-(1H-imidazol-1-yl)-1H-pyrrolo[3,2-b]pyridin-2-yl)(4-(2-(trifluoromethyl)phenyl)piperidin-1-yl)methanone; (5-chloro-1H-pyrrolo[3,2-b]pyridin-2-yl)(4-(2-(trifluoromethyl)phenyl)piperidin-1-yl)methanone; (5-fluoro-1H-pyrrolo[3,2-b]pyridin-2-yl)(4-(2-(trifluoromethyl)phenyl)piperidin-1-yl)methanone; (5-methyl-1H-pyrrolo[3,2-b]pyridin-2-yl)(4-(2-(trifluoromethyl)phenyl)piperidin-1-yl)methanone; (6-methoxy-1H-pyrrolo[3,2-b]pyridin-2-yl)(4-(2-(trifluoromethyl)phenyl)piperidin-1-yl)methanone; imidazo[1,2-a]pyridin-2-yl(4-(2-(trifluoromethyl)phenyl)piperidin-1-yl)methanone; (6-chloro-2-methylimidazo[1,2-b]pyridazin-3-yl)(4-(2-(trifluoromethyl)phenyl)piperidin-1-yl)methanone; imidazo[1,2-b]pyridazin-6-yl(4-(2-(trifluoromethyl)phenyl)piperidin-1-yl)methanone; (1H-pyrrolo[2,3-b]pyridin-2-yl)(4-(2-(trifluoromethyl)phenyl)piperidin-1-yl)methanone; (1H-pyrrolo[3,2-c]pyridin-2-yl)(4-(2-(trifluoromethyl)phenyl)piperidin-1-yl)methanone; (6-chloro-1H-pyrrolo[3,2-b]pyridin-2-yl)(4-(2-(trifluoromethyl)phenyl)piperidin-1-yl)methanone; (6-morpholino-1H-pyrrolo[3,2-b]pyridin-2-yl)(4-(2-(trifluoromethyl)phenyl)piperidin-1-yl)methanone; (6-(1H-imidazol-1-yl)-1H-pyrrolo[3,2-b]pyridin-2-yl)(4-(2-(trifluoromethyl)phenyl)piperidin-1-yl)methanone; (1-methyl-1H-pyrrolo[3,2-b]pyridin-2-yl)(4-(2-(trifluoromethyl)phenyl)piperidin-1-yl)methanone; (5-methoxy-1H-pyrrolo[3,2-b]pyridin-2-yl)(4-(2-(trifluoromethyl)phenyl)piperidin-1-yl)methanone; (6-fluoro-1H-pyrrolo[3,2-b]pyridin-2-yl)(4-(2-(trifluoromethyl)phenyl)piperidin-1-yl)methanone; (1H-imidazo[4,5-b]pyridin-2-yl)(4-(2-(trifluoromethyl)phenyl)piperidin-1-yl)methanone; (6-methyl-1H-pyrrolo[3,2-b]pyridin-2-yl)(4-(2-(trifluoromethyl)phenyl)piperidin-1-yl)methanone; (1H-indol-2-yl)(4-(2-(trifluoromethyl)phenyl)piperidin-1-yl)methanone; (1H-pyrrolo[3,2-b]pyridin-2-yl)(4-(2-(trifluoromethyl)phenyl)piperidin-1-yl)methanone; (1H-pyrrolo[2,3-c]pyridin-2-yl)(4-(2-(trifluoromethyl)phenyl)piperidin-1-yl)methanone; (1H-pyrazol-3-yl)(4-(2-(trifluoromethyl)phenyl)piperidin-1-yl)methanone; (1H-1,2,3-triazol-5-yl)(4-(2-(trifluoromethyl)phenyl)piperidin-1-yl)methanone; pyrazin-2-yl(4-(2-(trifluoromethyl)phenyl)piperidin-1-yl)methanone; (6-methoxypyridazin-3-yl)(4-(2-(trifluoromethyl)phenyl)piperidin-1-yl)methanone; (6-methylpyridazin-3-yl)(4-(2-(trifluoromethyl)phenyl)piperidin-1-yl)methanone; (4-methyl-1,2,3-thiadiazol-5-yl)(4-(2-(trifluoromethyl)phenyl)piperidin-1-yl)methanone; (6-chloropyridazin-3-yl)(4-(2-(trifluoromethyl)phenyl)piperidin-1-yl)methanone; pyridazin-3-yl(4-(2-(trifluoromethyl)phenyl)piperidin-1-yl)methanone; pyridazin-4-yl(4-(2-(trifluoromethyl)phenyl)piperidin-1-yl)methanone; 4-(2-(trifluoromethyl)phenyl)piperidine-1-carboxylic acid; or 3-oxo-3-(4-(2-(trifluoromethyl)phenyl)piperidin-1-yl)propanoic acid.

Preparation of Compounds

The compounds used in the chemical reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (CostaMesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Alternatively, specific and analogous reactants can be identified through the indices of known chemicals and reactions prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the heterocyclic RBP4 inhibitory compound described herein is P. H. Stahl & C. G. Wermuth "Handbook of Pharmaceutical Salts", Verlag Helvetica Chimica Acta, Zurich, 2002.

Retinol Binding Protein 4 (RBP4)

Retinol-binding protein 4 (RBP4), the sole retinol transporter in blood, is secreted from adipocytes and the liver. Lowering levels of RBP4 can lead to reduction in the accumulation of lipofuscin that leads to vision loss in diseases like Age-Related Macular Degeneration, dry (atrophic) Age-Related Macular Degeneration, Juvenile Macular Degeneration (Stargardt Disease), Best disease, adult vitelliform maculopathy, Geographic Atrophy, Stargardt-like macular dystrophy, diabetic retinopathy, or ABCA4 gene associated retinal diseases. In some instances, lowering RBP4 reduces the accumulation of lipofuscin in the retina. In some embodiments, compounds and formulations described herein lower serum or plasma RBP4 and thus delay or stop vision loss from excessive accumulation of lipofuscin in the retina.

In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 30% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 20% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 25% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 300% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 40% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 50% from baseline. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 65% from baseline. In certain embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 80% from baseline. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 85% from baseline.

In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 48 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 1 mg/dL. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 2 mg/dL. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 5 mg/dL. In certain embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 10 mg/dL. In some embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced by at least 15 mg/dL.

In some embodiments, after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1 µM. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1 µM. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1 µM. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1 µM. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1 µM.

In some embodiments, after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1.5 µM. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of are reduced to below 1.5 µM. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1.5 µM. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1.5 µM. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 1.5 µM.

In some embodiments, after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 2 µM. In other embodiments, 6 hours after administration of a compound of Formula (I), a pharmaceutically acceptable salt, solvate, polymorph, prodrug, metabolite, N-oxide, stereoisomer, or isomer thereof, the serum or plasma levels of are reduced to below 2 µM. In some embodiments, 12 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 2 µM. In certain embodiments, 24 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 2 µM. In some embodiments, 36 hours after administration of a compound of Formula (I), a pharmaceutically acceptable salt, solvate, polymorph, prodrug, metabolite, N-oxide, stereoisomer, or isomer thereof, the serum or plasma levels of RBP4 are reduced to below 2 µM.

Methods of Treatment

In some embodiments, a compound disclosed herein is used to treat or ameliorate a disease associated with altered RBP4 pathways when administered to a subject in need thereof. In some cases, a compound disclosed herein is used to treat or ameliorate the effects of a disease associated with altered RBP4 pathway when administered to a subject in need thereof. Exemplary diseases associated with altered RBP4 include eye diseases. In some instances, the eye disease is characterized by excessive lipofuscin accumulation in the retina. In some instances, a compound disclosed herein is used to treat or ameliorate an eye disease when administered to a subject in need thereof. Exemplary eye disease include Age-Related Macular Degeneration, dry (atrophic) Age-Related Macular Degeneration, Juvenile Macular Degeneration (Stargardt Disease), Best disease, adult vitelliform maculopathy, Geographic Atrophy, Stargardt-like macular dystrophy, diabetic retinopathy, or an ABCA4 gene associated retinal disease.

Age-Related Macular Degeneration

Age-related macular degeneration (AMD) is a common eye condition and a leading cause of vision loss among people age 50 and older. It causes damage to the macula, a small spot n ear the center of the retina and the part of the eye needed for sharp, central vision. As AMD progresses, a blurred area near the center of vision is a common symptom. Overtime, the blurred area may grow larger and the subject may develop blank spots in his or her central vision.

Some embodiments provided herein describe the use of the compounds of Formula (I) described herein for treating AMD in a subject in need thereof. In some embodiments, the compounds of Formula (I) inhibit AMD. In certain embodiments, the compounds of Formula (I) arrest development of AMD or its clinical symptoms. In certain embodiments, the compounds of Formula (I) reduce development of AMD or its clinical symptoms. In certain embodiments, the compounds of Formula (I) relieve the subject of AMD. In certain embodiments, the compounds of Formula (I) cause regression, reversal, or amelioration of AMD. In certain embodiments, the compounds of Formula (I) reduce the number, frequency, duration, or severity of AMD clinical symptoms.

In some embodiments, the compounds of Formula (I) are used prophylactically. In certain embodiments, the compounds of Formula (I) are used to prevent or reduce the risk of developing AMD. In certain embodiments, the compounds of Formula (I) cause the clinical symptoms of AMD to not develop in a subject who may be predisposed to AMD but who doe s not yet experience or display symptoms of AMD.

Dry (Atrophic) Age-Related Macular Degeneration

Approximately 85% to 90% of the cases of macular degeneration are the "dry" (atrophic) type. It is estimated that 62.9 million individuals worldwide have this form of AMD; 8 million of them are Americans. Due to increasing life expectancy and current demographics this number is expected to triple by 2020. There is currently no FDA-approved treatment for dry AMD. Given the lack of treatment and high prevalence, development of drugs for dry AMD is of upmost importance. Clinically, atrophic AMD represents a slowly progressing neurodegenerative disorder in which specialized neurons (rod and cone photoreceptors) die in the central part of the retina called the macula. Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD. The major cytotoxic component of RPE lipofuscin is pyridinium bisretinoid A2E (FIG. 1). Additional cytotoxic bisretinoids are isoA2E, atRAL di-PE, and A2-DHP-PE. Formation of A2E and other lipofuscin bisretinoids, such as A2-DHP-PE (A2-dihydropyridine-phosphatidylethanolamine) and atRALdi-PE (all-trans-retinal dimer-phosphatidyletha-nolamine), begins in photoreceptor cells in a non-enzymatic manner and can be considered as a by-product of the properly functioning visual cycle.

Some embodiments provided herein describe the use of the compounds of Formula (I) described herein for treating dry (atrophic) AMD in a subject in need thereof. In some embodiments, the compounds of Formula (I) inhibit dry (atrophic) AMD. In certain embodiments, the compounds of Formula (I) arrest development of dry (atrophic) AMD or its clinical symptoms. In certain embodiments, the compounds of Formula (I) reduce development of dry (atrophic) AMD or its clinical symptoms. In certain embodiments, the compounds of Formula (I) relieve the subject of dry (atrophic) AMD. In certain embodiments, the compounds of Formula (I) cause regression, reversal, or amelioration of dry (atrophic) AMD. In certain embodiments, the compounds of Formula (I) reduce the number, frequency, duration, or severity of dry (atrophic) AMD clinical symptoms.

In some embodiments, the compounds of Formula (I) are used prophylactically. In certain embodiments, the compounds of Formula (I) are used to prevent or reduce the risk of developing dry (atrophic) AMD. In certain embodiments, the compounds of Formula (I) cause the clinical symptoms of dry (atrophic) AMD to not develop in a subject who may be predisposed to dry (atrophic) AMD but who does not yet experience or display symptoms of dry (atrophic) AMD.

Juvenile Macular Degeneration (Stargardt Disease)

Stargardt Disease (STGD) is an inherited form of juvenile-onset macular degeneration. STGD is characterized by the dramatic accumulation of lipofuscin in the retina. STGD is linked to defects in the ABCA4 gene. Excessive production of lipofuscin bisretinoids is thought to be the sole biochemical trigger of monogenic STGD caused by recessive mutations in the ABCA4 gene. Symptoms include wavy vision, blind spots, blurriness, loss of depth perception, sensitivity to glare, impaired color vision, and difficulty adapting to dim lighting. Symptoms typically develop before age 20.

Some embodiments provided herein describe the use of the compounds of Formula (I) described herein for treating STGD in a subject in need thereof. In some embodiments, the compounds of Formula (I) inhibit STGD. In certain embodiments, the compounds of Formula (I) arrest development of STGD or its clinical symptoms. In certain embodiments, the compounds of Formula (I) reduce development of STGD or its clinical symptoms. In certain embodiments, the compounds of Formula (I) relieve the subject of STGD. In certain embodiments, the compounds of Formula (I) cause regression, reversal, or amelioration of STGD. In certain embodiments, the compounds of Formula (I) reduce the number, frequency, duration, or severity of STGD clinical symptoms.

In some embodiments, the compounds of Formula (I) are used prophylactically. In certain embodiments, the compounds of Formula (I) are used to prevent or reduce the risk of developing STGD. In certain embodiments, the compounds of Formula (I) cause the clinical symptoms of STGD to not develop in a subject who may be predisposed to STGD but who does not yet experience or display symptoms of STGD.

Best Disease

Vitelliform dystrophy, or Best disease, is a hereditary retinal dystrophy involving the retinal pigment epithelium (RPE), and leads to a characteristic bilateral yellow "egg-yolk" appearance of the macula. This disease tends to present itself in childhood or early adulthood. Best disease is caused by mutations in the BEST1 gene, which encodes the transmembrane protein bestrophin 1. The mutations lead to a buildup of lipofuscin between the outer retina and the retinal pigment epithelium.

Some embodiments provided herein describe the use of the compounds of Formula (I) described herein for treating Best disease in a subject in need thereof. In some embodiments, the compounds of Formula (I) inhibit Best disease. In certain embodiments, the compounds of Formula (I) arrest development of Best disease or its clinical symptoms. In certain embodiments, the compounds of Formula (I) reduce development of Best disease or its clinical symptoms. In certain embodiments, the compounds of Formula (I) relieve the subject of Best disease. In certain embodiments, the compounds of Formula (I) cause regression, reversal, or amelioration of Best disease. In certain embodiments, the compounds of Formula (I) reduce the number, frequency, duration, or severity of Best disease clinical symptoms.

In some embodiments, the compounds of Formula (I) are used prophylactically. In certain embodiments, the compounds of Formula (I) are used to prevent or reduce the risk of developing Best disease. In certain embodiments, the compounds of Formula (I) cause the clinical symptoms of Best disease to not develop in a subject who may be predisposed to Best disease but who does not yet experience or display symptoms of Best disease.

Geographic Atrophy

Geographic atrophy is a chronic progressive degeneration of the macula and can be seen as part of late-stage age-related macular degeneration (AMD). The condition leads to central scotomas and permanent loss of visual acuity. The disease is characterized by localized sharply demarcated atrophy of outer retinal tissue, retinal pigment epithelium and choriocapillaris.

Some embodiments provided herein describe the use of the compounds of Formula (I) described herein for treating geographic atrophy in a subject in need thereof. In some embodiments, the compounds of Formula (I) inhibit geographic atrophy. In certain embodiments, the compounds of Formula (I) arrest development of geographic atrophy or its clinical symptoms. In certain embodiments, the compounds of Formula (I) reduce development of geographic atrophy or its clinical symptoms. In certain embodiments, the compounds of Formula (I) relieve the subject of geographic atrophy. In certain embodiments, the compounds of Formula (I) cause regression, reversal, or amelioration of geographic atrophy. In certain embodiments, the compounds of Formula (I) reduce the number, frequency, duration, or severity of geographic atrophy clinical symptoms.

In some embodiments, the compounds of Formula (I) are used prophylactically. In certain embodiments, the compounds of Formula (I) are used to prevent or reduce the risk of developing geographic atrophy. In certain embodiments, the compounds of Formula (I) cause the clinical symptoms of geographic atrophy to not develop in a subject who may be predisposed to geographic atrophy but who does not yet experience or display symptoms of geographic atrophy.

Adult Vitelliform Maculopathy

Adult vitelliform maculopathy is an eye disorder that can cause progressive vision loss. The condition causes the accumulation of lipofuscin in the cells underlying the macula. The condition typically manifests after the age of 40. The condition can be caused by mutations in the RDS and VMD2 genes.

Some embodiments provided herein describe the use of the compounds of Formula (I) described herein for treating adult vitelliform maculopathy in a subject in need thereof. In some embodiments, the compounds of Formula (I) inhibit adult vitelliform maculopathy. In certain embodiments, the compounds of Formula (I) arrest development of adult vitelliform maculopathy or its clinical symptoms. In certain embodiments, the compounds of Formula (I) reduce development of adult vitelliform maculopathy clinical symptoms or its clinical symptoms. In certain embodiments, the compounds of Formula (I) relieve the subject of adult vitelliform maculopathy. In certain embodiments, the compounds of Formula (I) cause regression, reversal, or amelioration of adult vitelliform maculopathy. In certain embodiments, the compounds of Formula (I) reduce the number, frequency, duration, or severity of adult vitelliform maculopathy clinical symptoms.

In some embodiments, the compounds of Formula (I) are used prophylactically. In certain embodiments, the compounds of Formula (I) are used to prevent or reduce the risk of developing adult vitelliform maculopathy. In certain embodiments, the compounds of Formula (I) cause the clinical symptoms of adult vitelliform maculopathy to not develop in a subject who may be predisposed to adult vitelliform maculopathy but who does not yet experience or display symptoms of adult vitelliform maculopathy.

Stargardt-Like Macular Dystrophy

Stargardt-like macular dystrophy is similar in symptoms and presentation to Stargardt disease, but typically presents later in childhood than Stargardt disease. Stargardt-like macular dystrophy is linked with mutations in the EVOVL4 gene.

Some embodiments provided herein describe the use of the compounds of Formula (I) described herein for treating Stargardt-like macular dystrophy in a subject in need thereof. In some embodiments, the compounds of Formula (I) inhibit Stargardt-like macular dystrophy. In certain embodiments, the compounds of Formula (I) arrest development Stargardt-like macular dystrophy or its clinical symptoms. In certain embodiments, the compounds of Formula (I) reduce development of Stargardt-like macular dystrophy or its clinical symptoms. In certain embodiments, the compounds of Formula (I) relieve the subject of Stargardt-like macular dystrophy. In certain embodiments, the compounds of Formula (I) cause regression, reversal, or amelioration of Stargardt-like macular dystrophy. In certain embodiments, the compounds of Formula (I) reduce the number, frequency, duration, or severity of Stargardt-like macular dystrophy clinical symptoms.

In some embodiments, the compounds of Formula (I) are used prophylactically. In certain embodiments, the compounds of Formula (I) are used to prevent or reduce the risk of developing Stargardt-like macular dystrophy. In certain embodiments, the compounds of Formula (I) cause the clinical symptoms of Stargardt-like macular dystrophy to not develop in a subject who may be predisposed to Stargardt-like macular dystrophy but who does not yet experience or display symptoms of Stargardt-like macular dystrophy.

Diabetic Retinopathy

Diabetic retinopathy is a diabetes complication that affects the eyes. It may be caused by damage to the blood vessels of the light sensitive tissue at the back of the eye, and can eventually cause blindness. Diabetic retinopathy can be caused when new blood vessels in the retina fail to grow. Diabetic retinopathy may also result from blood vessels becoming damaged and closing off, causing the growth of new, abnormal blood vessels in the retina.

Some embodiments provided herein describe the use of the compounds of Formula (I) described herein for treating diabetic retinopathy in a subject in need thereof. In some embodiments, the compounds of Formula (I) inhibit diabetic retinopathy. In certain embodiments, the compounds of Formula (I) arrest development diabetic retinopathy or its clinical symptoms. In certain embodiments, the compounds of Formula (I) reduce development of diabetic retinopathy or its clinical symptoms. In certain embodiments, the compounds of Formula (I) relieve the subject's diabetic retinopathy. In certain embodiments, the compounds of Formula (I) cause regression, reversal, or amelioration of diabetic retinopathy. In certain embodiments, the compounds of Formula (I) reduce the number, frequency, duration, or severity of diabetic retinopathy clinical symptoms.

In some embodiments, the compounds of Formula (I) are used prophylactically. In certain embodiments, the compounds of Formula (I) are used to prevent or reduce the risk of developing diabetic retinopathy. In certain embodiments, the compounds of Formula (I) cause the clinical symptoms of diabetic retinopathy to not develop in a subject who may be predisposed to diabetic retinopathy but who does not yet experience or display symptoms of diabetic retinopathy.

ABCA4 Gene Associated Retinal Diseases

ATP-binding cassette, subfamily A, member 4 (ABCA4) is a protein encoded by the ABCA4 gene in humans and other eukaryotes. The ABCA4 protein is expressed almost exclusively in the retina and is implicated in Stargardt and other eye diseases, including but not limited to fundus flavimaculatus, cone-rod dystrophy, retinitis pigmentosa, and age-related macular degeneration. Diminished ABCA4 activity is linked with excessive accumulation of toxic retinoids and lipofuscin. Such mutations in some instances are detected by sequencing a subject's DNA or RNA.

Some embodiments provided herein describe the use of the compounds of Formula (I) described herein for treating ABCA4 gene associated retinal diseases in a subject in need thereof. In some embodiments, the compounds of Formula (I) inhibit ABCA4 gene associated retinal diseases. In certain embodiments, the compounds of Formula (I) arrest development ABCA4 gene associated retinal diseases or their clinical symptoms. In certain embodiments, the compounds of Formula (I) reduce development of ABCA4 gene associated retinal diseases or their clinical symptoms. In certain embodiments, the compounds of Formula (I) relieve the subject ABCA4 gene associated retinal diseases. In certain embodiments, the compounds of Formula (I) cause regression, reversal, or amelioration ABCA4 gene associated retinal diseases. In certain embodiments, the compounds of Formula (I) reduce the number, frequency, duration, or severity of ABCA4 gene associated retinal disease clinical symptoms.

In some embodiments, the compounds of Formula (I) are used prophylactically. In certain embodiments, the compounds of Formula (I) are used to prevent or reduce the risk of developing ABCA4 gene associated retinal diseases. In certain embodiments, the compounds of Formula (I) cause the clinical symptoms ABCA4 gene associated retinal diseases to not develop in a subject who may be predisposed to ABCA4 gene associated retinal diseases but who does not yet experience or display symptoms of ABCA4 gene associated retinal diseases.

Pharmaceutical Compositions

In certain embodiments, the compound of Formula (I) as described herein is administered as a pure chemical. In other embodiments, the heterocyclic RBP4 inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, $21^{st}$ Ed. Mack Pub. Co., Easton, PA (2005)).

Provided herein is a pharmaceutical composition comprising at least one heterocyclic RBP4 inhibitory compound, or a stereoisomer, pharmaceutically acceptable salt, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject or patient) of the composition.

One embodiment provides a pharmaceutical composition comprising a compound of Formula (I), or a pharmaceutically acceptable salt thereof, and a pharmaceutically acceptable excipient. In one embodiment, the pharmaceutical compositions are provided in a dosage form for oral administration, which comprise a compound provided herein, and one or more pharmaceutically acceptable excipients or carriers.

In certain embodiments, the heterocyclic RBP4 inhibitory compound as described by Formula (I) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

In some embodiments, the pharmaceutical compositions provided herein are formulated for oral administration in tablet, capsule, powder, or liquid form. In some embodiments, the pharmaceutical formulation is formulated as a tablet. In some embodiments, the pharmaceutical formulation is formulated as a capsule. In some embodiments, a tablet comprises a solid carrier or an adjuvant. Liquid pharmaceutical compositions generally comprise a liquid carrier such as water, petroleum, animal or vegetable oils, mineral oil, or synthetic oil. In some embodiments, physiological saline solution, dextrose or other saccharide solution, or glycols are optionally included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions are formulated for intravenous, cutaneous or subcutaneous injection, the active ingredient is in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included.

In yet another embodiment, the pharmaceutical compositions are provided in a dosage form for topical administration, which comprise a compound provided herein, and one or more pharmaceutically acceptable excipients or carriers.

Solid Dispersions

In certain embodiments, the pharmaceutical compositions of the present invention comprise solid dispersions. In some instances, a pharmaceutical composition comprises a solid dispersion comprising a compound of Formula (I). A solid dispersion is in some instances a solid composition having at least two components, for example a drug and a polymer. Components of a solid dispersion may be molecularly dispersed, wherein there is a random distribution of drug, polymer, and any additional elements in the dispersion. In some embodiments, the molecular dispersion is amorphous. In some embodiments, the compound of Formula (I) is amorphous within the molecular dispersion.

Solid dispersions can be prepared using many methods known in the art. In certain embodiments, the solid dispersion is prepared by a melting method, a solvent evaporation method, a fusion method, a kneading method, a melting method, a spray drying method, a co-grinding method, a lyophilization technique, hot melt extrusion, melt agglomeration, or supercritical fluid (SCF) technology. In certain embodiments, the solid dispersion is prepared using a spray drying method. In certain embodiments, the solid dispersion is prepared using a hot melt extrusion method.

In certain embodiments, the solid dispersion comprises a compound of Formula (I) and a dispersion polymer. In certain embodiments, the dispersion polymer is selected from the group consisting of hydroxypropyl methylcellulose (HPMC), hydroxypropyl methylcellulose-acetate succinate (HPMC-AS or HPMCAS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, and derivatives or combinations thereof.

In certain embodiments, the dispersion polymer comprises about 1-99% by weight of the solid dispersion. In certain embodiments, the dispersion polymer comprises about 20-80% by weight of the solid dispersion. In certain embodiments, the dispersion polymer comprises about 40-60% by weight of the solid dispersion. In certain embodiments, the dispersion polymer comprises about 95% by weight of the solid dispersion. In certain embodiments, the dispersion polymer comprises about 90% by weight of the solid dispersion. In certain embodiments, the dispersion polymer comprises about 80% by weight of the solid dispersion. In certain embodiments, the dispersion polymer comprises about 70% by weight of the solid dispersion. In certain embodiments, the dispersion polymer comprises about 60% by weight of the solid dispersion. In certain embodiments, the dispersion polymer comprises about 50% by weight of the solid dispersion. In certain embodiments, the dispersion polymer comprises about 40% by weight of the solid dispersion. In certain embodiments, the dispersion polymer comprises about 30% by weight of the solid dispersion. In certain embodiments, the dispersion polymer comprises about 20% by weight of the solid dispersion. In certain embodiments, the dispersion polymer comprises about 10% by weight of the solid dispersion.

In certain embodiments, the dispersion polymer comprises at least about 10% by weight of the solid dispersion. In certain embodiments, the dispersion polymer comprises at least about 20% by weight of the solid dispersion. In certain embodiments, the dispersion polymer comprises at least about 30% by weight of the solid dispersion. In certain embodiments, the dispersion polymer comprises at least about 40% by weight of the solid dispersion. In certain embodiments, the dispersion polymer comprises at least about 50% by weight of the solid dispersion. In certain embodiments, the dispersion polymer comprises at least about 60% by weight of the solid dispersion. In certain embodiments, the dispersion polymer comprises at least about 70% by weight of the solid dispersion. In certain embodiments, the dispersion polymer comprises at least about 80% by weight of the solid dispersion. In certain embodiments, the dispersion polymer comprises at least about 90% by weight of the solid dispersion. In certain embodiments, the dispersion polymer comprises at least about 95% by weight of the solid dispersion.

In certain embodiments, the dispersion polymer comprises up to about 10% by weight of the solid dispersion. In certain embodiments, the dispersion polymer comprises up to about 20% by weight of the solid dispersion. In certain embodiments, the dispersion polymer comprises up to about 30% by weight of the solid dispersion. In certain embodiments, the dispersion polymer comprises up to about 40% by weight of the solid dispersion. In certain embodiments, the dispersion polymer comprises up to about 50% by weight of the solid dispersion. In certain embodiments, the dispersion polymer comprises up to about 60% by weight of the solid dispersion. In certain embodiments, the dispersion polymer comprises up to about 70% by weight of the solid dispersion. In certain embodiments, the dispersion polymer comprises up to about 80% by weight of the solid dispersion. In certain embodiments, the dispersion polymer comprises up to about 90% by weight of the solid dispersion. In certain embodiments, the dispersion polymer comprises up to about 95% by weight of the solid dispersion.

In certain embodiments, the dispersion polymer is HPMC-AS. The HPMC-AS can be of any grade, including HPMC-AS, LF; HPMC-AS, M; HPMC-AS, H; HPMC-AS, HF; and HPMC-AS, HG. The HPMC-AS can also be of any viscosity, including low, normal, and high. In certain embodiments, the dispersion polymer comprises HPMC-AS, LF. In certain embodiments, the dispersion polymer comprises HPMC-AS, M. In certain embodiments, the dispersion polymer comprises HPMC-AS, HF. In certain embodiments, the dispersion polymer comprises HPMC-AS, HG. In some embodiments, the indicator "L," "M," or "H" refers to a low, medium, or high ratio of acetyl to succinyl substituents on the HPMC backbone, respectively. In some embodiments, the indicator "F" or "G" refers to either a fine or granular particle size, respectively.

In certain embodiments, a particular grade of HPMC-AS is specified, such as L, M, or H. In some embodiments, the grade refers to the ratio of acetyl to succinyl substituents on the HPMC backbone, with "L" grade being a low ratio, "M" grade being a medium ratio, and "H" grade being a high ratio. In some embodiments, HPMC-AS, L comprises an acetyl content of about 5-9% and a succinyl content of about 14-18%. In some embodiments, the HPMC-AS, L further comprises a methoxyl content of about 20-24% and a hydroxypropyl content of about 5-9%. In some embodiments, HPMC-AS, M comprises an acetyl content of about 7-11% and a succinyl content of about 10-14%. In some embodiments, the HPMC-AS, M further comprises a methoxyl content of about 21-25% and a hydroxypropyl content of about 5-9%. In some embodiments, HPMC-AS, H comprises an acetyl content of about 10-14% and a succinyl content of about 4-8%. In some embodiments, the HPMC-AS, H further comprises a methoxyl content of 22-26% and a hydroxypropyl content of about 60-10%. The percentages referred to in this paragraph refer to percentages by weight of the HPMC-AS composition.

In certain embodiments, the dispersion polymer is HPMC. In certain embodiments, the HPMC is an HPMC derivative. The HPMC or HPMC derivative can be of any grade, including low, normal, or high viscosity grades. Non-limiting examples of suitable HPMC or HPMC derivatives include Methocel™ K100M, K15M, F4M, E4M, K4M, K100LV, K3, E15LV, E15LN, E15CLV, E50, E5, E5LV, E3, and E3LV (available from Dow Chemical, Midland Mich.). In certain embodiments, the dispersion polymer is HPMC E3LV.

In certain embodiments, the compound of Formula (I) comprises about 1-99% by weight of the solid dispersion. In certain embodiments, the compound of Formula (I) comprises about 10-80% by weight of the solid dispersion. In certain embodiments, the compound of Formula (I) comprises about 10-60% by weight of the solid dispersion. In certain embodiments, the compound of Formula (I) comprises about 10-50% by weight of the solid dispersion. In certain embodiments, the compound of Formula (I) comprises about 10-40% by weight of the solid dispersion. In certain embodiments, the compound of Formula (I) comprises about 20-80% by weight of the solid dispersion. In certain embodiments, the compound of Formula (I) comprises about 20-60% by weight of the solid dispersion. In certain embodiments, the compound of Formula (I) comprises about 20-50% by weight of the solid dispersion. In certain embodiments, the compound of Formula (I) comprises about 20-40% by weight of the solid dispersion. In certain embodiments, the compound of Formula (I) comprises about 40-60% by weight of the solid dispersion. In certain embodiments, the compound of Formula (I) comprises about 95% by weight of the solid dispersion. In certain embodiments, the compound of Formula (I) comprises about 90% by weight of the solid dispersion. In certain embodiments, the compound of Formula (I) comprises about 80% by weight of the solid dispersion. In certain embodiments, the compound of Formula (I) comprises about 70% by weight of the solid dispersion. In certain embodiments, the compound of Formula (I) comprises about 60% by weight of the solid dispersion. In certain embodiments, the compound of Formula (I) comprises about 50% by weight of the solid dispersion. In certain embodiments, the compound of Formula (I) comprises about 40% by weight of the solid dispersion. In certain embodiments, the compound of Formula (I) comprises about 300% by weight of the solid dispersion. In certain embodiments, the compound of Formula (I) comprises about 20% by weight of the solid dispersion. In certain embodiments, the compound of Formula (I) comprises about 10% by weight of the solid dispersion. In certain embodiments, the compound of Formula (I) comprises about 5% by weight of the solid dispersion.

In certain embodiments, the compound of Formula (I) comprises at least about 5% by weight of the solid dispersion. In certain embodiments, the compound of Formula (I) comprises at least about 10% by weight of the solid dispersion. In certain embodiments, the compound of Formula (I) comprises at least about 20% by weight of the solid dispersion. In certain embodiments, the compound of Formula (I) comprises at least about 30% by weight of the solid dispersion. In certain embodiments, the compound of Formula (I) comprises at least about 40% by weight of the solid dispersion. In certain embodiments, the compound of Formula (I) comprises at least about 50% by weight of the solid dispersion. In certain embodiments, the compound of Formula (I) comprises at least about 60% by weight of the solid dispersion. In certain embodiments, the compound of Formula (I) comprises at least about 70% by weight of the solid dispersion. In certain embodiments, the compound of Formula (I) comprises at least about 80% by weight of the solid dispersion. In certain embodiments, the compound of Formula (I) comprises at least about 90% by weight of the solid dispersion. In certain embodiments, the compound of Formula (I) comprises at least about 95% by weight of the solid dispersion.

In certain embodiments, the compound of Formula (I) comprises up to about 5% by weight of the solid dispersion. In certain embodiments, the compound of Formula (I) comprises up to about 10% by weight of the solid dispersion. In certain embodiments, the compound of Formula (I) comprises up to about 20% by weight of the solid dispersion. In certain embodiments, the compound of Formula (I) comprises up to about 30% by weight of the solid dispersion. In certain embodiments, the compound of Formula (I) comprises up to about 40% by weight of the solid dispersion. In certain embodiments, the compound of Formula (I) comprises up to about 50% by weight of the solid dispersion. In certain embodiments, the compound of Formula (I) comprises up to about 60% by weight of the solid dispersion. In certain embodiments, the compound of Formula (I) comprises up to about 70% by weight of the solid dispersion.

In certain embodiments, the compound of Formula (I) comprises up to about 80% by weight of the solid dispersion. In certain embodiments, the compound of Formula (I) comprises up to about 90% by weight of the solid dispersion. In certain embodiments, the compound of Formula (I) comprises up to about 95% by weight of the solid dispersion.

In certain embodiments, the ratio of the compound of Formula (I):dispersion polymer is about 5:95 (w/w) in the solid dispersion. In certain embodiments, the ratio of the compound of Formula (I):dispersion polymer is about 10:90 (w/w) in the solid dispersion. In certain embodiments, the ratio of the compound of Formula (I):dispersion polymer is about 20:80 (w/w) in the solid dispersion. In certain embodiments, the ratio of the compound of Formula (I):dispersion polymer is about 30:70 (w/w) in the solid dispersion. In certain embodiments, the ratio of the compound of Formula (I):dispersion polymer is about 40:60 (w/w) in the solid dispersion. In certain embodiments, the ratio of the compound of Formula (I):dispersion polymer is about 50:50 (w/w) in the solid dispersion. In certain embodiments, the ratio of the compound of Formula (I):dispersion polymer is about 60:40 (w/w) in the solid dispersion. In certain embodiments, the ratio of the compound of Formula (I):dispersion polymer is about 70:30 (w/w) in the solid dispersion. In certain embodiments, the ratio of the compound of Formula (I):dispersion polymer is about 80:20 (w/w) in the solid dispersion. In certain embodiments, the ratio of the compound of Formula (I):dispersion polymer is about 90:10 (w/w) in the solid dispersion. In certain embodiments, the ratio of the compound of Formula (I):dispersion polymer is about 95:5 (w/w) in the solid dispersion.

In certain embodiments, the solid dispersion comprises Compound 1 and HPMC-AS in a ratio of from about 5:95 to about 50:50. In certain embodiments, the solid dispersion comprises Compound 1 and HPMC-AS in a ratio of from about 5:95 to about 50:50. In certain embodiments, the solid dispersion comprises Compound 1 and HPMC-AS in a ratio of from about 10:90 to about 50:50. In certain embodiments, the solid dispersion comprises Compound 1 and HPMC-AS in a ratio of from about 15:85 to about 50:50. In certain embodiments, the solid dispersion comprises Compound 1 and HPMC-AS in a ratio of from about 20:80 to about 50:50. In certain embodiments, the solid dispersion comprises Compound 1 and HPMC-AS in a ratio of from about 5:95 to about 40:60. In certain embodiments, the solid dispersion comprises Compound 1 and HPMC-AS in a ratio of from about 10:90 to about 40:60. In certain embodiments, the solid dispersion comprises Compound 1 and HPMC-AS in a ratio of from about 15:85 to about 40:60. In certain embodiments, the solid dispersion comprises Compound 1 and HPMC-AS in a ratio of from about 20:80 to about 40:60. In certain embodiments, the solid dispersion comprises Compound 1 and HPMC-AS in a ratio of about 10:90. In certain embodiments, the solid dispersion comprises Compound 1 and HPMC-AS in a ratio of about 20:80. In certain embodiments, the solid dispersion comprises Compound 1 and HPMC-AS in a ratio of about 30:70. In certain embodiments, the solid dispersion comprises Compound 1 and HPMC-AS in a ratio of about 40:60. In certain embodiments, the solid dispersion comprises Compound 1 and HPMC-AS in a ratio of about 50:50.

In certain embodiments, the solid dispersion comprises Compound 1 and HPMC-AS, H in a ratio of from about 5:95 to about 50:50. In certain embodiments, the solid dispersion comprises Compound 1 and HPMC-AS, H in a ratio of from about 5:95 to about 50:50. In certain embodiments, the solid dispersion comprises Compound 1 and HPMC-AS, H in a ratio of from about 10:90 to about 50:50. In certain embodiments, the solid dispersion comprises Compound 1 and HPMC-AS, H in a ratio of from about 15:85 to about 50:50. In certain embodiments, the solid dispersion comprises Compound 1 and HPMC-AS, H in a ratio of from about 20:80 to about 50:50. In certain embodiments, the solid dispersion comprises Compound 1 and HPMC-AS, H in a ratio of from about 5:95 to about 40:60. In certain embodiments, the solid dispersion comprises Compound 1 and HPMC-AS, H in a ratio of from about 10:90 to about 40:60. In certain embodiments, the solid dispersion comprises Compound 1 and HPMC-AS, H in a ratio of from about 15:85 to about 40:60. In certain embodiments, the solid dispersion comprises Compound 1 and HPMC-AS, H in a ratio of from about 20:80 to about 40:60. In certain embodiments, the solid dispersion comprises Compound 1 and HPMC-AS, H in a ratio of about 10:90. In certain embodiments, the solid dispersion comprises Compound 1 and HPMC-AS, H in a ratio of about 20:80. In certain embodiments, the solid dispersion comprises Compound 1 and HPMC-AS, H in a ratio of about 30:70. In certain embodiments, the solid dispersion comprises Compound 1 and HPMC-AS, H in a ratio of about 40:60. In certain embodiments, the solid dispersion comprises Compound 1 and HPMC-AS, H in a ratio of about 50:50. In some embodiments, the HPMC-AS, H comprises an acetyl content of about 10-14% and a succinyl content of about 4-8%.

In certain embodiments, the solid dispersion comprises Compound 1 and HPMC-AS, M in a ratio of from about 5:95 to about 50:50. In certain embodiments, the solid dispersion comprises Compound 1 and HPMC-AS, M in a ratio of from about 5:95 to about 50:50. In certain embodiments, the solid dispersion comprises Compound 1 and HPMC-AS, M in a ratio of from about 10:90 to about 50:50. In certain embodiments, the solid dispersion comprises Compound 1 and HPMC-AS, M in a ratio of from about 15:85 to about 50:50. In certain embodiments, the solid dispersion comprises Compound 1 and HPMC-AS, M in a ratio of from about 20:80 to about 50:50. In certain embodiments, the solid dispersion comprises Compound 1 and HPMC-AS, M in a ratio of from about 5:95 to about 40:60. In certain embodiments, the solid dispersion comprises Compound 1 and HPMC-AS, M in a ratio of from about 10:90 to about 40:60. In certain embodiments, the solid dispersion comprises Compound 1 and HPMC-AS, M in a ratio of from about 15:85 to about 40:60. In certain embodiments, the solid dispersion comprises Compound 1 and HPMC-AS, M in a ratio of from about 20:80 to about 40:60. In certain embodiments, the solid dispersion comprises Compound 1 and HPMC-AS, M in a ratio of about 10:90. In certain embodiments, the solid dispersion comprises Compound 1 and HPMC-AS, M in a ratio of about 20:80. In certain embodiments, the solid dispersion comprises Compound 1 and HPMC-AS, M in a ratio of about 30:70. In certain embodiments, the solid dispersion comprises Compound 1 and HPMC-AS, M in a ratio of about 40:60. In certain embodiments, the solid dispersion comprises Compound 1 and HPMC-AS, M in a ratio of about 50:50. In some embodiments, the HPMC-AS, M comprises an acetyl content of about 7-11% and a succinyl content of about 10-14%.

In certain embodiments, the solid dispersion comprises Compound 1 and PVP. In some embodiments, the ratio of Compound 1:PVP is from about 1:10 to about 1:1. In some embodiments, the ratio of Compound 1:PVP is from about 1:10 to about 1:2. In some embodiments, the ratio of Compound 1:PVP is from about 1:5 to about 1:2. In some embodiments, the ratio of Compound 1:PVP is from about 1:5 to about 1:1. In some embodiments, the ratio of Compound 1:PVP is about 1:1, about 1:2, about 1:3, about 1:4, about 1:5, or about 1:10. In some embodiments, the ratio of Compound 1:PVP is about 1:2. In some embodiments, the ratio of Compound 1:PVP is about 1:3. In some embodiments, the ratio of Compound 1:PVP is about 1:5. In some embodiments, molecular weight of the PVP is from about 7,000 Daltons to about 11,000 Daltons.

In certain embodiments, the solid dispersion has an average particle size of less than 5 µm. In certain embodiments, the solid dispersion has an average particle size of less than 10 µm. In certain embodiments, the solid dispersion has an average particle size of less than 20 µm. In certain embodiments, the solid dispersion has an average particle size of less than 30 µm. In certain embodiments, the solid dispersion has an average particle size of less than 40 µm. In certain embodiments, the solid dispersion has an average particle size of less than 50 µm. In certain embodiments, the solid dispersion has an average particle size from about 1 µm to 20 µm. In certain embodiments, the solid dispersion has an average particle size from about 5 µm to 20 µm. In certain embodiments, the solid dispersion has an average particle size from about 10 µm to 20 µm. In certain embodiments, the solid dispersion has an average particle size from about 15 µm to 20 µm. In certain embodiments, the solid dispersion has an average particle size from about 1 µm to 5 µm. In certain embodiments, the solid dispersion has an average particle size from about 1 µm to 10 µm. In certain embodiments, the solid dispersion has an average particle size from about 5 µm to 10 µm.

In certain embodiments, the solid dispersion comprises 1-100% by weight of the pharmaceutical composition. In certain embodiments, the solid dispersion comprises 20-80% by weight of the pharmaceutical composition. In certain embodiments, the solid dispersion comprises 40-60% by weight of the pharmaceutical composition. In certain embodiments, the solid dispersion comprises about 10%, 20%, 30%, 40%, 50%, 60%, 70%, 80%, 90%, or 100% by weight of the pharmaceutical composition.

In certain embodiments, the pharmaceutical composition comprising a solid dispersion comprises a therapeutically effective amount of a compound of Formula (I). In certain embodiments, the pharmaceutical composition comprises about 1 mg of a compound of Formula (I). In certain embodiments, the pharmaceutical composition comprises about 5 mg of a compound of Formula (I). In certain embodiments, the pharmaceutical composition comprises about 10 mg of a compound of Formula (I). In certain embodiments, the pharmaceutical composition comprises about 25 mg of a compound of Formula (I). In certain embodiments, the pharmaceutical composition comprises about 50 mg of a compound of Formula (I). In certain embodiments, the pharmaceutical composition comprises about 100 mg of a compound of Formula (I). In certain embodiments, the pharmaceutical composition comprises about 200 mg of a compound of Formula (I). In certain embodiments, the pharmaceutical composition comprises about 400 mg of a compound of Formula (I).

In certain embodiments, the solid dispersion improves the solubility of a compound of Formula (I). In certain embodiments, the solid dispersion improves the solubility of a compound of Formula (I) by at least two-fold. In certain embodiments, the solid dispersion improves the solubility of a compound of Formula (I) by at least four-fold. In certain embodiments, the solid dispersion improves the solubility of a compound of Formula (I) by at least eight-fold. In certain embodiments, the solid dispersion improves the solubility of a compound of Formula (I) by at least ten-fold. In certain embodiments, the solid dispersion improves the solubility of a compound of Formula (I) by at least 20-fold. In certain embodiments, the solid dispersion improves the solubility of a compound of Formula (I) by at least 30-fold. In certain embodiments, the solid dispersion improves the solubility of a compound of Formula (I) by at least 40-fold. In certain embodiments, the solid dispersion improves the solubility of a compound of Formula (I) by at least 50-fold. In certain embodiments, the solid dispersion improves the solubility of a compound of Formula (I) by at least 60-fold. In some embodiments, the improvement is measured as compared to a crystalline form of the compound of Formula (I). In some embodiments, the improvement is measured as compared to an amorphous form of the compound of Formula (I). In some embodiments, Additional Elements In certain embodiments, the pharmaceutical composition further comprises a filler, a sweetener, a disintegrant, a wetting agent, a glidant, a lubricant, or a surfactant, or any combinations thereof. In certain embodiments, the solid dispersion of the pharmaceutical composition further comprises a filler, a sweetener, a disintegrant, a wetting agent, a glidant, a lubricant, or a surfactant, or any combinations thereof.

Fillers

In certain embodiments, the pharmaceutical composition further comprises a filler. In certain embodiments, the solid dispersion of the pharmaceutical composition further comprises a filler. Fillers may be any biocompatible substance that is unreactive with the compound of Formula (I) and the compound of Formula (I). Non-limiting examples of fillers include lactose monohydrate, mannitol, sorbitol, cellulose, calcium phosphate, starch, sugar, cellulose, modified cellulose, sodium carboxymethyl cellulose, ethyl cellulose hydroxymethyl cellulose, hydroxypropylcellulose, cellulose acetate, microcrystalline cellulose, dibasic calcium phosphate, sucrose, lactose, corn starch, potato starch, or any combination thereof.

In certain embodiments, the filler comprises about 1-99% by weight of the pharmaceutical composition. In certain embodiments, the filler comprises about 10% by weight of the pharmaceutical composition. In certain embodiments, the filler comprises about 20% by weight of the pharmaceutical composition. In certain embodiments, the filler comprises about 30% by weight of the pharmaceutical composition. In certain embodiments, the filler comprises about 40% by weight of the pharmaceutical composition. In certain embodiments, the filler comprises about 50% by weight of the pharmaceutical composition. In certain embodiments, the filler comprises about 60% by weight of the pharmaceutical composition. In certain embodiments, the filler comprises about 70% by weight of the pharmaceutical composition. In certain embodiments, the filler comprises about 80% by weight of the pharmaceutical composition. In certain embodiments, the filler comprises about 90% by weight of the pharmaceutical composition.

In certain embodiments, the filler comprises up to about 10% by weight of the pharmaceutical composition. In certain embodiments, the filler comprises up to about 20% by weight of the pharmaceutical composition. In certain embodiments, the filler comprises up to about 30% by weight of the pharmaceutical composition. In certain embodiments, the filler comprises up to about 40% by weight of the pharmaceutical composition. In certain embodiments, the filler comprises up to about 50% by weight of the pharmaceutical composition. In certain embodiments, the filler comprises up to about 60% by weight of the pharmaceutical composition. In certain embodiments, the filler comprises up to about 70% by weight of the pharmaceutical composition. In certain embodiments, the filler comprises up to about 80% by weight of the pharmaceutical composition. In certain embodiments, the filler comprises up to about 90% by weight of the pharmaceutical composition.

In certain embodiments, the filler comprises at least about 10% by weight of the pharmaceutical composition. In certain embodiments, the filler comprises at least about 20% by weight of the pharmaceutical composition. In certain embodiments, the filler comprises at least about 30% by weight of the pharmaceutical composition. In certain embodiments, the filler comprises at least about 40% by weight of the pharmaceutical composition. In certain embodiments, the filler comprises at least about 50% by weight of the pharmaceutical composition. In certain embodiments, the filler comprises at least about 60% by weight of the pharmaceutical composition. In certain embodiments, the filler comprises at least about 70% by weight of the pharmaceutical composition. In certain embodiments, the filler comprises at least about 80% by weight of the pharmaceutical composition. In certain embodiments, the filler comprises at least about 90% by weight of the pharmaceutical composition.

Sweeteners

In certain embodiments, the pharmaceutical composition comprising a compound of Formula (I) further comprises a sweetener. In certain embodiments, the solid dispersion of the pharmaceutical composition further comprises a sweetener. Non-limiting examples of sweeteners include water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenylglycine, L-aspartyl-2,5-dihydro-L-phenylalanine, L-aspartyl-L-(1-cyclohexyen)-alanine, and the like; and water-soluble sweeteners derived from naturally occurring water-soluble sweeteners, such as a chlorinated derivatives of ordinary sugar (sucrose), known, for example, as sucralose.

In certain embodiments, the sweetener comprises about 1-99% by weight of the pharmaceutical composition. In certain embodiments, the sweetener comprises about 10% by weight of the pharmaceutical composition. In certain embodiments, the sweetener comprises about 20% by weight of the pharmaceutical composition. In certain embodiments, the sweetener comprises about 30% by weight of the pharmaceutical composition. In certain embodiments, the sweetener comprises about 40% by weight of the pharmaceutical composition. In certain embodiments, the sweetener comprises about 50% by weight of the pharmaceutical composition. In certain embodiments, the sweetener comprises about 60% by weight of the pharmaceutical composition. In certain embodiments, the sweetener comprises about 70% by weight of the pharmaceutical composition. In certain embodiments, the sweetener comprises about 80% by weight of the pharmaceutical composition. In certain embodiments, the sweetener comprises about 90% by weight of the pharmaceutical composition.

In certain embodiments, the sweetener comprises up to about 10% by weight of the pharmaceutical composition. In certain embodiments, the sweetener comprises up to about 20% by weight of the pharmaceutical composition. In certain embodiments, the sweetener comprises up to about 30% by weight of the pharmaceutical composition. In certain embodiments, the sweetener comprises up to about 40% by weight of the pharmaceutical composition. In certain embodiments, the sweetener comprises up to about 50% by weight of the pharmaceutical composition. In certain embodiments, the sweetener comprises up to about 60% by weight of the pharmaceutical composition. In certain embodiments, the sweetener comprises up to about 70% by weight of the pharmaceutical composition. In certain embodiments, the sweetener comprises up to about 80% by weight of the pharmaceutical composition. In certain embodiments, the sweetener comprises up to about 90% by weight of the pharmaceutical composition.

In certain embodiments, the sweetener comprises at least about 10% by weight of the pharmaceutical composition. In certain embodiments, the sweetener comprises at least about 20% by weight of the pharmaceutical composition. In certain embodiments, the sweetener comprises at least about 30% by weight of the pharmaceutical composition. In certain embodiments, the sweetener comprises at least about 40% by weight of the pharmaceutical composition. In certain embodiments, the sweetener comprises at least about 50% by weight of the pharmaceutical composition. In certain embodiments, the sweetener comprises at least about 60% by weight of the pharmaceutical composition. In certain embodiments, the sweetener comprises at least about 70% by weight of the pharmaceutical composition. In certain embodiments, the sweetener comprises at least about 80% by weight of the pharmaceutical composition. In certain embodiments, the sweetener comprises at least about 90% by weight of the pharmaceutical composition.

Disintegrants

In certain embodiments, the pharmaceutical composition comprising a compound of Formula (I) further comprises a disintegrant. In certain embodiments, the solid dispersion of the pharmaceutical composition further comprises a disintegrant. Non-limiting examples of disintegrants include agar-agar, algins, calcium carbonate, carboxymethylcellulose, cellulose, hydroxypropylcellulose, low substituted hydroxypropylcellulose, clays, croscarmellose sodium, crospovidone, gums, magnesium aluminum silicate, methylcellulose, polacrilin potassium, sodium alginate, sodium starch glycolate, maize starch, potato starch, tapioca starch, or any combination thereof.

In certain embodiments, the disintegrant comprises about 1-99% by weight of the pharmaceutical composition. In certain embodiments, the disintegrant comprises about 10% by weight of the pharmaceutical composition. In certain embodiments, the disintegrant comprises about 20% by weight of the pharmaceutical composition. In certain embodiments, the disintegrant comprises about 30% by weight of the pharmaceutical composition. In certain embodiments, the disintegrant comprises about 40% by weight of the pharmaceutical composition. In certain embodiments, the disintegrant comprises about 50% by weight of the pharmaceutical composition. In certain embodiments, the disintegrant comprises about 60% by weight of the pharmaceutical composition. In certain embodiments, the disintegrant comprises about 70% by weight of the pharmaceutical composition. In certain embodiments, the disintegrant comprises about 80% by weight of the pharmaceutical composition. In certain embodiments, the disintegrant comprises about 90% by weight of the pharmaceutical composition.

In certain embodiments, the disintegrant comprises up to about 10% by weight of the pharmaceutical composition. In certain embodiments, the disintegrant comprises up to about 20% by weight of the pharmaceutical composition. In certain embodiments, the disintegrant comprises up to about 30% by weight of the pharmaceutical composition. In certain embodiments, the disintegrant comprises up to about 40% by weight of the pharmaceutical composition. In certain embodiments, the disintegrant comprises up to about 50% by weight of the pharmaceutical composition. In certain embodiments, the disintegrant comprises up to about 60% by weight of the pharmaceutical composition. In certain embodiments, the disintegrant comprises up to about 70% by weight of the pharmaceutical composition. In certain embodiments, the disintegrant comprises up to about 80% by weight of the pharmaceutical composition. In certain embodiments, the disintegrant comprises up to about 90% by weight of the pharmaceutical composition.

In certain embodiments, the disintegrant comprises at least about 10% by weight of the pharmaceutical composition. In certain embodiments, the disintegrant comprises at least about 20% by weight of the pharmaceutical composition. In certain embodiments, the disintegrant comprises at least about 30% by weight of the pharmaceutical composition. In certain embodiments, the disintegrant comprises at least about 40% by weight of the pharmaceutical composition. In certain embodiments, the disintegrant comprises at least about 50% by weight of the pharmaceutical composition. In certain embodiments, the disintegrant comprises at least about 60% by weight of the pharmaceutical composition. In certain embodiments, the disintegrant comprises at least about 70% by weight of the pharmaceutical composition. In certain embodiments, the disintegrant comprises at least about 80% by weight of the pharmaceutical composition. In certain embodiments, the disintegrant comprises at least about 90% by weight of the pharmaceutical composition.

Wetting Agents

In certain embodiments, the pharmaceutical composition comprising a compound of Formula (I) further comprises a wetting agent. In certain embodiments, the solid dispersion of the pharmaceutical composition further comprises a wetting agent. Non-limiting examples of wetting agents include sodium lauryl sulfate, cetostearyl alcohol, cetomacrogol emulsifying wax, gelatin, casein, docusate sodium, benzalkonium chloride, calcium stearate, polyethylene glycols, phosphates, polyoxyethylene sorbitan fatty acid esters, gum acacia, cholesterol, tragacanth, polyoxyethylene 20 stearyl ethers, polyoxyethylene alkyl ethers, polyoxyethylene castor oil derivatives, PEGylated hydrogenated castor oils, sorbitan esters of fatty acids, Vitamin E or tocopherol derivatives, vitamin E TPGS, tocopheryl esters, lecithin, phospholipids and their derivatives, poloxamers, stearic acid, oleic acid, oleic alcohol, cetyl alcohol, mono and diglycerides, propylene glycol esters of fatty acids, glycerol esters of fatty acids, ethylene glycol palmitostearate, polyoxylglycerides, propylene glycol monocaprylate, propylene glycol monolaurate, alkyl aryl polyether alcohols and polyglyceryl oleate or combinations thereof.

In certain embodiments, the wetting agent comprises about 1-99% by weight of the pharmaceutical composition. In certain embodiments, the wetting agent comprises about 10% by weight of the pharmaceutical composition. In certain embodiments, the wetting agent comprises about 20% by weight of the pharmaceutical composition. In certain embodiments, the wetting agent comprises about 30% by weight of the pharmaceutical composition. In certain embodiments, the wetting agent comprises about 40% by weight of the pharmaceutical composition. In certain embodiments, the wetting agent comprises about 50% by weight of the pharmaceutical composition. In certain embodiments, the wetting agent comprises about 60% by weight of the pharmaceutical composition. In certain embodiments, the wetting agent comprises about 70% by weight of the pharmaceutical composition. In certain embodiments, the wetting agent comprises about 80% by weight of the pharmaceutical composition. In certain embodiments, the wetting agent comprises about 90% by weight of the pharmaceutical composition.

In certain embodiments, the wetting agent comprises up to about 10% by weight of the pharmaceutical composition. In certain embodiments, the wetting agent comprises up to about 20% by weight of the pharmaceutical composition. In certain embodiments, the wetting agent comprises up to about 30% by weight of the pharmaceutical composition. In certain embodiments, the wetting agent comprises up to about 40% by weight of the pharmaceutical composition. In certain embodiments, the wetting agent comprises up to about 50% by weight of the pharmaceutical composition. In certain embodiments, the wetting agent comprises up to about 60% by weight of the pharmaceutical composition. In certain embodiments, the wetting agent comprises up to about 70% by weight of the pharmaceutical composition. In certain embodiments, the wetting agent comprises up to about 80% by weight of the pharmaceutical composition. In certain embodiments, the wetting agent comprises up to about 90% by weight of the pharmaceutical composition.

In certain embodiments, the wetting agent comprises at least about 10% by weight of the pharmaceutical composition. In certain embodiments, the wetting agent comprises at least about 20% by weight of the pharmaceutical composition. In certain embodiments, the wetting agent comprises at least about 30% by weight of the pharmaceutical composition. In certain embodiments, the wetting agent comprises at least about 40% by weight of the pharmaceutical composition. In certain embodiments, the wetting agent comprises at least about 50% by weight of the pharmaceutical composition. In certain embodiments, the wetting agent comprises at least about 60% by weight of the pharmaceutical composition. In certain embodiments, the wetting agent comprises at least about 70% by weight of the pharmaceutical composition. In certain embodiments, the wetting agent comprises at least about 80% by weight of the pharmaceutical composition. In certain embodiments, the wetting agent comprises at least about 90% by weight of the pharmaceutical composition.

Glidants

In certain embodiments, the pharmaceutical composition comprising a compound of Formula (I) further comprises a glidant. In certain embodiments, the solid dispersion of the pharmaceutical composition further comprises a glidant. Non-limiting examples of glidants include colloidal silicon dioxide, talk, corn starch, metal silicates, higher fatty acid metal salts, metal oxides, alkaline earth metal salts, and metal hydroxides or any combination thereof.

In certain embodiments, the glidant comprises about 1-99% by weight of the pharmaceutical composition. In certain embodiments, the glidant comprises about 10% by weight of the pharmaceutical composition. In certain embodiments, the glidant comprises about 20% by weight of the pharmaceutical composition. In certain embodiments, the glidant comprises about 30% by weight of the pharmaceutical composition. In certain embodiments, the glidant comprises about 40% by weight of the pharmaceutical composition. In certain embodiments, the glidant comprises about 50% by weight of the pharmaceutical composition. In certain embodiments, the glidant comprises about 60% by weight of the pharmaceutical composition. In certain embodiments, the glidant comprises about 70% by weight of the pharmaceutical composition. In certain embodiments, the glidant comprises about 80% by weight of the pharmaceutical composition. In certain embodiments, the glidant comprises about 90% by weight of the pharmaceutical composition.

In certain embodiments, the glidant comprises up to about 10% by weight of the pharmaceutical composition. In certain embodiments, the glidant comprises up to about 20% by weight of the pharmaceutical composition. In certain embodiments, the glidant comprises up to about 30% by weight of the pharmaceutical composition. In certain embodiments, the glidant comprises up to about 40% by weight of the pharmaceutical composition. In certain embodiments, the glidant comprises up to about 50% by weight of the pharmaceutical composition. In certain embodiments, the glidant comprises up to about 60% by weight of the pharmaceutical composition. In certain embodiments, the glidant comprises up to about 70% by weight of the pharmaceutical composition. In certain embodiments, the glidant comprises up to about 80% by weight of the pharmaceutical composition. In certain embodiments, the glidant comprises up to about 90% by weight of the pharmaceutical composition.

In certain embodiments, the glidant comprises at least about 10% by weight of the pharmaceutical composition. In certain embodiments, the glidant comprises at least about 20% by weight of the pharmaceutical composition. In certain embodiments, the glidant comprises at least about 30% by weight of the pharmaceutical composition. In certain embodiments, the glidant comprises at least about 40% by weight of the pharmaceutical composition. In certain embodiments, the glidant comprises at least about 50% by weight of the pharmaceutical composition. In certain embodiments, the glidant comprises at least about 60% by weight of the pharmaceutical composition. In certain embodiments, the glidant comprises at least about 70% by weight of the pharmaceutical composition. In certain embodiments, the glidant comprises at least about 80% by weight of the pharmaceutical composition. In certain embodiments, the glidant comprises at least about 90% by weight of the pharmaceutical composition.

Lubricants

In certain embodiments, the pharmaceutical composition comprising a compound of Formula (I) further comprises a lubricant. In certain embodiments, the solid dispersion of the pharmaceutical composition further comprises a lubricant. Non-limiting examples of lubricants include magnesium stearate, calcium stearate, zinc stearate, sodium stearate, stearic acid, aluminum stearate, leucine, glyceryl behenate, hydrogenated vegetable oil, sodium stearyl fumarate, or any combination thereof.

In certain embodiments, the lubricant comprises about 1-99% by weight of the pharmaceutical composition. In certain embodiments, the lubricant comprises about 10% by weight of the pharmaceutical composition. In certain embodiments, the lubricant comprises about 20% by weight of the pharmaceutical composition. In certain embodiments, the lubricant comprises about 30% by weight of the pharmaceutical composition. In certain embodiments, the lubricant comprises about 40% by weight of the pharmaceutical composition. In certain embodiments, the lubricant comprises about 50% by weight of the pharmaceutical composition. In certain embodiments, the lubricant comprises about 60% by weight of the pharmaceutical composition. In certain embodiments, the lubricant comprises about 70% by weight of the pharmaceutical composition. In certain embodiments, the lubricant comprises about 80% by weight of the pharmaceutical composition. In certain embodiments, the lubricant comprises about 90% by weight of the pharmaceutical composition.

In certain embodiments, the lubricant comprises up to about 10% by weight of the pharmaceutical composition. In certain embodiments, the lubricant comprises up to about 20% by weight of the pharmaceutical composition. In certain embodiments, the lubricant comprises up to about 30% by weight of the pharmaceutical composition. In certain embodiments, the lubricant comprises up to about 40% by weight of the pharmaceutical composition. In certain embodiments, the lubricant comprises up to about 50% by weight of the pharmaceutical composition. In certain embodiments, the lubricant comprises up to about 60% by weight of the pharmaceutical composition. In certain embodiments, the lubricant comprises up to about 70% by weight of the pharmaceutical composition. In certain embodiments, the lubricant comprises up to about 80% by weight of the pharmaceutical composition. In certain embodiments, the lubricant comprises up to about 90% by weight of the pharmaceutical composition.

In certain embodiments, the lubricant comprises at least about 10% by weight of the pharmaceutical composition. In certain embodiments, the lubricant comprises at least about 20% by weight of the pharmaceutical composition. In certain embodiments, the lubricant comprises at least about 30% by weight of the pharmaceutical composition. In certain embodiments, the lubricant comprises at least about 40% by weight of the pharmaceutical composition. In certain embodiments, the lubricant comprises at least about 50% by weight of the pharmaceutical composition. In certain embodiments, the lubricant comprises at least about 60% by weight of the pharmaceutical composition. In certain embodiments, the lubricant comprises at least about 70% by weight of the pharmaceutical composition. In certain embodiments, the lubricant comprises at least about 80% by weight of the pharmaceutical composition. In certain embodiments, the lubricant comprises at least about 90% by weight of the pharmaceutical composition.

Surfactant

In some embodiments of pharmaceutical composition comprising a compound of Formula (I), the pharmaceutical composition further comprises a surfactant. In certain embodiments, the solid dispersion of the pharmaceutical composition further comprises a surfactant. Non limiting examples of surfactants include sodium dodecyl sulfate (SDS), sodium laurel sulfate (SLS), macroglycerol ricinoleate (Kolliphor EL® or Cremophor EL®), caprylocaproyl polyoxyl-8 glyceride (Labrasol®), lauroyl polyoxyl-6 glycerides (Labrafil® M 2130 CS), lauroyl polyoxyl-32 glyceride (Gelucire® 44/14), polyethylene glycol monostearate (Gelucire®48/16), polyoxyethylene hydrogenated castor oil 60 (HCO-60), polysorbate 80 (Tween®-80), polyethylene glycol sorbitan monolaurate (Tween®-20), polyoxyethylene sorbitan trioleate (Tween®-85), polyoxyethyelene glyceryl trioleate (tagot-TO), sorbitan monooleate (Span®-80), sorbitan monolaurate (Span®-20), or any combinations thereof.

In certain embodiments, the surfactant comprises about 1-99% by weight of the pharmaceutical composition. In certain embodiments, the surfactant comprises about 10% by weight of the pharmaceutical composition. In certain embodiments, the surfactant comprises about 20% by weight of the pharmaceutical composition. In certain embodiments, the surfactant comprises about 30% by weight of the pharmaceutical composition. In certain embodiments, the surfactant comprises about 40% by weight of the pharmaceutical composition. In certain embodiments, the surfactant comprises about 50% by weight of the pharmaceutical composition. In certain embodiments, the surfactant comprises about 60% by weight of the pharmaceutical composition. In certain embodiments, the surfactant comprises about 70% by weight of the pharmaceutical composition. In certain embodiments, the surfactant comprises about 80% by weight of the pharmaceutical composition. In certain embodiments, the surfactant comprises about 90% by weight of the pharmaceutical composition.

In certain embodiments, the surfactant comprises up to about 10% by weight of the pharmaceutical composition. In certain embodiments, the surfactant comprises up to about 20% by weight of the pharmaceutical composition. In certain embodiments, the surfactant comprises up to about 30% by weight of the pharmaceutical composition. In certain embodiments, the surfactant comprises up to about 40% by weight of the pharmaceutical composition. In certain embodiments, the surfactant comprises up to about 50% by weight of the pharmaceutical composition. In certain embodiments, the surfactant comprises up to about 60% by weight of the pharmaceutical composition. In certain embodiments, the surfactant comprises up to about 70% by weight of the pharmaceutical composition. In certain embodiments, the surfactant comprises up to about 80% by weight of the pharmaceutical composition. In certain embodiments, the surfactant comprises up to about 90% by weight of the pharmaceutical composition.

In certain embodiments, the surfactant comprises at least about 10% by weight of the pharmaceutical composition. In certain embodiments, the surfactant comprises at least about 20% by weight of the pharmaceutical composition. In certain embodiments, the surfactant comprises at least about 30% by weight of the pharmaceutical composition. In certain embodiments, the surfactant comprises at least about 40% by weight of the pharmaceutical composition. In certain embodiments, the surfactant comprises at least about 50% by weight of the pharmaceutical composition. In certain embodiments, the surfactant comprises at least about 60% by weight of the pharmaceutical composition. In certain embodiments, the surfactant comprises at least about 70% by weight of the pharmaceutical composition. In certain embodiments, the surfactant comprises at least about 80% by weight of the pharmaceutical composition. In certain embodiments, the surfactant comprises at least about 90% by weight of the pharmaceutical composition.

Methods of Manufacturing a Solid Dispersion

Described herein are methods of manufacturing pharmaceutical compositions, such as those comprising a compound of Formula (I). The methods provided herein may be used to prepare any of the solid dispersion formulations provided herein. In certain embodiments, a method of manufacturing a solid dispersion comprises the steps of
i. adding a solvent to a vessel;
ii. adding a compound of Formula (I) or its pharmaceutically acceptable salt to the vessel;
iii. adding a dispersion polymer to the vessel to obtain a first mixture;
iv. mixing the first mixture until the compound of Formula (I) or its pharmaceutically acceptable salt and the dispersion polymer are dissolved in the solvent to obtain a first solution;
v. dry spraying the first solution to obtain a first solid; and
vi. drying the first solid to obtain the solid dispersion.

In certain embodiments of methods of manufacturing a solid dispersion, the solvent is an organic solvent. In certain embodiments, the solvent is selected from the group consisting of ethanol, methanol, acetone, isopropyl alcohol, n-butanol, tetrahydrofuran, dichloromethane, ethyl acetate, methyl acetate, acetonitrile, chloroform, carbon tetrachloride, benzene, toluene, diethyl ether, dioxane, pentane, hexane, cyclohexane, heptane, methyl t-butyl ether, petroleum ether, 1-propanol, methyl ethyl ketone, and combinations thereof.

In certain embodiments, the solvent is a mixture of a non-polar solvent and polar solvent. In certain embodiments, the solvent is 95:5 non-polar:polar. In certain embodiments, the solvent is 95:5 non-polar:polar. In certain embodiments, the solvent is 90:10 non-polar:polar. In certain embodiments, the solvent is 85:15 non-polar:polar. In certain embodiments, the solvent is 80:20 non-polar:polar. In certain embodiments, the solvent is 75:25 non-polar:polar. In certain embodiments, the solvent is 70:30 non-polar:polar. In certain embodiments, the solvent is 60:40 non-polar:polar. In certain embodiments, the solvent is 50:50 non-polar:polar. In certain embodiments, the solvent is 40:60 non-polar:polar. In certain embodiments, the solvent is 30:70 non-polar:polar. In certain embodiments, the solvent is 20:80 non-polar:polar. In certain embodiments, the solvent is 10:90 non-polar:polar.

In certain embodiments, the solvent is a mixture of chloroform and methanol. In certain embodiments, the solvent is 95:5 chloroform:methanol. In certain embodiments, the solvent is 95:5 chloroform:methanol. In certain embodiments, the solvent is 90:10 chloroform:methanol. In certain embodiments, the solvent is 85:15 chloroform:methanol. In certain embodiments, the solvent is 80:20 chloroform:methanol. In certain embodiments, the solvent is 75:25 chloroform:methanol. In certain embodiments, the solvent is 70:30 chloroform:methanol. In certain embodiments, the solvent is 60:40 chloroform:methanol. In certain embodiments, the solvent is 50:50 chloroform:methanol. In certain embodiments, the solvent is 40:60 d chloroform:methanol. In certain embodiments, the solvent is 30:70 chloroform:methanol. In certain embodiments, the solvent is 20:80 chloroform:methanol. In certain embodiments, the solvent is 10:90 chloroform:methanol In certain embodiments, the solvent is a mixture of dichloromethane and methanol. In certain embodiments, the solvent is 95:5 dichloromethane:methanol. In certain embodiments, the solvent is 95:5 dichloromethane:methanol. In certain embodiments, the solvent is 90:10 dichloromethane:methanol. In certain embodiments, the solvent is 85:15 dichloromethane:methanol. In certain embodiments, the solvent is 80:20 dichloromethane:methanol. In certain embodiments, the solvent is 75:25 dichloromethane:methanol. In certain embodiments, the solvent is 70:30 dichloromethane:methanol. In certain embodiments, the solvent is 60:40 dichloromethane:methanol. In certain embodiments, the solvent is 50:50 dichloromethane:methanol. In certain embodiments, the solvent is 40:60 dichloromethane:methanol. In certain embodiments, the solvent is 30:70 dichloromethane:methanol. In certain embodiments, the solvent is 20:80 dichloromethane:methanol. In certain embodiments, the solvent is 10:90 dichloromethane:methanol.

In certain embodiments, the solvent is a mixture of dichloromethane and ethanol. In certain embodiments, the solvent is 95:5 dichloromethane:ethanol. In certain embodiments, the solvent is 95:5 dichloromethane:ethanol. In certain embodiments, the solvent is 90:10 dichloromethane:ethanol. In certain embodiments, the solvent is 85:15 dichloromethane:ethanol. In certain embodiments, the solvent is 80:20 dichloromethane:ethanol. In certain embodiments, the solvent is 75:25 dichloromethane:ethanol. In certain embodiments, the solvent is 70:30 dichloromethane:ethanol. In certain embodiments, the solvent is 60:40 dichloromethane:ethanol. In certain embodiments, the solvent is 50:50 dichloromethane:ethanol. In certain embodiments, the solvent is 40:60 dichloromethane:ethanol. In certain embodiments, the solvent is 30:70 dichloromethane:ethanol. In certain embodiments, the solvent is 20:80 dichloromethane:ethanol. In certain embodiments, the solvent is 10:90 dichloromethane:ethanol.

In certain embodiments, the solvent is a mixture of acetone and methanol. In certain embodiments, the solvent is 95:5 acetone:methanol. In certain embodiments, the solvent is 90:10 acetone:methanol. In certain embodiments, the solvent is 85:15 acetone:methanol. In certain embodiments, the solvent is 80:20 acetone:methanol. In certain embodiments, the solvent is 75:25 acetone:methanol. In certain embodiments, the solvent is a 70:30 acetone:methanol. In certain embodiments, the solvent is 60:40 acetone:methanol. In certain embodiments, the solvent is 50:50 acetone:methanol. In certain embodiments, the solvent is 40:60 acetone:methanol. In certain embodiments, the solvent is 30:70 acetone:methanol. In certain embodiments, the solvent is 20:80 dichloromethane:methanol. In certain embodiments, the solvent is 10:90 acetone:methanol.

In certain embodiments, the solvent is a mixture of ethyl acetate and acetonitrile. In certain embodiments, the solvent is 95:5 ethyl acetate:acetonitrile. In certain embodiments, the solvent is 95:5 ethyl acetate:acetonitrile. In certain embodiments, the solvent is 90:10 ethyl acetate:acetonitrile. In certain embodiments, the solvent is 85:15 ethyl acetate:acetonitrile. In certain embodiments, the solvent is 80:20 ethyl acetate:acetonitrile. In certain embodiments, the solvent is 75:25 ethyl acetate:acetonitrile. In certain embodiments, the solvent is 70:30 ethyl acetate:acetonitrile. In certain embodiments, the solvent is 60:40 ethyl acetate:acetonitrile. In certain embodiments, the solvent is 50:50 ethyl acetate:acetonitrile. In certain embodiments, the solvent is 40:60 ethyl acetate:acetonitrile. In certain embodiments, the solvent is 30:70 ethyl acetate:acetonitrile. In certain embodiments, the solvent is 20:80 ethyl acetate:acetonitrile. In certain embodiments, the solvent is 10:90 ethyl acetate:acetonitrile.

In certain embodiments of methods of manufacturing a solid dispersion, the dispersion polymer is selected from the group consisting of hydroxypropyl methylcellulose (HPMC), hydroxypropyl methylcellulose-acetate succinate (HPMC-AS or HPMCAS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, and derivatives or combinations thereof. In certain embodiments, the dispersion polymer is HPMC-AS. In certain embodiments, the dispersion polymer is HPMC. In some embodiments, the dispersion polymer is PVP.

In some embodiments, the dispersion polymer is a particular grade of HPMC-AS. In some embodiments, the dispersion polymer is HPMC-AS, L. In some embodiments, the dispersion polymer is HPMC-AS, M. In some embodiments, the dispersion polymer is HPMC-AS, H. In some embodiments, the dispersion polymer is PVP. In some embodiments, the PVP has a molecular weight from about 7000 Daltons to about 11000 Daltons.

In certain embodiments of methods of manufacturing a solid dispersion, the method further comprises the step of adding an additional element to the first mixture. In certain embodiments, the additional element is a filler, a sweetener, a disintegrant, a wetting agent, a glidant, a lubricant, a surfactant, or any combinations thereof.

In certain embodiments, the compound of Formula (I) has the structure:

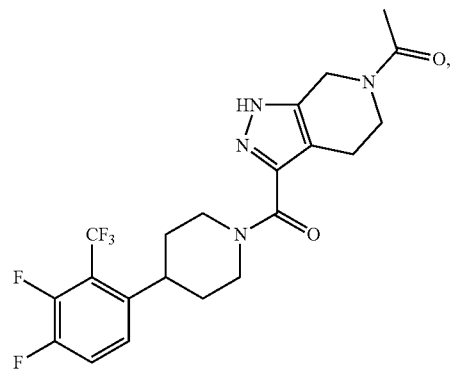 [SMILES: CC(=O)N1CCc2c(C(=O)N3CCC(c4ccc(F)c(F)c4C(F)(F)F)CC3)n[nH]c2C1]

or a pharmaceutically acceptable salt, solvate, polymorph, prodrug, metabolite, N-oxide, stereoisomer, or isomer thereof. In certain embodiments, the compound of Formula (I) has the structure:

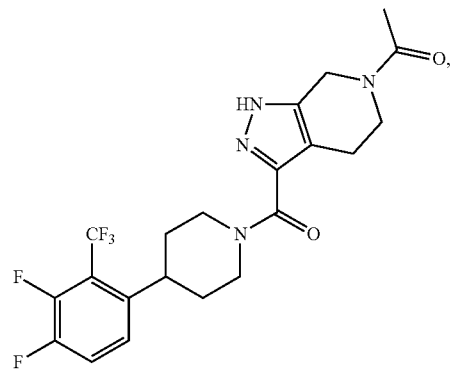 [SMILES: CC(=O)N1CCc2c(C(=O)N3CCC(c4ccc(F)c(F)c4C(F)(F)F)CC3)n[nH]c2C1]

or a pharmaceutically acceptable salt, solvate, polymorph, prodrug, metabolite, N-oxide, stereoisomer, or isomer thereof is formulated as a solid dispersion.

Nanosuspension Pharmaceutical Formulations

Also provided herein are nanosuspension pharmaceutical compositions comprising compounds of Formula (I), especially Compound 1. Nanosuspensions are formulations ideally suited to compounds with low solubility in pharmaceutically acceptable solvents. Such formulations can offer improved bioavailability of such compounds. Nanosuspension typically comprises the desired API in a stable polymorphic form with an average particle size of less than 1000 nm, which is then suspended in a liquid (such as water). Ideally, the API will remain stably suspended in the formulation for an extended period of time without any change to the polymorphic form of the API. Such formulations often comprise additional reagents, such as surfactants or emulsifiers to aid in keeping the API in the suspension.

In one aspect, provided herein, is a nanosuspension pharmaceutical composition comprising: a compound of Formula (I), a pharmaceutically acceptable salt, crystalline, solvate, polymorph, prodrug, metabolite, N-oxide, stereoisomer, or isomer thereof, suspended in a pharmaceutically acceptable solvent. In some embodiments, the compound of Formula (I) is Compound 1. In some embodiments, Compound 1 is the polymorph "Form C" provided herein.

In some embodiments, the nanosuspension pharmaceutical formulation comprises an indicated amount of the compound of Formula (I). In some embodiments, the compound of Formula (I) is present in an amount of about 1 mg/mL to about 500 mg/mL. In some embodiments, the compound of Formula (I) is present in an amount of about 1 mg/mL to about 200 mg/mL. In some embodiments, the compound of Formula (I) is present in an amount of about 1 mg/mL to about 5 mg/mL, about 1 mg/mL to about 10 mg/mL, about 1 mg/mL to about 25 mg/mL, about 1 mg/mL to about 50 mg/mL, about 1 mg/mL to about 100 mg/mL, about 1 mg/mL to about 200 mg/mL, about 5 mg/mL to about 10 mg/mL, about 5 mg/mL to about 25 mg/mL, about 5 mg/mL to about 50 mg/mL, about 5 mg/mL to about 100 mg/mL, about 5 mg/mL to about 200 mg/mL, about 10 mg/mL to about 25 mg/mL, about 10 mg/mL to about 50 mg/mL, about 10 mg/mL to about 100 mg/mL, ab out 10 mg/mL to about 200 mg/mL, about 25 mg/mL to about 50 mg/mL, about 25 mg/mL to about 100 mg/mL, about 25 mg/mL to about 200 mg/mL, about 50 mg/mL to about 100 mg/mL, about 50 mg/mL to about 200 mg/mL, or about 100 mg/mL to about 200 mg/mL. In some embodiments, the compound of Formula (I) is present in an amount of about 1 mg/mL, about 5 mg/mL, about 10 mg/mL, about 25 mg/mL, about 50 mg/mL, about 100 mg/mL, or about 200 mg/mL. In some embodiments, the compound of Formula (I) is present in an amount of at least about 1 mg/mL, about 5 mg/mL, about 10 mg/mL, about 25 mg/mL, about 50 mg/mL, or about 100 mg/mL. In some embodiments, the compound of Formula (I) is present in an amount of at most about 5 mg/mL, about 10 mg/mL, about 25 mg/mL, about 50 mg/mL, about 100 mg/mL, or about 200 mg/mL. In some embodiments, the compound of Formula (I) is present in an amount of about 1 mg/mL to about 200 mg/mL. In some embodiments, the compound of Formula (I) is present in an amount of about 1 mg/mL to about 10 mg/mL. In some embodiments, the compound of Formula (I) is present in an amount of about 5 mg/mL to about 10 mg/mL In some embodiments, the compound of Formula (I) is present in an amount of about 5 mg/mL or about 10 mg/mL.

In some embodiments, the compound of Formula (I) has an average particle size of less than 1000 nm. In some embodiments, the compound of Formula (I) has an average particle size of about 50 nm to about 1,000 nm. In some embodiments, the compound of Formula (I) has an average particle size of about 50 nm to about 100 nm, about 50 nm to about 250 nm, about 50 nm to about 500 nm, about 50 nm to about 750 nm, about 50 nm to about 1,000 nm, about 100 nm to about 250 nm, about 100 nm to about 500 nm, about 100 nm to about 750 nm, about 100 nm to about 1,000 nm, about 250 nm to about 500 nm, about 250 nm to about 750 nm, about 250 nm to about 1,000 nm, about 500 nm to about 750 nm, about 500 nm to about 1,000 nm, or about 750 nm to about 1,000 nm. In some embodiments, the compound of Formula (I) has an average particle size of about 50 nm, about 100 nm, about 250 nm, about 500 nm, about 750 nm, or about 1,000 nm. In some embodiments, the compound of Formula (I) has an average particle size of at least about 50 nm, about 100 nm, about 250 nm, about 500 nm, or about 750 nm. In some embodiments, the compound of Formula (I) has an average particle size of at most about 100 nm, about 250 nm, about 500 nm, about 750 nm, or about 1,000 nm.

The particle size distribution of the resultant suspensions can be measured using any instrumentation. An example is laser diffraction using a Cilas Particle Size Analyser 1190. The images of the particles can be taken using, for example, the microscope "Olympus". The resolution rates can be determined, for example, by a pION µDISS Profiler.

In some embodiments, the compound of Formula (I) is micronized. The compound can be micronized by any suitable method, such as milling or jet milling. In some embodiments, the compound is milled in a solution comprising any additional additives that will be in the final formulation, such as surfactant or excipients.

In some embodiments, the solvent is water. In some embodiments, the solvent is water and an additional solvent. Solvents include, but are not limited to, ethanol, t-butanol, hexane and glycol.

The pH of the aqueous dispersion media can be adjusted by techniques known to those skilled in the art. Ideally, the pH should be one that will be tolerable by the subject, such as near neutral. In some embodiments, the pH of the nanosuspension pharmaceutical formulation is about 7. In some embodiments, the pH of the nanosuspension pharmaceutical formulation is about 6. In some embodiments, the pH of the nanosuspension pharmaceutical formulation is from about 6 to about 8. In some embodiments, the pH of the nanosuspension pharmaceutical formulation is from about 5 to about 9. In some embodiments, the pH of the nanosuspension pharmaceutical formulation is from about 6 to about 7. In some embodiments, the pH of the nanosuspension pharmaceutical formulation is from about 5 to about 7.

In some embodiments, the nanosuspension pharmaceutical formulation further comprises a surfactant. Surfactants are wetting agents that lower the surface tension of a liquid allowing easier spreading and lower the interfacial tension between two liquids. Surfactants are usually organic compounds that are amphiphilic, therefore, they are soluble in both organic solvents and water. Surfactants reduce the surface tension of water by adsorbing at the liquid-gas interface. They also reduce the interfacial tension between oil and water by adsorbing at the liquid-liquid interface.

Surfactants are classified into two primary groups: ionic (anionic, cationic and zwitterionic) (dual charge) and non-ionic.

The examples of non-ionic surfactants include, but are limited to, alkyl poly(ethylene oxide), copolymers of poly (ethylene oxide) and poly(propylene oxide) (a.k.a. poloxamers), (alkyl polyglucosides, such as octyl glucoside, decyl maltoside, fatty alcohols, cetyl alcohol, oleyl alcohol, cocamide MEA, cocamide DEA, polysorbates, such as Tween 20, Tween 80, and dodecyl dimethylamine oxide. In some embodiments, the surfactant comprises a poloxamer. In some embodiments, the surfactant comprises a polysorbate.

The examples of ionic surfactants include, but are limited to, rerfluorooctanoate (PFOA or PFO), pertluorooctanesulfonate (PFOS), sodium dodecyl sulfate (SDS), ammonium lauryl sulfate, sodium lauryl ether sulfate (SLES), alkyl benzene sulfonate, soaps, or a fatty acid salts (anionic), cetyl tri ammonium bromide (CTAB) a.k.a. hexadecyl trimethyl ammonium bromide, and other alkyltrimethylammonium salts, cetylpyridinium chloride (CPC), Polyethoxylated tallow amine (POEA), Benzalkonium chloride (BAC), benzethonium chloride (BZT) (cationic), dodecyl betaine, cocamidopropyl betaine and coco ampho glycinate (zwitterionic). In some embodiments, the surfactant comprises SDS.

In some embodiments, nanosuspension comprises a surfactant at a concentration of about 0.01% to about 1%. In some embodiments, nanosuspension comprises a surfactant at a concentration of about 0.01% to about 0.05%, about 0.01% to about 0.1%, about 0.01% to about 0.2%, about 0.01% to about 0.35%, about 0.01% to about 0.5%, about 0.01% to about 0.75%, about 0.01% to about 1%, about 0.05% to about 0.1%, about 0.05% to about 0.2%, about 0.05% to about 0.35%, about 0.05% to about 0.5%, about 0.05% to about 0.75%, about 0.05% to about 1%, about 0.1% to about 0.2%, about 0.1% to about 0.35%, about 0.1% to about 0.5%, about 0.1% to about 0.75%, about 0.1% to about 1%, about 0.2% to about 0.35%, about 0.2% to about 0.5%, about 0.2% to about 0.75%, about 0.2% to about 1%, about 0.35% to about 0.5%, about 0.35% to about 0.75%, about 0.35% to about 1%, about 0.5% to about 0.75%, about 0.5% to about 1%, or about 0.75% to about 1%. In some embodiments, nanosuspension comprises a surfactant at a concentration of about 0.01%, about 0.05%, about 0.1%, about 0.2%, about 0.35%, about 0.5%, about 0.75%, or about 1%. In some embodiments, nanosuspension comprises a surfactant at a concentration of at least about 0.01%, about 0.05%, about 0.1%, about 0.2%, about 0.35%, about 0.5%, or about 0.75%. In some embodiments, nanosuspension comprises a surfactant at a concentration of at most about 0.05%, about 0.1%, about 0.2%, about 0.35%, about 0.5%, about 0.75%, or about 1%.

In some embodiments, nanosuspension comprises SDS at a concentration of about 0.01% to about 1%. In some embodiments, nanosuspension comprises SDS at a concentration of about 0.01% to about 0.05%, about 0.01% to about 0.1%, about 0.01% to about 0.2%, about 0.01% to about 0.35%, about 0.01% to about 0.5%, about 0.01% to about 0.75%, about 0.01% to about 1%, about 0.05% to about 0.1%, about 0.05% to about 0.2%, about 0.05% to about 0.35%, about 0.05% to about 0.5%, about 0.05% to about 0.75%, about 0.05% to about 1%, about 0.1% to about 0.2%, about 0.1% to about 0.35%, about 0.1% to about 0.5%, about 0.1% to about 0.75%, about 0.1% to about 1%, about 0.2% to about 0.350%, about 0.2% to about 0.5%, about 0.2% to about 0.75%, about 0.2% to about 1%, about 0.35% to about 0.5%, about 0.350% to about 0.75%, about 0.35% to about 10%, about 0.5% to about 0.75%, about 0.5% to about 1%, or about 0.75% to about 1%. In some embodiments, nanosuspension comprises SDS at a concentration of about 0.01%, about 0.05%, about 0.1%, about 0.2%, about 0.35%, about 0.5%, about 0.75%, or about 1%. In some embodiments, nanosuspension comprises SDS at a concentration of at least about 0.01%, about 0.05%, about 0.1%, about 0.2%, about 0.35%, about 0.5%, or about 0.75%. In some embodiments, nanosuspension comprises SDS at a concentration of at most about 0.05%, about 0.1%, about 0.2%, about 0.35%, about 0.5%, about 0.75%, or about 1%.

In some embodiments, the nanosuspension comprises one or more excipients. Suitable excipients include, but are not limited to, PVP, CMC, HPMC, HPC, PEG, PEO, transcutol and glycerin. In some embodiments, the excipient comprises hydroxypropyl methylcellulose (HPMC), hydroxypropyl methylcellulose-acetate succinate (HPMC-AS), hydroxypropyl cellulose (HPC), methyl cellulose, hydroxyethyl methyl cellulose, hydroxyethyl cellulose acetate, hydroxyethyl ethyl cellulose, polyvinyl alcohol polyvinyl acetate copolymers, polyethylene glycol, polyethylene glycol polypropylene glycol copolymers, polyvinylpyrrolidone (PVP), polyethylene polyvinyl alcohol copolymers, polyoxyethylene-polyoxypropylene block copolymers, or any combinations thereof. In some embodiments, the excipient is a low molecular weight polymer.

In some embodiments, the excipient is HPMC, HPMC-AS, HPC, or PVP. In some embodiments, the excipient is HPC.

In some embodiments, nanosuspension comprises an excipient at a concentration of about 0.1% to about 5%. In some embodiments, nanosuspension comprises an excipient at a concentration of about 0.1% to about 0.5%, about 0.1% to about 1%, about 0.1% to about 1.5%, about 0.1% to about 2%, about 0.1% to about 3%, about 0.1% to about 4%, about 0.1% to about 5%, about 0.5% to about 1%, about 0.5% to about 1.5%, about 0.5% to about 2%, about 0.5% to about 3%, about 0.5% to about 4%, about 0.5% to about 5%, about 1% to about 1.5%, about 1% to about 2%, about 1% to about 3%, about 1% to about 4%, about 1% to about 5%, about 1.5% to about 2%, about 1.5% to about 3%, about 1.5% to about 4%, about 1.5% to about 5%, about 2% to about 3%, about 2% to about 4%, about 2% to about 5%, about 3% to about 4%, about 3% to about 5%, or about 4% to about 5%. In some embodiments, nanosuspension comprises an excipient at a concentration of about 0.1%, about 0.5%, about 1%, about 1.5%, about 2%, about 3%, about 4%, or about 5%. In some embodiments, nanosuspension comprises an excipient at a concentration of at least about 0.1%, about 0.5%, about 1%, about 1.5%, about 2%, about 3%, or about 4%. In some embodiments, nanosuspension comprises an excipient at a concentration of at most about 0.5%, about 1%, about 1.5%, about 2%, about 3%, about 4%, or about 5%.

In some embodiments, nanosuspension comprises HPC at a concentration of about 0.1% to about 5%. In some embodiments, nanosuspension comprises HPC at a concentration of about 0.1% to about 0.5%, about 0.1% to about 1%, about 0.1% to about 1.5%, about 0.1% to about 2%, about 0.1% to about 3%, about 0.1% to about 4%, about 0.1% to about 5%, about 0.5% to about 1%, about 0.5% to about 1.5%, about 0.5% to about 2%, about 0.5% to about 3%, about 0.5% to about 4%, about 0.5% to about 5%, about 1% to about 1.5%, about 1% to about 2%, about 1% to about 3%, about 1% to about 4% about 1% to about 5%, about 1.5% to about 2%, about 1.5% to about 3%, about 1.5% to about 4%, about 1.5% to about 5%, about 2% to about 3%, about 2% to about 4%, about 2% to about 5%, about 3% to about 4%, about 3% to about 5%, or about 4% to about 5%. In some embodiments, nanosuspension comprises HPC at a concentration of about 0.1%, about 0.5%, about 1%, about 1.5%, about 2%, about 3%, about 4%, or about 5%. In some embodiments, nanosuspension comprises HPC at a concentration of at least about 0.1%, about 0.5%, about 1%, about 1.5%, about 2%, about 3%, or about 4%. In some embodiments, nanosuspension comprises HPC at a concentration of at most about 0.5%, about 1%, about 1.5%, about 2%, about 3%, about 4%, or about 5%.

In certain embodiments, provided is a nanosuspension wherein the resulting nanosuspension is stable for more than 1, 5, 10, 15, 20 or 25 days at a room temperature (22° C.). In certain embodiments, provided is a nanosuspension wherein the resulting nanosuspension is stable for more than 1, 2, 3 or 4 weeks at a room temperature (22° C.). In certain embodiments, provided is a nanosuspension wherein the resulting nanosuspension is stable for more than 1, 3, 6, 12, 18 or 24 months at a room temperature (22° C.). In some embodiments, stability is measured by a change in particle size or particle size distribution of the compound. In some embodiments, stability is measured by the chemical stability of the compound. In some embodiments, stability is measured by a change in the polymorph of the compound.

Polymorphs of Compound 1

Provided herein is a new, unique polymorph of Compound 1. This polymorph, described herein as "Form C." This polymorph was found to be readily prepared from a variety of methods provided in the Examples section. Form C is a crystalline solid having high thermodynamic stability, making it well suited for pharmaceutical formulations of Compound 1.

Figure 16:
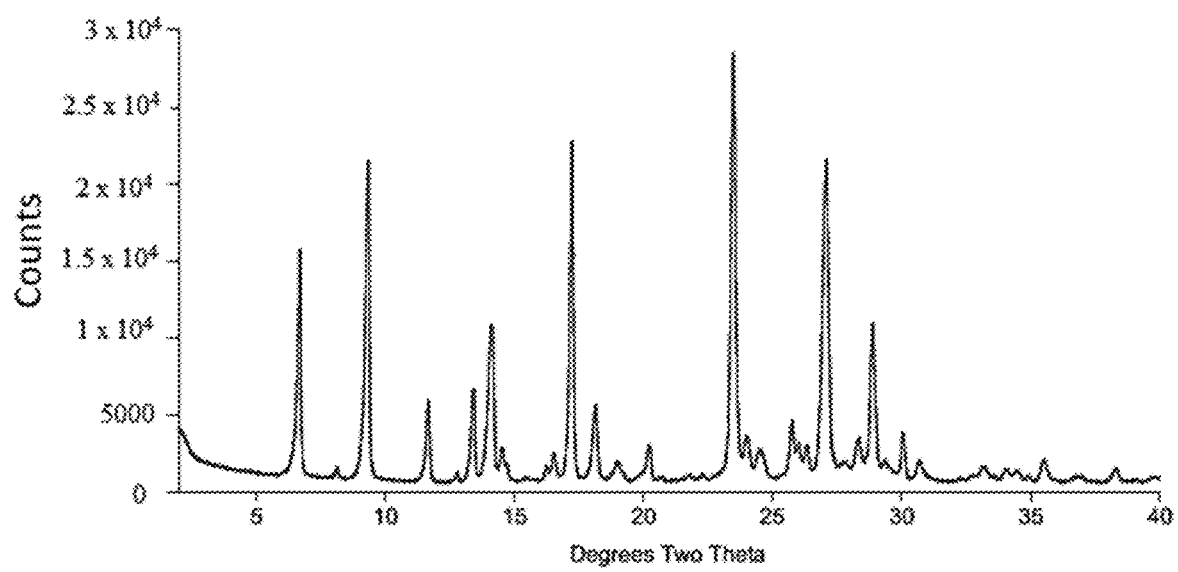
FIG. 16 shows an XRPD pattern of Compound 1 in polymorph Form C.

Provided herein is a polymorph of Compound 1 having an X-ray powder diffraction pattern shown in FIG. 16. FIG. 16 shows numerous peaks at many degrees two theta, including with limitation at approximately 6.7, 9.3, 14.1, 17.2, 23.5, 27.1, and/or 29.0. XRPD peak values in the application refer to those obtained using a copper source with a wavelength of 1.5406 angstrom unless otherwise noted.

In one aspect, provided herein, is polymorph of a compound of Formula (I) having the structure

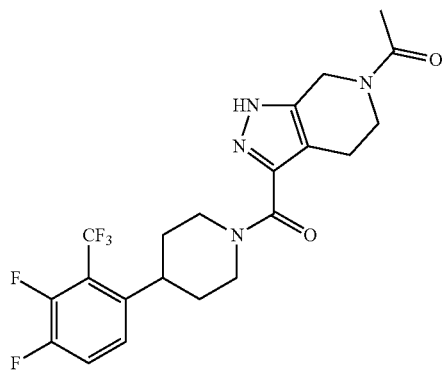 [SMILES: CC(=O)N1CCc2c(C(=O)N3CCC(c4ccc(F)c(F)c4C(F)(F)F)CC3)n[nH]c2C1]

wherein the compound of Formula (I) exhibits an x-ray powder diffraction pattern having at least three characteristic peaks expressed in degrees two theta (+/−0.5 degree theta) at 6.7, 9.3, 14.1, 17.2, 23.5, 27.1, and/or 29.0. In some embodiments, the polymorph exhibits an x-ray powder diffraction pattern having at least four characteristic peaks expressed in degrees two theta (+/−0.5 degree theta) at 6.7, 9.3, 14.1, 17.2, 23.5, 27.1, and/or 29.0. In some embodiments, the polymorph exhibits an x-ray powder diffraction pattern having at least five characteristic peaks expressed in degrees two theta (+/−0.5 degree theta) at 6.7, 9.3, 14.1, 17.2, 23.5, 27.1, and/or 29.0. In some embodiments, the polymorph exhibits an x-ray powder diffraction pattern having at least six characteristic peaks expressed in degrees two theta (+/−0.5 degree theta) at 6.7, 9.3, 14.1, 17.2, 23.5, 27.1, and/or 29.0. In some embodiments, the polymorph exhibits an x-ray powder diffraction pattern having characteristic peaks expressed in degrees two theta (+/−0.5 degree theta) at 6.7, 9.3, 14.1, 17.2, 23.5, 27.1, and/or 29.0.

In one aspect, provided herein, is polymorph of a compound of Formula (I) having the structure

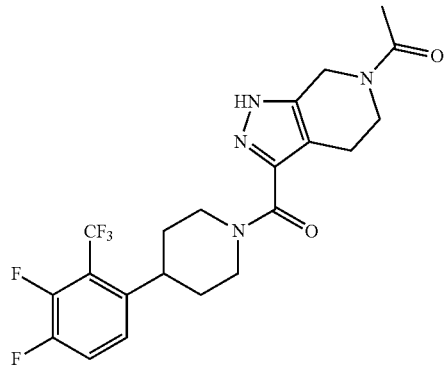 [SMILES: CC(=O)N1CCc2c(C(=O)N3CCC(c4ccc(F)c(F)c4C(F)(F)F)CC3)n[nH]c2C1]

wherein the polymorph exhibits an x-ray powder diffraction pattern having at least three characteristic peaks expressed in degrees two theta (+/−1.0 degree theta) at 6.7, 9.3, 14.1, 17.2, 23.5, 27.1, and/or 29.0. In some embodiments, the polymorph exhibits an x-ray powder diffraction pattern having at least four characteristic peaks expressed in degrees two theta (+/−1.0 degree theta) at 6.7, 9.3, 14.1, 17.2, 23.5, 27.1, and/or 29.0. In some embodiments, the polymorph exhibits an x-ray powder diffraction pattern having at least five characteristic peaks expressed in degrees two theta (+/−1.0 degree theta) at 6.7, 9.3, 14.1, 17.2, 23.5, 27.1, and/or 29.0. In some embodiments, the polymorph exhibits an x-ray powder diffraction pattern having at least six characteristic peaks expressed in degrees two theta (+/−1.0 degree theta) at 6.7, 9.3, 14.1, 17.2, 23.5, 27.1, and/or 29.0. In some embodiments, the polymorph exhibits an x-ray powder diffraction pattern having characteristic peaks expressed in degrees two theta (+/−1.0 degree theta) at 6.7, 9.3, 14.1, 17.2, 23.5, 27.1, and/or 29.0.

In one aspect, provided herein, is polymorph of a compound of Formula (I) having the structure

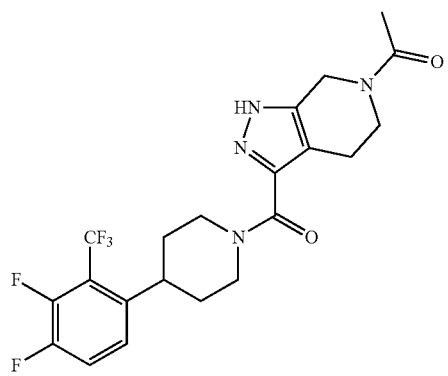 [SMILES: CC(=O)N1CCc2c(C(=O)N3CCC(c4ccc(F)c(F)c4C(F)(F)F)CC3)n[nH]c2C1]

wherein the polymorph exhibits an x-ray powder diffraction pattern having at least three characteristic peaks expressed in degrees two theta (+/−0.2 degree theta) at 6.7, 9.3, 14.1, 17.2, 23.5, 27.1, and/or 29.0. In some embodiments, the polymorph exhibits an x-ray powder diffraction pattern having at least four characteristic peaks expressed in degrees two theta (+/−0.2 degree theta) at 6.7, 9.3, 14.1, 17.2, 23.5, 27.1, and/or 29.0. In some embodiments, the polymorph exhibits an x-ray powder diffraction pattern having at least five characteristic peaks expressed in degrees two theta (+/−0.2 degree theta) at 6.7, 9.3, 14.1, 17.2, 23.5, 27.1, and/or 29.0. In some embodiments, the polymorph exhibits an x-ray powder diffraction pattern having at least six characteristic peaks expressed in degrees two theta (+/−0.2 degree theta) at 6.7, 9.3, 14.1, 17.2, 23.5, 27.1, and/or 29.0. In some embodiments, the polymorph exhibits an x-ray powder diffraction pattern having characteristic peaks expressed in degrees two theta (+/−0.2 degree theta) at 6.7, 9.3, 14.1, 17.2, 23.5, 27.1, and/or 29.0.

In some embodiments, the polymorph exhibits an x-ray powder diffraction pattern comprising characteristic peaks expressed in degrees two theta (+/−0.2 degree theta) at 6.7, 9.3, and 14.1. In some embodiments, the polymorph exhibits an x-ray powder diffraction pattern comprising characteristic peaks expressed in degrees two theta (+/−0.2 degree theta) at 6.7, 9.3, and 17.2. In some embodiments, the polymorph exhibits an x-ray powder diffraction pattern comprising characteristic peaks expressed in degrees two theta (+/−0.2 degree theta) at 6.7, 9.3, and 23.5. In some embodiments, the polymorph exhibits an x-ray powder diffraction pattern comprising characteristic peaks expressed in degrees two theta (+/−0.2 degree theta) at 6.7, 9.3, and 27.1. In some embodiments, the polymorph exhibits an x-ray powder diffraction pattern comprising characteristic peaks expressed in degrees two theta (+/−0.2 degree theta) at 6.7, 9.3, and 29.0.

In some embodiments, the polymorph exhibits an x-ray powder diffraction pattern comprising characteristic peaks expressed in degrees two theta (+/−0.2 degree theta) at 6.7, 14.1, and 17.2. In some embodiments, the polymorph exhibits an x-ray powder diffraction pattern comprising characteristic peaks expressed in degrees two theta (+/−0.2 degree theta) at 6.7, 14.1, and 23.5. In some embodiments, the polymorph exhibits an x-ray powder diffraction pattern comprising characteristic peaks expressed in degrees two theta (+/−0.2 degree theta) at 6.7, 14.1, and 27.1. In some embodiments, the polymorph exhibits an x-ray powder diffraction pattern comprising characteristic peaks expressed in degrees two theta (+/−0.2 degree theta) at 6.7, 14.1, and 29.0.

In some embodiments, the polymorph exhibits an x-ray powder diffraction pattern comprising characteristic peaks expressed in degrees two theta (+/−0.2 degree theta) at 9.3, 14.1, and 17.2. In some embodiments, the polymorph exhibits an x-ray powder diffraction pattern comprising characteristic peaks expressed in degrees two theta (+/−0.2 degree theta) at 9.3, 14.1, and 23.5. In some embodiments, the polymorph exhibits an x-ray powder diffraction pattern comprising characteristic peaks expressed in degrees two theta (+/−0.2 degree theta) at 9.3, 14.1, and 27.1. In some embodiments, the polymorph exhibits an x-ray powder diffraction pattern comprising characteristic peaks expressed in degrees two theta (+/−0.2 degree theta) at 9.3, 14.1, and 29.0.

In some embodiments, the polymorph exhibits an x-ray powder diffraction pattern comprising characteristic peaks expressed in degrees two theta (+/−0.2 degree theta) at 9.3, 14.1, and 17.2. In some embodiments, the polymorph exhibits an x-ray powder diffraction pattern comprising characteristic peaks expressed in degrees two theta (+/−0.2 degree theta) at 9.3, 14.1, and 23.5. In some embodiments, the polymorph exhibits an x-ray powder diffraction pattern comprising characteristic peaks expressed in degrees two theta (+/−0.2 degree theta) at 9.3, 14.1, and 27.1. In some embodiments, the polymorph exhibits an x-ray powder diffraction pattern comprising characteristic peaks expressed in degrees two theta (+/−0.2 degree theta) at 9.3, 14.1, and 29.0.

In some embodiments, the polymorph exhibits an x-ray powder diffraction pattern comprising characteristic peaks expressed in degrees two theta (+/−0.2 degree theta) at 14.1, 17.2, and 23.5. In some embodiments, the XRPD pattern further comprises a peak at 29.0 (+/−0.2 degree theta). In some embodiments, the XRPD pattern further comprises a peak at 27.1 (+/−0.2 degree theta). In some embodiments, the XRPD pattern further comprises a peak at 9.3 (+/−0.2 degree theta). In some embodiments, the XRPD pattern further comprises a peak at 6.7 (+/−0.2 degree theta).

In some embodiments, the polymorph exhibits an x-ray powder diffraction pattern comprising characteristic peaks expressed in degrees two theta (+/−0.2 degree theta) at 9.3, 17.2, 23.5, and 27.1. In some embodiments, the XRPD pattern further comprises a peak at 14.1(+/−0.2 degree theta). In some embodiments, the XRPD pattern further comprises a peak at 29.0 (+/−0.2 degree theta). In some embodiments, the XRPD pattern further comprises a peak at 6.7 (+/−0.2 degree theta).

In some embodiments, the polymorph exhibits an x-ray powder diffraction pattern comprising characteristic peaks expressed in degrees two theta (+/−0.2 degree theta) at 6.7, 9.3, 17.2, and 23.5. In some embodiments, the XRPD pattern further comprises a peak at 14.1(+/−0.2 degree theta). In some embodiments, the XRPD pattern further comprises a peak at 29.0 (+/−0.2 degree theta). In some embodiments, the XRPD pattern further comprises a peak at 27.1 (+/−0.2 degree theta).

In some embodiments, the polymorph exhibits an x-ray powder diffraction pattern comprising characteristic peaks expressed in degrees two theta (+/−0.2 degree theta) at 6.7, 9.3, 17.2, 23.5, and 27.1. In some embodiments, the XRPD pattern further comprises a peak at 14.1(+/−0.2 degree theta). In some embodiments, the XRPD pattern further comprises a peak at 29.0 (+/−0.2 degree theta).

In some embodiments, the polymorph exhibits an x-ray powder diffraction pattern comprising characteristic peaks expressed in degrees two theta (+/−0.5 degree theta) at 6.7, 9.3, 17.2, 23.5, and 27.1. In some embodiments, the XRPD pattern further comprises a peak at 14.1(+/−0.5 degree theta). In some embodiments, the XRPD pattern further comprises a peak at 29.0 (+/−0.5 degree theta).

In some embodiments, the XRPD pattern comprises peaks substantially identical to those shown in FIG. 16.

In some embodiments, the polymorph exhibits Differential Scanning calorimetry (DSC) of an endotherm at about 228° C.

Figure 15:
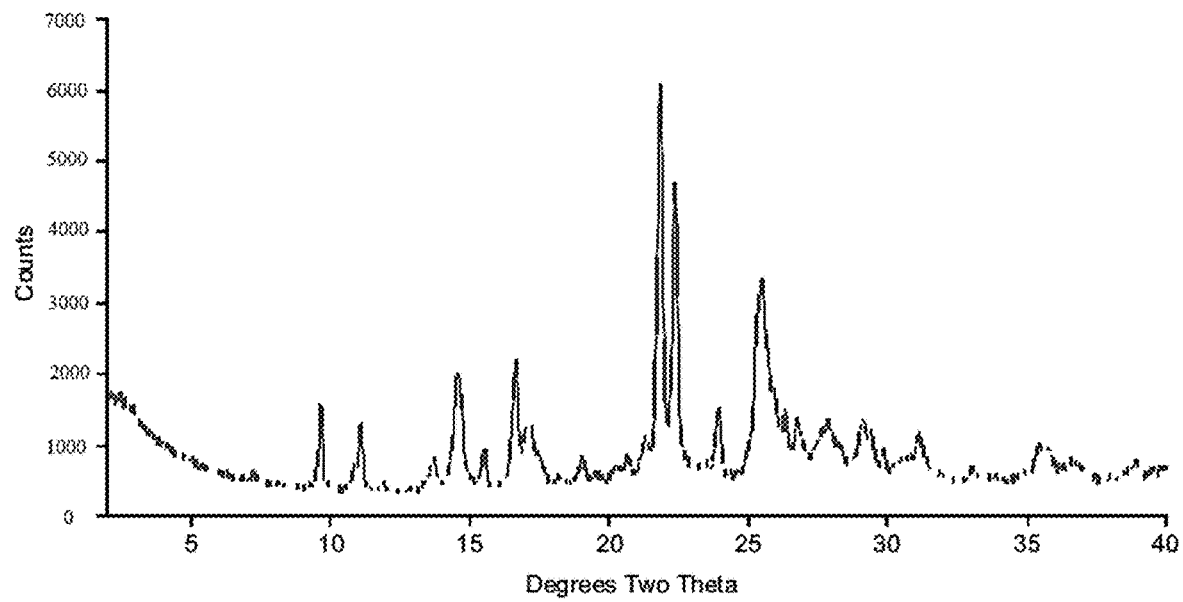
FIG. 15 shows an XRPD pattern of Compound 1 in polymorph Form A.

Also provided herein is a polymorph of Compound 1, referred to herein as Form A, having an XRPD pattern substantially identical to that shown in FIG. 15.

Methods of Dosing and Treatment Regimens

The dose of the composition comprising at least one compound of Formula (I) as described herein differ, depending upon the patient's condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome), or a lessening of symptom severity. Optimal doses are generally determined using experimental models and/or clinical trials. The optimal dose depends upon the body mass, weight, or blood volume of the patient.

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, in which the mammal previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Oral doses typically range from about 1.0 mg to about 1000 mg, one to four times, or more, per day. In general, however, doses employed for adult human treatment are typically in the range of 0.01 mg to 5000 mg per day. In certain embodiments, oral doses range from about 0.1 mg to about 20 mg per day. In certain embodiments, oral doses range from about 0.5 mg to about 50 mg per day. In certain embodiments, oral dosages range from about 1 mg to about 10 mg per day. In one aspect, doses employed for adult human treatment are from about 1 mg to about 1000 mg per day. In one embodiments, the desired dose is conveniently presented in a single dose or in divided doses administered simultaneously or at appropriate intervals, for example as two, three, four or more sub-doses per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, ab out 185 mg, about 190 mg, about 195 mg, about 200 mg, about 225 mg, about 240 mg, about 250 mg, about 275 mg, about 300 mg, about 325 mg, about 350 mg, about 375 mg, about 400 mg, about 425 mg, about 450 mg, about 475 mg, or about 500 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg, about 1 mg, about 5 mg, about 10 mg, about 15 mg, or about 20 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to about 0.1 mg, up to about 0.5 mg, up to about 1 mg, up to about 5 mg, up to about 10 mg, up to about 15 mg, up to about 20 mg, up to about 25 mg, up to about 30 mg, up to about 35 mg, up to about 40 mg, up to about 45 mg, up to about 50 mg, up to about 55 mg, up to about 60 mg, up to about 65 mg, up to about 70 mg, up to about 75 mg, up to about 80 mg, up to about 85 mg, up to about 90 mg, up to about 95 mg, up to about 100 mg, up to about 105 mg, up to about 110 mg, up to about 115 mg, up to about 120 mg, up to about 125 mg, up to about 130 mg, up to about 135 mg, up to about 140 mg, up to about 145 mg, up to about 150 mg, up to about 155 mg, up to about 160 mg, up to about 165 mg, up to about 170 mg, up to about 175 mg, up to about 180 mg, up to about 185 mg, up to about 190 mg, up to about 195 mg, up to about 200 mg, up to about 225 mg, up to about 240 mg, up to about 250 mg, up to about 275 mg, up to about 300 mg, up to about 325 mg, up to about 350 mg, up to about 375 mg, up to about 400 mg, up to about 425 mg, up to about 450 mg, up to about 475 mg, or up to about 500 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to about 0.1 mg, up to about 0.5 mg, up to about 1 mg, up to about 5 mg, up to about 10 mg, up to about 15 mg, or up to about 20 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 0.1 mg, least 0.5 mg, least 1 mg, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, at least 240 mg, at least 250 mg, at least 275 mg, at least 300 mg, at least 325 mg, at least 350 mg, at least 375 mg, at least 400 mg, at least 425 mg, at least 450 mg, at least 475 mg, or at least 500 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 0.1 mg, at least 0.5 mg, at least 1 mg, at least 5 mg, at least 10 mg, at least 15 mg, at least 20 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg, about 1 mg, about 5 mg, about 10 mg, about 25 mg, about 50 mg, about 75 mg, about 100 mg, about 150 mg, about 200 mg, or about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg, about 1 mg, about 5 mg, about 10 mg, about 15 mg, or about 20 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.1 mg, up to 0.5 mg, up to 1 mg, up to 5 mg, up to 10 mg, up to 25 mg, up to 50 mg, up to 100 mg, or up to 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 0.1 mg, at least 0.5 mg, at least 1 mg, at least 5 mg, at least 10 mg, at least 25 mg, at least 50 mg, at least 100 mg, or at least 200 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg per day, about 0.5 mg per day, about 1 mg per day, about 5 mg per day, about 10 mg per day, about 15 mg per day, about 20 mg per day, about 25 mg per day, about 50 mg per day, about 75 mg per day, about 100 mg per day, about 150 mg per day, about 200 mg per day, or about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg per day, about 0.5 mg per day, about 1 mg per day, about 5 mg per day, about 10 mg per day, about 25 mg per day, or about 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.1 mg per day, up to 0.5 mg per day, up to 1 mg per day, up to 5 mg per day, up to 10 mg per day, up to 25 mg per day, up to 50 mg per day, up to 100 mg per day, or up to 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least 0.1 mg per day, at least 0.5 mg per day, at least 1 mg per day, at least 5 mg per day, at least 10 mg per day, at least 25 mg per day, at least 50 mg per day, at least 100 mg per day, or at least 200 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 20 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 10 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg to about 20 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.5 mg to about 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg to about 10 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg to about 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 500 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of up to 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 10 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 1 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.1 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of up to 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 25 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 10 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 1 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.1 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 10 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 25 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 10 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg per day.

In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 400 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 200 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 150 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 100 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 75 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 50 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 25 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 10 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 1 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 0.5 mg. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 0.1 mg.

In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 400 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 200 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 150 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 100 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 75 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 50 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 25 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 10 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 1 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 0.5 mg per day. In some embodiments, a compound of Formula (I), a pharmaceutically acceptable salt, solvate, polymorph, prodrug, metabolite, N-oxide, stereoisomer, or isomer thereof is administered to a subject or patient in an amount of at least about 0.1 mg per day.

In one embodiment, the daily dosages appropriate for the compound of Formula (I) described herein, or a pharmaceutically acceptable salt thereof, are from about 0.01 to about 50 mg/kg per body weight. In certain embodiments the daily dosages are from about 0.01 to about 25, about 0.01 to about 1, about 0.1 to about 5, about 1 to about 10, about 1 to about 5, about 0.5 to about 5 or about 5 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal. In some embodiments, a compound of Formula (I), a pharmaceutically acceptable salt, solvate, polymorph, prodrug, metabolite, N-oxide, stereoisomer, or isomer thereof is administered orally or parenterally to the subject in need thereof. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration. In some embodiments, a compound of Formula (I), a pharmaceutically acceptable salt, solvate, polymorph, prodrug, metabolite, N-oxide, stereoisomer, or isomer thereof is administered orally or intravenously to a subject in need thereof. In some embodiments, a compound of Formula (I), a pharmaceutically acceptable salt, solvate, polymorph, prodrug, metabolite, N-oxide, stereoisomer, or isomer thereof is administered orally to a subject in need thereof. In some embodiments, a compound of Formula (I), a pharmaceutically acceptable salt, solvate, polymorph, prodrug, metabolite, N-oxide, stereoisomer, or isomer thereof is administered intravenously to a subject in need thereof.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily. In some embodiments, the compounds of Formula (I) described herein are administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the heterocyclic RBP4 inhibitory compounds described herein, or a pharmaceutically acceptable salt, solvate, polymorph, prodrug, metabolite, N-oxide, stereoisomer, or isomer thereof, are administered daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 4%5% 50%, 55%, 60%, 65%, 70%, 75%, 80%, 85%, 90%, 95%, and 100%. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 7 days. In one embodiment, the length of the drug holiday is 7 days. In one embodiment, the length of the drug holiday is 14 days. In one embodiment, the length of the drug holiday is 28 days.

In some embodiments, a compound of Formula (I) is administered as a pharmaceutical composition. In any of the aforementioned aspects are further embodiments wherein a compound of Formula (I) is administered to a subject as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg, about 1 mg, about 5 mg, about 10 mg, about 25 mg, about 50 mg, about 75 mg, about 100 mg, about 150 mg, about 200 mg, or about 400 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg, about 0.5 mg about 1 mg, about 5 mg, about 10 mg, about 15 mg, or about 20 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of up to 0.1 mg, up to 0.5 mg, up to 1 mg, up to 5 mg, up to 10 mg, up to 25 mg, up to 50 mg, up to 100 mg, or up to 200 mg as part of a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of at least 0.1 mg, at least 0.5 mg, at least 1 mg at least 5 mg, at least 10 mg, at least 25 mg, at least 50 mg, at least 100 mg, or at least 200 mg as a pharmaceutical composition comprising a solid dispersion comprising the compound of Formula (I).

In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg as a pharmaceutical composition comprising a solid dispersion comprising a compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.5 mg as a pharmaceutical composition comprising a solid dispersion comprising a compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg as a pharmaceutical composition comprising a solid dispersion comprising a compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 5 mg as a pharmaceutical composition comprising a solid dispersion comprising a compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 10 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 15 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 20 mg as a pharmaceutical composition comprising a solid dispersion comprising the compound of Formula (I).

In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 20 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 100 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 1 mg to about 500 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg to about 1000 mg as a pharmaceutical composition comprising a solid dispersion comprising the compound of Formula (I). In some embodiments, a compound of Formula (I), a pharmaceutically acceptable salt, solvate, polymorph, prodrug, metabolite, N-oxide, stereoisomer, or isomer thereof is administered to a subject or patient in an amount of about 0.1 mg to about 20 mg as a pharmaceutical composition comprising a solid dispersion comprising the compound of Formula (I).

EXAMPLES

Example 1: Compound 1 Treatment of a Macular Degeneration Mouse Model

Figure 2:
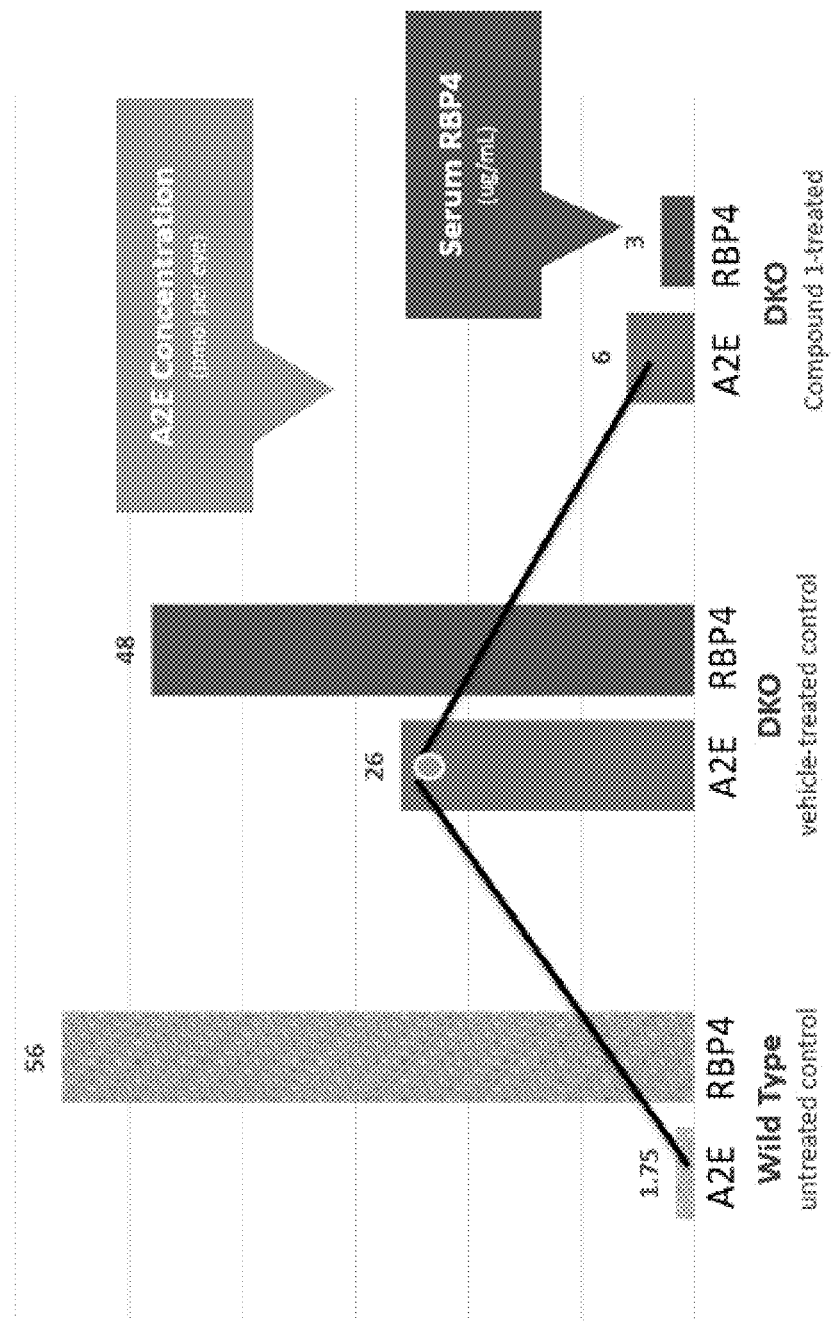
FIG. 2 is a graph of bisretinoid A2E (pmol in the eye) and RBP4 (serum) levels for ABCA4−/−RDH8−/− mice either untreated, treated with vehicle, or treated with Compound 1. Mice treated with Compound 1 had an 80% reduction in bisretinoid accumulation (p=0.003; unpaired t-test).
Figure 3:
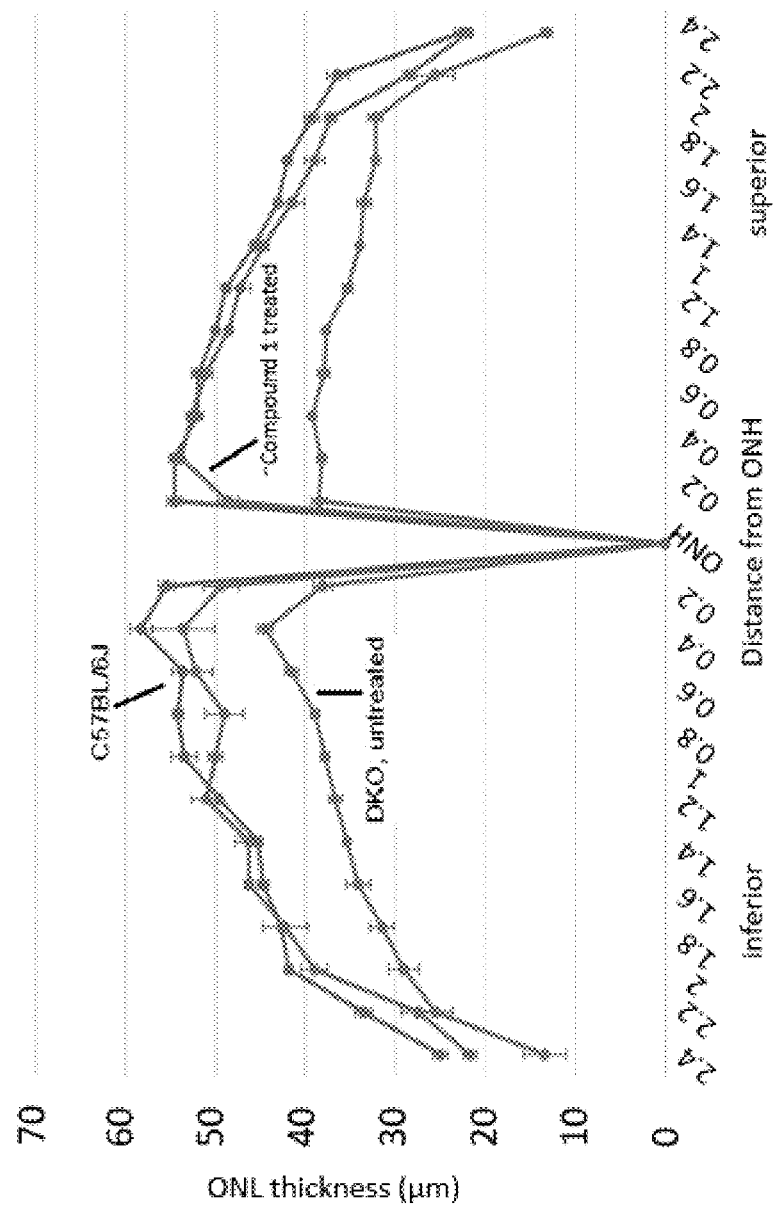
FIG. 3 is a graph of outer nuclear layer (ONL) thickness (μm) as a function of distance (μm) from the optic nerve (ONH). ONL is the cell layer consisting of photoreceptor cell bodies (rods and cones). Dry AMD or STGD is often associated with thinning of the ONL and the loss of photoreceptor cells, indicating macular degeneration. ONL thickness was significantly decreased in the diseased group (abcd4/rdh8 knockout mice), as compared to the diseased group treated with Compound 1 wherein the ONL was preserved.

Abcd4/rdh8 double knockout mice were either untreated or treated with Compound 1. Wild type C57BL/6J mice were also used as a normal control. Mice treated with Compound 1 had significantly lower levels of A2E in the retina, and lower levels of RBP4 in serum. (FIG. 2). Diseases such as dry AMD or Stargardt are associated with thinning of the outer nuclear layer (ONL) of the eye and the loss of photoreceptor cells, indicating macular degeneration. ONL thickness was significantly decreased in the diseased group (abcd4/rdh8 knockout mice), as compared to the diseased group treated with Compound 1, wherein the ONL was preserved (FIG. 3).

Example 2: Phase 1 Single-Dose Human Clinical Study for Compound 1

Subjects. The subject population consisted of 40 healthy volunteers.

Objectives. Objectives of the study were to characterize the systemic and ocular safety of single doses of Compound 1, characterize the pharmacokinetics (PK) of single doses of Compound 1, and determine effects of single doses of Compound 1 on serum levels of retinol binding protein 4 (RBP4), a pharmacodynamics (PD) marker.

Study Design and Duration. The study was a randomized, double blind, placebo-controlled, sequential single dose study. There were 5 dose levels. Each cohort consisted of 8 subjects, 6 receiving Compound 1 and 2 subjects receiving placebo.

Single Ascending Dose Treatment Group. Cohorts 1-3 resided in the research unit from Day −1 through Day 3; Cohorts 4 and 5 on Days −1 to 4. On Day −1 baseline safety and PD markers were obtained. Subjects received a single oral dose on the morning of Day 1. Safety, PK and PD were obtained through Day 3 in early cohorts, though Day 4 in later.

Number of Subjects. 40 subjects were in the single dose ascending group.

Safety evaluation. Safety was evaluated by collecting adverse events, physical examination, Ocular examination (including slit lamp biomicroscopy, dilated ophthalmoscopy and intraocular pressure), Visual acuity, D-28 color vision text, Visual fields, Night vision questionnaire (multiple dose only), Vital signs (blood pressure, heart rate, temperature, respiratory rate), Weight, CBC with differential and platelets, serum chemistry, urinalysis, and ECG.

Twelve lead ECG were performed following recommendations in ICH E14 regarding evaluation of QTc prolongation in patients in early stage clinical trials. ECGs were performed in triplicate on Days 1, 2, 8, 15, and 16. Visual acuity was measured using Early Treatment of Diabetic Retinopathy Study (ETDRS) Visual Acuity charts 1 and 2. The chart was placed on an ETDRS light box which is hung at eye level on the wall or placed on a stand. Room lighting was at office levels and uniform between the subject and the light box. The distance from the patient's eyes to the Visual Acuity Chart was 4.0 meters. If vision tests were performed on the same day as an ERG, they were completed prior to pupil dilation.

Outcome Measures (PK). PK sampling of plasma was conducted in all subjects (for example predose, 0.5, 1, 1.5, 2, 3, 4, 8, 8, 10, 12, 16, 24, 36 and 48 hours post dose on Days 1-3 and 15-17; trough predose on other days; and times were finalized based on toxicokinetics). Compound 1 concentrations were determined using a high-pressure liquid chromatography coupled with a mass spectrometer (LC/MS/MS) method.

Outcome Measures (PD). Serum RBP4 was measured using a validated commercial ELISA assay. Full-field ERG measurements were recorded after pupil dilation using 10% tropicamide and 30 minutes of dark adaptation at baseline and on Day 1 (approximately 6 hours), Day 2 (24-36 hours post dose), and Day 4 (highest dose cohorts only). Responses were obtained from both eyes simultaneously and include the International Society for Clinical Electrocardiography of Vision (ISCEV) standard rod response (0.03 cd/m$^2$-seconds) and combined response (1.5 cd/m$^2$-seconds) in the dark, and the 31-Hz flicker response (2.25 cd/m$^2$-seconds) and 1-Hz cone response (2.25 cd/m$^2$-seconds) in the presence of a background illumination (34 cd/m$^2$).

Inhibition of the visual cycle was evidenced by the delay in restoration of the ERG b-wave amplitude following the photobleach is measured. After a 10-minute exposure to a full-field bleaching light (556 cd/m$^2$), recovery of the ERG was measured for 60 minutes at 10-minute intervals.

Investigational Product. Compound 1 was provided as micronized powder in capsules. The dose levels were 25 mg, 50 mg, 100 mg, 200 mg, and 400 mg.

Target therapeutic range. Defined as reducing and maintaining RBP4 serum concentration below 1 µM (2 mg/dL) was defined in Fenretinides Phase 2b trial in dry AMD patients with geographic atrophy.

Statistical Analysis. All subjects who received IP are included in the safety population. All subjects who received IP and have at least one post-treatment sample or determination were included in the PK analysis population. Analysis was by treatment assignment. Safety was evaluated by monitoring AEs, and by change from baseline on examinations and laboratory studies. The AEs were coded using the Medical Dictionary for Regulatory Activities (MedDRA) and summarized by system organ class (SOC) and preferred term, by severity, by relationship to study drug and study procedure, and by study drug dose. ECG parameters analyzed include heart rate, PR, QRS, QT, QTcB and QTcF intervals. Analysis of other examinations were specified in the protocol.

PK parameters were summarized using descriptive statistics (mean, standard deviation, coefficient of variation [CV], median, minimum, and maximum) by treatment. Geometric means were determined for $AUC_{0-inf}$, $AUC_{0-t}$, and $C_{max}$. The following PK parameters were determined: maximum observed plasma concentration ($C_{max}$) and time of the maximum observed plasma concentration ($T_{max}$), obtained directly from the data without interpolation; the apparent terminal elimination rate constant ($\lambda_Z$), determined by log-linear regression of the terminal plasma concentrations; area under the plasma concentration-time curve from time 0 to the time of the last measureable concentration ($AUC_{0-t}$), calculated by the linear trapezoidal method; apparent plasma terminal elimination half-life ($t_{1/2}$), calculated as $0.693/\lambda_Z$; area under the plasma concentration-time curve from time 0 to infinity ($AUC_{0-inf}$) where $AUC_{0-inf}=AUC_{0-t}+C_t/\lambda_Z$ and $C_t$ was the last measureable concentration; and apparent total plasma clearance (CL/F); and apparent volume of distribution during the terminal phase ($V_z/F$).

The following outcome measures were calculated for ERGs: Absolute dark adapted prebleach rod amplitude at each time point; dark adapted prebleach rod amplitude at each time point as % baseline; recovery from photobleaching—% rod amplitude at 60 minutes recovery versus rod amplitude immediately prior to bleaching; and time to >90% recovery of rod amplitude from photobleaching.

Figure 4A:
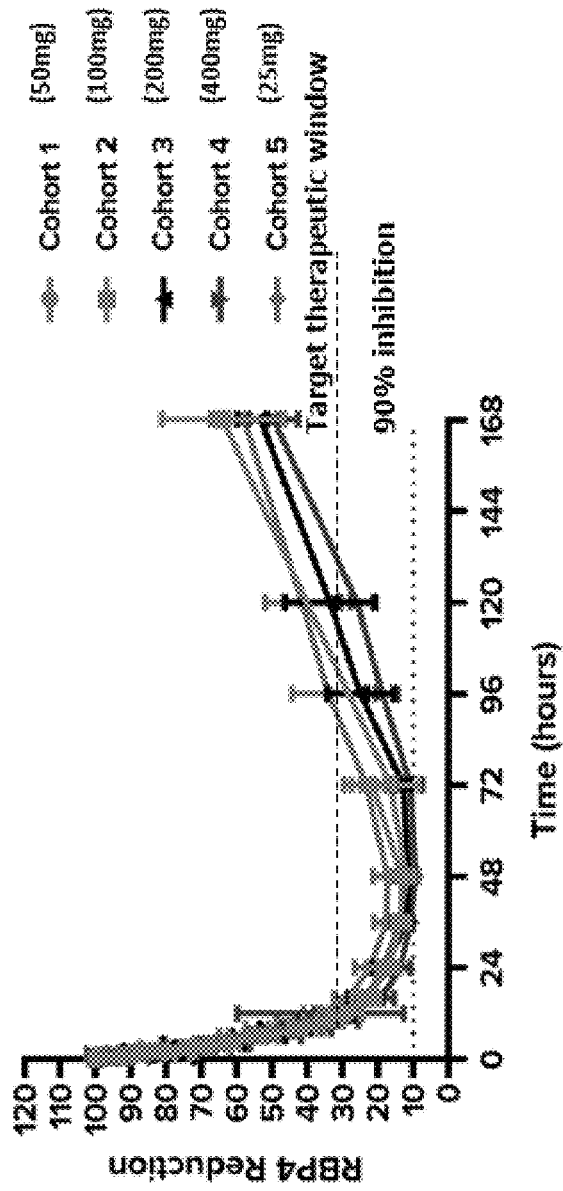
FIG. 4A is a graph of percent mean RBP4 reduction from baseline as a function of time (hours) for five cohorts comprising a total of 32 healthy adults in a randomized, double-blind, placebo-controlled Phase 1 clinical trial. Each cohort was given a single dose of 50 mg (Cohort 1), 100 mg (Cohort 2), 200 mg (Cohort 3), 400 mg (Cohort 4), 25 mg (Cohort 5) of Compound 1, or a placebo. Individuals receiving placebo were not included in the graph.
Figure 4B:
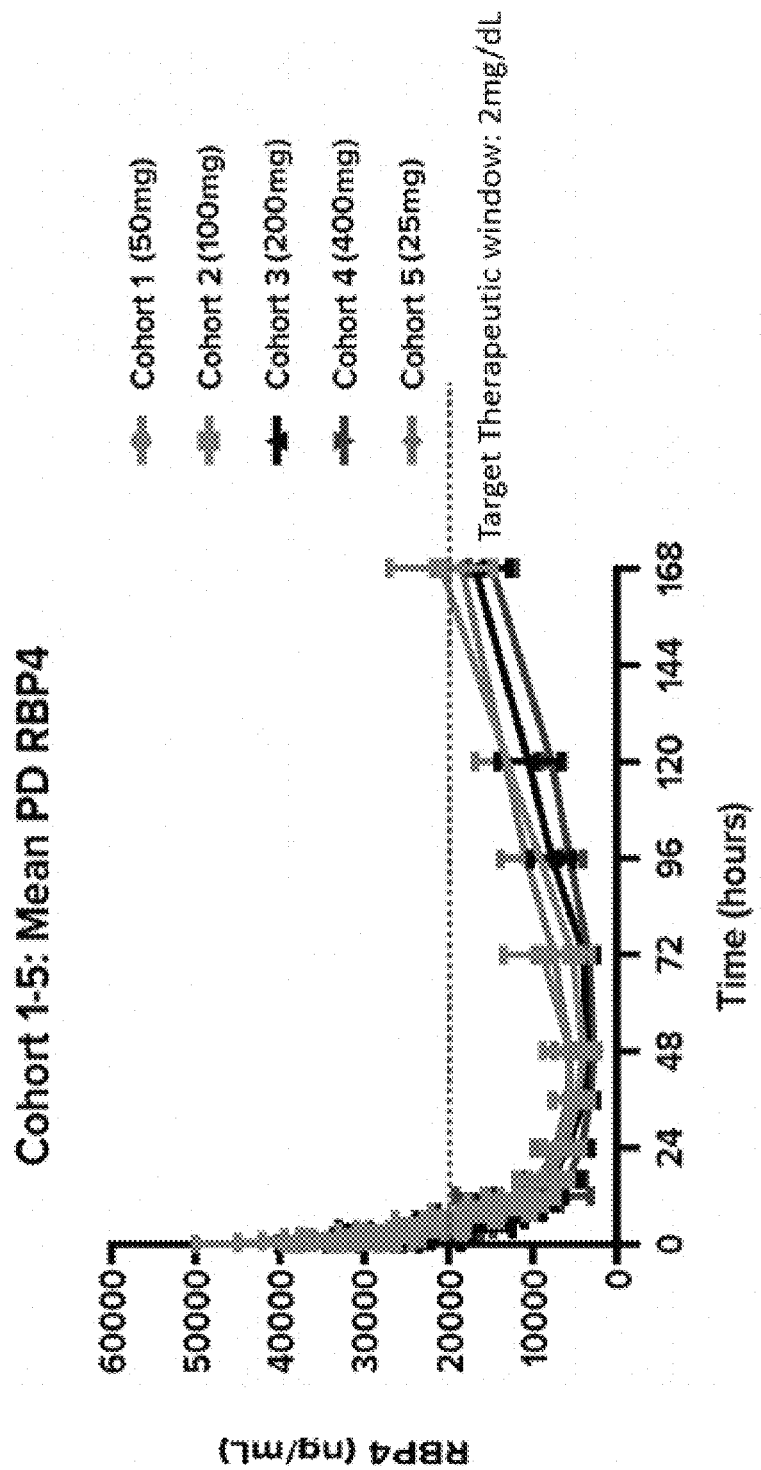
FIG. 4B is a graph of RBP4 concentration (ng/mL) as a function of time (hours) for five cohorts comprising a total of 32 healthy adults in a randomized, double-blind, placebo-controlled Phase 1 clinical trial. Each cohort was given a single dose of 50 mg (Cohort 1), 100 mg (Cohort 2), 200 mg (Cohort 3), 400 mg (Cohort 4), 25 mg (Cohort 5) of Compound 1, or a placebo. Individuals receiving placebo were not included in the graph
Figure 5:
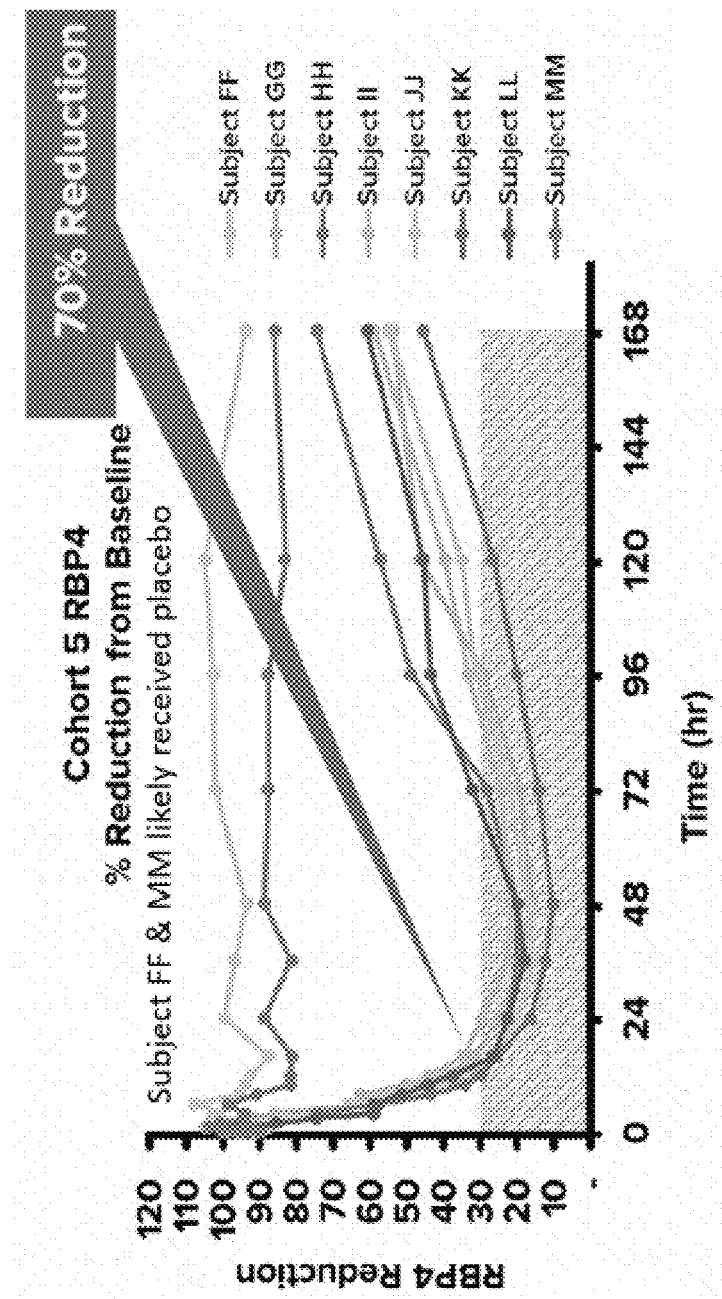
FIG. 5 is a graph of percent mean RBP4 reduction from baseline as a function of time (hours) for cohort 5 in a randomized, double-blind, placebo-controlled Phase 1 clinical trial. Each subject in the cohort was given a single dose of 25 mg of Compound 1, or a placebo. Six subjects received Compound 1 and two subjects were dosed with placebo. Subjects FF and GG likely received the placebo.
Figure 6:
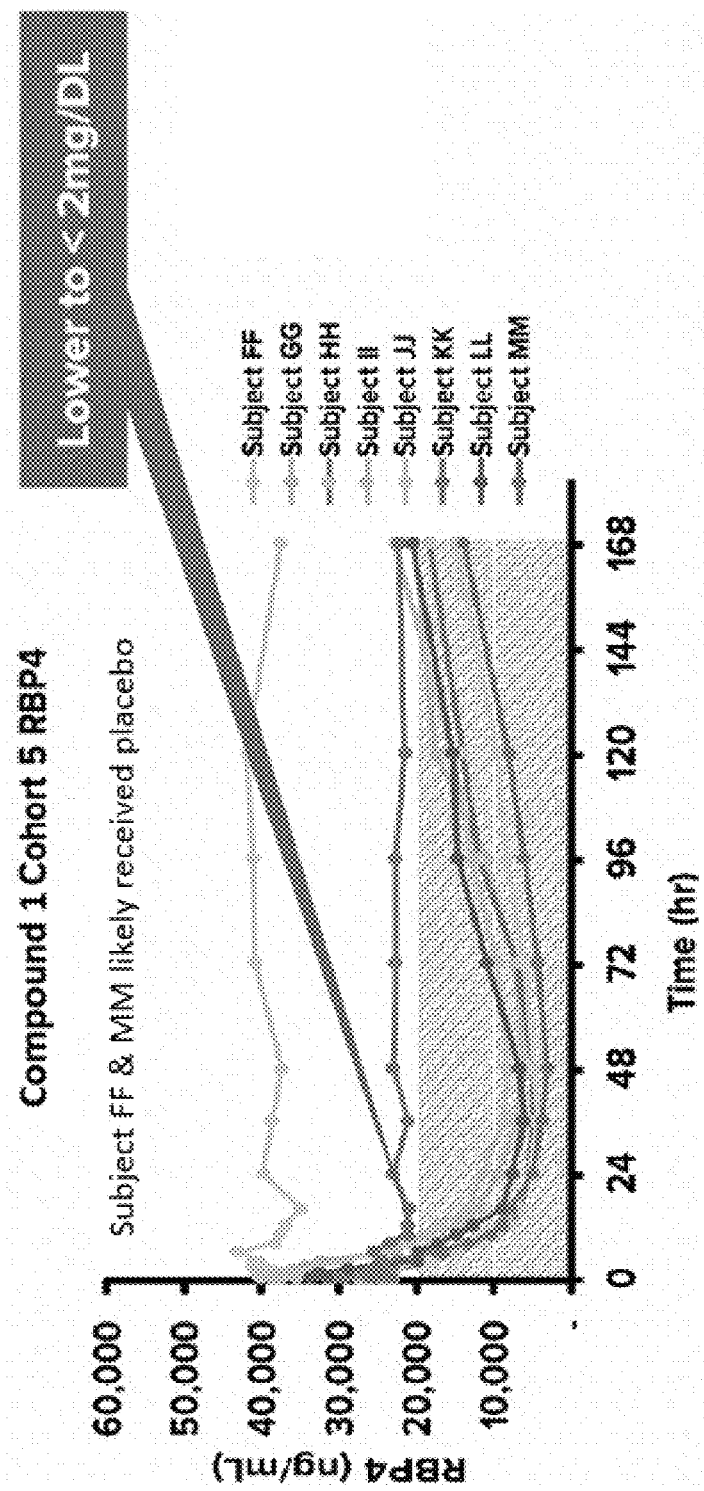
FIG. 6 is a graph of RBP4 concentration (ng/mL) as a function of time (hours) for cohort 5 in a randomized, double-blind, placebo-controlled Phase 1 clinical trial. Each subject in the cohort was given a single dose of 25 mg of Compound 1, or a placebo. Six subjects received Compound 1 and two subjects were dosed with placebo. Subjects FF and GG likely received the placebo.
Figure 7:
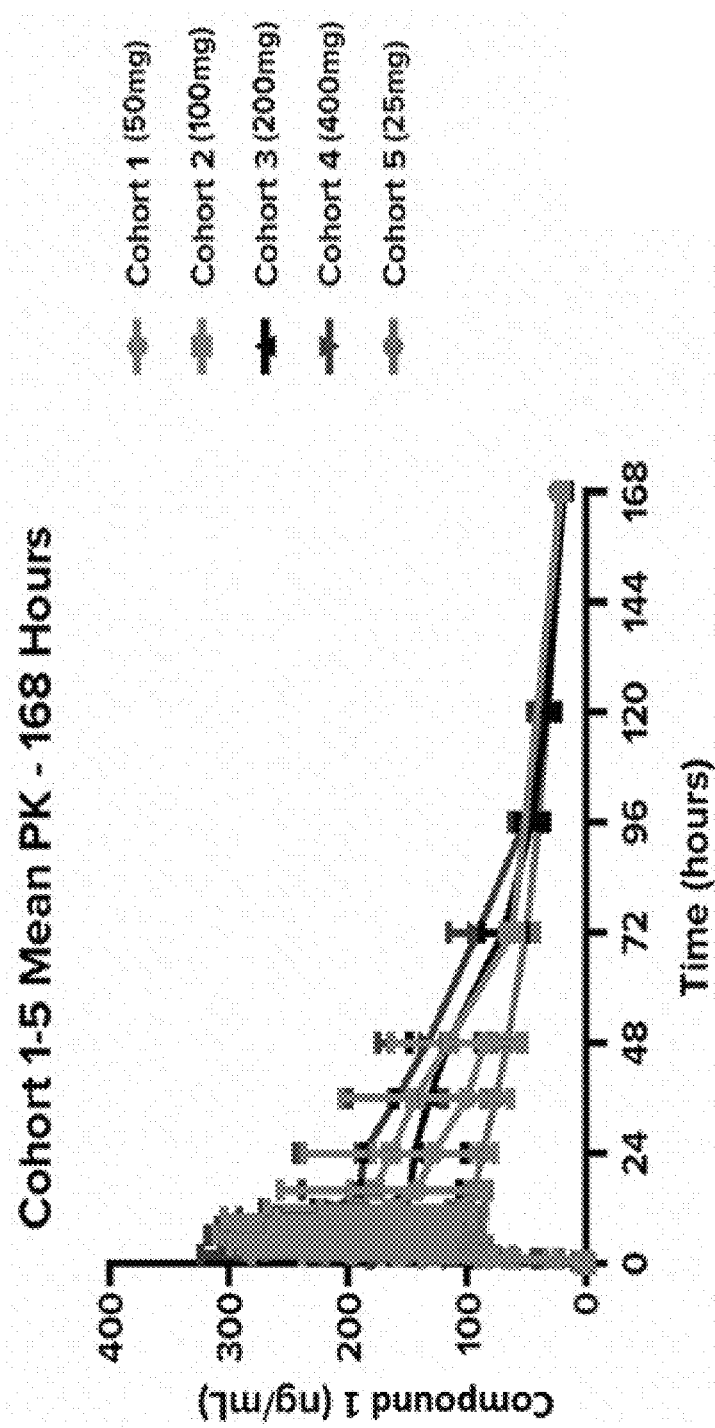
FIG. 7 is a graph of Compound 1 concentration (ng/mL) as a function of time (hours) for five cohorts comprising a total of 32 healthy adults in a randomized, double-blind, placebo-controlled Phase 1 clinical trial. Each cohort was given a single dose of 50 mg (Cohort 1), 100 mg (Cohort 2), 200 mg (Cohort 3), 400 mg (Cohort 4), 25 mg (Cohort 5) of Compound 1, or a placebo. Individuals receiving placebo were not included in the graph.
Figure 8:
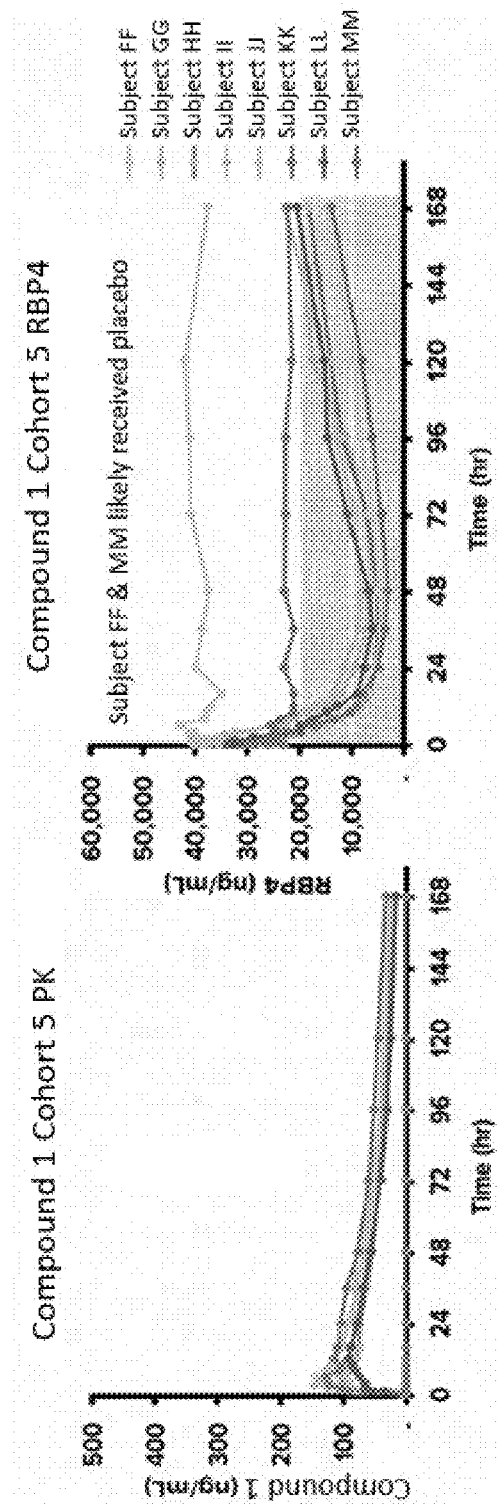
FIG. 8 are graphs of Compound 1 concentration (ng/mL) as a function of time (hours) (left) and RBP4 concentration (ng/mL) as a function of time (hours) (right) for cohort 5 in a randomized, double-blind, placebo-controlled Phase 1 clinical trial. Each subject in the cohort was given a single dose of 25 mg of Compound 1, or a placebo. Subjects FF and GG likely received the placebo.
Figure 9:
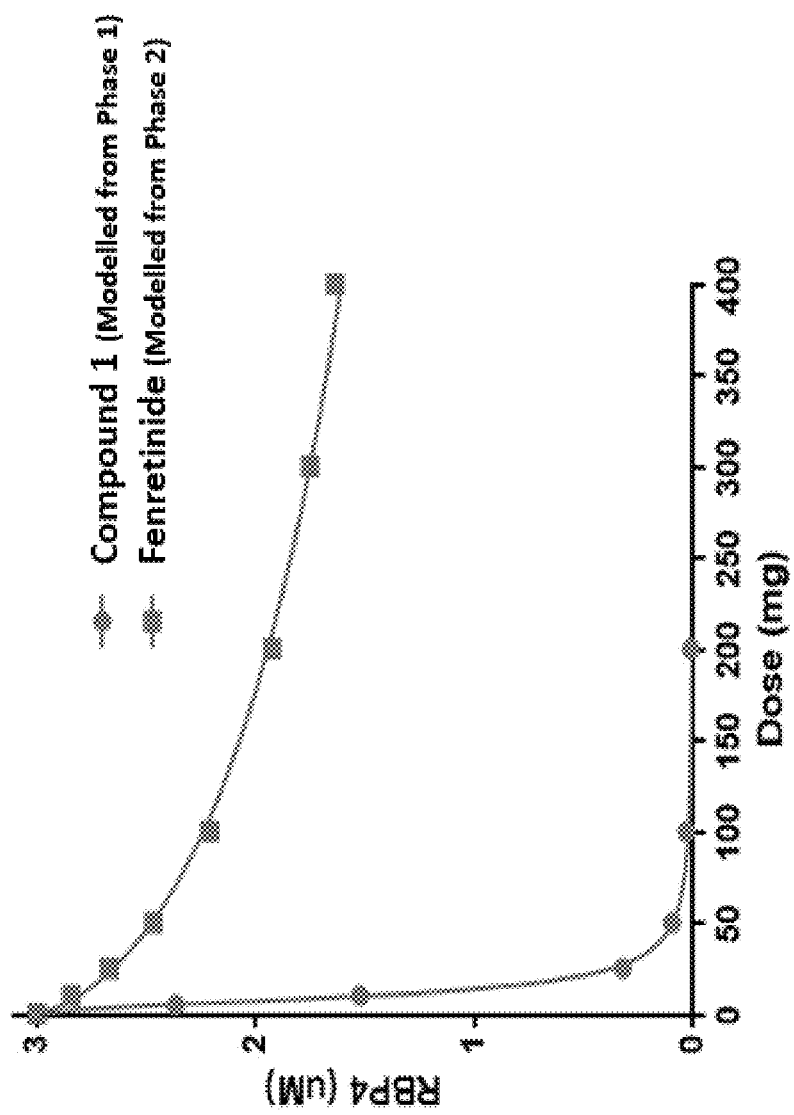
FIG. 9 is a graph of the RBP4 concentration (μm) as a function of dose of compound 1 (mg, modeled from a Phase 1 clinical study) and fenretinide (modeled from a Phase 2 clinical study). The Phase 2 fenretinide study showed that a sub-population with significant RBP4 lowering had slower lesion growth. Compound 1 is more potent than fenretinide and can lower RBP4 significantly at doses with clinical relevance.

Results. All Cohorts demonstrated a significant reduction in RBP4 levels from baseline (FIG. 4A), reaching less than 2 mg/dL (FIG. 4B). Results for an example individual Cohorts (cohort 5) are shown in FIGS. 5 and 6. The other Cohorts showed similar results. Subjects in Cohort 5 had an 80% reduction in RBP4 serum levels and at least a 70% reduction that was maintained for 3 days. Subjects in Cohorts 1 and 2 had a 90% reduction in RBP4 serum levels and at least a 70% reduction that was maintained for 3 days. Subjects in Cohort 3 had a 90% reduction in RBP4 serum levels and at least a 70% reduction that was maintained for 4 days. Subjects in Cohort 4 had a 90% reduction in RBP4 serum levels and at least a 70% reduction that was maintained for 5 days. PK data for all five Cohorts is shown in FIG. 7, and PK/PD data for each subject in Cohort 5 is shown in FIG. 8. Results from other cohorts showed similar results. The results were also modeled with results from a phase 2 Fenretinide clinical study (FIG. 9).

Example 3: Phase 1 Multiple Escalating Dose Human Clinical Study for Compound 1

The general format of the clinical study of Example 2 was followed, with modification. The study comprises up to 3 cohorts, and up to a total of 24 subjects (8 subjects per cohort). The starting dose of Compound 1 is 10 mg and doses for subsequent cohorts are 25 mg an d 50 mg.

Compound 1 was administered as a formulation described herein. Doses will be administered daily. The study will consist of a screening period (Days −28 to −1), Check-in (Day −1), study drug administration (Day 1-14), treatment period (Days 2 to 17), a follow-up telephone call (Day 20), and an end-of-study (EOS) visit (Day 23). Subjects will be randomly assigned to receive a pharmaceutical composition of Compound 1 or placebo as follows: 6 subjects will receive active drug and 2 subjects will receive placebo. Additional cohorts (8 subjects per cohort) may be enrolled if after evaluation it is determined that an intermediate or higher dose level should be tested. The institutional review board (IRB) will be notified of this revised approach. Safety data through Day 23 will be reviewed by the safety review committee in a blinded fashion for each dose cohort before escalating to the next dose cohort. Additional data (e.g., PK data) may be reviewed as deemed necessary by the committee. Subjects will fast overnight (nothing to eat or drink except water) for at least 10 hours before study drug administration on Days 1-14. Subjects will remain fasted for 4 hours after dosing with study drug. Subjects will be confined to the clinical unit from Day −1 until discharge on Day 17. The duration of the study, including a 28-day screening period, is approximately 51 days.

FIG. 5F shows results from a study carried out as indicated above. Subjects in this cohort received repeated daily doses of 10 mg of Compound 1 over a period of 14 days. This treatment regimen consistently reduced RBP4 to below 1 μM serum concentration (equivalent to 70% RBP4 reduction from baseline) in all subjects receiving Compound 1. Subjects displayed 50% RBP4 reduction after the first initial dose on day 1, which was further reduced down to 90% after subsequent doses. 90% RBP4 reduction was maintained throughout the two weeks of 10 mg daily dosing.

Example 4: Treatment of STGD1 Pediatric Patients 10 patients aged 10-20 with symptoms associated with autosomal recessive Stargardt disease (STGD1), including at least two pathogenic mutations of the ABCA4 gene and a defined lesion size are treated with a pharmaceutical composition of Compound 1 or placebo, for up to 18 months. Primary outcomes are PK/PD and RBP4 reduction. The results are analyzed following methods well known to the skilled artisan.

Example 5: Treatment of STGD1 Patients 120 patients aged 12-40 with symptoms associated with autosomal recessive Stargardt disease (STGD1), including at least two pathogenic mutations of the ABCA4 gene and a defined lesion size are randomly assigned to receive a pharmaceutical composition of Compound 1 or placebo, for up to 18 months. Primary outcomes are PK/PD, RBP4 reduction, and the mean rate of change in the area of ellipsoid zone defect measured by en face SD-OCT, as measured by spectral Domain-Optical Coherence Tomography (SD-OCT). The results are analyzed following methods well known to the skilled artisan.

Example 6: Treatment of (Dry) Age-Related Macular Degeneration (AMD) in Humans 100 patients at least 18 years of age with symptoms associated with dry AMD are randomly assigned to receive a pharmaceutical composition of Compound 1 or the standard of care, for up to 48 weeks. Primary outcomes are change from baseline of geographical atrophy (GA, mm$^2$) size, change from baseline of retinal drusen volume (mm$^3$), change in macular sensitivity (DB), change in monocular reading speed from baseline (words/min). The results are analyzed following methods well known to the skilled artisan.

Example 7: Treatment of (Wet) Age-Related Macular Degeneration (AMD) in Humans 100 patients at least 50 years of age with symptoms associated with neovascular/wet AMD, including active primary or recurrent subfoveal choroidal neovascularization (CNV) secondary to age-related macular degeneration (AMD) are randomly assigned to receive a pharmaceutical composition of Compound 1 or the standard of care, for up to 48 weeks. Primary outcomes are change in the best corrected visual acuity score measured using the Early Treatment Diabetic Retinopathy Study (ETDRS) protocol by Week 16. Secondary outcomes are percent of subjects gaining >/=15 letters in the best corrected visual acuity score at 16 weeks compared to baseline, as measured using the ETDRS protocol; mean change from Baseline over time (16 weeks) in the best corrected visual acuity score, as measured using the ETDRS protocol; incidence and severity of ocular adverse events identified by ophthalmic examination and or spontaneously reported (at 48 weeks); change from baseline to weeks 4, 8, 12, and 16 in retinal central subfield thickness and retinal lesion thickness assessed by OCT; incidence and severity of systemic adverse events identified by physical examination, changes in vital signs, clinical laboratory abnormalities and or spontaneously reported (at 48 weeks); and change from baseline in lesion size on FFA at Week 16. The results are analyzed following methods well known to the skilled artisan.

Example 8: Treatment of Best Disease in Humans 50 patients at least 18 years of age with symptoms associated with Best disease or other eye disease caused by mutations in the gene BEST1 are randomly assigned to receive a pharmaceutical composition of Compound 1 or the standard of care, for up to 24 months. Primary outcomes are mean change in central retinal thickness as measured by OCT at month 12 compared to baseline and change in leakage area seen during fluorescein angiography at month 12 as compared with baseline. The results are analyzed following methods well known to the skilled artisan.

Example 9: Treatment of Adult Vitelliform Maculopathy in Humans 50 patients at least 18 years of age with symptoms associated with Adult Vitelliform Maculopathy are randomly assigned to receive a pharmaceutical composition of Compound 1 or the standard of care, for up to 24 months. Primary outcomes are mean change in central retinal thickness as measured by OCT at month 12 compared to baseline and change in leakage area seen during fluorescein angiography at month 12 as compared with baseline. The results are analyzed following methods well known to the skilled artisan.

Example 10: Treatment of Diabetic Retinopathy in Humans 50 patients 45-75 years of age with symptoms associated with diabetic retinopathy are randomly assigned to receive a pharmaceutical composition of Compound 1 or the standard of care, for up to 24 months. Primary outcomes are Best Corrected Visual Acuity (BCVA) assessed by ETDRS (Early Treatment Diabetic Retinopathy Study) scale; Retinal Nerve Fiber Layer (RNFL), Ganglion Cell Layer (GCL), Retinal thickness, and central Retinal thickness assessed by Spectral Domain Optical Coherence Tomography (SD-OCT); and icroaneurysm turnover assessed by Colour Fundus Photography. Outcomes are assessed at 0, 6, 12, 18, and 24 months. The results are analyzed following methods well known to the skilled artisan.

Example 11: Treatment of Geographic Atrophy in Humans 50 patients at least 50 years of age with symptoms associated with geographic atrophy are randomly assigned to receive a pharmaceutical composition of Compound 1 or the standard of care, for up to 12 months. Primary outcomes are the change in square root geographic atrophy (GA) lesion size from baseline at week 24 as measured by FAF (Fundus Autofluorescence). A positive change from baseline indicates an increase in size of geographic atrophy lesion area (worsening; disease progression). The results are analyzed following methods well known to the skilled artisan.

Example 12: Characterization of Compound 1

XRPD Characterization of Compound 1

Figure 10A:
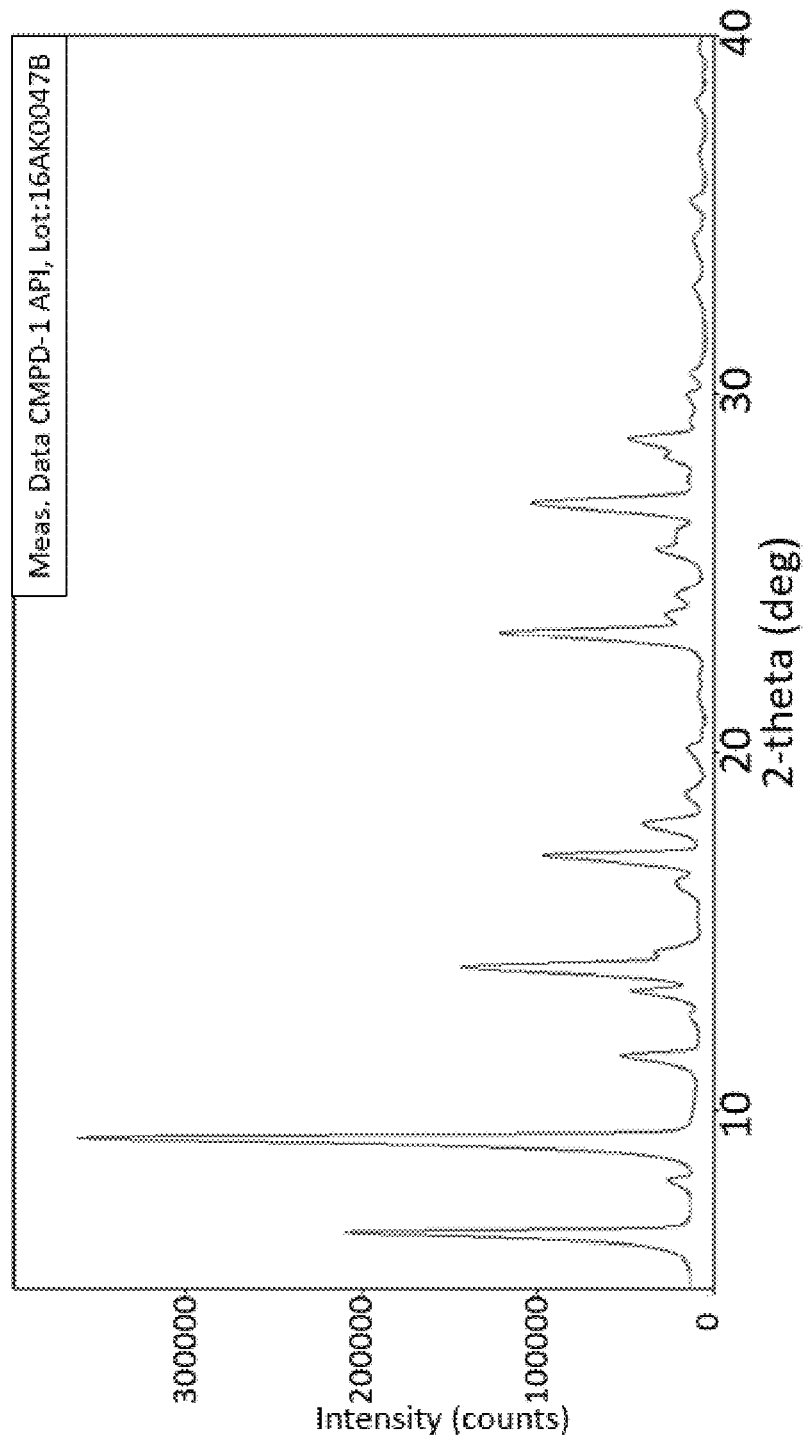
FIG. 10A is a graph generated in an X-ray powder diffraction (XRPD) experiment of crystalline Compound 1.

An X-Ray Powder Diffraction (XRPD) diffractogram of Compound 1 (CMPD-1) was acquired using Rigaku Miniflex 6G according to standard instrument procedures provided by manufacturer. Parameters used for the analysis are shown below in Table 2. The resulting diffractogram is shown in FIG. 10A. The diffraction pattern was consistent with Compound 1 being a crystalline material.

TABLE 2

| XRPD Parameters | |
| --- | --- |
| Instrument: | RigakuMiniflex6G |
| Radiation Source: | Cu—Kα (1.5406 Å) |
| Scan Mode: | Coupled 2θ/θ |
| Scan Range: | 5°-40° |
| Scan Speed: | 0.9°/min |
| Step Increment: | 0.005° |
| Voltage: | 40 kV |
| Current: | 15 mA |
| Rotation: | 30 rpm |
| Divergence Slit: | 0.625 mm |
| Sample Holder: | Zero-BackgroundCup |

DSC Characterization of Compound 1

A sample of Compound 1 was analyzed by Differential Scanning Calorimetry using a TA Discovery DSC2500 with RCS90 chiller according to standard instrument procedures provided by manufacturer. Parameters used for the analysis are shown below in Table 3. Two replicates of the experiment were run with reproducible results. The resulting thermogram, shown in FIG. 10B, indicated a melting temperature ($T_m$) of Compound 1 of about 229° C. and no degradation up to 275° C.

TABLE 3

| DSC Parameters | |
| --- | --- |
| Instrument: | TA DiscoveryDSC2500 with RCS90 chiller |
| Scan Mode: | Ramp |
| Temp. Range: | 35° C.-275° C. |
| Heating Rate: | 10.0° C./min |
| Mod. Period: | NA |
| Mod. Amplitude: | NA |
| Pan/Lid type: | Non-Hermetic |
| Replicates | n = 2 |

Melt-Quench by DSC Characterization of Compound 1

A sample of Compound 1 was analyzed by Modulated Differential Scanning Calorimetry using a TA Discovery DSC2500 with RCS90 chiller according to standard instrument procedures provided by manufacturer. Parameters used for the analysis are shown below in Table 4. Two replicates of the experiment were run with reproducible results. The resulting thermogram, shown in FIG. 10C, indicates a glass transition temperature ($T_g$) of about 93° C., a crystallization temperature ($T_c$) of about 136° C., and a $T_m/T_g$ ratio of 1.37. The $T_m/T_g$ ratio of 1.37 is indicative of moderate physical stability. Without being bound by theory, the $T_e$ observed quickly after Compound 1 entering a rubbery state was indicative of a propensity to crystallize.

TABLE 4

| DSC Parameters | |
| --- | --- |
| Instrument: | TA Discovery DSC2500 with RCS90 chiller |
| Melt Parameters: | |
| Scan Mode: | Ramp |
| Temp. Range: | 0° C.-245° C. |
| Heating Rate: | 10° C./min. |
| Isothermal Time: | 1 min |
| Quench Parameters: | |
| Equilibration Temp: | 0° C. |
| Isothermal Time: | 5 min |
| Quench Temp. | Liquid N2 |
| Isothermal Time: | 10 s |
| ModulatedDSC Parameters: | |
| ScanMode: | Modulated |
| Temp. Range: | 0° C.-275° C. |
| Heating Rate: | 2° C./min. |
| Modulation Period: | 60 sec. |
| Modulation Amplitude: | ±1.0° C. |
| Replicates | n = 2 |

SEM Characterization of Compound 1

A sample of Compound 1 (CMPD-1) was analyzed by scanning electron microscopy (SEM). Resulting images form this analysis can be seen in FIG. 10D. Compound 1 morphology consisted of high aspect ratio orthogonal acicular crystals. This morphology was favorable for the detection of low level crystallinity in amorphous solid dispersions by SEM.

Solvent Shift Assay Characterization of Compound 1

Figure 10B:
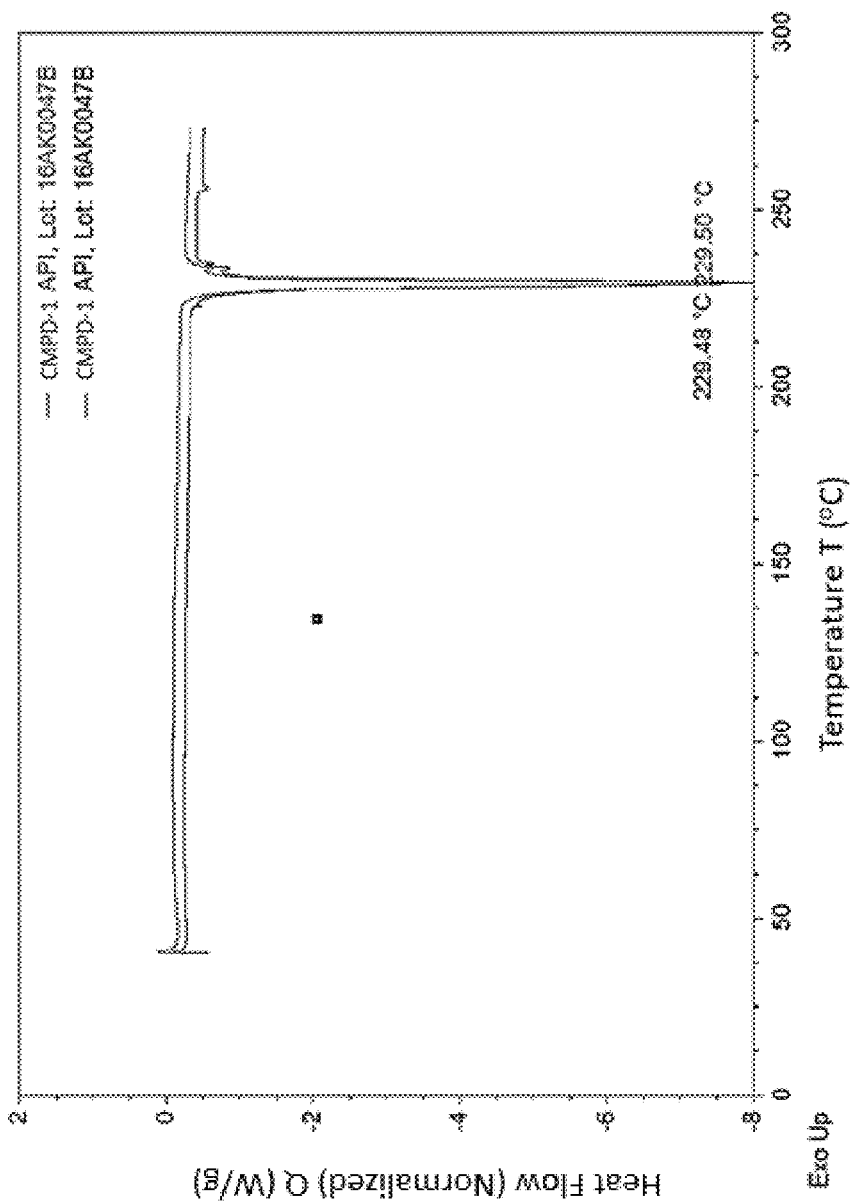
FIG. 10B is a graph generated in a differential scanning calorimetry (DSC) experiment of crystalline Compound 1 showing heat flow Q (W/g) as a function of temperature (deg C.).
Figure 10C:
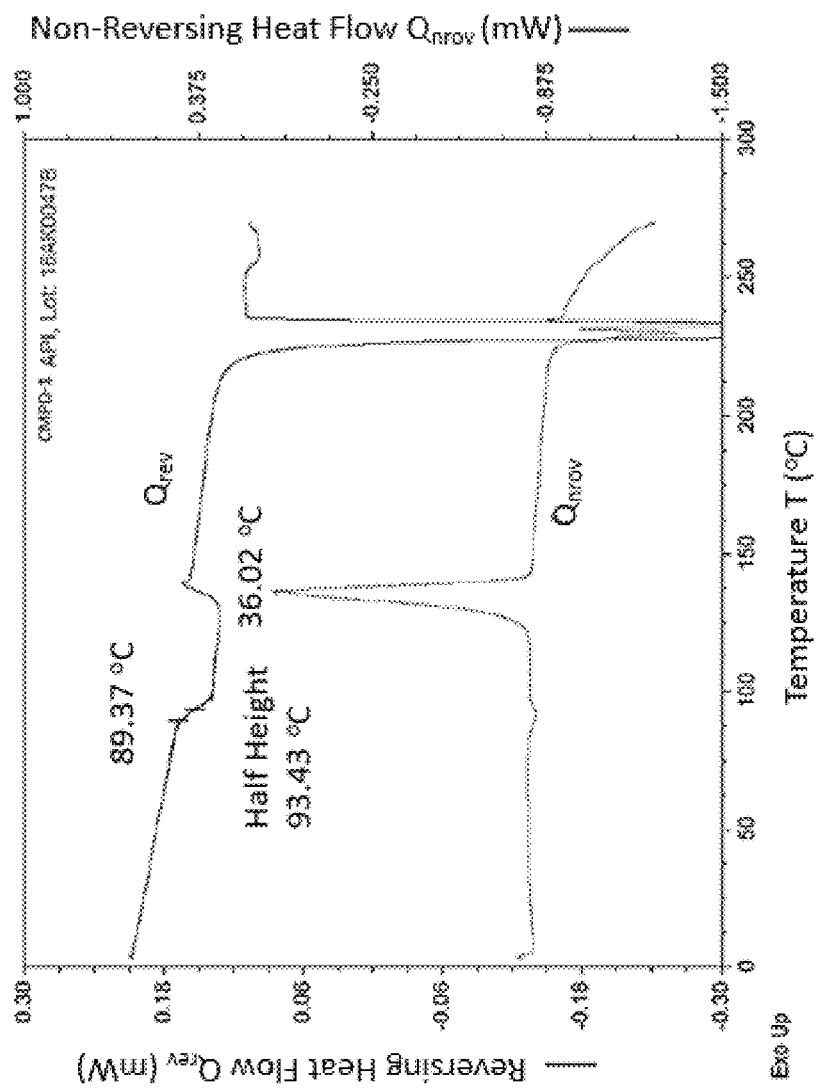
FIG. 10C is a graph generated in a differential scanning calorimetry (DSC) experiment of crystalline Compound 1 showing reverse heat flow $Q_{rev}$ (mW) as a function of temperature (deg C.).
Figure 10D:
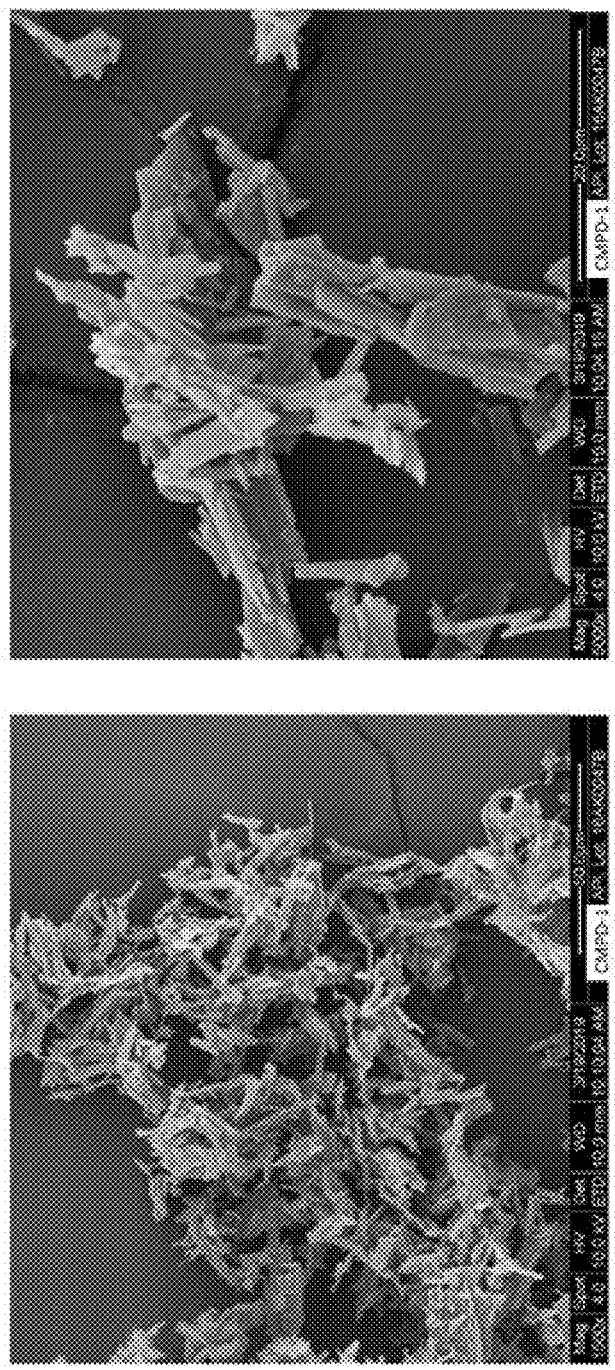
FIG. 10D are images of crystalline Compound 1 generated by SEM (scanning electron microscope). Compound 1's morphology consists of high aspect ratio orthogonal acicular crystals.
Figure 10E:
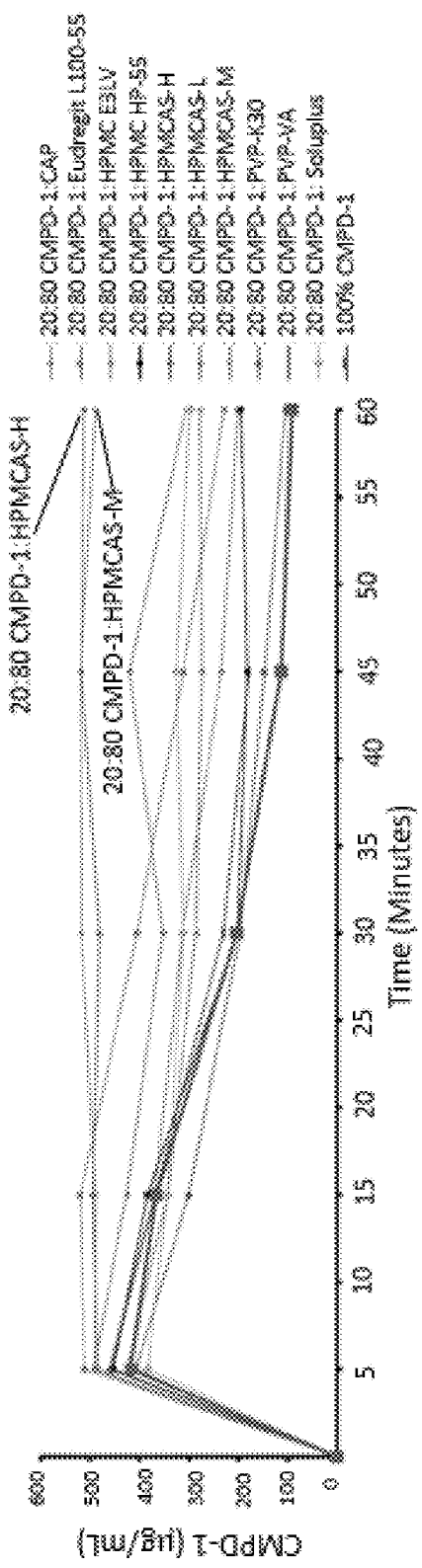
FIG. 10E is a graph of Compound 1 solubility (μgA/mL) as a function of time (minutes) for mixtures of Compound 1 and various polymers in a 20:80 ratio.
Figure 10F:
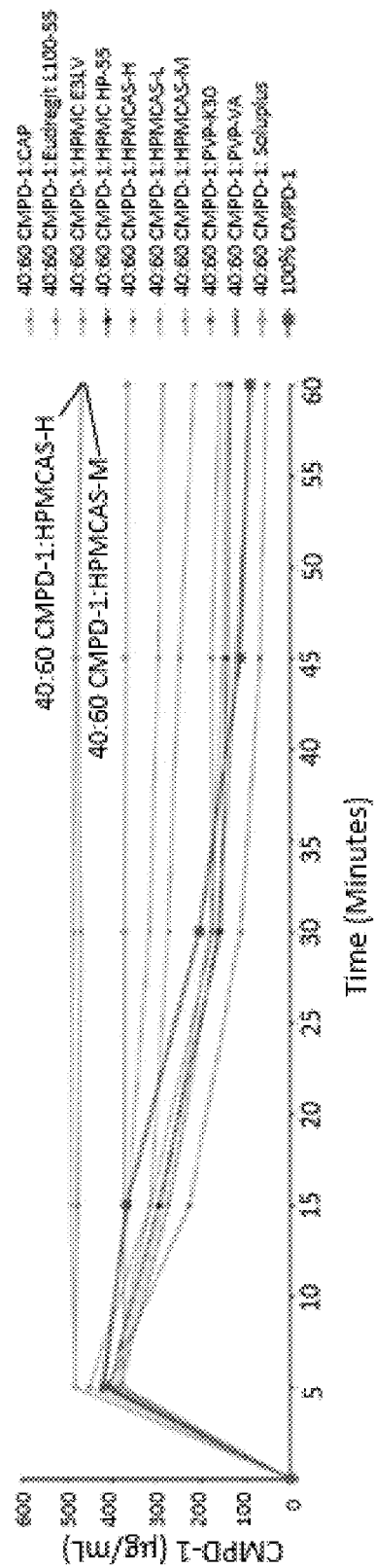
FIG. 10F is graph of Compound 1 solubility (μgA/mL) as a function of time (minutes) for mixtures of Compound 1 and various polymers in a 40:60 ratio.

A solvent shift assay was performed in order to assess the effect of polymer excipients in improving supersaturation and sustainment in biorelevant media. Compound 1 was dissolved in DMSO to generate concentrated dissolved stock solution at 25 mg/mL. Stock API solution was then added to Fasted State Simulated Intestinal Fluid (FaSSIF) solution or FaSSIF solution containing predissolved polymer excipients to final concentration of compound 1 at 0.5 mg/mL. Ratios of Compound 1:polymer excipient in the final solution were either 20:80 or 40:60 (w/w). Samples were analyzed by HPLC to assess dynamic solubility of Compound 1 at various time points over a one hour period. The resulting chromatograms are shown in FIG. 10E and FIG. 10F. Table 5 below shows calculations of polymer performance in maintaining Compound 1 in solution during the experiment.

tures of Compound 1 and the desired amount of polymer were mixed in a spray solvent, then spray dried on a Buchi B-290 Lab Scale Spray Dryer with 2-fluid nozzle, 1.5 mm AirCap, and 0.7 mm Liquid tip. The spray drier was operated according to standard instrument procedures provided by manufacturer. Specific parameters used for each composition are shown below in Table 6B and Table 7 below.

TABLE 5

| Sample | Total DrugCmaxFaSSIF (μgA/mL) | Total DrugAUCFaSSIF (min*μgA/mL) | Total DrugC60 (μgA/mL) | Increase in AUC over API AUC |
|---|---|---|---|---|
| 20:80 CMPD-1:HPMCAS-M | 519.0 | 29000 | 489.3 | 2.2 |
| 20:80 CMPD-1:HPMCAS-H | 517.0 | 28600 | 512.3 | 2.2 |
| 40:60 CMPD-1:HPMCAS-M | 489.3 | 27800 | 467.8 | 2.1 |
| 40:60 CMPD-1:HPMCAS-H | 481.6 | 27300 | 466.5 | 2.1 |
| 20:80 CMPD-1:HPMC E3LV | 493.2 | 22900 | 306.4 | 1.7 |
| 20:80 CMPD-1:Eudragit L100-55 | 519.2 | 22800 | 228.1 | 1.7 |
| 40:60 CMPD-1:Soluplus | 373.9 | 21300 | 364.9 | 1.6 |
| 20:80 CMPD-1:Soluplus | 383.2 | 19000 | 211.1 | 1.5 |
| 40:60 CMPD-1:HPMC E3LV | 422.6 | 19000 | 285.5 | 1.5 |
| 20:80 CMPD-1:HPMCAS-L | 425.1 | 18000 | 278.2 | 1.4 |
| 20:80 CMPD-1:CAP | 461.5 | 17800 | 200.9 | 1.4 |
| 40:60 CMPD-1:HPMCAS-L | 403.0 | 16400 | 216.1 | 1.3 |
| 20:80 CMPD-1:HPMCP HP-55 | 452.7 | 15400 | 194.7 | 1.2 |
| 20:80 CMPD-1:PVP-VA | 457.9 | 15300 | 110.2 | 1.2 |
| 40:60 CMPD-1:Eudragit L100-55 | 449.8 | 13700 | 159.1 | 1.0 |
| 20:80 CMPD-1:PVP-K30 | 407.9 | 12700 | 104.7 | 1.0 |
| 40:60 CMPD-1:CAP | 392.7 | 12600 | 145.6 | 1.0 |
| 40:60 CMPD-1:HPMCP HP-55 | 405.4 | 12200 | 133.9 | 0.9 |
| 40:60 CMPD-1:PVP-VA | 381.6 | 11200 | 88.9 | 0.9 |
| 40:60 CMPD-1:PVP-K30 | 408.2 | 9000 | 52.8 | 0.7 |
| 100% CMPD-1 | 418.0 | 13100 | 91.3 | NA |

Example 13: Preparation and Characterization of Solid Dispersions Containing Compound 1
Dispersion Preparation Solid dispersions of Compound 1 and lead polymers identified from the solvent shift assay in Example 12 (HPMC E3LV, HPMCAS-H, HPMCAS-M, and Soluplus) were prepared in ratios of Compound 1:polymer of 20:80 and 40:60. The HPMCAS-L, HPMCAS-M, and HPMCAS-H were Ashland Aquasolv® brand. Characteristics of these polymers are shown below in Table 6A Mix-

TABLE 6A

Properties of HPMCAS Used

| HMPCAS Grade | Acetyl Content (wt %) | Succinyl Content (wt %) | Methoxyl Content (wt %) | Hydroxypropyl Content (wt %) |
|---|---|---|---|---|
| L | 5-9% | 14-18% | 20-24% | 5-9% |
| M | 7-11% | 10-14% | 21-25% | 5-9% |
| H | 10-14% | 4-8% | 22-26% | 6-10% |

TABLE 6B

| Formulation | 20:80 CMPD-1:HPMCE3LV | 20:80 CMPD-1:HPMCAS-H | 20:80 CMPD-1:HPMCAS-M | 20:80 CMPD-1:Soluplus |
|---|---|---|---|---|
| Batch Size, TotalSolids | 45.0 grams (9.0 grams Active) | | | |
| Spray Solvent | 100% Methanol | 90:10 DCM:MeOH | | |
| Spray Solution Composition (wt % total solids) | 5.0 | 10.0 | | |
| Drying Gas Mode | Recycle | | | |
| Cyclone Used | High Efficiency | | | |
| Solution Flow Rate (Average) | 17 g/min | 26 g/min | 26 g/min | 26 g/min |
| Atomization Pressure | 28 psi | | | |
| Inlet Temperature | 155° C. | 78° C. | 86° C. | 85° C. |
| Outlet Temperature | 54° C. | 36° C. | 36° C. | 36° C. |
| Condenser Temperature | −20° C. | −20° C. | −20° C. | −20° C. |
| Secondary Drying | 29 h | 29 h | 24.5 h | 24.5 h |
| Time/Temperature | 40° C. | 40° C. | 40° C. | 40° C. |
| SDD Yield | 73% | 56% | 66% | 48% |
| Residual MeOH(ppm) | <200 | <200 | ND | ND |
| Residual DCM (ppm) | ND | ND | ND | ND |

*ND: Not Detected

TABLE 7

| Formulation | 40:60 CMPD-1:HPMC E3LV | 40:60 CMPD-1:HPMCAS-H | 40:60 CMPD-1:HPMCAS-M | 40:60 CMPD-1:Soluplus |
|---|---|---|---|---|
| Batch Size, TotalSolids | 22.5 grams (9.0 grams Active) | | | |
| Spray Solvent | 100% Methanol | 90:10 DCM:MeOH | | |
| Spray Solution Composition (wt % total solids) | 2.5 | 10.0 | | |
| Drying Gas Mode | Recycle | | | |
| Cyclone Used | High Efficiency | | | |
| Solution Flow Rate (Average) | 17 g/min | 27 g/min | 26 g/min | 24 g/min |
| Atomization Pressure | 28 psi | | | |
| Inlet Temperature | 164° C. | 77° C. | 80° C. | 74° C. |
| Outlet Temperature | 55° C. | 37° C. | 36° C. | 35° C. |
| Condenser Temperature | −20° C. | −20° C. | −20° C. | −20° C. |
| Secondary Drying | 29 h | 29 h | 24.5 h | 24.5 h |
| Time/Temperature | 40° C. | 40° C. | 40° C. | 40° C. |
| SDD Yield | 70% | 65% | 55% | 73% |
| Residual MeOH(ppm) | ND | ND | ND | ND |
| Residual DCM (ppm) | ND | ND | ND | ND |

*ND: Not Detected

XRPD Characterization of Solid Dispersions Containing Compound 1

Figure 11A:
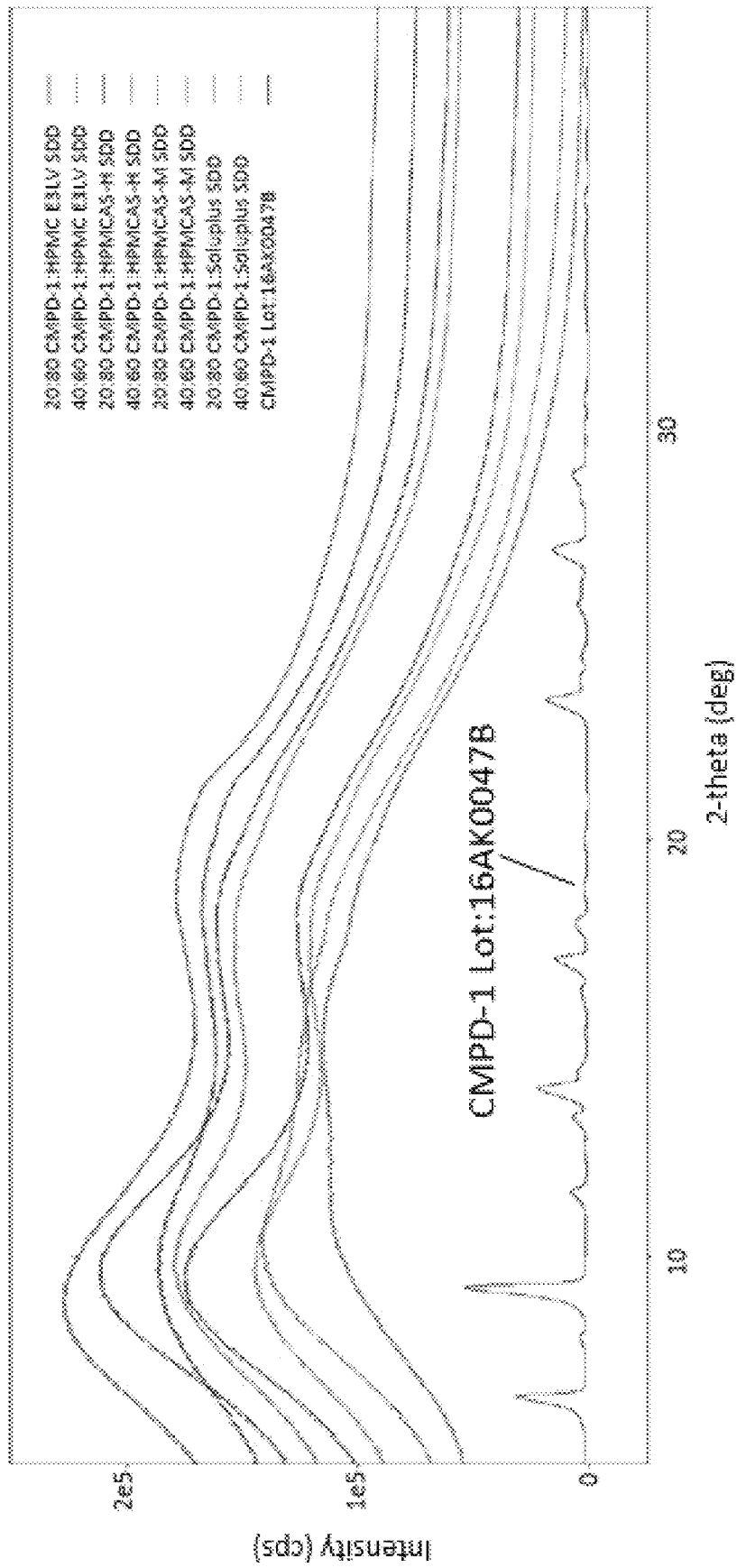
FIG. 11A is a graph generated of X-ray powder diffraction (XRPD) experiments of multiple spray-dried dispersions of Compound 1 and polymers. They are compared to crystalline API and show the spray-dried dispersions are amorphous.

X-Ray Powder Diffraction (XRPD) diffractograms of the solid dispersions containing Compound 1 prepared above were acquired using a Rigaku Miniflex 6G according to standard instrument procedures provided by manufacturer. Parameters used for the analysis are shown below in Table 8. The resulting diffractograms are shown in FIG. 11A. The diffraction patterns indicate that amorphous dispersions were obtained for each preparation of polymers and Compound 1.

TABLE 8

XRPD Parameters

| | |
|---|---|
| Instrument: | RigakuMiniflex6G |
| Radiation Source: | Cu—Kα (1.5406 Å) |
| Scan Mode: | Coupled 2θ/θ |
| Scan Range: | 5°-40° |
| Scan Speed: | 0.9°/min |
| Step Increment: | 0.005° |
| Voltage: | 40 kV |
| Current: | 15 mA |
| Rotation: | 30 rpm |
| Divergence Slit: | 0.625 mm |
| Sample Holder: | Zero-BackgroundCup |

MDSC Characterization of Solid Dispersions Containing Compound 1

Figure 11B:
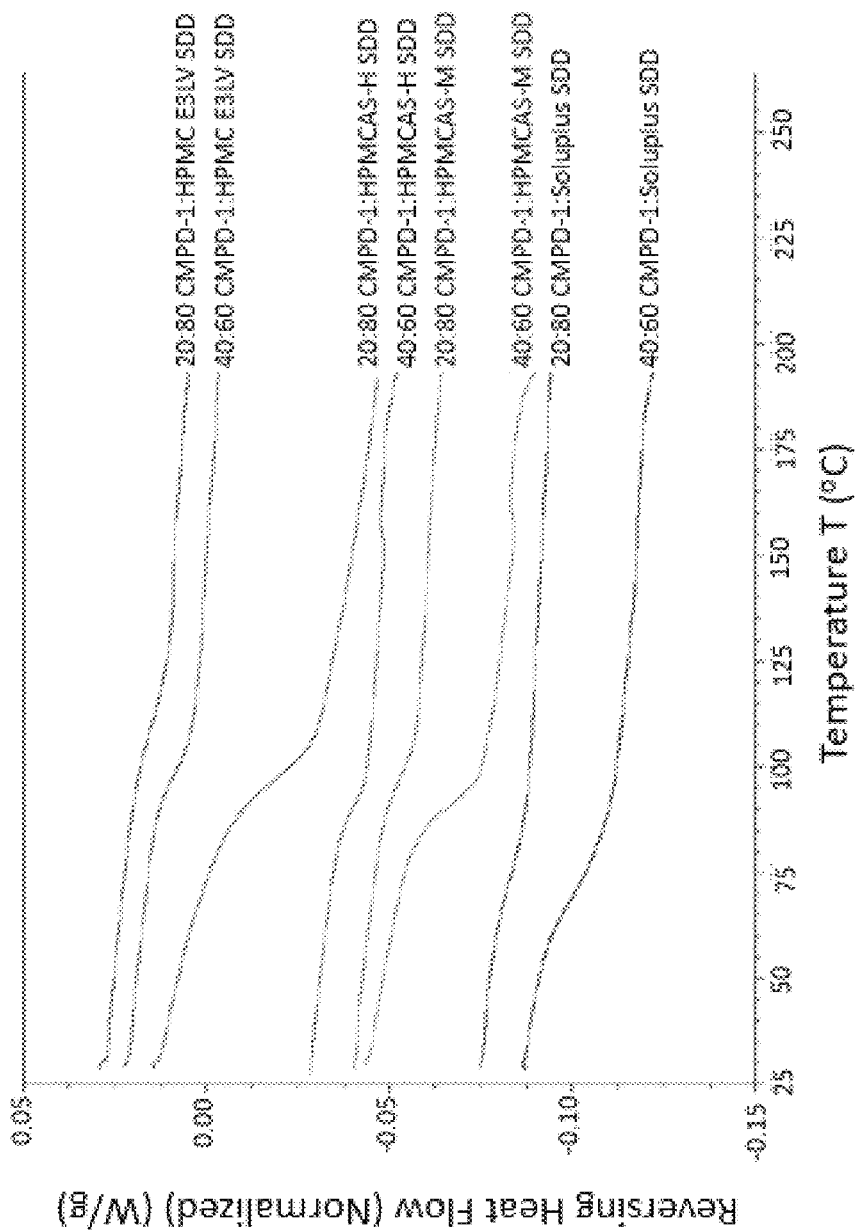
FIG. 11B is a graph generated in a differential scanning calorimetry (DSC) experiment of spray-dried dispersions of Compound 1:and polymers showing reverse heat flow $Q_{rev}$ (mW) as a function of temperature (deg C.).
Figure 11C:
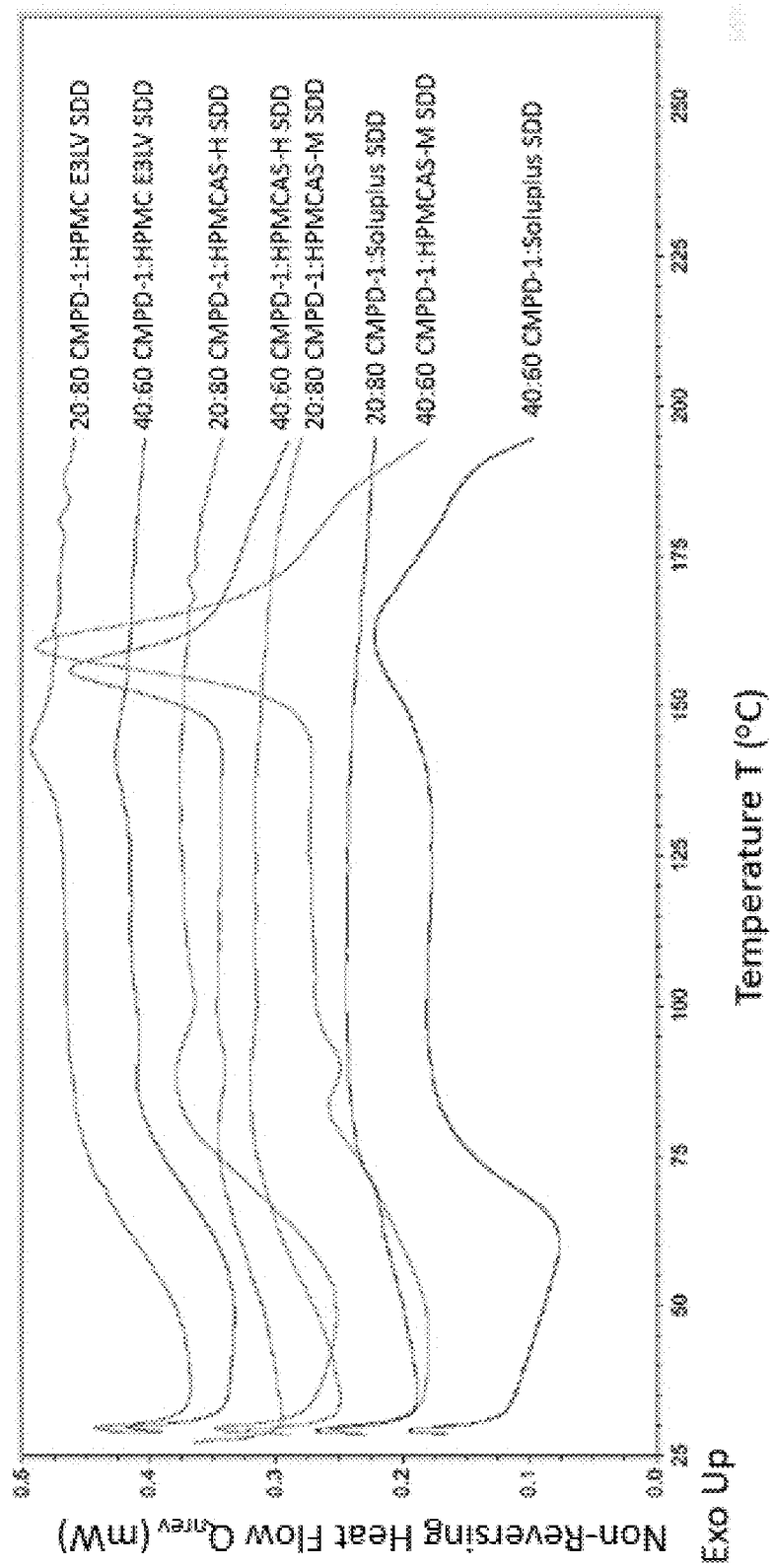
FIG. 11C is a graph generated in a differential scanning calorimetry (DSC) experiment of spray-dried dispersions of Compound 1:and polymers showing heat flow Q (W/g) as a function of temperature (deg C.).

Samples of the solid dispersions containing Compound 1 were analyzed by Differential Scanning Calorimetry using a TA Discovery DSC2500 with RCS90 chiller according to standard instrument procedures provided by manufacturer. Parameters used for the analysis are shown below in Table 9. Three replicates of the experiment were run for each dispersion. The resulting thermograms showing reversing heat flow are shown in FIG. 11B. Glass transition temperatures and glass transition temperature onsets are shown in Table 10 below. Notable, all the samples showed a single glass transition temperature in FIG. 11B, indicating good homogeneity. Additionally, all samples except the dispersions containing Soluplus exhibited glass transition temperatures above 90° C., which is a good indication of stability of the dispersions. FIG. 11C shows the thermograms of non-reversing heat flow. The samples containing 40:60 Compound 1:HPMCAS-H and 40:60 Compound 1:HPMCAS-M displayed an exothermic event occurring at around 150-160° C., indicating a possible recrystallization event.

TABLE 9

MDSC Parameters

| | |
|---|---|
| Instrument: | TA Discovery DSC2500 with RCS90 chiller |
| Scan Mode: | Ramp |
| Temp. Range: | 35° C.-200° C. |
| Heating Rate: | 2.0° C./min |
| Mod. Period: | 60 s |
| Mod. Amplitude: | ±1.0° C. |
| Pan/Lid type: | Non-Hermetic |
| Replicates | n = 3 |

TABLE 10

| Sample Description | TgOnset (° C.) | Tg(° C.) |
|---|---|---|
| CMPD-1 | 89.4 | 93.4 |
| 20:80 CMPD-1:HPMC E3LV SDD | 96.9 | 111.4 |
| 40:60 CMPD-1:HPMC E3LV SDD | 89.7 | 98.5 |
| 20:80 CMPD-1:HPMCAS-H SDD | 88.1 | 96.9 |
| 40:60 CMPD-1:HPMCAS-H SDD | 83.7 | 90.2 |
| 20:80 CMPD-1:HPMCAS-M SDD | 88.5 | 97.1 |
| 40:60 CMPD-1:HPMCAS-M SDD | 83.5 | 90.2 |
| 20:80 CMPD-1:Soluplus SDD | 57.4 | 71.5 |
| 40:60 CMPD-1:Soluplus SDD | 57.4 | 71.8 |

SEM Characterization of Solid Dispersions Containing Compound 1

Figure 11D:
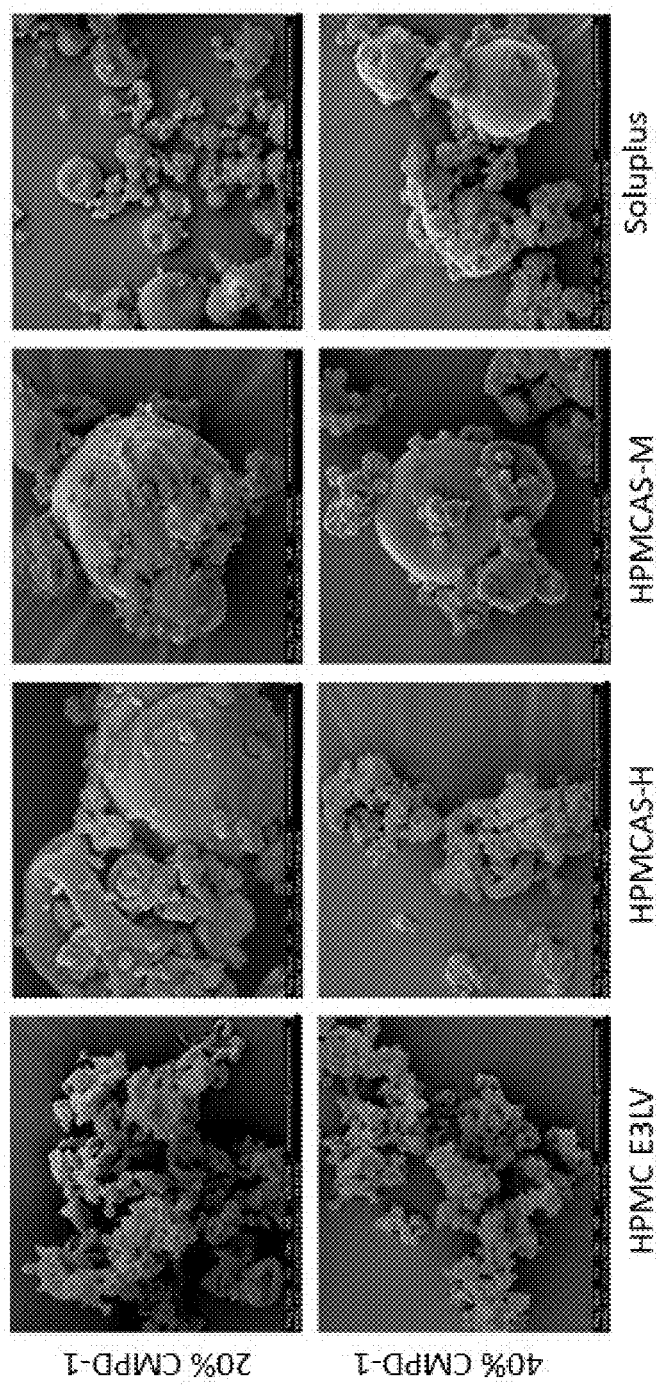
FIG. 11D are images of spray-dried Compound 1/polymer mixtures generated by SEM (scanning electron microscope). The dispersions' morphology consists of collapsed spheres. The majority of particles are less than 20 microns in diameter for all polymers.

Sample of solid dispersions containing Compound 1 were analyzed by scanning electron microscopy (SEM). Resulting images from this analysis can be seen in FIG. 11D. All dispersions displayed collapsed sphere morphology, which is typical of spray dried dispersions. All polymers tested had a majority of particles smaller than 20 μm, with the HPMC E3LV containing samples having a majority of particles of less than 10 μm.

Non-Sink Dissolution Characterization of Solid Dispersion Containing Compound 1

Figure 11E:
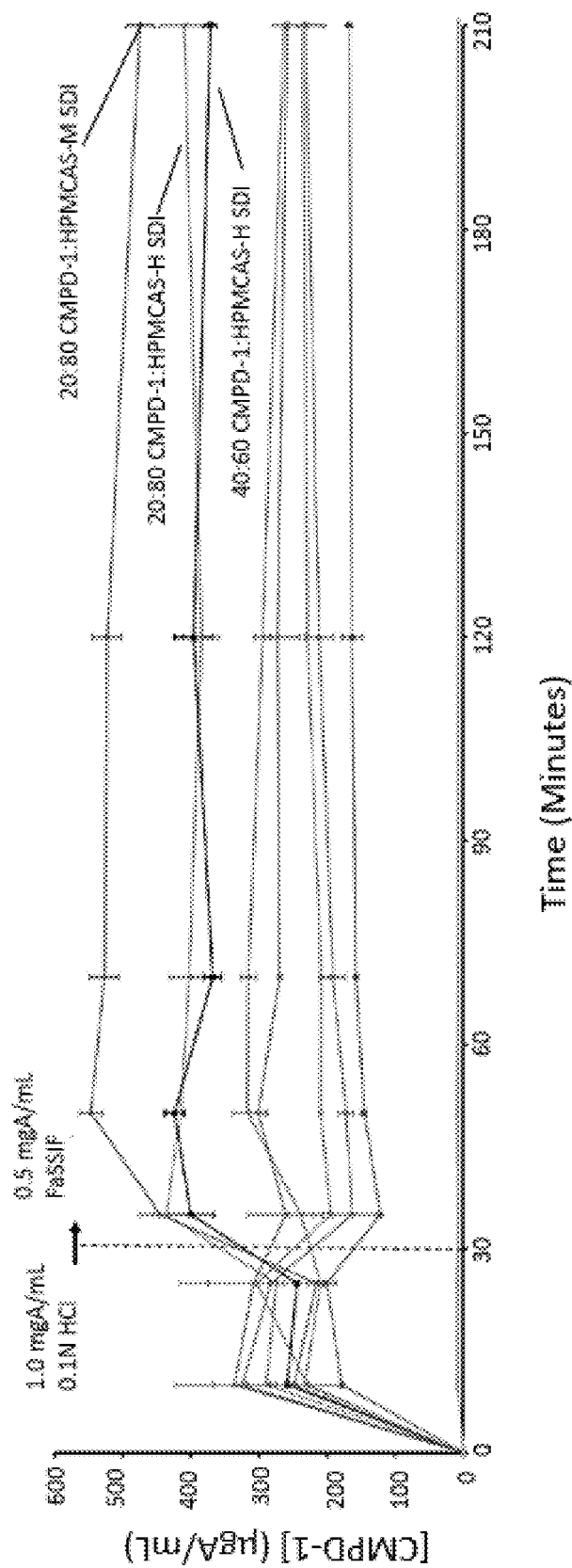
FIG. 11E is graph of Compound 1 solubility (μgA/mL) as a function of time (minutes) in a non-sink dissolution experiment for spray-dispersions of Compound 1 and a polymer.

Sample of solid dispersions containing Compound 1 were analyzed in a non-sink dissolution experiment. Dispersion samples and neat Compound 1 were suspended in 0.1N HCl media at a concentration of 1000 ug/mL Compound 1. Concentration of each sample was then measured by centrifugation to pellet undissolved material, and an aliquot of the supernatant was assessed by HPLC for concentration. Material was then agitated in a Distek 2100 C Dissolution apparatus, USP Type II. Instrument was operated according to standard instrument procedures provided by manufacturer. Parameters used for the experiment are shown below in Table 11. After 30 minutes, the media was modulated to FaSSIF by adding equivalent volume of FaSSIF buffer with bile salts, bringing the theoretical concentration of compound 1 to 500 μg/mL. Dissolved concentration of Compound 1 in each sample was then assessed periodically by HPLC. A plot of the resulting concentrations at each time point can be shown in FIG. 11E. From this data, max concentration of Compound 1 in 0.1N HCl ($C_{maxGB}$), max concentration of Compound 1 in FaSSIF ($C_{maxIB}$), area under the curve ($AUC_{5-180\ IB}$, measured in min*μgA/mL), final concentration of Compound 1 ($C_{210}$), and increase in area under the curve relative to neat Compound 1 ($AUC_{5-180\ IB}$ increase over API) were all calculated. These resulting values can be seen in Table 12 below.

TABLE 11

Figure 12A:
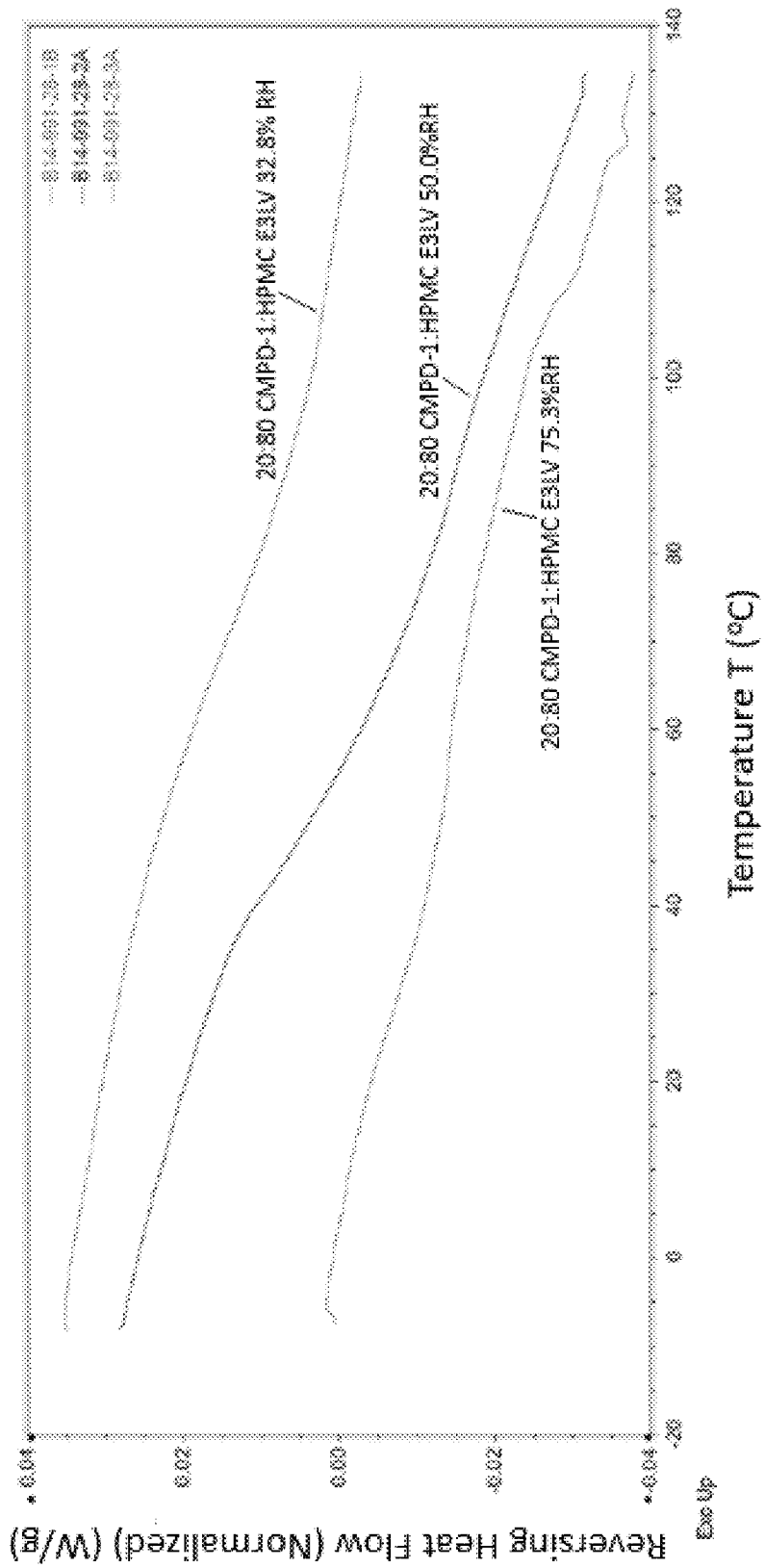
FIG. 12A is a graph generated in a differential scanning calorimetry (DSC) experiment of spray-dried Compound 1 compositions showing reverse heat flow $Q_{rev}$ (mW) as a function of temperature (deg C.) for various relative humidity samples.
Figure 12B:
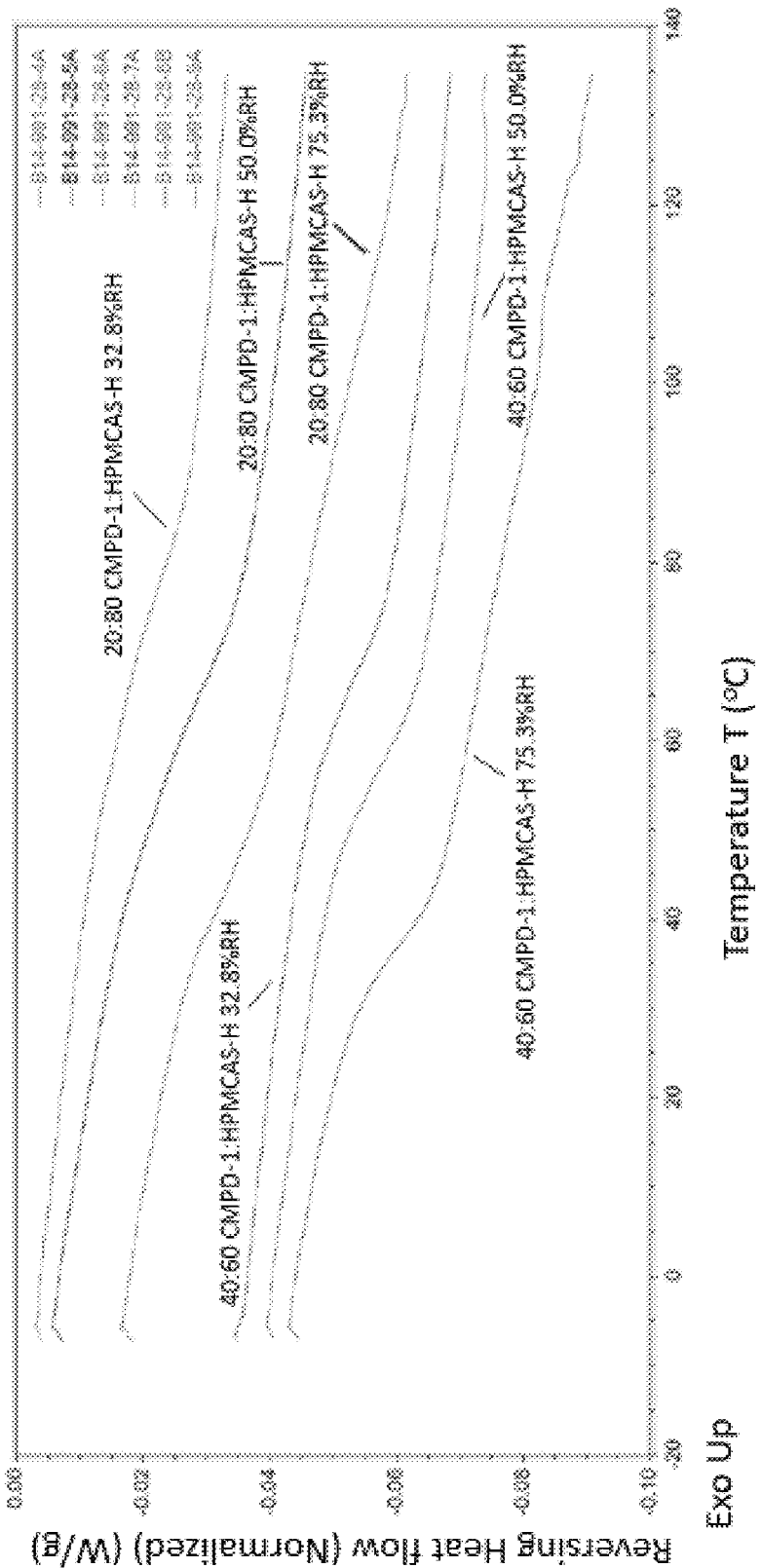
FIG. 12B is a graph generated in a differential scanning calorimetry (DSC) experiment of spray-dried Compound 1 compositions showing reverse heat flow $Q_{rev}$ mW) as a function of temperature (deg C.) for various relative humidity samples.
Figure 12C:
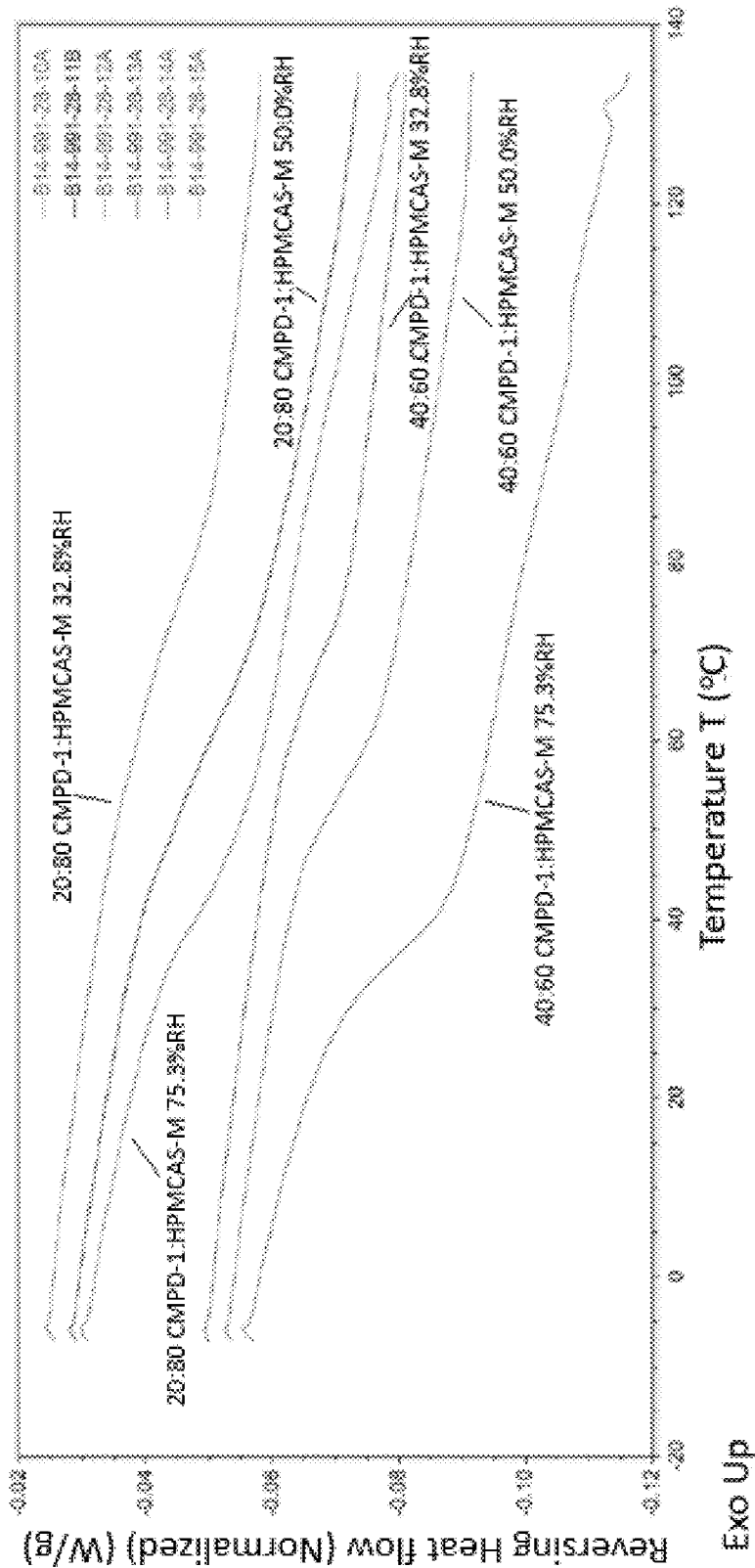
FIG. 12C is a graph generated in a plurality of differential scanning calorimetry (DSC) experiment of spray-dried Compound 1 compositions showing the glass transition temperature (deg C.) vs. relative humidity (percent).
Figure 12D:
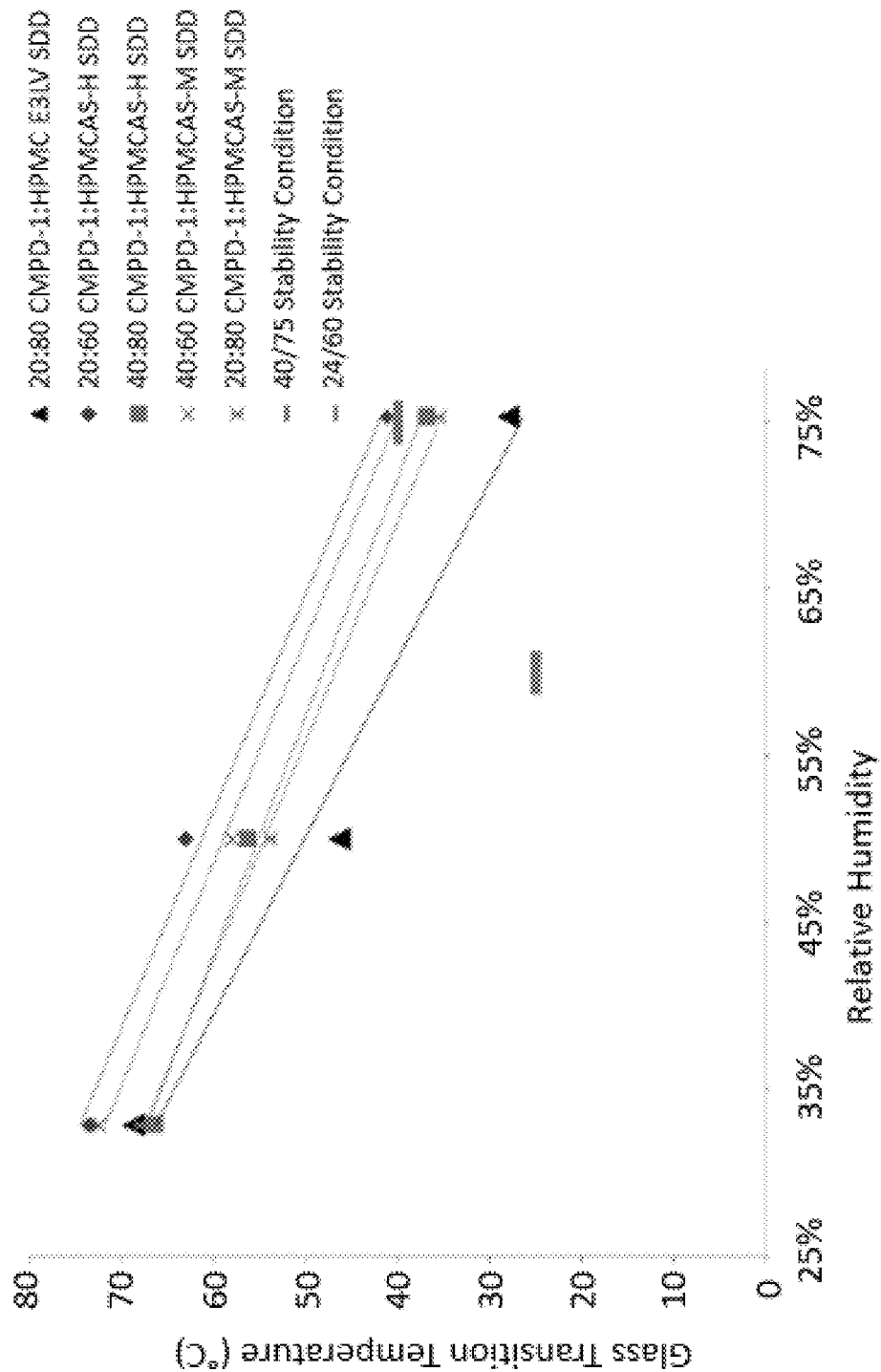
FIG. 12D is a graph showing the effect of RH on the glass transition temperature of various solid dispersion formulations of Compound 1.

| Parameter | Value |
| --- | --- |
| Apparatus | Distek2100 C Dissolution Apparatus, USP Type II |
| Gastric Media (SGF) | 0.1 NHCl |
| Gastric Dose | 1000 μgA/mL |
| Intestinal Media (FaSSIF) | 2.24 mg/mL FaSSIF in 100 mM PBS buffer |
| Intestinal Dose | 500 μgA/mL |
| Paddle RPM | 100 |
| Bath Temp | 37.0 ± 0.5° C. |
| Vessel Volume | 100 mL |
| Centrifuged | 3 min @ 13k RPM | calculated from earlier runs at 0% RH were used as a comparison. Two replicates of the experiment were run for each dispersion at each relative humidity. The resulting thermograms showing reversing heat flow for the 20:80 CMPD-1:HPMC E3LV dispersion are shown in FIG. 12A. Thermograms showing reversing heat flow for the 20:80 CMPD-1:HPMCAS-H and 40:60 CMPD-1:HPMCAS-H dispersion are shown in FIG. 12B. Thermograms showing reversing heat flow for the 20:80 CMPD-1:HPMCAS-M and 40:60 CMPD-1:HPMCAS-M dispersion are shown in FIG. 12C. Glass transition temperatures for each experiment were determined and are shown in Table 14 below. Additionally, a plot showing the effect of RH on the glass transition temperature of each sample was prepared and can be seen in FIG. 12D. For each dispersion, increased relative humidity was associated with a lower glass transition temperature.

TABLE 13

| DSC Parameters | |
| --- | --- |
| Instrument: | TA Discovery DSC2500 with RCS90 chiller |
| ModulatedDSC Parameters: | |
| ScanMode: | Modulated |
| Temp. Range: | −10° C.-140° C. |
| Heating Rate: | 2° C./min. |
| Modulation Period: | 60 sec. |
| Modulation Amplitude: | ±1.0° C. |
| Sample Pan | TzeroHermetic |
| Replicates | n = 2 |
| Method | DM-0204 |

TABLE 12

| Sample | CmaxGB(μgA/mL) | CmaxIB (μgA/mL) | AUC 5-180 IB (min*μgA/mL) | C210(μgA/mL) | AUC 5-180 IB increase over API |
| --- | --- | --- | --- | --- | --- |
| 20:80 CMPD-1:HPMCAS-M SDI | 248 | 546.4 | 89300 | 473.8 | 68.7 |
| 20:80 CMPD-1:HPMCAS-H SDI | 289 | 436.2 | 69900 | 409.6 | 53.8 |
| 40:60 CMPD-1:HPMCAS-H SDI | 259 | 424.2 | 67700 | 370.9 | 52.1 |
| 40:60 CMPD-1:HPMCAS-M SDI | 233 | 316.0 | 50800 | 262.4 | 39.1 |
| 20:80 CMPD-1:HPMC E3LV SDI | 336 | 301.5 | 47400 | 258.5 | 36.5 |
| 20:80 CMPD-1:Soluplus SDI | 303 | 235.4 | 39000 | 235.4 | 30.0 |
| 40:60 CMPD-1:HPMC E3LV SDI | 324 | 232.1 | 36200 | 232.1 | 27.8 |
| 40:60 CMPD-1:Soluplus SDI | 200 | 167.6 | 27900 | 167.6 | 21.5 |
| CMPD-1 API | 8 | 8.1 | 1300 | 7.1 | NA |

Characterization of $T_g$ vs RH of Solid Dispersions Containing Compound 1

Samples of selected solid dispersions containing Compound 1 were analyzed by Differential Scanning Calorimetry using a TA Discovery DSC2500 with RCS90 chiller according to standard instrument procedures provided by manufacturer. Parameters used for the experiment are shown below in Table 13. Each dispersion was tested at multiple % relative humidities (RH) (32.8%, 50.0%, and 75.30%). $T_g$s

TABLE 14

| Sample Description | % RH | Avg. $T_g$ (° C.) | STD DEV (° C.) |
| --- | --- | --- | --- |
| 20:80 CMPD-1:HPMC E3LV | 0.0% | 111 | 0.4 |
| | 32.8% | 69 | 0 |
| | 50.0% | 46 | 0.4 |
| | 75.3% | 27 | 1.6 |
| 20:80 CMPD-1:HPMCAS-H | 0.0% | 97 | 0.5 |
| | 32.8% | 74 | 0.2 |

TABLE 14-continued

| Sample Description | % RH | Avg. $T_g$ (° C.) | STD DEV (° C.) |
|---|---|---|---|
|  | 50.0% | 63 | 0.3 |
|  | 75.3% | 43 | 2.2 |
| 40:60 CMPD-1:HPMCAS-H | 0.0% | 90 | 0.1 |
|  | 32.8% | 67 | 0.2 |
|  | 50.0% | 56 | NA |
|  | 75.3% | 37 | 1.6 |
| 20:80 CMPD-1:HPMCAS-M | 0.0% | 97 | 0.4 |
|  | 32.8% | 72 | 0.2 |
|  | 50.0% | 58 | NA |
|  | 75.3% | 41 | 0.2 |
| 40:60 CMPD-1:HPMCAS-M | 0.0% | 90 | 0.4 |
|  | 32.8% | 68 | 0.1 |
|  | 50.0% | 54 | 0.1 |
|  | 75.3% | 36 | 0.7 |

Suspension Evaluation of Solid Dispersions Containing Compound 1

Figure 13A:
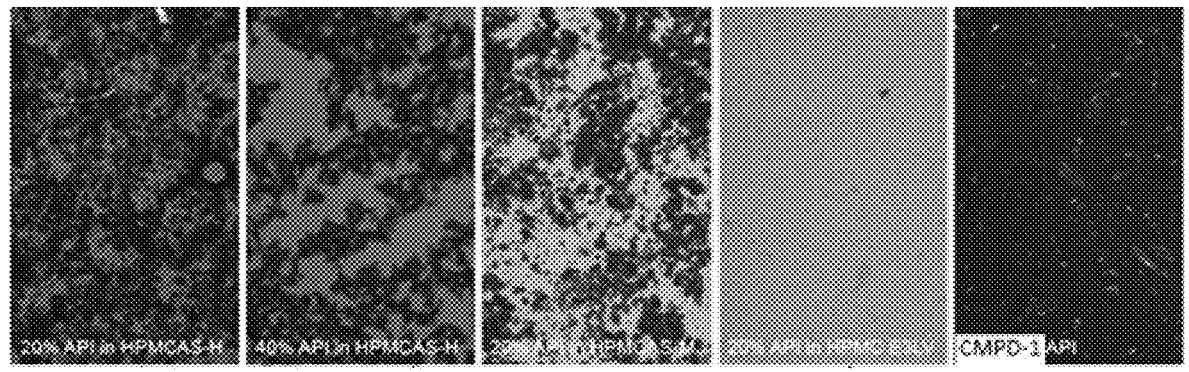
FIG. 13A is an image of Compound 1 compositions suspended in 0.5% Methocel A4M comprising a polymer as a spray dried dispersion composition or an API control. Images were taken at time point 0. All suspensions were amorphous.
Figure 13B:
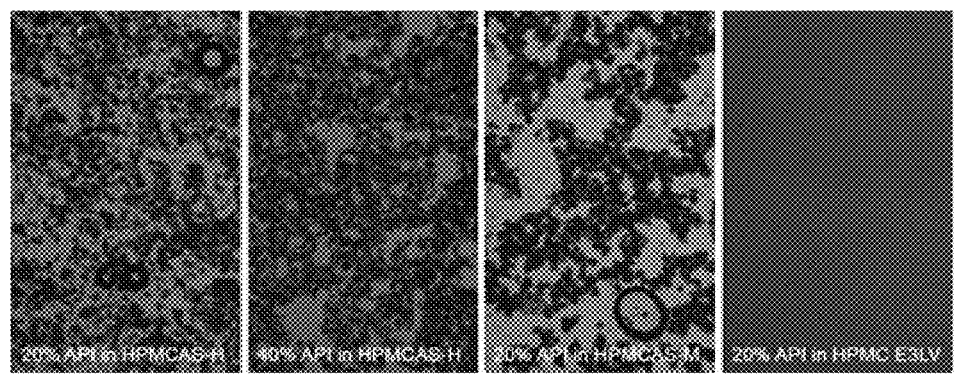
FIG. 13B is an image of Compound 1 compositions suspended in 0.5% Methocel A4M comprising a polymer as a spray dried dispersion composition or an API control. Images were taken at time point 2 hours. All suspensions were amorphous.
Figure 13C:
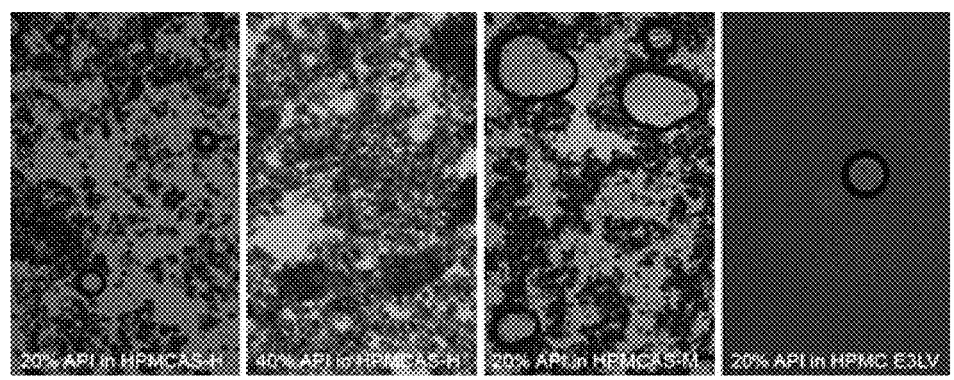
FIG. 13C is an image of Compound 1 compositions suspended in 0.5% Methocel A4M comprising a polymer as a spray dried dispersion composition or an API control. Images were taken at time point 6 hours. All suspensions were amorphous.

Suspensions of selected solid dispersions containing Compound 1 were prepared in 0.5 wt % Methocel A4M in order to assess suspension stability. 5 mL of 100 mg/mL concentrations of suspension (20 mg/mL Compound 1 or 40 mg/mL Compound 1) were prepared in mortar and pestle and transferred to scintillation vials. The samples were continuously stirred and characterized by polarized light microscopy (PLM) at t=0, 2, and 6 hours. FIG. 13A shows PLM images at the t=0 time point. These images indicate that all the suspensions of dispersions containing Compound 1 were amorphous and homogenous in appearance. At this time point, all suspensions were syringe able through 16 ga. gavage needles. FIG. 13B shows PLM data for the same samples at the two hour time point. All suspensions were still amorphous, with no change in visual appearance or consistency. FIG. 13C shows PLM data for the samples at the six hour time point. The 20% Compound 1 dispersions showed no change in visual appearance or syringeability after six hours. The 4000 Compound 1 dispersions showed a decrease in syringeability of the suspensions at this time point, likely due to increased agglomeration.

Example 14: Additional Solid Dispersions Comprising Compound 1 and Polyvinyl Pyrrolidine In addition to the solid dispersion provided above in Example 13, additional solid dispersions were prepared using analogous methods. A variety of mixtures of Compound 1 and Kollidon© 17 PF (BASF). Kollidon© 17 PF is a polyvinyl pyrrolidine polymer having a weight average molecular weight from about 7,000 to about 11,000 daltons and a bulk density of about 400-600 g/L.

Figure 14:
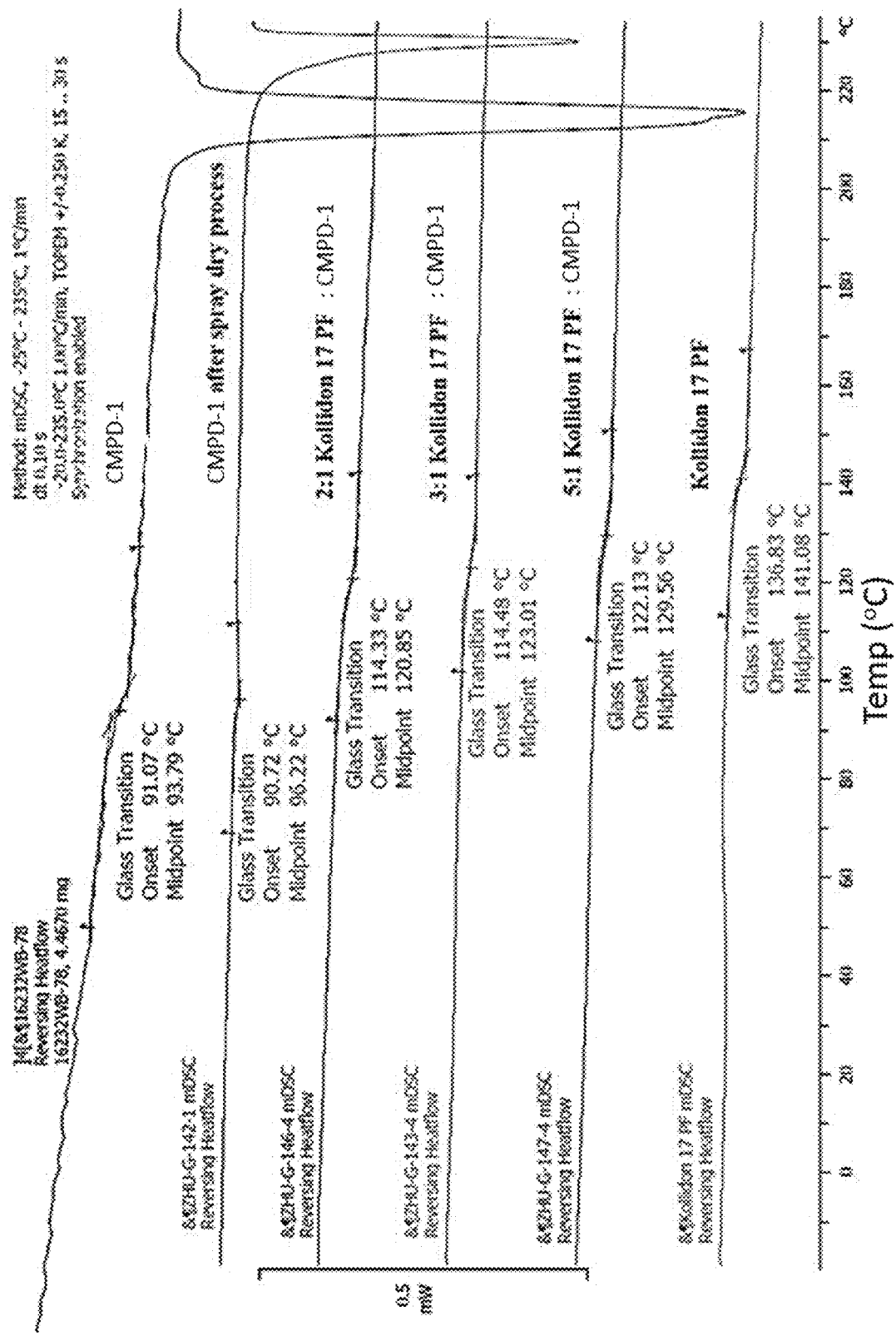
FIG. 14 is a graph generated in a plurality of differential scanning calorimetery (DSC) experiment of spray-dried Compound 1 compositions comprising polyvinyl pyrrolidine showing the glass transition temperature (deg C.) of each mixture

Mixtures of Kollidon© 17 PF and Compound 1 were prepared as spray dried dispersions in ratios of 2:1, 3:1, and 5:1 Kollidon 17 PF:Compound 1. The dispersions were characterized in a variety of manners, including DSC, XRPD, HPLC, TGA, and NMR. The results of each of these analyses can be shown below in Table 15. FIG. 14 shows the resulting DSC trace for each of the mixtures, as well as Compound 1 by itself both before and after being subject to the spray drying process.

TABLE 15

| Material | mDSC (Tg, C.) | XRPD | Moisture Sorption 60% RH | Moisture Sorption 90% RH | XRPD (Post DVS) | HPLC HPLC | TGA | NMR |
|---|---|---|---|---|---|---|---|---|
| Pure Compound 1 | 96.2 | Amorphous | No Data | No Data | No Data | 99.6 | 0.4 wt % loss at 44.7 C., onset 255.2 C. | Contains water, no EtOH |
| 2:1 Kollidon 17 PF/Compound 1 | 120.9 | Amorphous | No Data | No Data | No Data | 99.75 | 1.6 wt % loss at 40.3 C., 0.1 wt % loss at 120.3 C., onset 239.2 C. | Contains water, no EtOH |
| 3:1 Kollidon 17 PF/Compound 1 | 123 | Amorphous | 13.3 wt % | 31.0 wt % | Amorphous | 99.58 | 2.1 wt % loss at 40.0 C., 0.2 wt % loss at 128.0 C., onset at 245.4 C. | Contains water, no EtOH |
| 5:1 Kollidon 17 PF/Compound 1 | 129.6 | Amorphous | No Data | No Data | No Data | 99.48 | 2.5 wt % loss at 41.2 C., 0.2 wt % loss at 128.8 C., onset 248.7 C. | Contains water, no EtOH |

Example 15: Polymorph Analysis of Compound 1

One sample of Compound 1 was analyzed as received. It was unsolvated; Thermogravimetric Analysis (TG) results showed 0.77% weight loss below 230° C. Karl Fischer analysis showed a negligible amount of water, 0.22%. The endothermic event observed by differential scanning calorimetry (DSC) at 232.60° C. was likely melting. It was not hygroscopic. Compound 1 was also analyzed by XRPD (see FIG. 15). This polymorph of Compound 1 was designated as Form A.

Solubilities of Compound 1 in a few solvents were estimated. The experiments were carried out by adding the test solvent in aliquots to weighed portions of solid. Whether dissolution had occurred was judged by visual inspection after addition of each solvent aliquot. The results are shown in Table 16. Solubility numbers were calculated by dividing the total amount of solvent used to dissolve the sample by the weight of the sample. The actual solubilities may be greater than the numbers calculated because of the use of solvent aliquots that were too large or because of slow dissolution rates. The solubility number is expressed as "less than" if dissolution did not occur during the experiment. The solubility number is expressed as "greater than or equal to" if dissolution occurred on addition of the first solvent aliquot.

TABLE 16

| Solvent | Sample Weight (mg) | Solvent Amount (mL) | Solubility (mg/mL) |
|---|---|---|---|
| acetone | 3.4 | 2 | 2$^a$ |
| acetonitrile | 4.7 | 4 | <1 |
| dichloromethane | 4.4 | 2 | 2$^a$ |
| dimethylformamide | 4.4 | 0.3 | 15 |
| ethyl acetate | 3.5 | 3 | 1 |
| ethyl ether | 4.9 | 4 | <1 |
| ethanol (absolute) | 3.6 | 0.6 | 6 |
| methanol | 5.0 | 0.8 | 6 |
| 2-propanol | 3.3 | 0.8 | 4 |
| tetrahydrofuran | 4.8 | 0.8 | 6 |
| water | 4.8 | 4 | <1 |

$^a$Solid dissolved, then solid precipitated. Additional solvent then added to dissolve solids.

Polymorph Screen

Approximately 30 samples of Compound 1 were generated under various conditions in attempts to generate polymorphs. Three polymorphs were observed; designated forms A, B, and C. Samples generated and analyzed are listed in Table 17.

TABLE 17

| Method | Solvent$^a$ | Conditions$^b$ | XRPD Pattern |
|---|---|---|---|
| evaporation | acetone | foil w/3 pin holes, RT | C |
| | ACN | foil w/3 pin holes, RT | C |
| | DCM | foil w/3 pin holes, RT | B |
| | EtOH | foil w/3 pin holes, RT | C |
| | EtOAc | foil w/3 pin holes, RT | C |
| | MeOH | foil w/3 pin holes, RT | A + C |
| | 2-PrOH | foil w/3 pin holes, RT | C |
| | THF | foil w/3 pin holes, RT | C |
| cooling | acetone | 60 →, 0° C. | C |
| | ACN | 80 →, 0° C. | C |
| | DCM | 40 →, 0° C. | B |
| | EtOAc | 80 →, 0° C. | C |

TABLE 17-continued

| Method | Solvent$^a$ | Conditions$^b$ | XRPD Pattern |
|---|---|---|---|
| | EtOH | 80 →, 0° C. | C |
| | MeOH | 70 →, 0° C. | C |
| | 2-PrOH | 80 →, 0° C. | C |
| | THF | 70 →, 0° C. | C |
| slurry | acetone | RT, 4 days | C |
| | ACN | RT, 4 days | C |
| | DCM | RT, 4 days | B |
| | EtOAc | RT, 4 days | C |
| | Et$_2$O | RT, 4 days | C |
| | EtOH | RT, 4 days | C |
| | MeOH | RT, 4 days | C |
| | 2-PrOH | RT, 4 days | C |
| | THF | RT, 4 days | C |
| | water | RT, 4 days | C |
| | acetone/water (95/5) | RT, 4 days | C |
| | CH$_3$CN/water (95/5) | RT, 4 days | C |
| | 2-PrOH/water (95/5) | RT, 4 days | C |
| | THF/water (95/5) | RT, 4 days | C |

$^a$ACN = acetonitrile, DCM = dichloromethane, EtOAc = ethyl acetate; Et$_2$O = diethyl ether; EtOH = ethanol; MeOH = methanol; 2-PrOH = 2-propanol; THF = tetrahydrofuran.
$^b$RT = room temperature Based on the polymorphic behavior of Compound 1 in the first-stage polymorph screen, additional polymorph screening was conducted. Approximately 30 additional samples were generated under various conditions in attempts to generate additional polymorphs. No additional polymorphs were observed. Samples generated and analyzed are listed in Table 18 and Table 19.

TABLE 18

| Method | Solvent$^a$ | Conditions$^b$ | XRPD Pattern |
|---|---|---|---|
| precipitation | acetone | RT, dissolved, precipitated | NC/C |
| | DCM | RT, dissolved, precipitated | A + B |
| | EtOH | reflux → 0° C., Hex AS | C |
| | EtOH | reflux → 5° C., H$_2$O AS | C |
| | MeOH | reflux → 0° C., Et$_2$O AS | A |
| | MeOH | reflux → 5° C., H$_2$O AS | C |
| | 2-PrOH | reflux → 0° C., Hex AS | C |
| | 2-PrOH | reflux → 5° C., H$_2$O AS | C |
| | THF | reflux → 0° C., Hex AS | A |
| | THF | reflux → 5° C., water AS | C |
| rotary evaporation | EtOH | RT | A |
| | MeOH | RT | A |
| | 2-PrOH | RT | A |
| | THF | RT | A |
| milling | none | grind, 20 minutes | A |
| | acetone | grind, 20 minutes | C |
| | EtOAc | grind, 20 minutes | C |
| | EtOH | grind, 20 minutes | C |
| | H$_2$O | grind, 20 minutes | C |
| vapor diffusion | EtOH | ACN AS | — |
| | EtOH | H$_2$O as | C |
| | MeOH | ACN AS | NC/C |
| | MeOH | Hept AS | NC/C |
| | 2-PrOH | Et$_2$O AS | — |
| | 2-PrOH | MtBE AS | — |
| | THF | Et$_2$0 AS | C |
| | THF | Hex AS | C |
| heat/humidity | water | RT, 97% RH, 6 days | A |
| | | 40° C., 75% RH, 6 days | A |

$^a$EtOAc = ethyl acetate; Et$_2$O = diethy ether; EtOH = ethanol; MeOH = methanol; 2-PrOH = 2-propanol; THF = tetrahydrofuran.
$^b$AS = anti-solvent, Et$_2$O = ethyl ether, Hept = heptane, Hex = hexanes, MtBE = tert-Butyl Methyl Ether, RT = room temperature.

TABLE 19

| Method | Solvent[a] | Conditions[b] | XRPD Pattern |
|---|---|---|---|
| evaporation | dichloromethane | foil w/3 pin holes, RT | D + B |
| slurry | acetone | RT, 2 days | C |
|  | dichloromethane | RT, 2 days | D |
|  |  |  | D + B |
| air dry | n/a | 205-12-2 allowed to dry in ambient air 2 days | B |

It was decided to prepare forms B and C at larger scale for characterization (Table 19). A new form was observed from the scale-up experiments, designated form D. A sample of Compound 1 was crystallized using the AMRI process. The process was performed at a scale of approximately 0.5 g. Samples were collected periodically and analyzed by XRPD to monitor the polymorphic form throughout the experiment (Table 20). The XRPD pattern of the resulting material was a mixture of form A with a minor amount of form C.

TABLE 20

| Step | Details | XRPD Pattern |
|---|---|---|
| 1 | 477 mg of API dissolved in 30 mL of 4% MeOH in CH$_2$Cl$_2$. Washed twice with 5 mL 1N HCl and once with 5 mL 1N NaOH. Dried using Na$_2$SO$_4$. Vacuum filtered, mother liquor placed in sealed vial at ambient. Crystallization observed within 70 minutes. A subsample was filtered and analyzed by XRPD. | D + B (min) |
| 2 | Sample left at ambient overnight to allow for further crystallization. A subsample was filtered and analyzed | D + B (min) |
| 3 | Add 7.5 mL hexanes and let sample sit for 8 hours. The sample was filtered and analyzed by XRPD. | D + B (min) |
| 4 | Solid dried at ambient pressure, 75° C., T = 3 hours | D + B |
| 5 | Drying at 75° C. continued, T = 24 hours | A + B + C (min) |
| 6 | Drying at 75° C. continued, T = 72 hours | A + C (min) |

Characterization of New Polymorphs

Form B: Characterization data are shown in Table 21. It is a dichloromethane solvate; TG results show 6.51% weight loss below 125° C. which corresponds to 0.4 moles of dichloromethane. Approximately 0.25 moles of dichloromethane is observed in the NMR spectrum, suggesting it is a quarter-dichloromethane solvate. The discrepancy in the amount of dichloromethane calculated from the TG and NMR is likely due to solvent loss prior to NMR analysis. The amount of dichloromethane incorporated in the crystal structure may vary. Karl Fischer analysis shows a negligible amount of water, 0.19%. The endothermic event observed by DSC at 233.55° C. is likely melting. It is not hygroscopic.

TABLE 21

| Technique | Result |
|---|---|
| XRPD | crystalline, form B |
| DSC | endos 126.22, 233.55° C. |
| TG | 6.51% loss up to 125° C. 0.86% loss from 125 to 235° C. |
| KF | 0.19% water |
| DVS | 0.09% loss on drying at 5% RH 0.98% gain from 5 to 95% RH 2.46% loss from 95 to 5% RH |

TABLE 21-continued

| Technique | Result |
|---|---|
| Post-DVS XRPD | form B |
| NMR | consistent with structure |

A sample of form B was heated to 125° C. and held at that temperature for approximately 10 minutes. XRPD analysis of the resulting material shows that it converted to Form A (Table 22).

TABLE 22

| Experiment | TG Result | XRPD Pattern |
|---|---|---|
| Heat at 10° C./min to 125° C. Hold for 10 minutes. | 6.80% loss up to 125° C. | A |

Form C: Characterization data are shown in Table 23. It is unsolvated; TG results show 0.51% weight loss below 230° C. Karl Fischer analysis shows a negligible amount of water, 0.20%. The endothermic event observed by DSC at 227.82° C. is likely melting. It is not Hygroscopic. An exemplary XRPD pattern of form C can be seen in FIG. 15, which shows degrees 2 theta on the X-axis and counts on the Y axis.

TABLE 23

| Technique | Result |
|---|---|
| XRPD | crystalline, form C |
| DSC | endo 227.82° C. |
| TG | 0.51% loss up to 230° C. |
| KF | 0.20% water |
| DVS | 0.001% loss on drying at 5% RH 1.05% gain from 5 to 95% RH 1.15% loss from 95 to 5% RH |
| Post-DVS XRPD | form C |
| NMR | consistent with structure |

Form D: Characterization data are shown in Table 24. It is a dichloromethane solvate; TG results show 9.95% weight loss below 125° C. which corresponds to 0.6 moles of dichloromethane. However, that weight loss may not be a reliable measure of the volatile content since loss was occurring at the beginning of the experiment. Approximately 1.1 moles of dichloromethane is observed in the NMR spectrum, suggesting it is a mono-dichloromethane solvate. Karl Fischer analysis shows a negligible amount of water, 0.25%. The endothermic event observed by DSC at 233.37° C. is likely melting. It is not hygroscopic.

TABLE 24

| Technique | Result |
|---|---|
| XRPD | crystalline, form D |
| DSC | endos 125.46, 233.37° C. shoulder 223.68° C. |
| TG | 9.95% loss up to 125° C. 0.58% loss from 125 to 235° C. |
| DVS | 3.19% loss on drying to 5% RH 0.07% loss from 5 to 95% RH 2.57% loss from 95 to 5% RH |
| KF | 0.25% water |
| Post-DVS XRPD | form C + B |
| NMR | consistent with structure |

Relative Stability of Polymorphs

Competitive slurry experiments were performed to determine the most stable form over a range of temperatures (Table 10). Form C was found to be more thermodynamically stable than form A in the temperature range tested.

Form D was found to be unstable, and rapidly converts to form B under ambient conditions. Form B was found to convert to form A when heated.

Form C was found to be more thermodynamically stable than form A in the temperature range of 5 to 60° C. Form A has a higher melting point than form C, suggesting that the two forms are enantiotropically related. Form C was determined to be the best target polymorph form for crystallization and further development.

Example 16: Nanosuspension Formulation of Compound 1 Polymorph Form C

Raw material of Compound 1 in polymorph Form C was characterized by X-ray powder diffraction (XRPD) and polarized light microscopy (PLM). The material was found to be highly crystalline.
Nanosuspension Screening 0.4 mL vehicle (list in Table 24B) was mixed with the 0.2 mL milling beads (0.5 mm) at the ratio of 2:1 in 1.5 mL plastic tube, then adequate compound of Compound 1 was added to the system, aiming to obtain a target concentration of 200 mg/mL. Then place them on MM400 for continuous milling. From characterization results: 5 vehicles were tried at small scale of 0.4 mL by MM-400 instrument at 2500 rpm for 12.5 hours, 3 vehicles (F2, F3 and F5) showed better and similar results of PSD at 240~260 nm in D50 and 400-440 nm in D90.

TABLE 24B

| Prototype No. | Vehicle Composition |
|---|---|
| F1 | 0.5% HPMC E5/0.5% Tween 80 in water |
| F2 | 0.5% HPMC E5/0.5% PVP K30/0.2% SDS in water |
| F3 | 0.5% HPMC E5/0.2% SDS in water |
| F4 | 1% Poloxamer 188/05% Tween 80 |
| F5 | 2% HPC SL/0.2% SDS in water |

The obtained nanosuspensions were transferred into 2-mL glass vials, and then stored under 5° C. and 25° C. After storing for 1-4 week, the suspensions were sampled for XRPD, ZPPS and UPLC analysis to check possible physical and chemical changes. Based on stability results in, the particle size of prototype F1, F2, F,3 and D4 increased, but the particle size of prototype F5 (nanosuspension with vehicle 0.5% HPM SL/0.2% SDS in water) almost remained unchanged. All four formulations were physically and chemically stable. Prototype F5 was selected for the following scale up for PK and Tox study.
Nanosuspension Scale Up 0.9091 g of API was weighed into 12 mL stainless steel pot and 4.5 mL vehicle F5 was added to the system with target of 200 mg/mL, then 1.5 mL of 0.5 mm zirconium beads was added. The sample was ground with PM400 for 5 hours. The sample was transferred to 6 centrifuge tubes and continued grinding with MM400. The sample was ground with MM400 for 4 hours. The sample was tested by ZPPS and XRPD. The nanosuspension product was transferred to a 10 mL tube and diluted to 5 mg/mL (50 mL, Compound 1-suspension-5 mg/mL) and 10 mg/mL (50 mL, Compound 1—suspension-10 mg/mL) with the vehicle (FR00965-2-0505-vehicle) and test the samples (5 mg/mL and 10 mg/mL) by UPLC and ZPPS.

~200 mg of Compound 1 was weighed into 2 mL vial and 1 mL vehicle (FR00965-2-0505-vehicle) will be added to target of 200 mg/mL, then 0.5 mL of 0.5 mm zirconium beads was added. Make two samples in parallel. Grind the sample with MM400. The sample was test by ZPPS, purity and XRPD. The obtained nanosuspensions were transferred into 2-mL glass vials, and then stored under 4° C. and −20° C. After storing for 1 week~3 months, the suspensions were sampled for XRPD, ZPPS and UPLC analysis to check possible physical and chemical changes.

Based on the formulation screening and stability results of 5 prototypes, F5 (targeting 200 mg/mL, vehicle: 2% HPC SL/0.2% SDS) showed best performance with limited particle increase ~50 nm in 4 week (260 nm to 330 nm in D50, 388 nm to 493/579 nm in D90 at RT/5° C.). All the other stability characterization were kept same with initial.

Example 17: Further Analysis of Polymorphs

Figure 17:
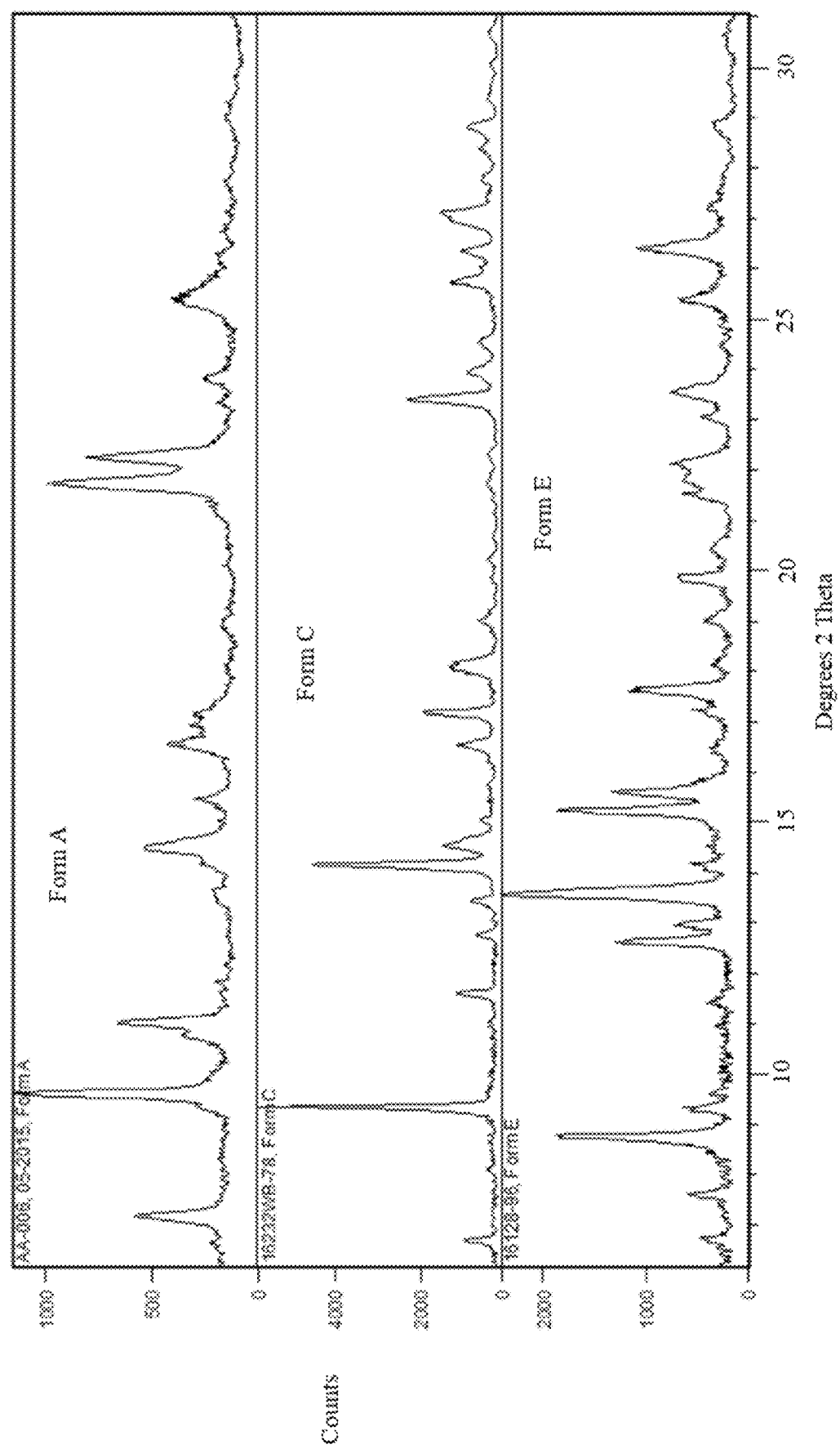
FIG. 17 shows, from top to bottom, XRPD patterns of Compound 1 in polymorph Form A, Form C, and Form E.

Physicochemical characterization of Compound 1 was performed to support formulation development. Experiments were conducted to study solid-state properties (e.g. physical state, thermal analysis, water vapor sorption, and polymorphism), physical properties (e.g. particle morphology and particle size), intrinsic stability (e.g. API chemical stability at elevated temperature), and biopharmaceutical properties (e.g. solubility, dissolution, and biopharmaceutical parameters) of the active pharmaceutical ingredient (API).
Polymorph Confirmation Three batches of Compound 1 were received and analyzed. The chemical structure of the material was confirmed by 1H NMR analysis. X-ray powder diffraction (XRPD) data (FIG. 17) showed that the three batches were in crystalline state. As demonstrated in Example 15 above, the XRPD patterns suggested that one batch was Form A, a second batch was Form C, and the third batch was yet another form, designated Form E (see Top, Middle, and Bottom of FIG. 17, respectively).

Since the third batch contained a polymorph not previously analyzed (Form E), there was a need to check whether this batch is reproducible by provided crystallization conditions at a relatively smaller scale of 500 mg. 500 mg of the compound was dissolved in approximately 20 mL of approximately 10:1 DCM/MeOH, solvent removed under vacuum, and the resulting solid dried for one day in vacuum oven. XRPD data indicated that both wet (before drying) and dried (after drying) solids were Form E. This demonstrated that the generation of Form E was reproducible. From pharmaceutical development point of view, the most thermodynamically stable form is highly preferred. Therefore, polymorphic relationship, in term of relative physical stability, needs to be further understood.
Humidity Effect Form C is a thermodynamically stable form (over the temperature range of 5 to 60 C) (Example 15). The determination of relative polymorphic stability between the reported stable form and newly discovered form was of importance. The relative physical stability between Form C and Form E was initially assessed by storage of the two samples at high relative humidity (RH) levels (e.g. 88% and 95% RH). There was no polymorph change when Form C was exposed to 88% RH for 7 days, followed by 95% RH for additional 8 days. As to Form E, the polymorph was also unchanged after 16 days storage at 88% RH. However, it turned to a mixture of Form A, C and E after the material was exposed to 95% RH for additional 7 days. This observation highly suggested that Form C could be more thermodynamically stable than Form E at ambient temperature and high RH % kinetically facilitated the conversion of Form E to Form C.

Slurry Experiments

To further systematically evaluate relative polymorph stability at elevated temperatures, slurries (solvent-mediated method) were set up for polymorph competitive study between Form A and C, Form C and E, and Form A and E under aqueous and organic conditions at temperatures of 60° C., 80° C., and 100° C. The original polymorphs in each mixture converted to Form C, confirmed by XRPD, after one day of stirring. Additionally, slurry of solely Form E under ambient conditions was set up in both water and IPA. Similarly, Form C was detected after one day of stirring. The data proved that Form C was the most thermodynamically stable polymorph at temperature of 100° C. or lower. These results indirectly supported the conclusion that Form C was relative more stable form. Therefore, Form C (the most thermodynamically stable form of the API) was selected for formulation development. In addition, the physicochemical characterization was conducted to have a comprehensive understanding of the solid-state properties of the polymorphs.

Solid-State Characterization of Polymorphs

Polarized-light optical microscopy showed that both Form A and C were in needle-like shape with presence of birefringence. However, Form E was irregular-shaped particles with presence of birefringence.

Gravimetric moisture sorption analysis indicated a slight moisture uptake (e.g. approximately 1.6% and 0.8% weight gain for Form E and Form C, respectively, at 90% relative humidity, suggesting nonhygroscopic nature of the polymorphic forms. The two full moisture adsorption isotherms at 25° C. did not exhibit pronounced phase transitions. In addition, as supported by XRPD analysis, the polymorphic forms, studied in gravimetric moisture sorption, was unchanged after being dried at 60° C./0% RH.

Thermal analysis was further employed to characterize the three batches of Compound 1. Differential scanning calorimetry (DSC) thermograms showed an endotherm peak at 234° C., 229° C., and 235° C. for batches of Form A, Form C, and Form E, respectively. In addition, thermogravimetric analysis (TGA) data indicated no weight loss for the Form E batch. The relatively lower melting temperature for Form C indicated that Form C is in enantiotropic relationship with Form A or Form E because a polymorph with higher thermodynamic stability based on slurry experiments is expected to show a higher melting temperature if it is in monotropic relationship with another polymorph. Relative stability of an enantiotropic polymorph pair of polymorphs reverses once a transition temperature is passed. In this case, the enantiotropic relationship of Form C versus Form A or Form E poses low risk on polymorph control in manufacturing process because the slurry study results in Section 2.1.2.2 showed Form C was stable below 100° C. and the manufacturing process is not expected to exceed 100° C. Therefore, determination of a transition temperature is not necessary.

Screening of Solubility Enhancement Approaches

Several biopharmaceutically relevant parameters of the API (Compound 1) were obtained for the API. The Log D7.4 of the API was determined to be 3.23 (Pion, Inc.) suggesting the API is likely a hydrophobic compound with a possible low solubility using shake-flask partitioning experiments. In addition, the API was categorized as high in absorption potential classification with no significant efflux determined by Absorption Systems by permeability through Caco-2 monolayers in both the apical-to-basolateral and basolateral-to-apical directions. Based on these two biopharmaceutical parameters, this compound is possibly a BCS Class II. Solubility enhancement is critical for bioavailability of the API for dosing. Therefore, to overcome the limitation from solubility, several experiments were conducted to assess various solubility enhancement approaches utilized in formulation development Solvent Screening—Ambient Temperature: To screen the API solubility (as a part of feasibility assessment of liquid dosage form in formulation development and dissolution method development), a number of solvent systems were selected for solubility enhancement at ambient temperature. The suspension of the material (Form C) in a variety of solvent was prepared and stirred at ambient temperature for three or four days. The equilibrated suspensions were isolated by centrifuge and the filtrates were injected into HPLC to determine equilibrium solubility of the API in each solvent system. The detailed equilibrium solubility data at ambient temperature are summarized in Table 5. Solubility higher than 10 mg/mL was observed in concentrated sodium lauryl sulfate (SLS) solutions at 100× critical micelle concentration (CMC). In addition, solubility of the API between 1 and 5 mg/mL were observed in EtOH, PEG 400, Propylene glycol, Capmul MCM, NF, Kolliphor EL, Capmul MCM, EP, Plurol Oleique CC 497, Peceol, Labrasol, SLS at 5× and 10×CMC, and Transcutol HP.

TABLE 25

| Solvent | Solubility by HPLC (mg/mL) | Comments** |
|---|---|---|
| Water | 0.0010* | Final pH: 8.99 |
| pH 1.0 buffer | 0.0012* | Final pH: 0.89 |
| pH 4.5 buffer | 0.0011* | Final pH: 4.80 |
| pH 6.8 buffer | 0.0008* | Final pH: 6.50 |
| FaSSIF | 0.0032* | Final pH: 6.78 |
| FaSSIF | 0.0051 | Final pH: 6.77 |
| FaSSIF | 0.039 | Final pH: 4.96 |
| FaSSIF | 0.047 | Final pH: 4.99 |
| Ethanol | 3.1 | — |
| PEG 400 | 2.0 | — |
| Propylene Glycol | 2.6 | — |
| Sulfobutylether β-CD | 0.75 | 40 wt % |
| Tween 80 | 0.56 | 1.2 mM (100× cmc) |
| Vitamin E TPGS | 0.020 | 0.2 wt % (10× cmc) |
|  | 0.040 | 2 wt % (100× cmc) |
| Gelucire 44/14 | 0.0008* | 1 mg/mL (500× cmc) |
| Captex 355, EP/NF | 0.049 | — |
| Captex 300, EP/NF | 0.064 | — |
| Castor Oil | 0.99 | — |
| Soybean Oil | 0.030 | — |
| Corn Oil | 0.031 | — |
| Canola Oil | 0.031 | — |
| Miglyol 810 | 0.053 | — |
| Miglyol 812 | 0.052 | — |
| Capmul MCM, NF | 4.4 | — |
| Capmul MCM, EP | 3.9 | — |
| Kolliphor P188 | 0.0016* | 0.4 mM (3.2× cmc) |
|  | 0.0031 | 4 mM (32× cmc) |
| Kolliphor HS-15 | 2.8 | Stirred at 35° C. |
| Oleic Acid | 0.39 | — |
| Plurol Oleique CC 497 | 1.2 | — |
| Peceol | 1.3 | — |
| Labrasol | 1.7 | — |

TABLE 25-continued

| Solvent | Solubility by HPLC (mg/mL) | Comments** |
|---|---|---|
| Labrafil M1944CS | 0.28 | — |
| Sodium Lauryl Sulfate | 0.15 | 8.2 mM (cmc) |
|  | 1.6 | 41 mM (5× cmc) |
|  | 2.4 | 82 mM (10× cmc) |
|  | 17 | 0.82M (100× cmc) |
|  | 19 | 0.82M (100× cmc) |
| Lecithin | 0.053 | 61 mg/mL (100× cmc) |
| Triacetic | 0.43 | — |
| Transcutol HP | 4.7 | — |

Solvent Screening—Elevated Temperature: In addition to equilibrium solubility at ambient temperature, the saturated solubility of the API at elevated temperature of 80° C. was visually estimated for gauging potential solubility enhancement in several selected excipients. Due to achievement of a high solubility of the API (16 or 20 mg/mL), the Capmul MCM was selected as a potential lipid vehicle for formulation development in soft gel capsule.

Amorphous Form

To assess the feasibility of solid dispersion approach in formulation development, the glass transition temperature of the material was determined by modulated differential scanning calorimetry (mDSC). Preliminary TGA data suggested that the material started a continuous weight loss due to decomposition as the API was heated up to 260° C. Therefore, as preparing an in-situ amorphous material in DSC pan, the end temperature should not ramp beyond 260° C. The amorphous samples were generated by heating the raw APIs from 25 to 250° C., followed by a rapid cooling to −60° C. The glass transition temperature (Tg) was measured by a slow heating of the generated amorphous samples from −60° C. to 250° C. The Tg for in-situ generated amorphous material from C and Form A was 93° C. and 97° C., respectively. The discrepancy in the two Tg values may simply due to the variation of water content in the samples or chemical purity.

Chemical Stability at Elevated Temperatures

To evaluate the chemical stability of the API at elevated temperatures (as another part of feasibility assessment of solid dispersion approach in formulation development), DSC experiments were conducted using the batch of Form C with a melting temperature (Tm) at 229° C. The API was heated to a variety of temperatures with several holding time periods in DSC. The resulted solids in DSC pan were extracted with DMSO. The solutions of API were prepared and injected into HPLC for determination of assay and related substances. The HPLC data indicated that an impurity (with RRT=0.8 in HPLC) were present in all prepared samples except the control sample. It directly suggested that feasibility of solid dispersion via hot-melt extrusion needed a further investigation. One of possible solution to the API degradation in hot-melt extrusion might be the addition of a plasticizer which may lower the process temperature for maintaining chemical integrity of the API.

Particle Size Reduction

To probe the impact of particle size reduction of the API on apparent solubility/dissolution for sake of facilitating formulation development, micronization of the batch with stable polymorph (Form C) was conducted. This powder batch was micronized using a 2-inch Sturtevant SDM2 Micronizer jet mill using 70 psi for feed pressure and 40 psi for grind pressure. The resulted micronized material was examined for particle morphology by polarized-light optical microscopy, particle sizing by particle size analyzer using a wet method, and physical form by XRPD. The micronized material lost regular needle-like morphology and converted into fine particles with particle size approximately less than 10 m. However, the birefringence of the particles remained, supported from crystalline nature of the material by XRPD analysis after micronization.

A wet-method of particle size analysis was adopted using a Sympatec Helos Particle Size Analyzer (SUCELL module). The particle sizing profiles of unmicronized and micronized materials highly agreed with the data from optical microscopy. The detailed particle sizing data are summarized in Table 26.

TABLE 26

| Batch | $X_{10}$ (μm) | $X_{50}$ (μm) | $X_{90}$ (μm) | Comments |
|---|---|---|---|---|
| Form C Batch Pre-Micronization | 1.9 | 11 | 35 | Form C |
| RSD (n = 9) | 7.9% | 12% | 2.2% |  |
| Form C Batch Post Micronization | 0.92 | 3.3 | 8.5 | Micronized Form C |
| RSD (n = 9) | 4.3% | 4.2% | 3.4% |  |

Dissolution

Figure 18:
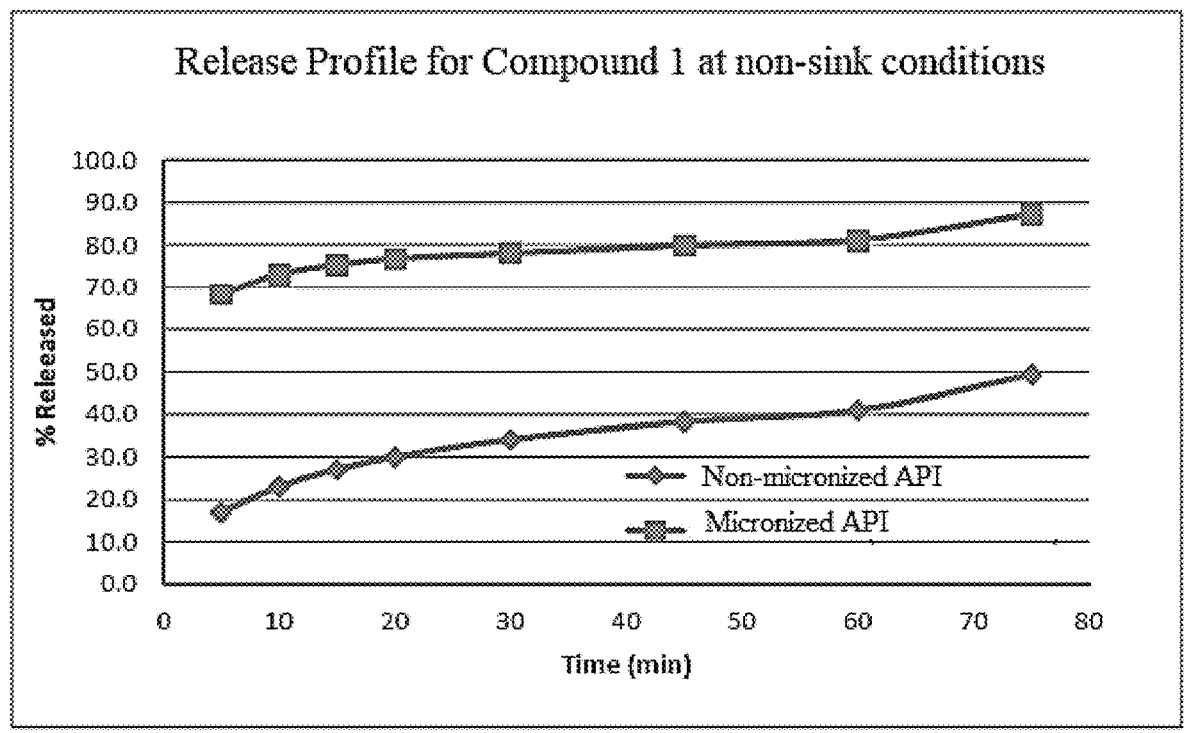
FIG. 18 shows a graph of the results of a solubility experiment comparing micronized and non-micronized Compound 1 in polymorph Form C.

To assess the impact of particle size reduction of the API on dissolution profile, the unmicronized Form C and micronized Form C API materials were evaluated for dissolution at non-sink conditions for a higher sensitivity of differentiating formulation effect (e.g. particle size). The required amount (approximately 222 mg) of each API was rinsed into dissolution vessel containing 500 mL of 0.366% SLS in water with nominal solubility of the API of ~0.46 mg/mL. The solubility of the API in 0.36% SLS in water was calculated as 0.4447 mg/mL based on SLS concentration vs solubility profile. With comparison to unmicronized counterpart, the micronized API exhibited an enhanced dissolution rate and overall release percentage up to 75 min, as is shown in FIG. 18. The enhancement in dissolution rate from micronized samples was likely due to the increase in surface area after micronization supported by microscopic images and particle sizing.

CONCLUSIONS

Compound 1 was comprehensively characterized for solid-state properties, physical properties, intrinsic stability, and biopharmaceutical properties. All the batches (e.g. Form A, C, and E) were in crystalline state with the presence of birefringence and low moisture adsorption. The Form C was the most thermodynamically stable polymorph below 100° C. confirmed by humidity and slurry studies.

An effect of particle size on dissolution rate was observed which can be utilized to develop a dosage form. The amorphous form of the API, for feasibility of solid dispersion approach, exhibited a glass transition temperature at 93 or 97° C. However, the degradation of the API was a concern for solid dispersion approach by hot-melt extrusion which can be mitigated by spray drying method.

Solubility enhancement of the API was screened for a list of solvent systems with solubility higher than 10 mg/mL in SLS at 100×CMC and solubility between 1 and 5 mg/mL in twelve solvent systems. In addition, higher solubility (e.g. 16 and 20 mg/mL) in Capmul MCM was achieved in threshold solubility study at elevated temperature, suggesting promising of dosing from soft gel capsule and for toxicology studies.

What is claimed is:

1. A polymorph of a compound of Formula (I) having the structure:

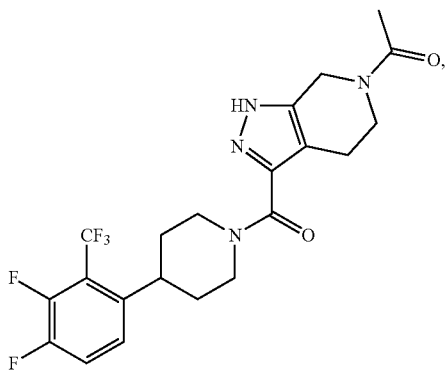 [SMILES: CC(=O)N1CCc2c(C(=O)N3CCC(c4ccc(F)c(F)c4C(F)(F)F)CC3)n[nH]c2C1]

wherein the polymorph exhibits an X-ray powder diffraction (XRPD) pattern having at least three characteristic peaks expressed in degrees two theta (+/−0.5 degree theta) at 6.7, 9.3, 14.1, 17.2, 23.5, 27.1, and 29.0.

2. The polymorph of claim 1, wherein the polymorph is crystalline.

3. The polymorph of claim 1, wherein the polymorph exhibits an X-ray powder diffraction (XRPD) pattern having at least five characteristic peaks expressed in degrees two theta (+/−0.5 degree theta) at 6.7, 9.3, 14.1, 17.2, 23.5, 27.1, and 29.0.

4. The polymorph of claim 1, wherein the polymorph exhibits an X-ray powder diffraction (XRPD) pattern having characteristic peaks expressed in degrees two theta (+/−0.5 degree theta) at 6.7, 9.3, 14.1, 17.2, 23.5, 27.1, and 29.0.

5. The polymorph of claim 1, wherein the polymorph exhibits an X-ray powder diffraction (XRPD) pattern having peaks substantially identical to those shown in FIG. 16.

6. The polymorph of claim 1, wherein the polymorph exhibits an endotherm at about 228° C. as determined by Differential Scanning calorimetry (DSC).

7. The polymorph of claim 1, wherein the polymorph exhibits a melting temperature ($T_m$) of about 229° C. as determined by Differential Scanning calorimetry (DSC).

8. The polymorph of claim 1, wherein the polymorph exhibits substantially no degradation up to 275° C. as determined by Thermogravimetric Analysis (TGA).

9. The polymorph of claim 1, wherein the polymorph exhibits a Differential Scanning calorimetry (DSC) thermogram that is substantially the same as shown in FIG. 10B.

10. The polymorph of claim 1, wherein the polymorph maintains its form after exposure to about 88% relative humidity (RH) for 7 days followed by exposure to about 95% RH for 8 days.

11. The polymorph of claim 1, wherein the polymorph is unsolvated.

12. The polymorph of claim 1, wherein the polymorph is micronized or unmicronized.

13. The polymorph of claim 12, wherein the polymorph has an average particle size of less than about 20 μm less than about 10 μm, less than about 1 μm, or less than about 100 nm.

14. A method of treating an eye disease, the method comprising administering a therapeutically effective amount of a pharmaceutical composition, the composition comprising a polymorph of a compound of Formula (I) having the structure:

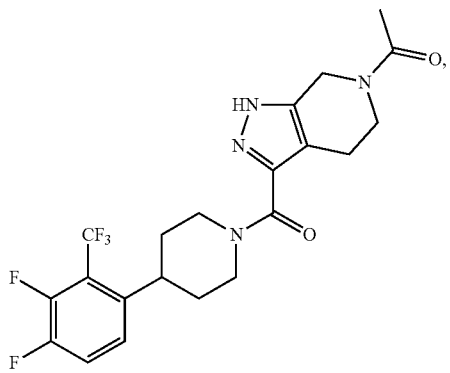 [SMILES: CC(=O)N1CCc2c(C(=O)N3CCC(c4ccc(F)c(F)c4C(F)(F)F)CC3)n[nH]c2C1]

wherein the polymorph exhibits an X-ray powder diffraction (XRPD) pattern having at least three characteristic peaks expressed in degrees two theta (+/−0.5 degree theta) at 6.7, 9.3, 14.1, 17.2, 23.5, 27.1, and 29.0.

15. The method of claim 14, wherein the polymorph is crystalline.

16. The method of claim 14, wherein the polymorph exhibits an X-ray powder diffraction (XRPD) pattern having at least five characteristic peaks expressed in degrees two theta (+/−0.5 degree theta) at 6.7, 9.3, 14.1, 17.2, 23.5, 27.1, and 29.0.

17. The method of claim 14, wherein the polymorph exhibits an X-ray powder diffraction (XRPD) pattern having characteristic peaks expressed in degrees two theta (+/−0.5 degree theta) at 6.7, 9.3, 14.1, 17.2, 23.5, 27.1, and 29.0.

18. The method of claim 14, wherein the eye disease is characterized by excessive lipofuscin accumulation in the retina.

19. The method of claim 18, wherein the eye disease characterized by excessive lipofuscin accumulation is Age-Related Macular Degeneration, dry (atrophic) Age-Related Macular Degeneration, Juvenile Macular Degeneration (Stargardt Disease), Best disease, adult vitelliform maculopathy, Geographic Atrophy, Stargardt-like macular dystrophy, diabetic retinopathy, or an ABCA4 gene associated retinal disease.

20. A pharmaceutical composition comprising the polymorph of claim 1 and at least one pharmaceutically acceptable excipient.

* * * * *